US011926614B2

(12) United States Patent
Krauss et al.

(10) Patent No.: US 11,926,614 B2
(45) Date of Patent: Mar. 12, 2024

(54) 1,2,4-TRIAZOLE DERIVATIVES AS TANKYRASE INHIBITORS

(71) Applicants: OSLO UNIVERSITETSSYKEHUS HF, Oslo (NO); FORSCHUNGSVERBUND BERLIN E.V., Berlin (DE); UNIVERSITY OF OULU, Oulu (FI)

(72) Inventors: Stefan Krauss, Eidsvoll Verk (NO); Marc Nazare, Berlin (DE); Lari Lehtio, Oulu (FI); Jo Waaler, Oslo (NO); Anita Wegert, Aldenhoven (DE); Ruben Gerardus George Leenders, Nijmegen (NL)

(73) Assignees: OSLO UNIVERSITETSSYKEHUS HF, Oslo (NO); FORSCHUNGSVERBUND BERLIN E.V., Berlin (DE); UNIVERSITY OF OULU, Oulu (FI)

(*) Notice: Subject to any disclaimer, the term of this patent is extended or adjusted under 35 U.S.C. 154(b) by 686 days.

(21) Appl. No.: 17/253,668

(22) PCT Filed: Jun. 19, 2019

(86) PCT No.: PCT/GB2019/051728
§ 371 (c)(1),
(2) Date: Dec. 18, 2020

(87) PCT Pub. No.: WO2019/243822
PCT Pub. Date: Dec. 26, 2019

(65) Prior Publication Data
US 2021/0269419 A1   Sep. 2, 2021

(30) Foreign Application Priority Data
Jun. 19, 2018   (GB) ..................... 1810071

(51) Int. Cl.
*C07D 401/14* (2006.01)
*C07D 403/04* (2006.01)
(Continued)

(52) U.S. Cl.
CPC ......... *C07D 401/14* (2013.01); *C07D 403/04* (2013.01); *C07D 403/14* (2013.01);
(Continued)

(58) Field of Classification Search
CPC .. C07D 401/14; C07D 403/04; C07D 403/14; C07D 405/14; C07D 409/14;
(Continued)

(56) References Cited

U.S. PATENT DOCUMENTS

2014/0031374 A1* 1/2014 Holsworth ........... C07D 413/14
546/256

FOREIGN PATENT DOCUMENTS

| JP | H072851 A | 1/1995 |
|---|---|---|
| JP | 2018500343 A | 1/2018 |

(Continued)

OTHER PUBLICATIONS

Notification of Reason(s) for Rejection dated Jun. 27, 2023 in Japanese Patent Application No. 2020-571480.
(Continued)

*Primary Examiner* — Timothy R Rozof
(74) *Attorney, Agent, or Firm* — Meunier Carlin & Curfman LLC

(57) ABSTRACT

The present invention relates to compounds of formula (I), tautomers, stereoisomers, pharmaceutically acceptable salts and pro-drugs thereof, to processes for their preparation, to pharmaceutical compositions containing such compounds and to their use in therapy wherein a dashed line indicates an optional bond; X represents: a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)2, and —SO$_2$R (where each R is independently H or $C_{1-6}$ alkyl, e.g. H or $C_{1-3}$ alkyl); a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or an aryl group optionally substituted by one or more (e.g. 1, 2 or 3) substituents independently selected from halogen (i.e. F, Cl, Br, I), $C_{1-6}$ alkyl (e.g $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); Y represents: an aryl or heteroaryl group optionally substituted by one or more (e.g. 1, 2 or 3) substituents independently selected from halogen (i.e. F, Cl, Br, I), $C_{1-6}$ alkyl (e.g $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); a 5- or 6-membered, saturated heterocyclic group optionally substituted by one or more (e.g. 1, 2 or 3) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and Z represents: an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or $C_{1-6}$ alkyl, e.g. H or $C_{1-3}$ alkyl); or an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or $C_{1-6}$ alkyl, e.g. H or $C_{1-3}$ alkyl).

(Continued)

These compounds find particular use in the treatment and/or prevention of a disease or disorder responsive to inhibition of tankyrase 1 and/or 2, for example a disorder which is mediated by tankyrase 1 and/or 2 such as cancer.

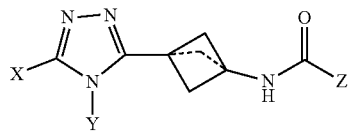

(I)

23 Claims, No Drawings

(51) Int. Cl.
*C07D 403/14* (2006.01)
*C07D 405/14* (2006.01)
*C07D 409/14* (2006.01)
*C07D 417/04* (2006.01)
*C07D 417/14* (2006.01)
*C07D 471/04* (2006.01)
*C07D 487/04* (2006.01)
*C07D 491/048* (2006.01)
*C07D 495/04* (2006.01)

(52) U.S. Cl.
CPC ......... *C07D 405/14* (2013.01); *C07D 409/14* (2013.01); *C07D 417/04* (2013.01); *C07D 417/14* (2013.01); *C07D 471/04* (2013.01); *C07D 487/04* (2013.01); *C07D 491/048* (2013.01); *C07D 495/04* (2013.01); *C07B 2200/07* (2013.01)

(58) Field of Classification Search
CPC .. C07D 417/14; C07D 417/04; C07D 471/04; C07D 487/04; C07D 491/048; C07D 495/04; C07B 2200/07
See application file for complete search history.

(56) References Cited

FOREIGN PATENT DOCUMENTS

| WO | 2010139966 A1 | 12/2010 |
| WO | 2012076898 A1 | 6/2012 |
| WO | 2016105477 A1 | 6/2016 |
| WO | 2018118868 A1 | 6/2018 |

OTHER PUBLICATIONS

International Search report and Written Opinion issued for Application No. PCT/GB2019/051728, dated Aug. 26, 2019.
International Preliminary Report on Patentability issued for Application No. PCT/GB2019/051728, dated Dec. 22, 2020.
Anumala, Upendra Rao, et al. "Discovery of a novel series of tankyrase inhibitors by a hybridization approach." Journal of medicinal chemistry 60.24 (2017): 10013-10025.
Search Report issued for Application No. GB1810071, dated Jan. 17, 2019.
Wang, Wenqi, et al. "Tankyrase inhibitors target YAP by stabilizing angiomotin family proteins." Cell reports 13.3 (2015): 524-532.
Chen, Baozhi, et al. "Small molecule—mediated disruption of Wnt-dependent signaling in tissue regeneration and cancer." Nature chemical biology 5.2 (2009): 100-107.
Waaler, Jo, et al. "Novel synthetic antagonists of canonical Wnt signaling inhibit colorectal cancer cell growth." Cancer research 71.1 (2011): 197-205.
Haikarainen, Teemu, Stefan Krauss, and Lari Lehtio. "Tankyrases: structure, function and therapeutic implications in cancer." Current pharmaceutical design 20.41 (2014): 6472-6488.
McGonigle, Sharon, et al. "E7449: A dual inhibitor of PARP1/2 and tankyrase1/2 inhibits growth of DNA repair deficient tumors and antagonizes Wnt signaling." Oncotarget 6.38 (2015): 41307.
Paine, Helen A., et al. "Exploration of the nicotinamide-binding site of the tankyrases, identifying 3-arylisoquinolin-1-ones as potent and selective inhibitors in vitro." Bioorganic & medicinal chemistry 23.17 (2015): 5891-5908.
Haikarainen, Teemu, et al. "Development and structural analysis of adenosine site binding tankyrase inhibitors." Bioorganic & medicinal chemistry letters 26.2 (2016): 328-333.

\* cited by examiner

1,2,4-TRIAZOLE DERIVATIVES AS TANKYRASE INHIBITORS

FIELD OF THE INVENTION

The present invention relates to novel compounds, to pharmaceutical formulations containing them and to their use in therapy, in particular as tankyrase (TNKS) inhibitors and, more specifically, as inhibitors of the WNT/β-catenin and hippo signalling pathways. The invention further relates to processes for the preparation of such compounds and to intermediates formed during these processes.

The compounds of the invention find particular use in the treatment of conditions mediated by tankyrase, including disorders associated with aberrant signalling in the WNT/β-catenin signalling pathway such as WNT/β-catenin signalling-related cancers, and disorders associated with aberrant signalling in the hippo signalling pathway such as hippo signalling-related cancers. They also find use in the treatment of other signalling disorders that are impacted by tankyrase such as proliferative diseases, fibrosis and viral infections (e.g. herpes simplex virus infections).

BACKGROUND OF THE INVENTION

WNT/β-catenin signalling is altered in a variety of tumors including tumors emerging from colorectal tissue, uterus, pancreas, skin, liver, thyroid, prostate, ovary, stomach, lung, lymphoid, bladder, brain, breast and kidney. Increased β-catenin levels have been identified as a central factor in T-cell infiltration in melanoma specimens (Spranger et al., Nature. 2015 Jul. 9; 523 (7559): 231-5) and a correlation between WNT/β-catenin pathway activation and immune exclusion has been observed across numerous human cancers (Luke et al., J. Clin. Oncol. 2016; 34 (suppl; abstract 3004)). The key effector in the hippo pathway, YAP, has also been identified as an oncoprotein whose expression is elevated in various human cancers (Wang et al., Cell Rep. 2015 Oct. 20; 13(3): 524-532).

Tankyrase 1 and 2 (TNKS1 and TNKS2) (PARP-5a, PARP-5b) are members of the poly-ADP-ribose polymerase (PARP) family of enzymes. Tankyrase 1/2 have been identified as regulators of the WNT/β-catenin signalling pathway via interactions with AXIN protein and a regulator of the hippo-signalling pathway via interactions with members of the AMOT family of proteins (Wang et al., Cell Rep. 2015 Oct. 20; 13(3):524-532). The inhibition of tankyrase 1/2 produces elevated AXIN protein levels and reduced levels of cellular β-catenin even in the absence of a dysfunctional and truncated form of APC protein. The inhibition of tankyrase 1/2 also stabilizes the AMOT family proteins, thereby suppressing YAP oncogenic functions.

Several groups of chemical substances (XAV939, MN-64, CMP8, CMP18, CMP11, CMP30, IWR-1, CMP40, CMP4, WIKI4, JW74, JW55, G007-LK, CMP24, CMP4b, MVP-TNKS656, AZ0108, E7449 and 3-arylisoquinolin-1-one inhibitors) have been identified which inhibit tankyrase 1 and 2 (Chen et al., Nat. Chem. Biol. 5: 100-107, 2009; Huang et al., Nature: 461: 614-620, 2009; Waaler et al., Cancer Res. 2011 Jan. 1; 71(1):197-205; Voronkov et al., J Med Chem. 2013 Apr. 11; 56(7): 3012-23; Bregman et al., J Med Chem. 2013 Feb. 14; 56(3): 1341-5; Bregman et al., J Med Chem. 2013 Jun. 13; 56(11): 4320-42; Haikarainen et al., Curr. Pharm. Des. 20(41): 6472-88, 2014; McGonigle et al., Oncotarget 6(38): 41307-23, 2015; Paine et al., Bioorg. Med. Chem. 23(17): 5891-908, 2015; Nkizinkiko et al., Bioorg. Med. Chem. 23(15): 4139-49, 2015; Haikarainen et al., Bioorg. Med. Chem. Lett. 26(2): 328-332016, 2016; Anumala et al., J Med Chem. 2017 Dec. 28; 60(24): 10013-10025; and Ferri et al., Eur J Med Chem. 2017 Dec. 15; 142: 506-522).

Compounds which exhibit activity in blocking tankyrase 1 and 2 are described in WO 2010/139966 and WO 2012/076898. Other compounds which display a high target affinity towards tankyrase 1 and 2 and which have been shown to be effective in a tumor xenograft model are described by Anumala et al. in J. Med. Chem. 60(24): 10013-10025, 2017.

Despite these developments, there is currently no viable tankyrase 1 and 2 inhibitor in clinical use. In view of the central importance of WNT/β-catenin signalling and hippo signalling in a wide range of cancers, there is an ongoing desire to identify further compounds which are useful in blocking tankyrase 1 and 2.

We have now found that the compounds described herein are effective in blocking tankyrase 1 and 2. Such compounds are thus suitable for inhibiting tumor cells in general and, in particular, those associated with colorectal cancers, non-small cell lung cancer, breast cancer, CNS cancers, ovary cancer, liver cancer, renal cancer, melanoma and pancreatic adenocarcinoma. The compounds are also suitable for cancer immunotherapy, for example when used in combination with checkpoint inhibitors such as PD-1 and PD-L1.

The compounds described herein also find use in the treatment of other disorders associated with tankyrase 1 and 2 activity, for example in treating fibrotic diseases and herpes simplex virus (HSV) infections.

SUMMARY OF THE INVENTION

In one aspect the invention relates to compounds of general formula (I), their tautomers, stereoisomers, pharmaceutically acceptable salts and pro-drugs:

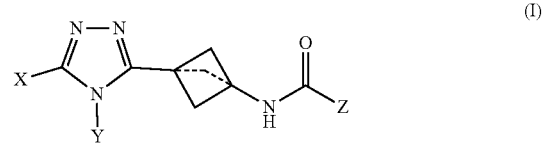

wherein:
a dashed line indicates an optional bond;
X represents:
  a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or $C_{1-6}$ alkyl, e.g. H or $C_{1-3}$ alkyl);
  a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);

Y represents:
   an aryl or heteroaryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);
   a 5- or 6-membered, saturated heterocyclic group optionally substituted by one or more (e.g. 1, 2 or 3) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or
   a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and Z represents:
   an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl); or
   an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl).

In another aspect the invention relates to a pharmaceutical composition comprising a compound of formula (I), a tautomer, a stereoisomer, a pharmaceutically acceptable salt, or a pro-drug thereof, together with one or more pharmaceutically acceptable carriers, excipients or diluents.

In a further aspect the invention relates to a compound of formula (I), a tautomer, a stereoisomer, a pharmaceutically acceptable salt, or a pro-drug thereof for use in therapy or for use as a medicament.

In a yet further aspect the invention relates to a compound of formula (I), a tautomer, a stereoisomer, a pharmaceutically acceptable salt, or a pro-drug thereof for use in the inhibition of tankyrase 1 and/or 2.

In a further aspect the invention relates to a compound of formula (I), a tautomer, a stereoisomer, a pharmaceutically acceptable salt, or a pro-drug thereof for use in the treatment or prevention of a disease or disorder responsive to inhibition of tankyrase 1 and/or 2, for example a disorder which is mediated by tankyrase 1 and/or 2, preferably for use in the treatment or prevention of a disorder such as cancer.

In a further aspect the invention relates to the use of a compound of formula (I), a tautomer, a stereoisomer, a pharmaceutically acceptable salt, or a pro-drug thereof in the manufacture of a medicament for use in the treatment or prevention of a disease or disorder responsive to inhibition of tankyrase 1 and/or 2, for example a disorder which is mediated by tankyrase 1 and/or 2, preferably a disorder such as cancer.

A yet further aspect of the invention relates to a method of treatment or prevention of a disease or disorder responsive to inhibition of tankyrase 1 and/or 2, for example a disorder which is mediated by tankyrase 1 and/or 2, preferably a method of treatment or prevention of a disorder such as cancer, said method comprising the step of administering to a patient in need thereof (e.g. a human patient) a pharmaceutically effective amount of a compound of formula (I), a tautomer, a stereoisomer, a pharmaceutically acceptable salt, or a pro-drug thereof.

DETAILED DESCRIPTION OF THE INVENTION

Definitions

As used herein, the term "alkyl" refers to a saturated hydrocarbon group and is intended to cover both straight-chained and branched alkyl groups. Examples of such groups include methyl, ethyl, n-propyl, iso-propyl, n-butyl, tert-butyl, sec-butyl, n-pentyl, iso-pentyl, neo-pentyl, n-hexyl, 2-methylbutyl, 2-methylpentyl, 2-ethylbutyl, 3-methylpentyl, and 4-methylpentyl. An alkyl group preferably contains from 1-6 carbon atoms, more preferably 1-4 carbon atoms, e.g. 1-3 carbon atoms. The term "alkyl" group also includes any saturated hydrocarbon group in which one or more (e.g. all) hydrogen atoms are replaced with deuterium. Examples of such groups include -$CD_3$, -$CD_2CD_3$, -$CD_2CD_2CD_3$, -$CD(CD_3)CD_3$, etc. Unless otherwise specified, any "alkyl" group may be substituted by one or more groups, which may be identical or different. Suitable substituents include hydroxyl, $C_{1-6}$ alkoxy, amino, cyano, or nitro groups, and halogen atoms (e.g. F, Cl or Br). For example, any alkyl group may be substituted by one or more hydroxyl groups, e.g. by one or two hydroxyl groups. Examples of such groups include —$CH(OH)CH_3$ and —$C(OH)(CH_3)(CH_3)$. In an embodiment, any alkyl group herein described may be unsubstituted.

The term "alkoxy" as used herein refers to an —O-alkyl or —O-cycloalkyl group, wherein alkyl and cycloalkyl are as defined herein and alkyl includes deuterated groups in which one or more (e.g. all) hydrogen atoms are replaced with deuterium. Examples of alkoxy groups include, but are not limited to, methoxy, ethoxy, propyloxy, cyclopropyloxy, etc. Unless otherwise specified, any alkoxy group may be substituted in one or more positions with a suitable substituent. Where more than one substituent group is present, these may be the same or different. Suitable substituents include hydroxy, $C_{1-6}$ alkoxy, amino, cyano, or nitro groups, and halogen atoms (e.g. F, Cl or Br).

The term "cycloalkyl" refers to a monovalent, saturated cyclic carbon system. Examples of cycloalkyl groups include, but are not limited to, cyclopropyl, cyclobutyl, cyclopentyl, and cyclohexyl. Unless otherwise specified, any cycloalkyl group may be substituted in one or more positions with a suitable substituent. Where more than one substituent group is present, these may be the same or different.

The term "halogen" or "halogen atom" refers to —F, —Cl, —Br or —I.

The term "haloalkyl" refers to an alkyl group as defined herein in which at least one of the hydrogen atoms of the alkyl group is replaced by a halogen atom, preferably F, Cl or Br. Examples of such groups include, but are not limited to, —$CH_2F$, —$CHF_2$, —$CF_3$, —$CCl_3$, —$CHCl_2$, —$CH_2CF_3$, etc.

As used herein, the term "unsaturated heterocyclic group" is intended to cover any unsaturated heterocyclic ring which contains at least one heteroatom selected from nitrogen, oxygen and sulphur. Such groups may be monocyclic or polycyclic, preferably mono- or bicyclic. Where these contain bicyclic rings, these may be fused. Where such rings are bicyclic these may contain up to 10 ring atoms in which at least one ring contains at least one heteroatom selected from nitrogen, oxygen and sulphur. The heterocyclic ring structure (whether mono- or bicyclic) may be linked to the remainder of the molecule through a carbon atom or, if present, through a nitrogen atom. Typically it will be linked to the remainder of the molecule through a carbon atom. In one embodiment the unsaturated heterocyclic group may contain one or two nitrogen atoms, e.g. two nitrogen atoms. In other embodiments, it may contain one sulphur atom, or one sulphur atom and one nitrogen atom. The unsaturated heterocyclic group may be aromatic or non-aromatic. In one embodiment it may be aromatic, i.e. it may be a "heteroaryl group". Unless otherwise stated, any unsaturated heterocyclic group mentioned herein may optionally be substituted by one or more groups as herein defined, which may be identical or different. Examples of "unsaturated heterocyclic groups" are the heterocycles pyrrole, 2H-pyrrole, pyrroline, pyrazole, imidazole, oxazole, isoxazole, pyrazoline, imidazoline, thiazole, isothiazole, thiadiazole, pyridine, pyridazine, pyrimidine, pyrazine, and triazole. Of these, pyrazole, imidazole, pyrazoline, imidazoline, pyridine, pyridazine, pyrimidine and pyrazine are preferred. Most preferred are pyrimidine and pyridine.

As used herein, the term "saturated heterocyclic ring" is intended to cover any heterocyclic ring which contains at least one heteroatom selected from nitrogen, oxygen and sulphur. The ring may be linked to the remainder of the molecule through a carbon atom or through a nitrogen atom. Typically, it will be linked via a carbon atom.

The term "aryl" as used herein refers to aromatic ring systems. Such ring systems may be monocyclic or bicyclic and contain at least one unsaturated aromatic ring. Where these contain bicyclic rings, these may be fused. Preferably such systems contain from 6-20 carbon atoms, e.g. either 6 or 10 carbon atoms. Examples of such groups include phenyl, 1-napthyl and 2-napthyl. A preferred aryl group is phenyl. Unless stated otherwise, any aryl group may be substituted by one or more substituents as described herein. Where more than one substituent group is present, these may be the same or different.

As used herein, the term "heteroaryl" refers to heterocyclic aromatic groups. Such groups may be monocyclic or bicyclic and contain at least one unsaturated heteroaromatic ring system. Where these are monocyclic, these comprise 5- or 6-membered rings which contain at least one heteroatom selected from nitrogen, oxygen and sulfur and contain sufficient conjugated bonds to form an aromatic system. Where these are bicyclic, these may contain from 9-11 ring atoms. Examples of "heteroaryl groups" include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless otherwise stated, any heteroaryl ring mentioned herein may optionally be substituted by one or more groups as described herein. Where more than one substituent group is present, these may be the same or different.

Where reference is made herein to one or more substituents, this refers to substitution by substituents that can be independently selected from the groups defined herein. In one embodiment, 1, 2, 3, 4, 5 or 6 substituents may be present, preferably 1, 2, or 3, more preferably 1 or 2, e.g. 1.

The compounds of the invention may contain one or more chiral centers and may therefore exist in different stereoisomeric forms. The term "stereoisomer" refers to compounds which have identical chemical constitution but which differ in respect of the spatial arrangement of the atoms or groups. Examples of stereoisomers are enantiomers and diastereomers. The term "enantiomers" refers to two stereoisomers of a compound which are non-superimposable mirror images of one another. The term "diastereoisomers" refers to stereoisomers with two or more chiral centres which are not mirror images of one another. The invention is considered to extend to diastereomers and enantiomers, as well as racemic mixtures.

The compounds herein described may be resolved into their enantiomers and/or diastereomers. For example, where these contain only one chiral center, these may be provided in the form of a racemate or racemic mixture (a 50:50 mixture of enantiomers) or may be provided as pure enantiomers, i.e. in the R- or S-form. Any of the compounds which occur as racemates may be separated into their enantiomers by methods known in the art, such as column separation on chiral phases or by recrystallization from an optically active solvent. Those compounds with at least two asymmetric carbon atoms may be resolved into their diastereomers on the basis of their physical-chemical differences using methods known per se, e.g. by chromatography and/or fractional crystallization, and where these compounds are obtained in racemic form, they may subsequently be resolved into their enantiomers.

The term "tautomer" as used herein refers to structural isomers which readily interconvert by way of a chemical reaction which may involve the migration of a proton accompanied by a switch of a single bond and adjacent double bond. It includes, in particular, keto-enol and amide-imidic acid tautomers, as well as tautomeric forms of any heterocyclic compounds which contain two or more ring nitrogen atoms (e.g. imidazoles, pyrazoles, tetrazoles, etc.). Dependent on the conditions, the compounds may predominantly exist in one of the tautomeric forms and the invention is not intended to be limited to the particular form shown in any of the structural formulae given herein.

The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilizes the charge on the parent compound. If the compound of the invention is a base, a suitable pharmaceutically acceptable salt may be prepared by reaction of the free base with an organic or inorganic acid. If the compound of the invention is an acid, a suitable pharmaceutically acceptable salt may be prepared by reaction of the free acid with an organic or inorganic base. Non-limiting examples of suitable salts are described herein.

The term "pharmaceutically acceptable" means that the compound or composition is chemically and/or toxicologically compatible with other components of the formulation or with the patient (e.g. human) to be treated.

By "a pharmaceutical composition" is meant a composition in any form suitable to be used for a medical purpose.

The term "pro-drug" refers to a derivative of an active compound which undergoes a transformation under the conditions of use, for example within the body, to release an active drug. A pro-drug may, but need not necessarily, be pharmacologically inactive until converted into the active drug. As used herein, the term "pro-drug" extends to any compound which under physiological conditions is converted into any of the active compounds herein described.

Suitable pro-drugs include compounds which are hydrolysed under physiological conditions to the desired molecule.

Pro-drugs may typically be obtained by masking one or more functional groups in the parent molecule which are considered to be, at least in part, required for activity using a pro-group. By "pro-group" as used herein is meant a group which is used to mask a functional group within an active drug and which undergoes a transformation, such as cleavage, under the specified conditions of use (e.g. administration to the body) to release a functional group and hence provide the active drug. Pro-groups are typically linked to the functional group of the active drug via a bond or bonds that are cleavable under the conditions of use, e.g. in vivo. Cleavage of the pro-group may occur spontaneously under the conditions of use, for example by way of hydrolysis, or it may be catalyzed or induced by other physical or chemical means, e.g. by an enzyme, by exposure to light, by exposure to a change in temperature, or to a change in pH, etc. Where cleavage is induced by other physical or chemical means, these may be endogenous to the conditions of use, for example pH conditions at a target tumor site, or these may be supplied exogenously.

As used herein, "treatment" includes any therapeutic application that can benefit a human or non-human animal (e.g. a non-human mammal). Both human and veterinary treatments are within the scope of the present invention, although primarily the invention is aimed at the treatment of humans. Treatment may be in respect of an existing disease or condition or it may be prophylactic.

As used herein, a "pharmaceutically effective amount" relates to an amount that will lead to the desired pharmacological and/or therapeutic effect, i.e. an amount of the agent which is effective to achieve its intended purpose. While individual patient needs may vary, determination of optimal ranges for effective amounts of the active agent is within the capability of one skilled in the art. Generally, the dosage regimen for treating a disease or condition with any of the compounds described herein is selected in accordance with a variety of factors including the nature of the medical condition and its severity.

Any reference herein to "tankyrase inhibition" with respect to a compound of the invention means a compound that can inhibit tankyrase activity, e.g. reduce and/or eliminate and/or mask and/or prevent the detrimental action of a tankyrase, e.g. tankyrase 1 and/or tankyrase 2. Any reduction in the action of a tankyrase need not be complete but will typically be a reduction of at least about 10%, 20%, 30%, 40%, 50%, 60%, 70%, 80%, or may be as high as at least 90% or at least 95%. Reference to a "tankyrase inhibitor" or "inhibition of tankyrase" should be construed accordingly.

The term "WNT signalling pathway" is used to refer to the chain of events normally mediated by WNT, LRP (LDL-receptor related protein), frizzled, AXIN and ß-catenin, among others, and resulting in changes in gene expression and other phenotypic changes typical of WNT activity.

The term "hippo signalling pathway" is used to refer to the chain of events normally mediated by the YAP/TAZ proteins, resulting in changes in gene expression and other phenotypic changes typical of hippo signalling pathway activity.

The invention is based, at least in part, on the finding that the compounds herein disclosed are tankyrase inhibitors, e.g. inhibitors of tankyrase 1 and/or 2. This discovery leads to the use of the compounds to treat conditions or diseases in subjects, e.g. in humans, which are mediated by tankyrase, including WNT signalling related disorders, hippo signalling related disorders and other tankyrase 1 and/or 2 (TNKS1/TNKS2) signalling related disorders.

In one aspect the invention relates to compounds of general formula (I), their tautomers, stereoisomers, pharmaceutically acceptable salts and pro-drugs:

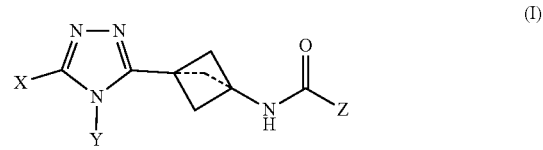

(I)

wherein:
a dashed line indicates an optional bond;
X represents:
  a 5- or 6-membered, unsaturated heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or $C_{1-6}$ alkyl, e.g. H or $C_{1-3}$ alkyl);
  a $C_{3-5}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);
Y represents:
  an aryl or heteroaryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), and $C_{1-6}$ alkoxy (e.g. $C_{1-3}$ alkoxy);
  a 5- or 6-membered, saturated heterocyclic group optionally substituted by one or more (e.g. 1, 2 or 3) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); or
  a $C_{3-6}$ cycloalkyl group optionally substituted by one or more (e.g. 1 or 2) substituents independently selected from $C_{1-6}$ alkyl (preferably $C_{1-3}$ alkyl), $C_{1-6}$ haloalkyl (e.g. $C_{1-3}$ haloalkyl), and $C_{1-6}$ alkoxy (e.g. $C_{1-3}$ alkoxy); and
Z represents:
  an aryl group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or $C_{1-6}$ alkyl, e.g. H or $C_{1-3}$ alkyl); or
  an unsaturated, 5- to 10-membered mono- or bicyclic heterocyclic group optionally substituted by one or more (e.g. 1, 2 or 3) substituents independently selected from halogen (i.e. F, Cl, Br, I), $C_{1-6}$ alkyl (e.g. $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —NO$_2$, —N(R)$_2$, and —SO$_2$R (where each R is independently H or C$_{1-6}$ alkyl, e.g. H or C$_{1-3}$ alkyl).

As will be understood, in formula (I) the group:

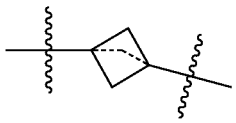

can be either one of the following groups:

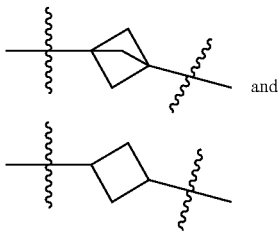

and

In one embodiment of formula (I), X represents:
a 5- or 6-membered, unsaturated heterocyclic group optionally substituted by one or more (e.g. 1, 2 or 3) substituents independently selected from halogen (i.e. F, Cl, Br, I), C$_{1-6}$ alkyl (e.g. C$_{1-3}$ alkyl), C$_{1-6}$ haloalkyl (e.g. C$_{1-3}$ haloalkyl), C$_{1-6}$ alkoxy (e.g. C$_{1-3}$ alkoxy), —CN, —NO$_2$, —N(R)$_2$, and —SO$_2$R (where each R is independently H or C$_{1-6}$ alkyl, e.g. H or C$_{1-3}$ alkyl); or
a C$_{3-5}$ cycloalkyl group optionally substituted by one or more (e.g. 1 or 2) substituents independently selected from C$_{1-6}$ alkyl (preferably C$_{1-3}$ alkyl), C$_{1-6}$ haloalkyl (e.g. C$_{1-3}$ haloalkyl), and C$_{1-6}$ alkoxy (e.g. C$_{1-3}$ alkoxy).

In one embodiment of formula (I), X is an optionally substituted, 5- or 6-membered, unsaturated heterocyclic group. Such groups will typically contain either at least one nitrogen atom, e.g. one or two nitrogen atoms, or one nitrogen atom and one sulphur atom. In an embodiment, X may be an optionally substituted heteroaryl group. Any substituent groups may be present either on a ring nitrogen or ring carbon atom. In another embodiment, X may be an unsubstituted.

X may, for example, be selected from any of the following groups: pyridine (e.g. 2-pyridine), pyrimidine (e.g. 2- or 4-pyrimidine), pyrrole (e.g. 2- or 3-pyrrole), pyrazine (e.g. 2-pyrazine), thiazole (e.g. 2- or 5-thiazole), pyrazole (e.g. 4-pyrazole), imidazole (e.g. 2-, 4- or 5-imidazole) and thiophene (e.g. 2-thiophene). Any of these groups may optionally be substituted by one or more of the substituent groups herein disclosed. In one embodiment, these groups may be unsubstituted.

Preferably, X is an optionally substituted pyridine or pyrimidine group, for example an optionally substituted 2-pyridine, 2-pyrimidine group or 4-pyrimidine group. In one embodiment, these groups may be unsubstituted.

In one embodiment of formula (I), X may represent an optionally substituted C$_{3-5}$ cycloalkyl group, e.g. an unsubstituted C$_{3-5}$ cycloalkyl group. Examples of such groups include cyclopropyl and cyclopentyl.

In one embodiment of formula (I), X may represent an optionally substituted aryl group, e.g. an optionally substituted phenyl group. For example, X may be an unsubstituted phenyl group.

Any of the X groups herein described may be substituted by one or more ring substituents. Where the groups X are substituted it is generally preferred that these are substituted by one or two substituent groups, e.g. by one substituent. Suitable substituents are as herein described and include, for example C$_{1-3}$ alkyl, C$_{1-3}$ alkoxy and —SO$_2$R (where R is H or C$_{1-6}$ alkyl, preferably H or C$_{1-3}$ alkyl, e.g. methyl). Examples of suitable substitutents include —OCH$_2$CH$_3$ (and deuterated analogs), —CH$_3$ and —SO$_2$CH$_3$.

In one embodiment, X is unsubstituted.

Specific examples of group X include the following:

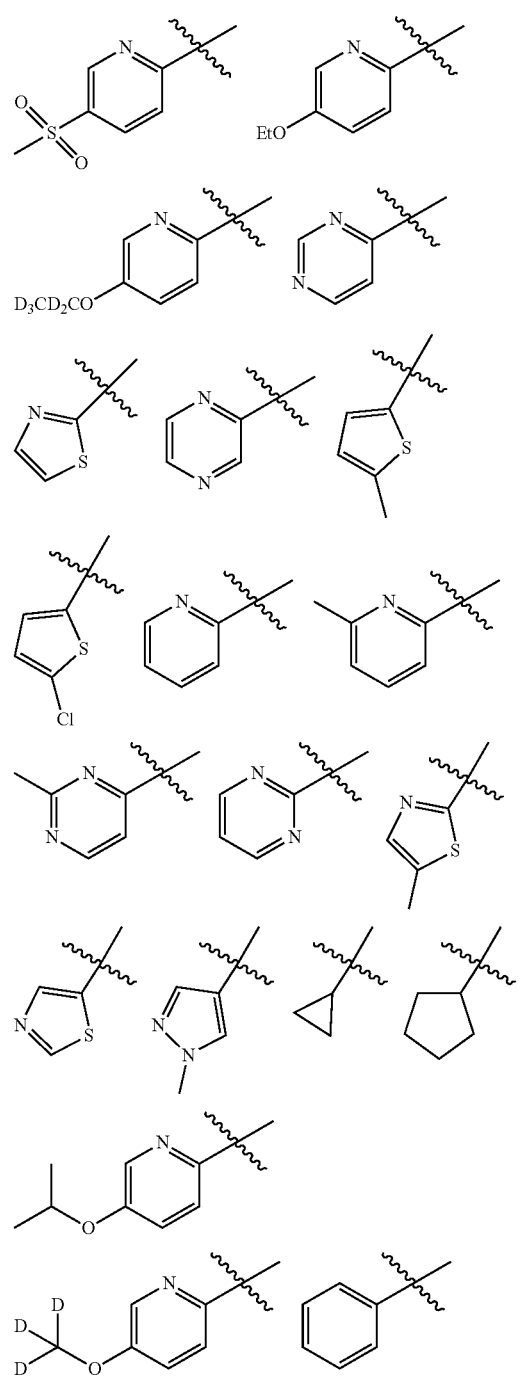

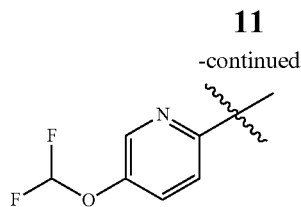

In one set of embodiments, group X may represent any of the following:

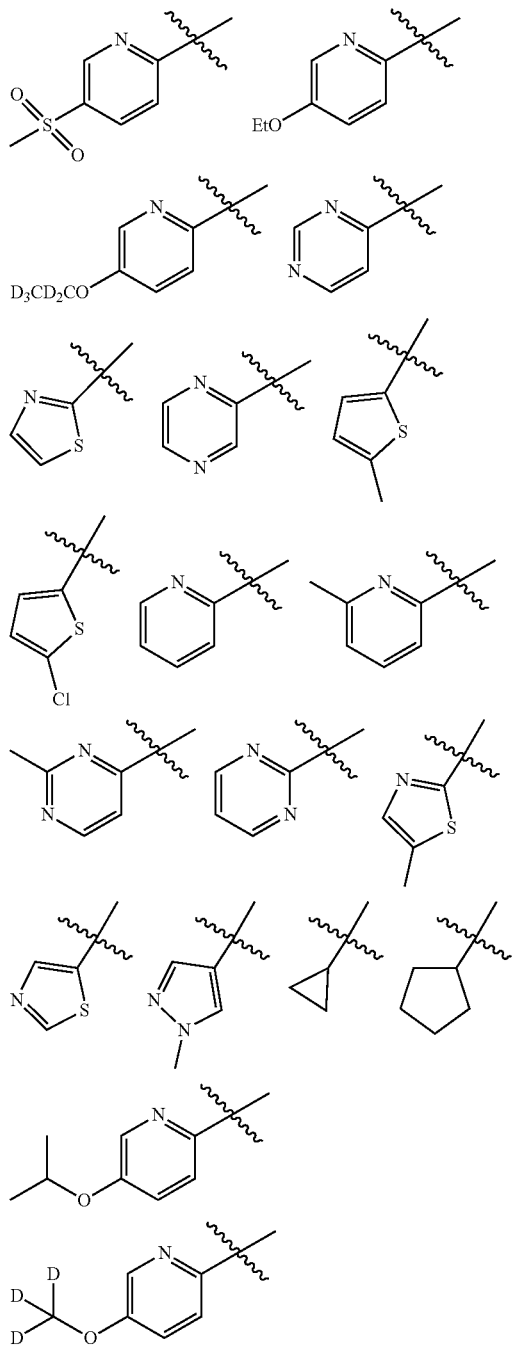

In certain embodiments, group X may be selected from any of the following:

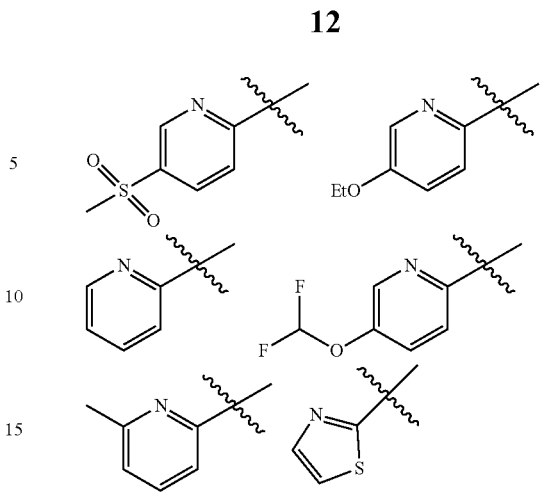

In one embodiment of formula (I), Y is an optionally substituted, aryl or heteroaryl group.

Where Y is an aryl group, this may be an optionally substituted phenyl group. When substituted, the ring substituents on the phenyl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. —$CF_3$), and halogen (e.g. F or Cl). One or more of such groups may be present on the ring in any ring positions. However, it is preferred that one or two groups will be present. In one embodiment, the phenyl ring will be substituted by a single halogen atom (e.g. F or Cl) either in the ortho-, meta- or para-position, e.g. in the ortho-position.

In another embodiment of formula (I), Y represents an optionally substituted heteroaryl group. Such groups will typically contain one or two heteroatoms, e.g. one heteroatom. Preferably, the heteroatom is either nitrogen or sulphur, e.g. nitrogen. Where the ring is 6-membered the heteroatom is preferably nitrogen. Where the ring is 5-membered the heteroatom is preferably sulphur. In one embodiment, Y represents pyridine, e.g. 2-pyridine. In a further embodiment, Y can be thiophene (e.g. 2-thiophene). When substituted, the ring substituents on the heteroaryl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. —$CF_3$), and halogen (e.g. F or Cl). One or more of such groups may be present on the ring in any ring positions. In one embodiment, a single substituent may be present.

Preferably Y may be an optionally substituted phenyl, pyridine (e.g. 2-pyridine) or thiophene (e.g. 2-thiophene) group.

In one embodiment, Y may represent a 5- or 6-membered, saturated heterocyclic group. This group may be substituted or unsubstituted, preferably it will be unsubstituted. Such groups will typically contain one or two heteroatoms, e.g. one heteroatom. Preferably the heteroatom is oxygen. An example of such a group is tetrahydropyranyl.

In another embodiment, Y may represent an optionally substituted $C_{3-6}$ cycloalkyl group. When substituted, suitable substituent groups include $C_{1-6}$ alkyl (e.g. $C_{1-3}$ alkyl). In one embodiment, the cycloalkyl ring may be unsubstituted. Examples of such groups include cyclopentyl and cyclohexyl.

Any of the Y groups herein described may be substituted by one or more ring substituents. Where these are substituted it is generally preferred that these are substituted by one or two substituent groups, e.g. by one substituent. Suitable substituents are as herein described and include, for example $C_{1-3}$ alkyl, $C_{1-3}$ alkoxy, $C_{1-3}$ haloalkyl, and halogen atoms. Examples of suitable substitutents include F, Cl, $C_{1-3}$ alkyl, and —$CF_3$.

In one embodiment, Y is unsubstituted.

Specific examples of group Y include the following:

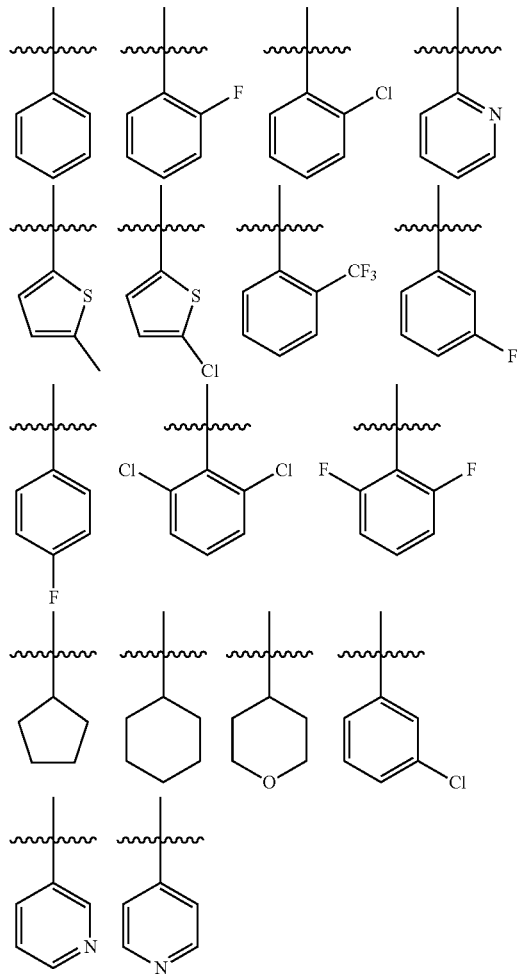

In certain embodiments, group Y may be selected from any of the following:

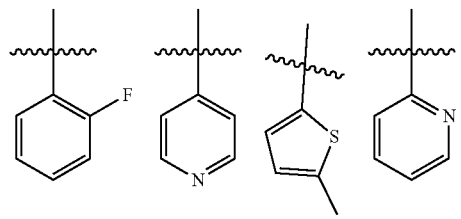

In one embodiment of formula (I), Z represents an aryl group optionally substituted by one or more (e.g. 1, 2 or 3) substituents. In one embodiment, Z is an optionally substituted phenyl group. When substituted, the ring substituents on the phenyl ring may independently be selected from $C_{1-3}$ alkyl (e.g. methyl or ethyl), $C_{1-3}$ alkoxy (e.g. methoxy or ethoxy), $C_{1-3}$ haloalkyl (e.g. —$CF_3$), and halogen (e.g. F or Cl). One or more of such groups may be present on the ring in any ring positions. However, it is preferred that one or two groups will be present. In one embodiment, the phenyl ring will be substituted by a single halogen atom (e.g. F or Cl) either in the ortho-, meta- or para-position. In another embodiment, the phenyl ring may be unsubstituted.

In another embodiment of formula (I), Z represents an optionally substituted, unsaturated, 5- to 10-membered mono- or bicyclic heterocyclic group. Such groups containing one or more nitrogen atoms, e.g. one or two nitrogen atoms, are preferred. For example, Z may represent a 6-membered, 5-5 fused, 5-6 fused, or 6-6 fused unsaturated heterocyclic ring containing one, two or three heteroatoms, e.g. one, two, or three nitrogen atoms, preferably one or two nitrogen atoms.

Z may, for example, be selected from any of the following groups:

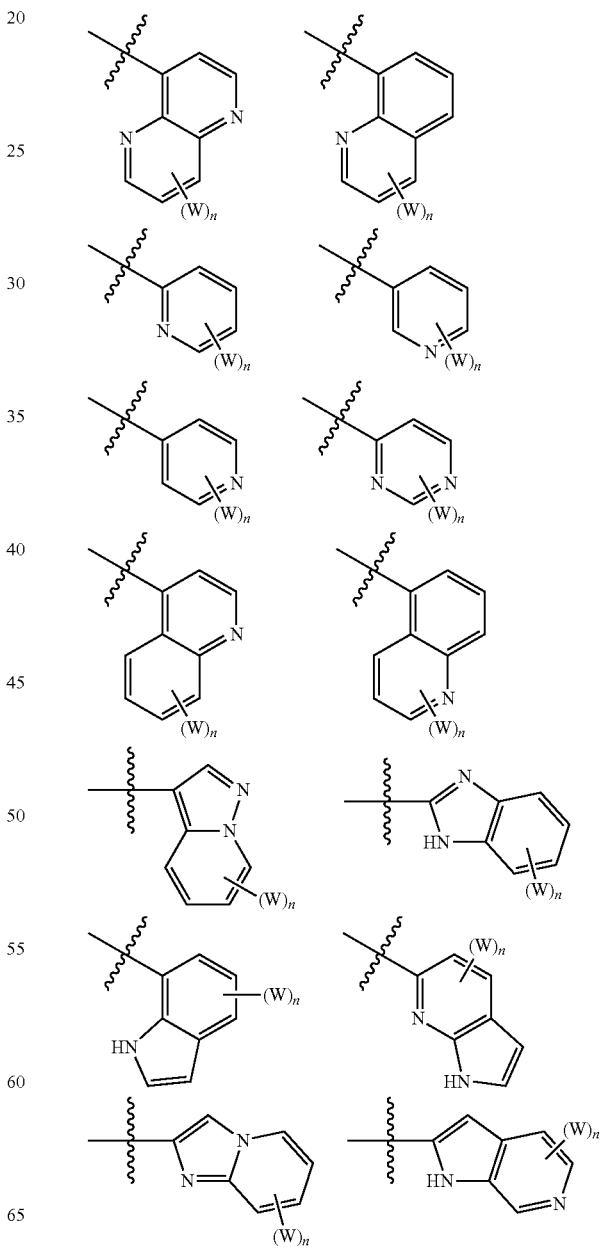

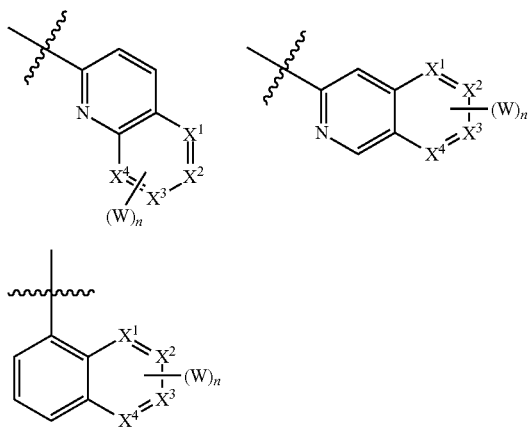

wherein n is 0, 1 or 2, preferably 0 or 1;

W is a substituent group selected from halogen (i.e. F, Cl, Br, I), $C_{1-6}$ alkyl (e.g $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl); and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH; or two of $X^1$, $X^2$, $X^3$ and $X^4$ (e.g. $X^1$ and $X^4$) are N and the remaining two of $X^1$, $X^2$, $X^3$ and $X^4$ (e.g. $X^2$ and $X^3$) are CH.

In one set of embodiments, group Z may be selected from any of the following groups:

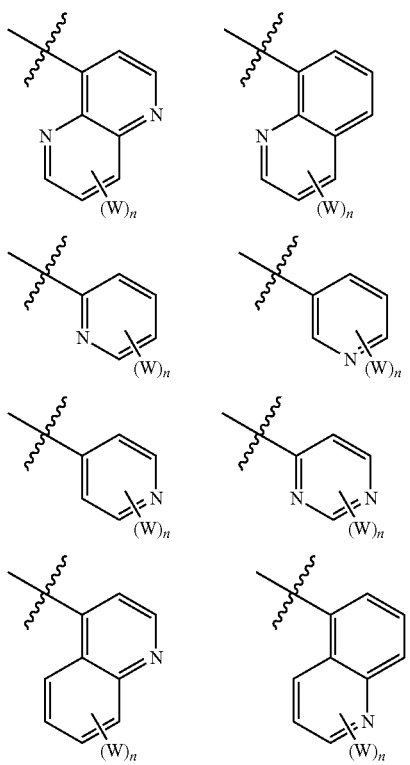

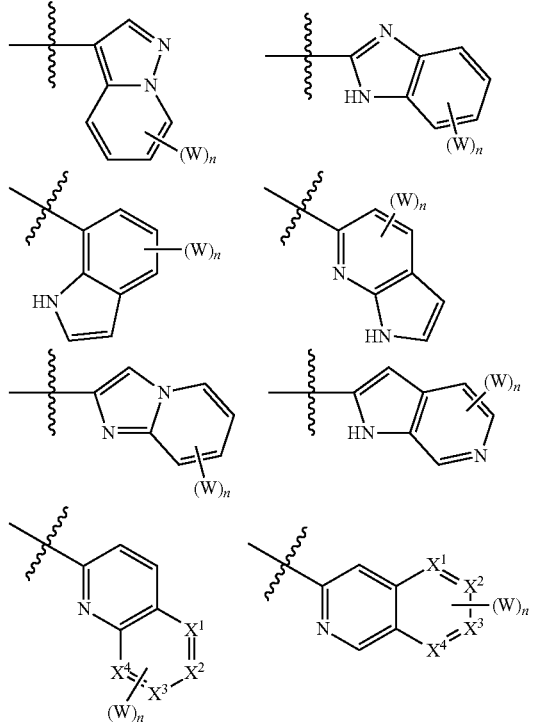

wherein n is 0, 1 or 2, preferably 0 or 1;

W is a substituent group selected from halogen (i.e. F, Cl, Br, I), $C_{1-6}$ alkyl (e.g $C_{1-3}$ alkyl), $C_{1-6}$ haloalkyl (e.g. $C_{1-3}$ haloalkyl), $C_{1-6}$ alkoxy (e.g. $C_{1-3}$ alkoxy), —CN, —$NO_2$, —$N(R)_2$, and —$SO_2R$ (where each R is independently H or $C_{1-6}$ alkyl, e.g. H or $C_{1-3}$ alkyl); and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH.

In one embodiment, n is 0. Where n is 1 or 2, each W may preferably be selected from halogen (e.g. F or $C_1$), $C_{1-3}$ alkyl, $C_{1-3}$ alkoxy, or —CN.

In one embodiment, Z is selected from optionally substituted phenyl, pyridine (e.g. 2-, 3- or 4-pyridine, preferably 2- or 3-pyridine), pyrimidine (e.g. 2- or 4-pyrimidine, preferably 4-pyrimidine), quinoline (e.g. 4-, 5- or 8-quinoline), 1,5-naphthyridine (e.g. 4-(1,5-naphthyridine)), benzimidazole (e.g. 2-benzimidazole), pyrazolo[1,5-a]pyridine (e.g. 3-(pyrazolo[1,5-a]pyridine)), diazanaphthalene (e.g. a naphthyridine, such as a 1,8-, 1,6- and 1,4-naphthyridine, or a benzodiazine, such as a 1,4-diazanaphthalene), an azaindole (e.g. a 4-, 5- or 7-azaindole), 1H-indole, furopyrrole (e.g. 4H-furo [3,2-6] pyrrole), and thienopyrrole (e.g. a 4-thieno [3,2-6] pyrrole). In another embodiment, Z is selected from optionally substituted phenyl, pyridine, quinoline, 1,5-naphthyridine and 1,4-diazanaphthalene.

Z is preferably selected from optionally substituted phenyl, pyridine (e.g. 2-, 3- or 4-pyridine, preferably 2- or 3-pyridine), pyrimidine (e.g. 2- or 4-pyrimidine, preferably 4-pyrimidine), quinoline (e.g. 4-, 5- or 8-quinoline), 1,5-naphthyridine (e.g. 4-(1,5-napthyridine)), benzimidazole (e.g. 2-benzimidazole), and pyrazolo[1,5-a]pyridine (e.g. 3-(pyrazolo[1,5-a]pyridine)). More preferably, Z is selected from optionally substituted phenyl, pyridine, quinoline and 1,5-naphthyridine.

In a further embodiment, Z is selected from optionally substituted 4-(1,5-napthyridine), phenyl, 8-quinoline and 2-pyridine.

Any of the Z groups herein described may be substituted by one or more ring substituents. Where these are substituted it is generally preferred that these are substituted by one or two substituent groups, e.g. by one substituent. Suitable substituents are as herein described and include, for example $C_{1-3}$ alkyl, $C_{1-3}$ alkoxy, $C_{1-3}$ haloalkyl, —CN and halogen atoms. Preferred examples of suitable substituents include F, CN, —OCH$_3$, and —OCH$_2$CH$_3$.

In one embodiment, Z is unsubstituted.

Specific examples of group Z include the following:

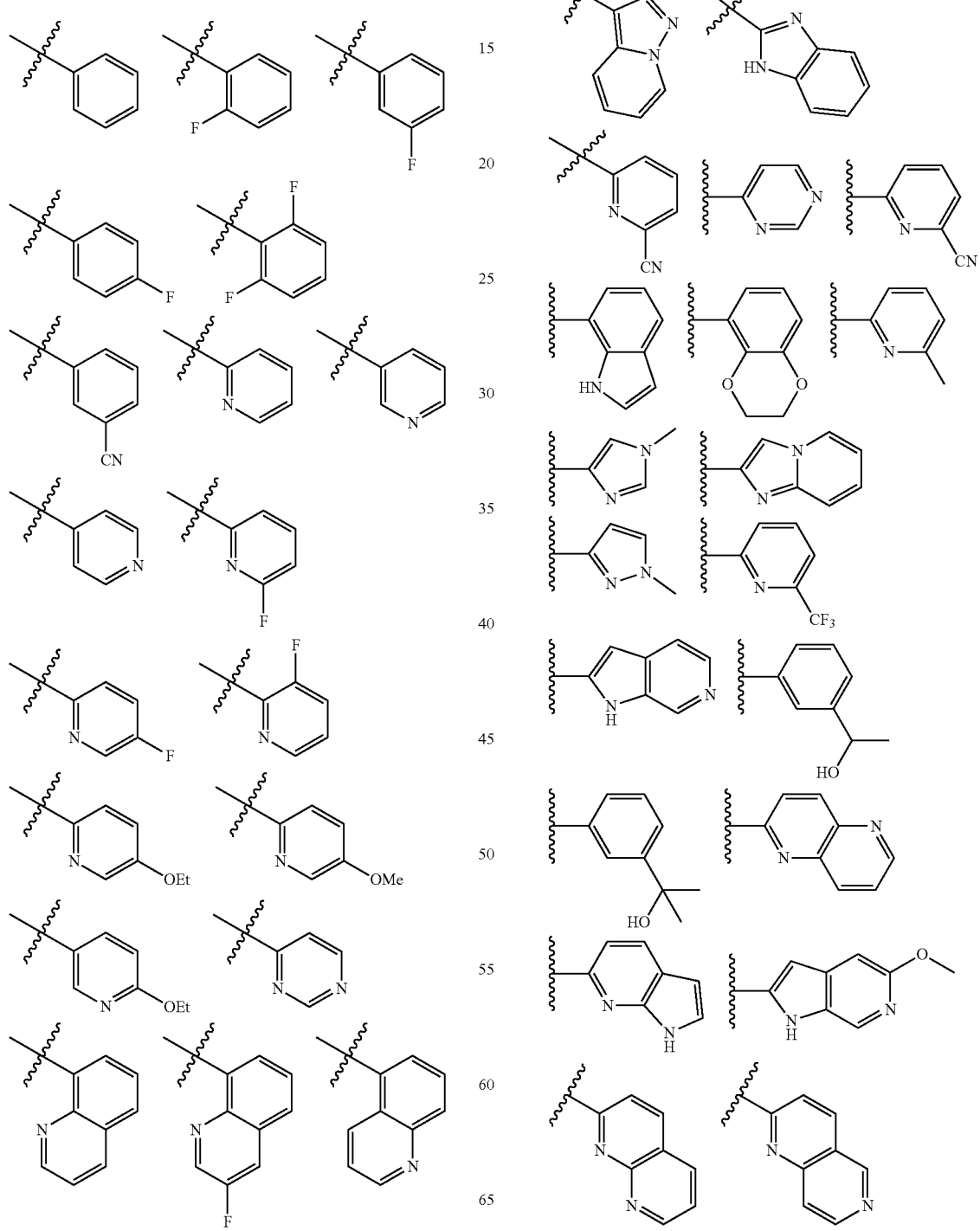

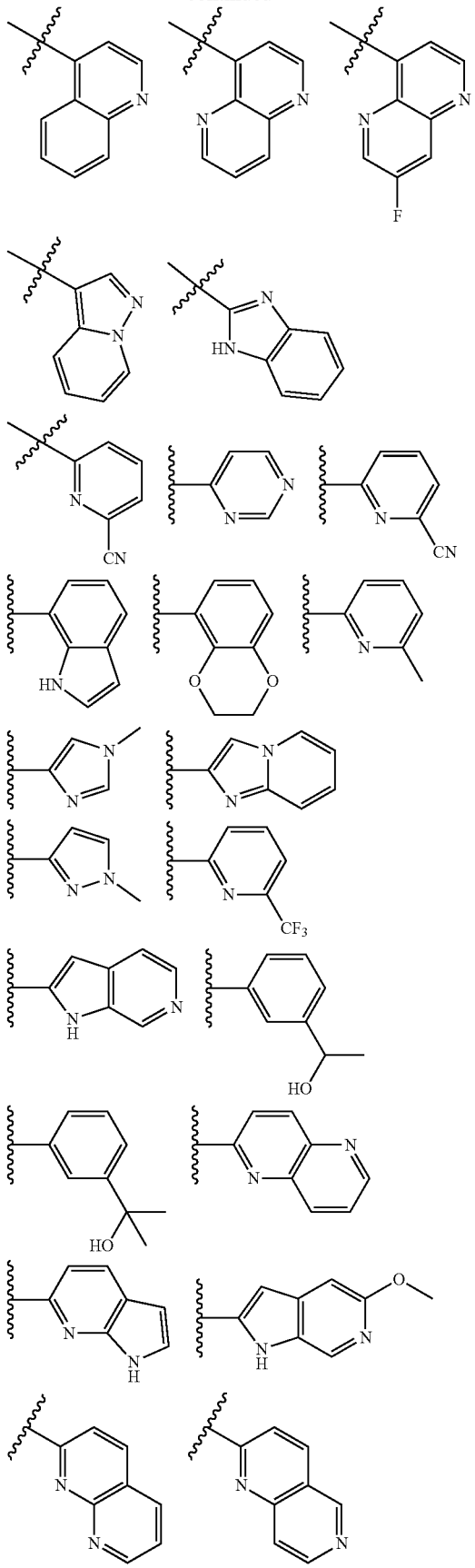

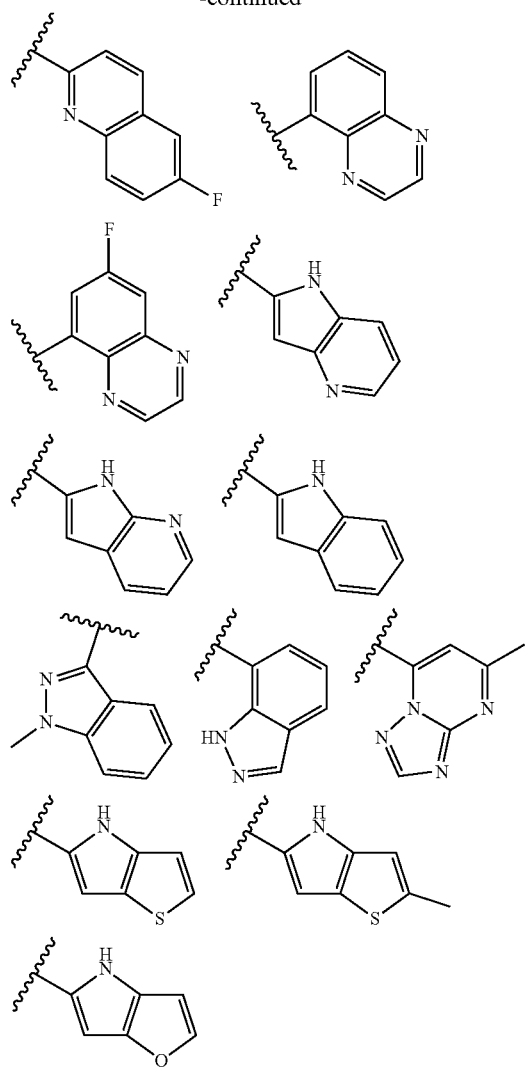
In certain embodiments, examples of group Z include the following:
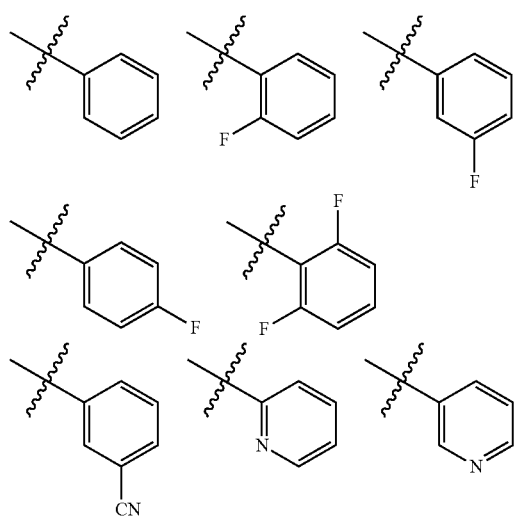
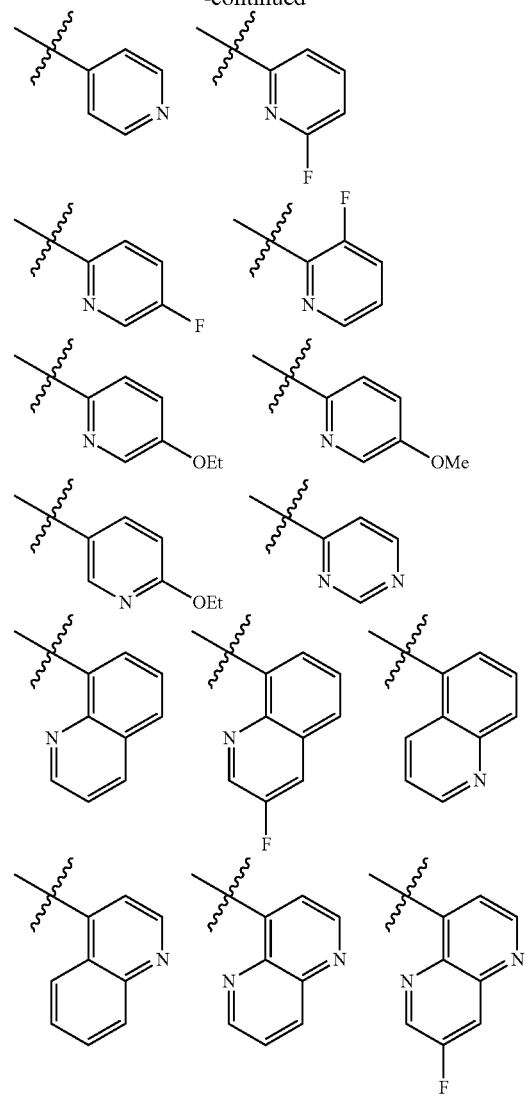
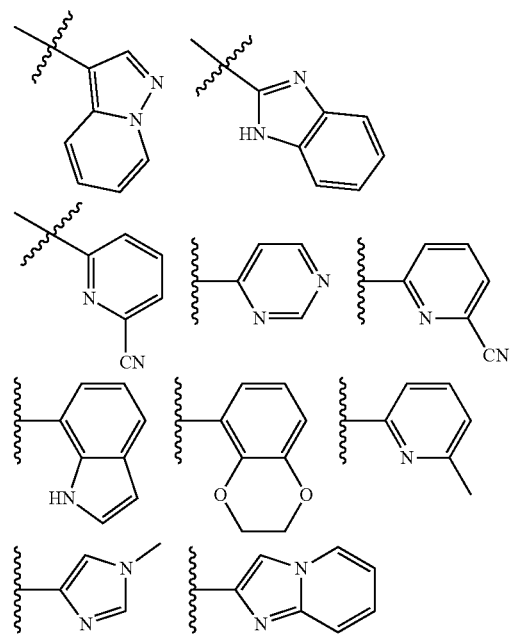

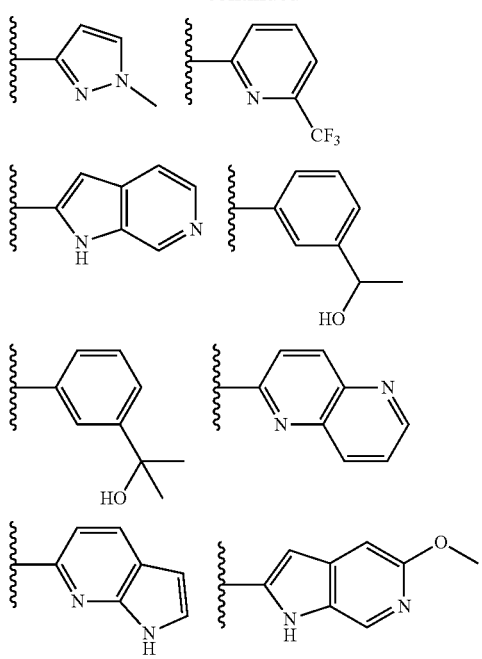
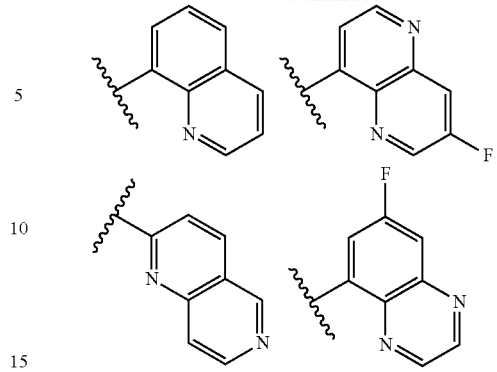

In another embodiment, examples of group Z include the following:

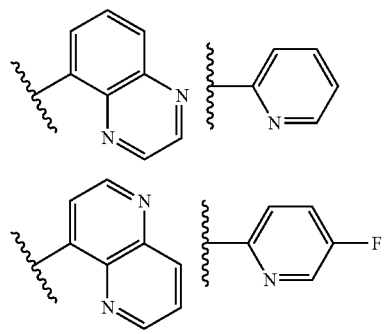

As will be understood, the compounds described herein may exist in various stereoisomeric forms, including enantiomers, diastereomers, and mixtures thereof. The invention encompasses all optical isomers of the compounds described herein and mixtures of optical isomers. Hence, compounds that exist as diastereomers, racemates and/or enantiomers are within the scope of the invention. In particular, the invention extends to the enantiomers, diastereomers, and mixtures of diastereomers and/or enantiomers, of any of the compounds having a chiral centre.

In particular, the invention extends to the enantiomers, diastereomers, and mixtures of diastereomers and/or enantiomers of any of the compounds herein described having a chiral centre in the cyclobutyl or bridged cyclobutyl linking moiety. In one embodiment the bonds between this linking moiety and the remainder of the molecule are in a trans-relationship. Thus, in one embodiment, the compounds of the invention may have the following general formula (Ia):

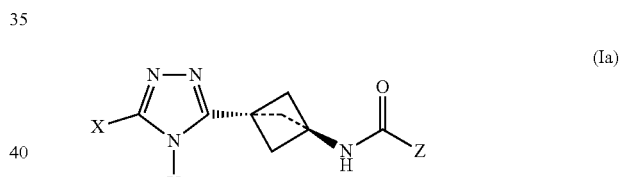

(Ia)

wherein X, Y and Z are as herein defined.

Examples of compounds according to the invention include the following, their tautomers, stereoisomers, pharmaceutically acceptable salts and pro-drugs:

| Example No. (where applicable) | Structure |
|---|---|
| 4 | 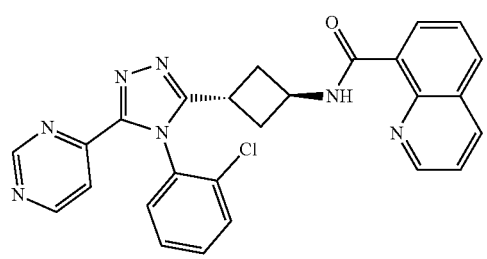 |

-continued
| Example No. (where applicable) | Structure |
|---|---|
| 5 | 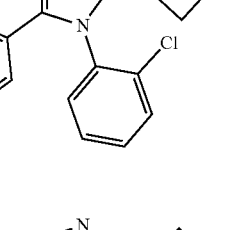 |
| 6 | 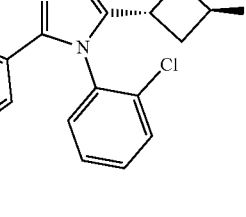 |
| 7 | 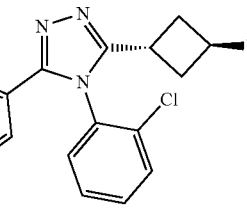 |
| 8 | 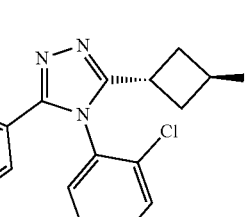 |
| 9 | 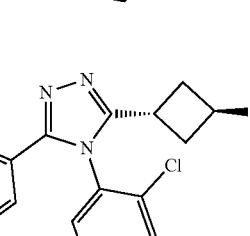 |
| 10 | 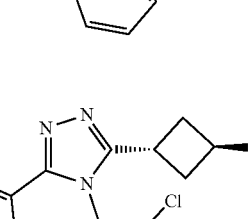 |

-continued
| Example No. (where applicable) | Structure |
|---|---|
| 11 | 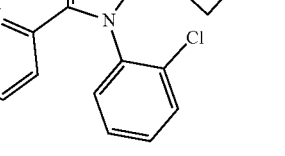 |
| 12 | 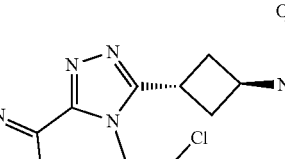 |
| 13 | 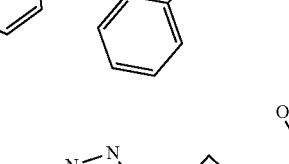 |
| 14 | 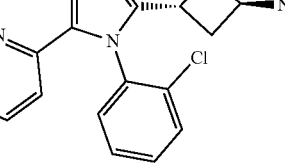 |
| 15 | 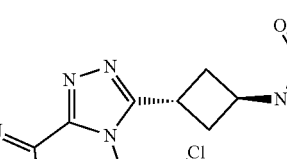 |
| 16 | 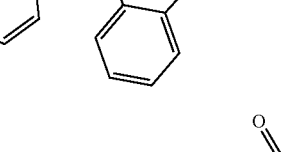 |

-continued
| Example No. (where applicable) | Structure |
|---|---|
| 17 | 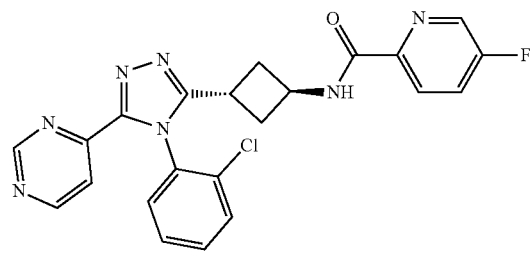 |
| 18 | 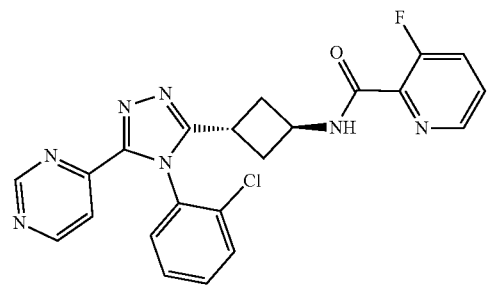 |
| 19 | 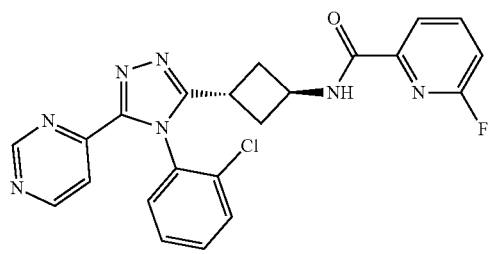 |
| 21 | 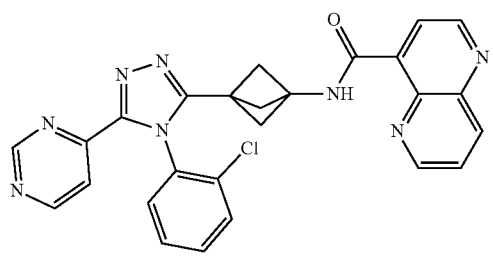 |
| 22 | 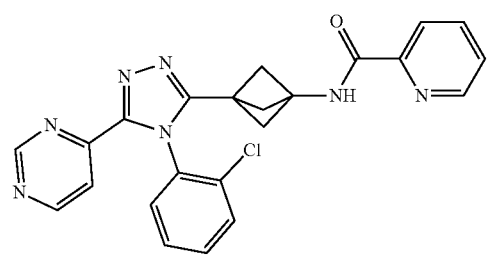 |

-continued
| Example No. (where applicable) | Structure |
|---|---|
| 23 | 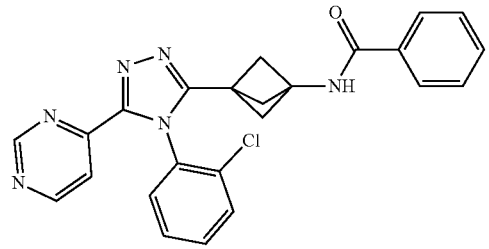 |
| 25 | 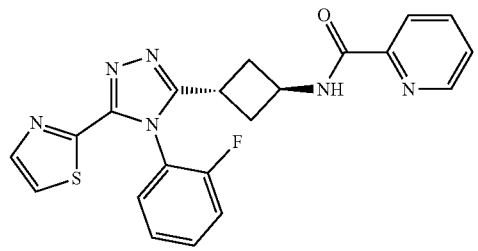 |
| 26 | 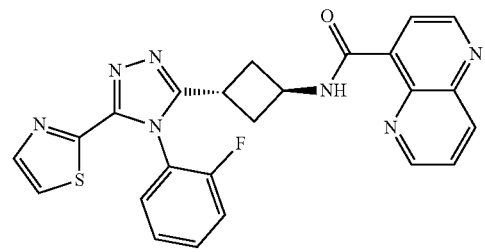 |
| 27 | 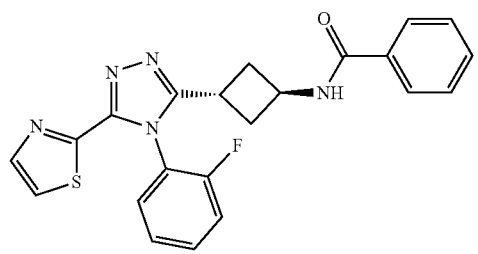 |
| 28 | 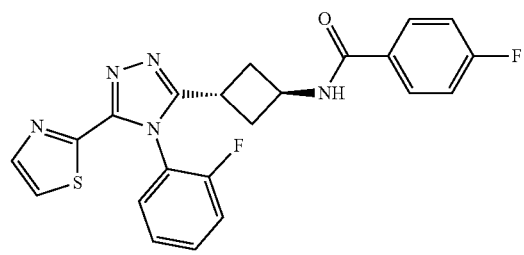 |
| 29 | 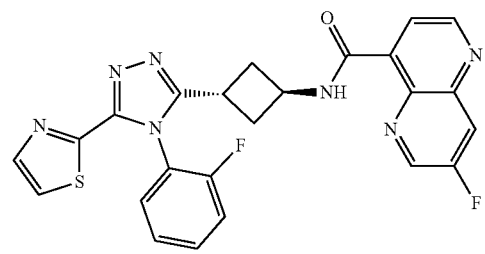 |

-continued
| Example No. (where applicable) | Structure |
|---|---|
| 30 | 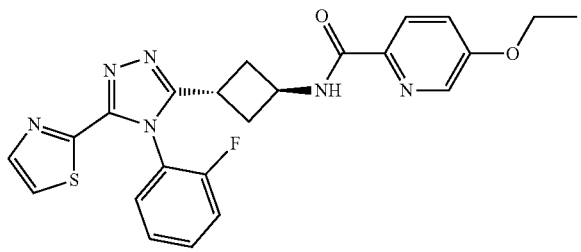 |
| 32 | 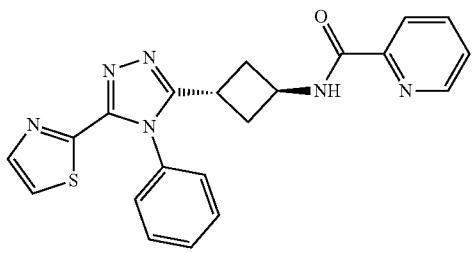 |
| 33 | 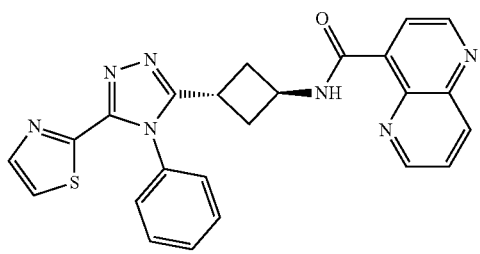 |
| 34 | 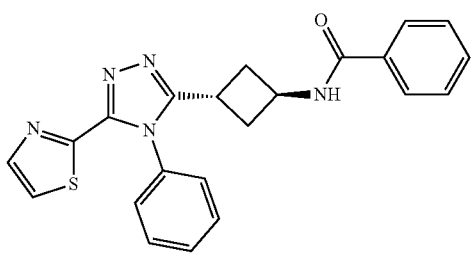 |
| 35 | 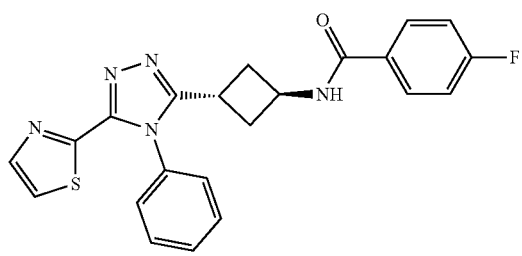 |
| 37 | 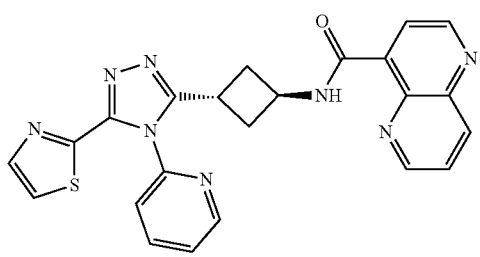 |

-continued
| Example No. (where applicable) | Structure |
|---|---|
| 38 | 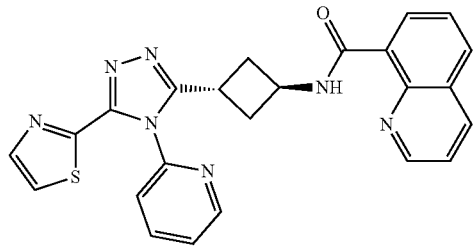 |
| 39 | 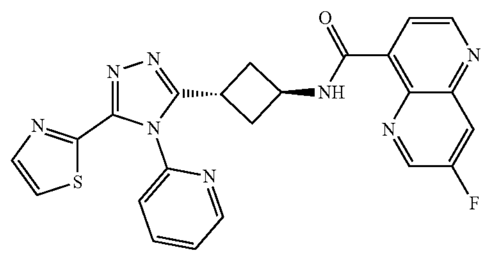 |
| 41 | 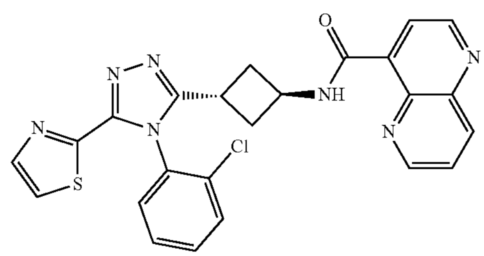 |
| 42 | 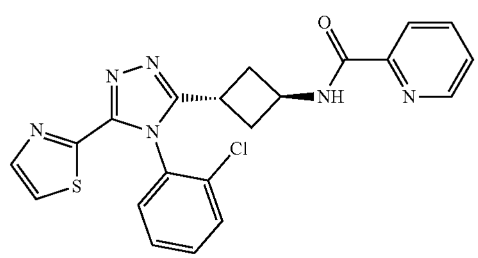 |
| 43 | 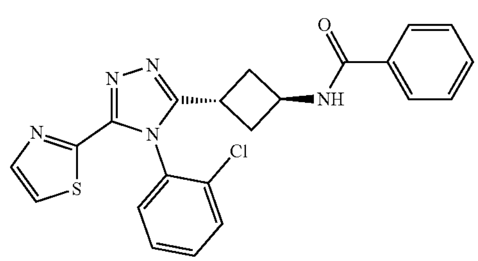 |
| 44 | 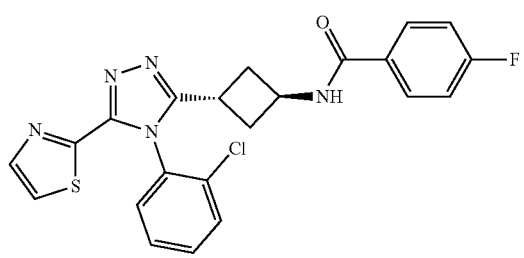 |

-continued
| Example No. (where applicable) | Structure |
|---|---|
| 46 | 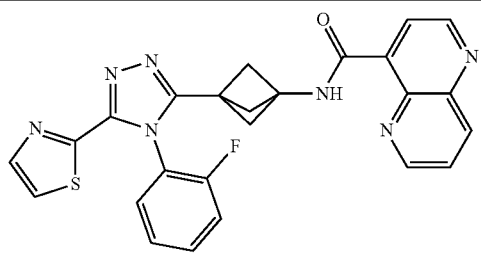 |
| 48 | 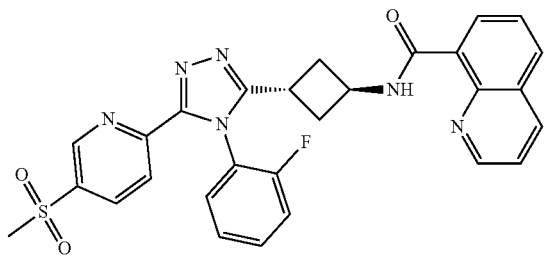 |
| 49 | 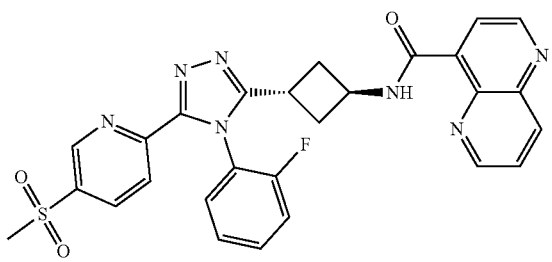 |
| 50 | 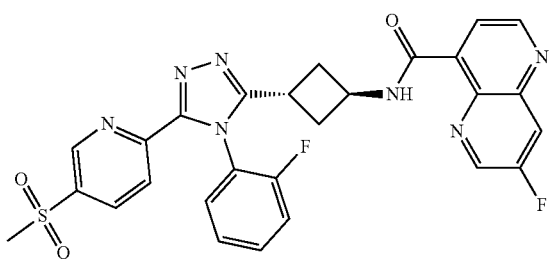 |
| 52 | 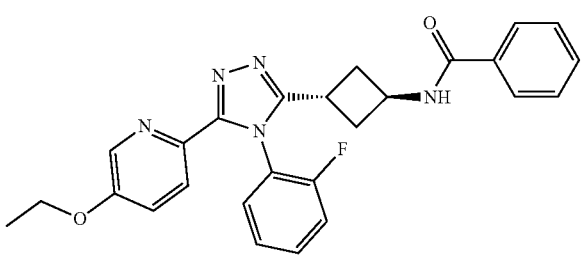 |
| 53 | 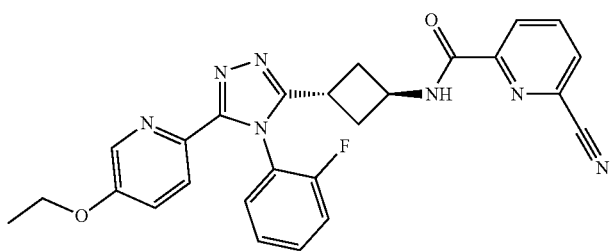 |

| Example No. (where applicable) | Structure |
|---|---|
| 54 | 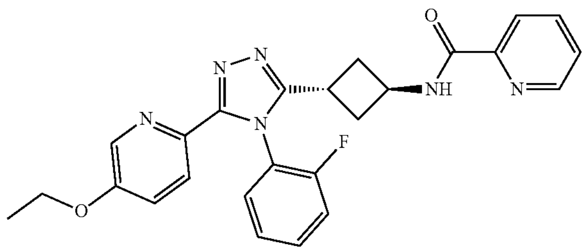 |
| 55 | 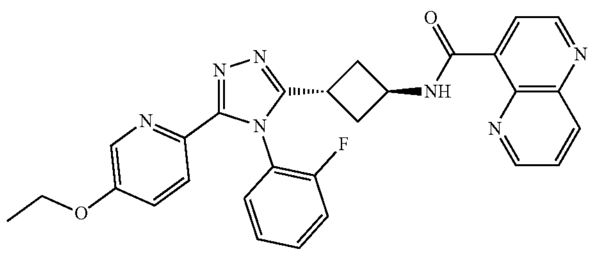 |
| 56 | 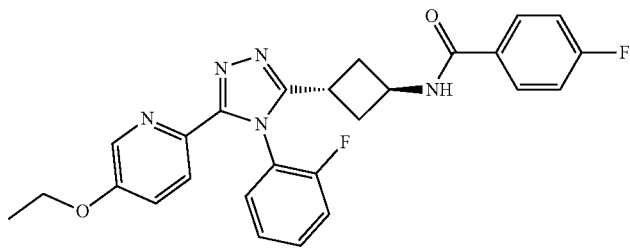 |
| 57 | 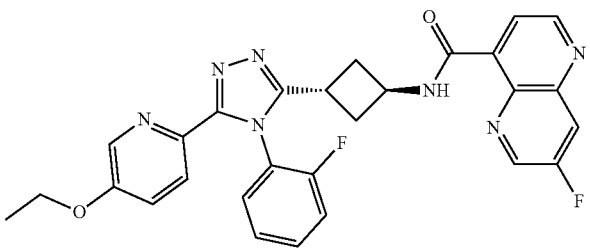 |
| 58 | 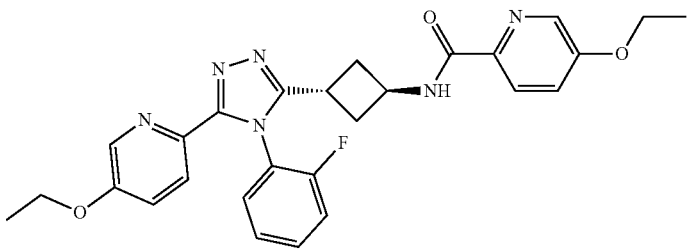 |
| 59 | 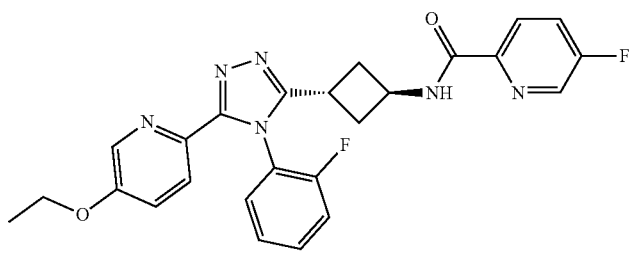 |

-continued
| Example No. (where applicable) | Structure |
|---|---|
| 60 | 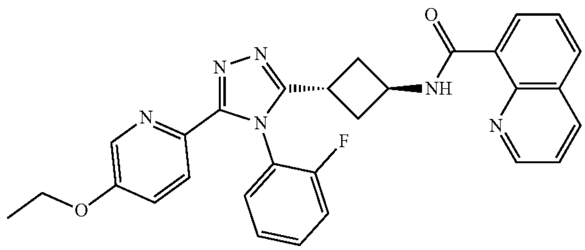 |
| 62 | 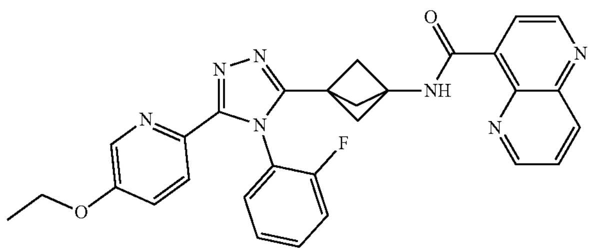 |
| 64 | 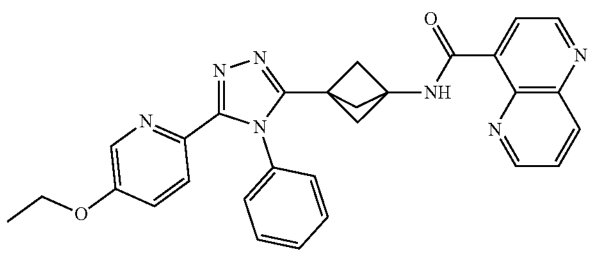 |
| 65 | 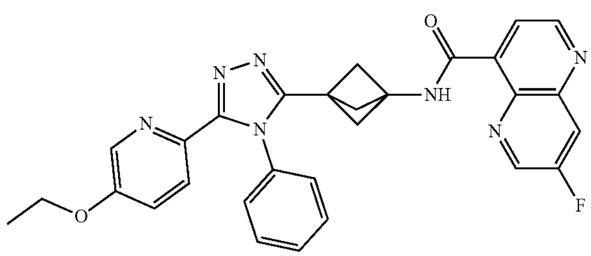 |
| 66 | 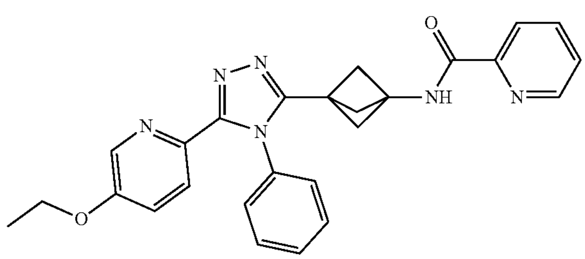 |
| 68 | 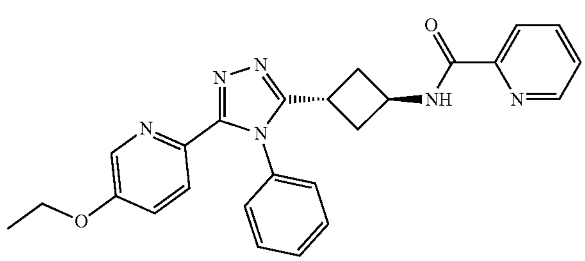 |

-continued
| Example No. (where applicable) | Structure |
|---|---|
| 69 | 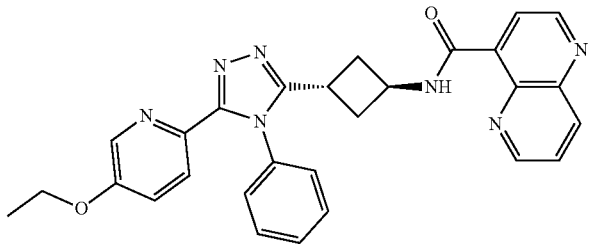 |
| 70 | 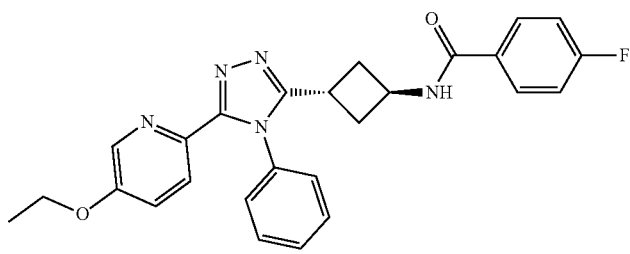 |
| 71 | 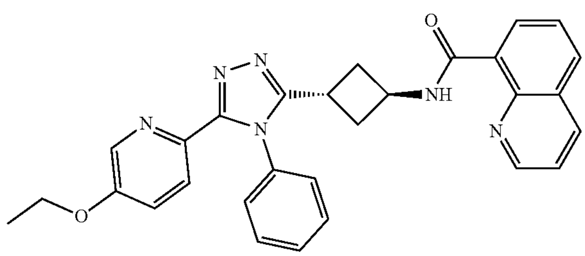 |
| 72 | 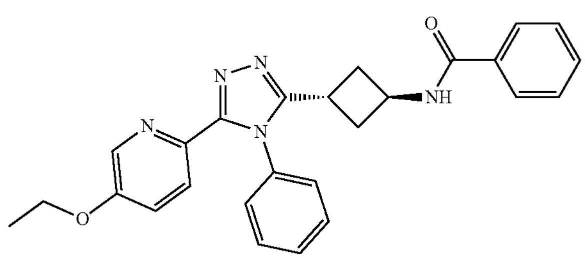 |
| 73 | 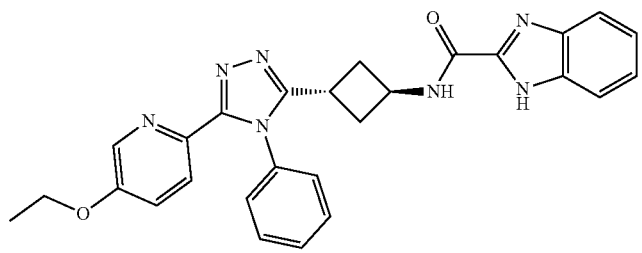 |
| 75 | 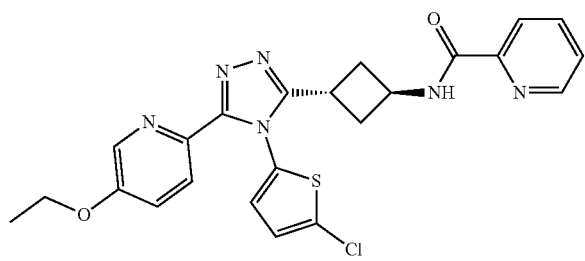 |

-continued
| Example No. (where applicable) | Structure |
|---|---|
| 76 | 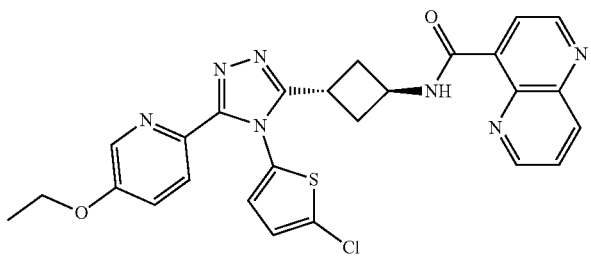 |
| 78 | 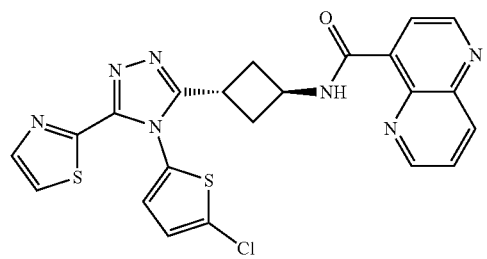 |
| 79 | 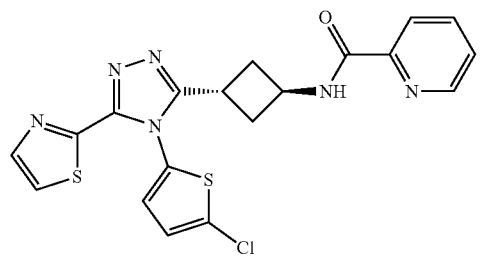 |
| 81 | 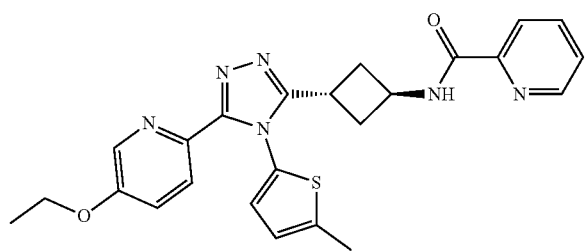 |
| 82 | 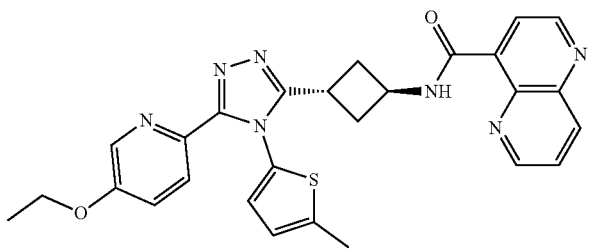 |
| 83 | 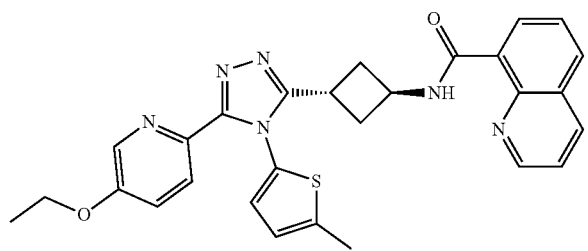 |

-continued
| Example No. (where applicable) | Structure |
|---|---|
| 84 | 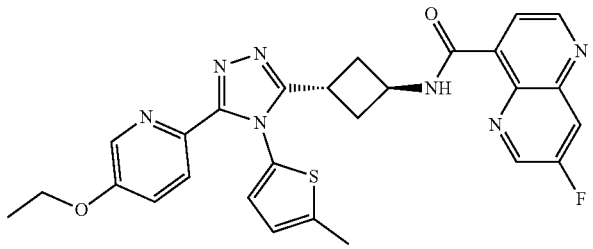 |
| 86 | 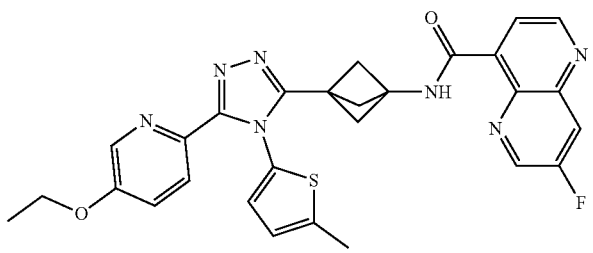 |
| 88 | 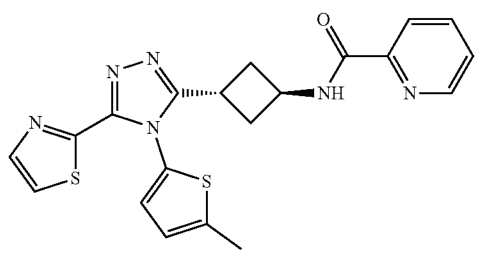 |
| 89 | 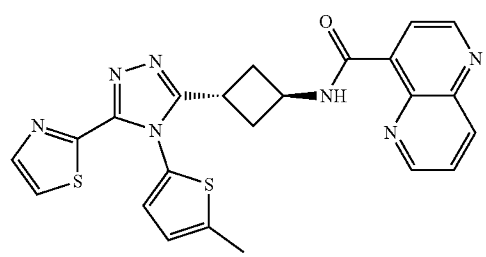 |
| 91 | 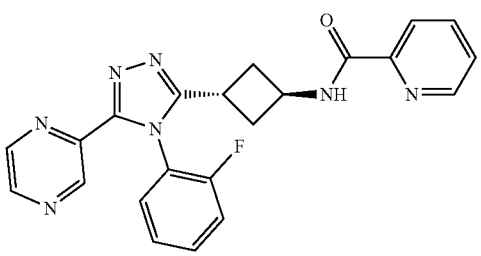 |
| 93 | 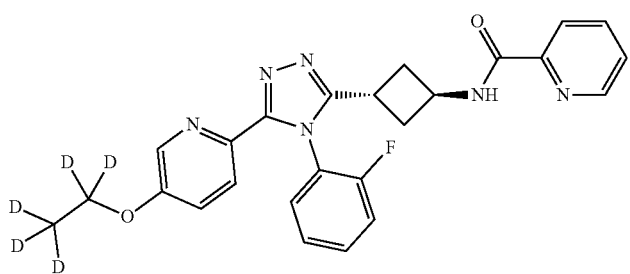 |

-continued
| Example No. (where applicable) | Structure |
|---|---|
| 94 | 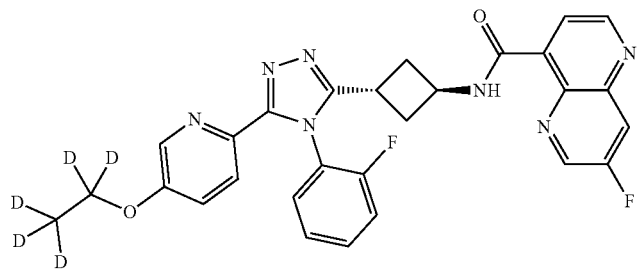 |
| 95 | 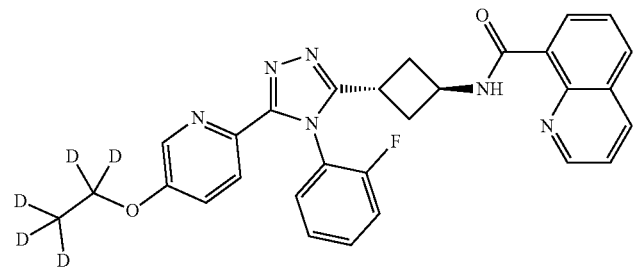 |
| 96 | 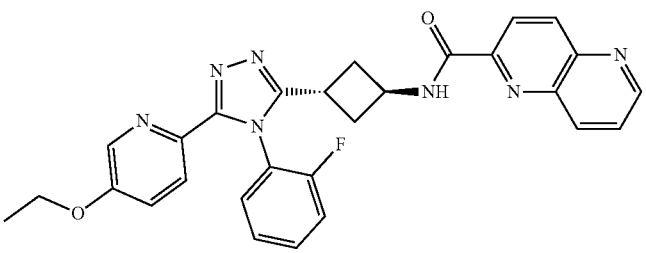 |
| 97 | 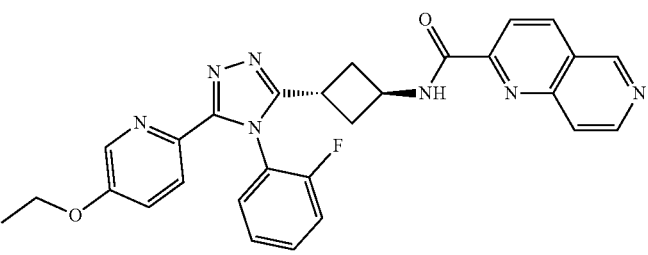 |
| 98 | 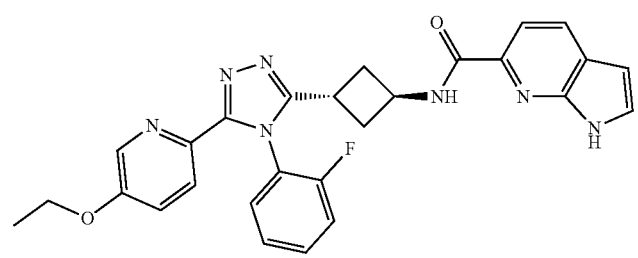 |

| Example No. (where applicable) | Structure |
|---|---|
| 99 | 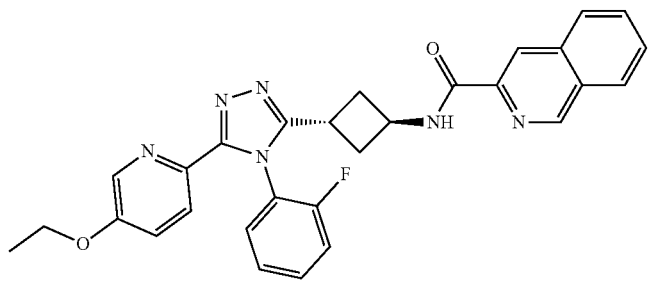 |
| 100 | 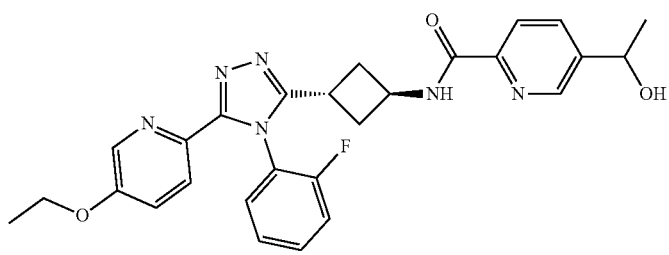 |
| 101 | 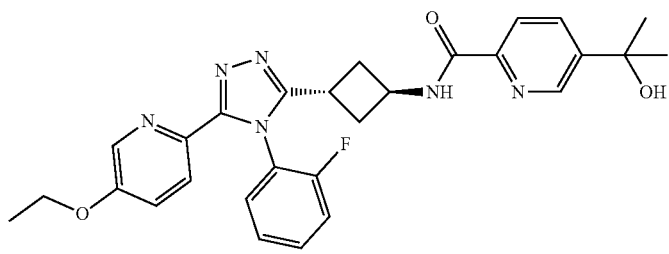 |
| 102 | 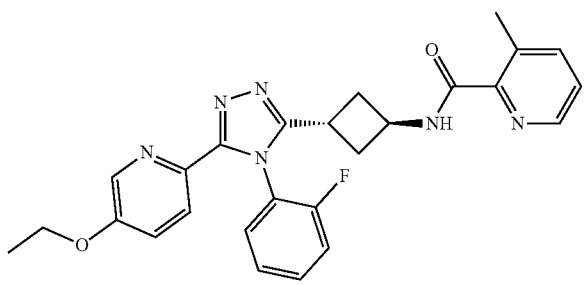 |
| 103 | 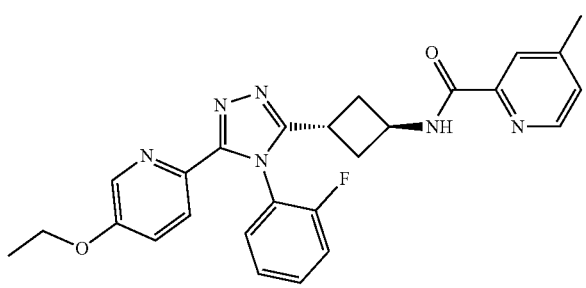 |

-continued
| Example No. (where applicable) | Structure |
|---|---|
| 104 | 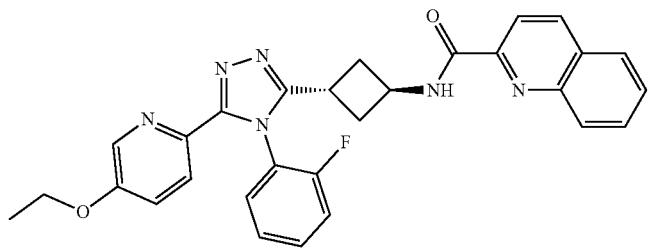 |
| 106 | 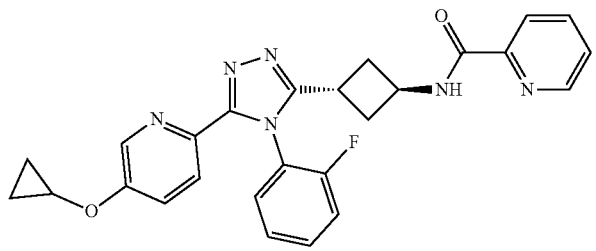 |
| 107 | 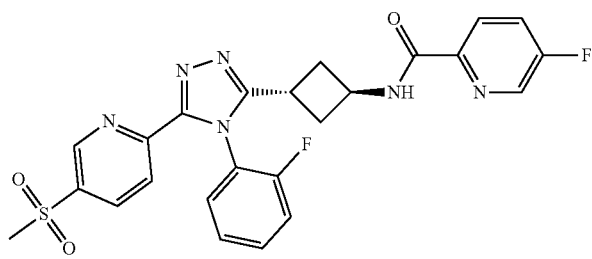 |
| 109 | 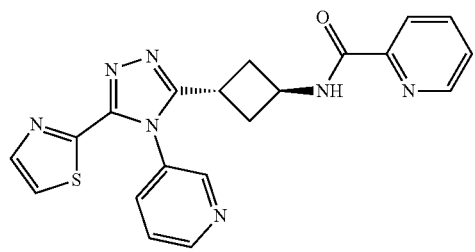 |
| 111 | 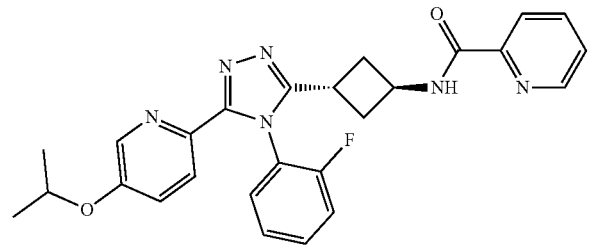 |
| 113 | 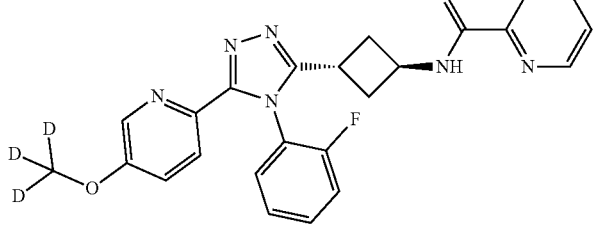 |

| Example No. (where applicable) | Structure |
|---|---|
| 114 | 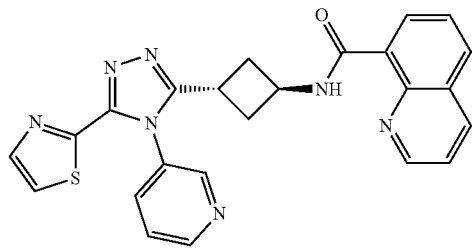 |
| 115 | 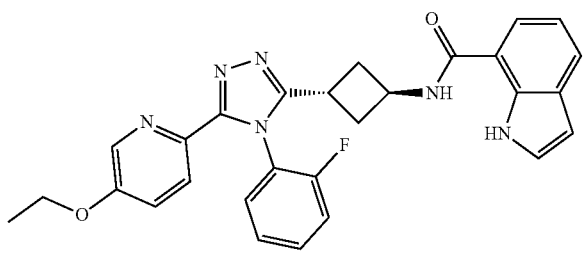 |
| 116 | 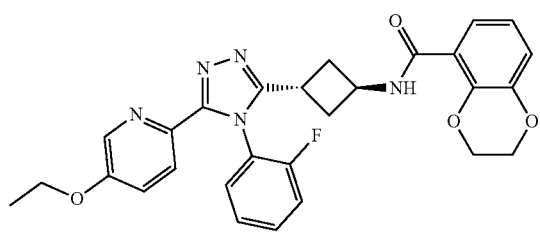 |
| 117 | 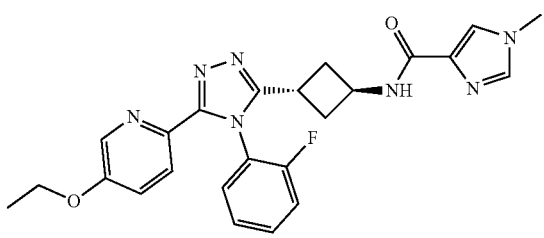 |
| 118 | 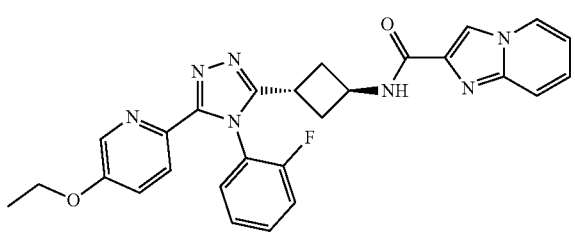 |
| 119 | 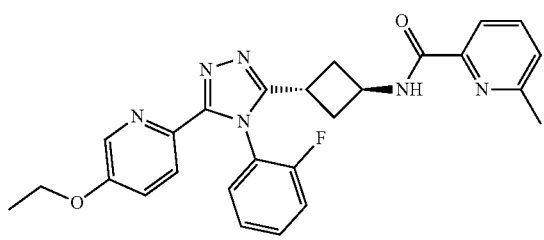 |

-continued
| Example No. (where applicable) | Structure |
|---|---|
| 120 | 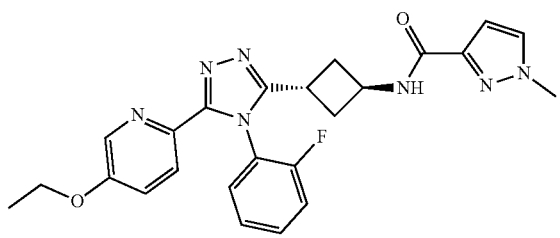 |
| 122 | 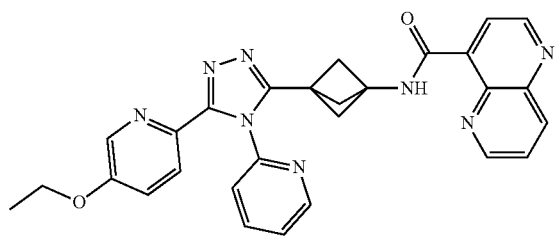 |
| 124 | 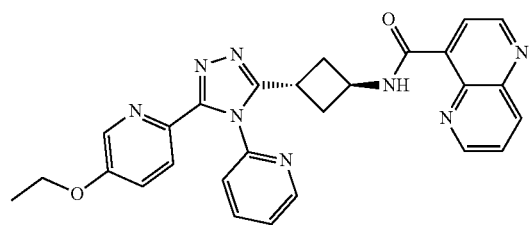 |
| 125 | 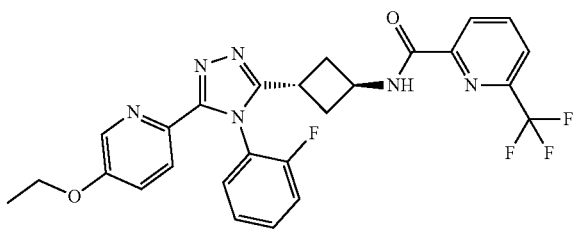 |
| 126 | 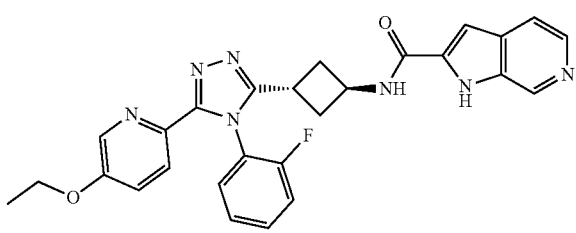 |
| 127 | 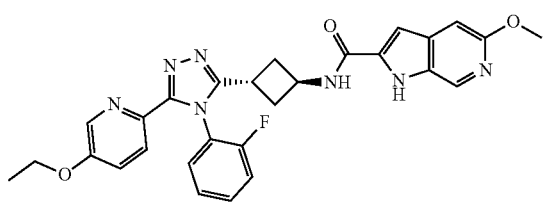 |

| Example No. (where applicable) | Structure |
|---|---|
| 128 | 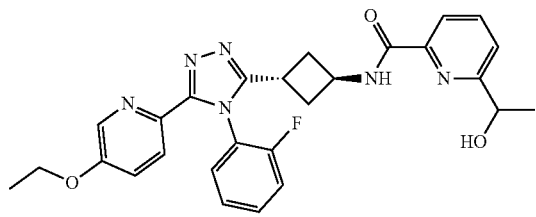 |
| 129 | 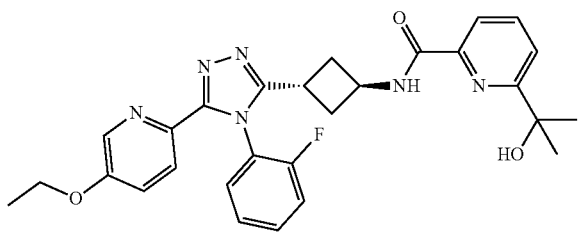 |
| 130 | 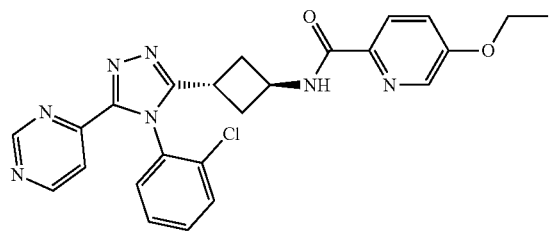 |
| 131 | 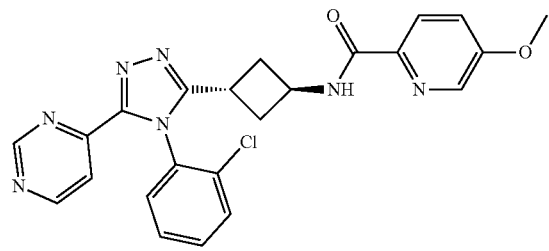 |
| 132 | 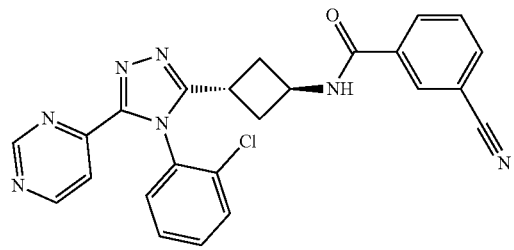 |
| 134 | 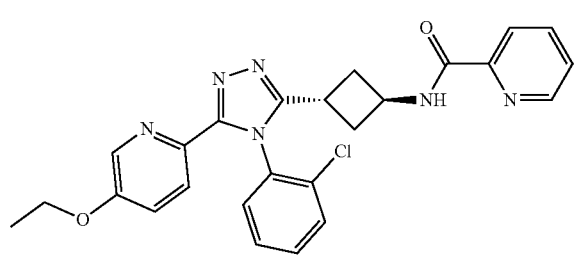 |

| Example No. (where applicable) | Structure |
|---|---|
| 135 | 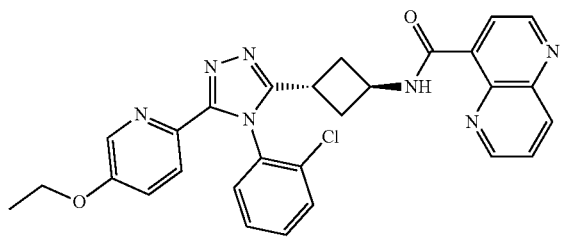 |
| 136 | 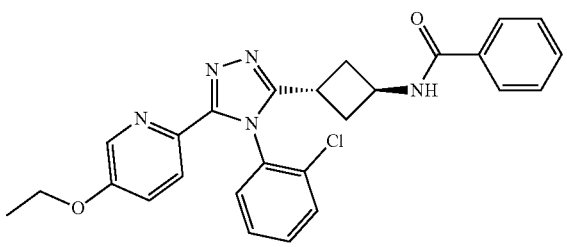 |
| 137 | 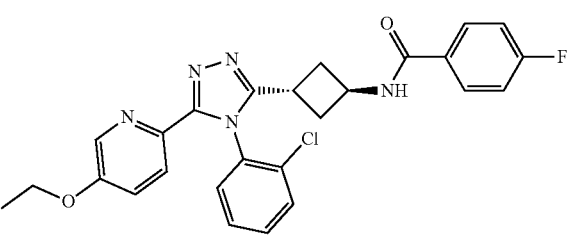 |
| 139 | 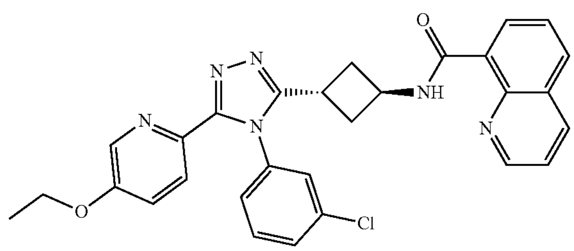 |
| 140 | 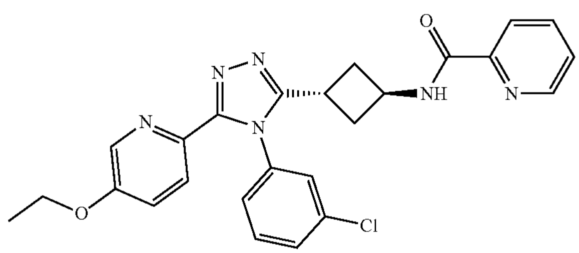 |
| 141 | 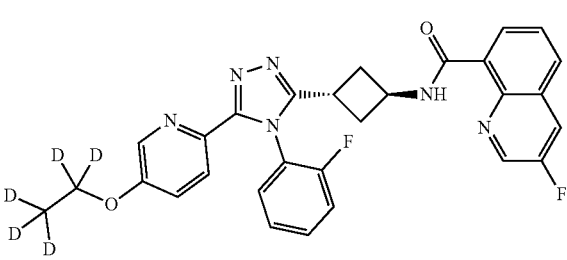 |

-continued
| Example No. (where applicable) | Structure |
|---|---|
| 142 | 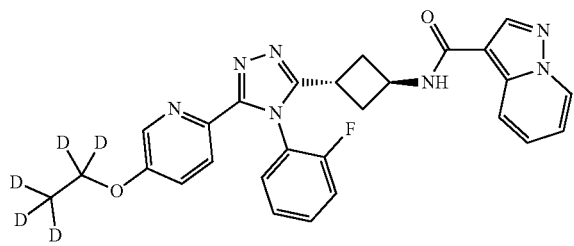 |
| 143 | 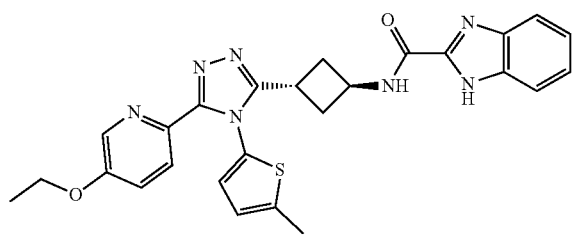 |
| 144 | 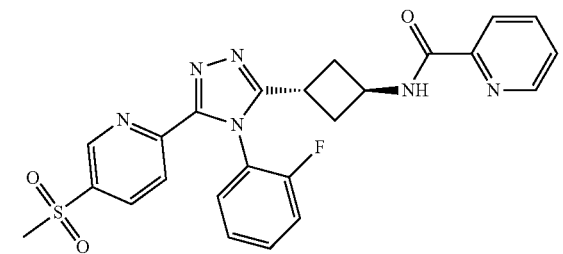 |
| 146 | 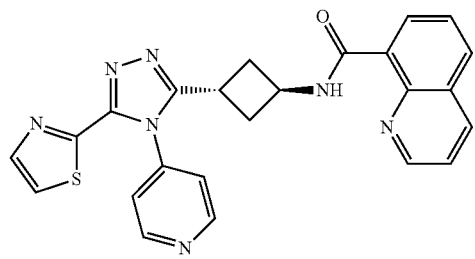 |
| 147 | 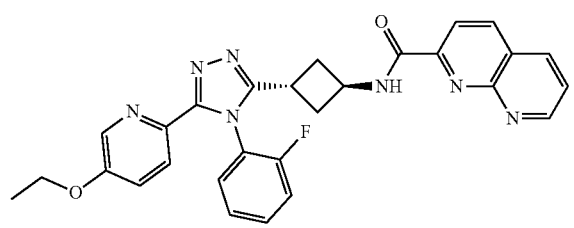 |
| 148 | 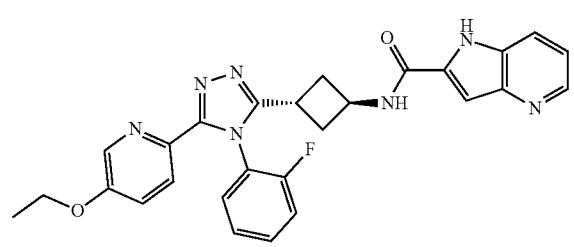 |

-continued
| Example No. (where applicable) | Structure |
|---|---|
| 149 | 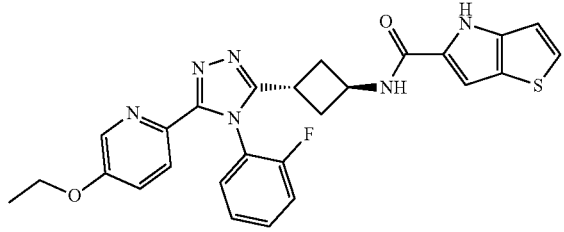 |
| 150 | 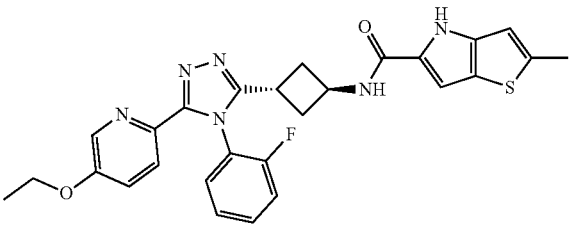 |
| 151 | 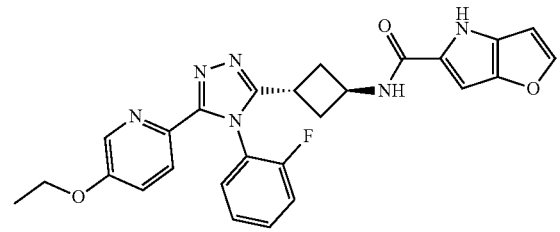 |
| 152 | 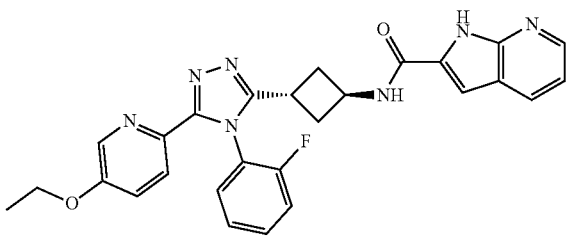 |
| 153 | 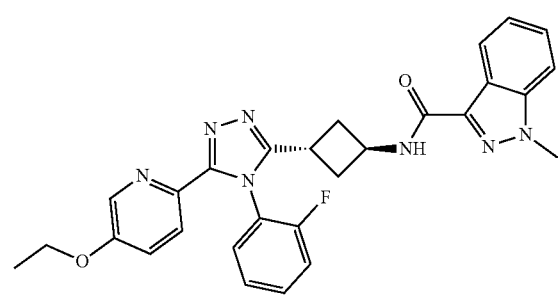 |
| 154 | 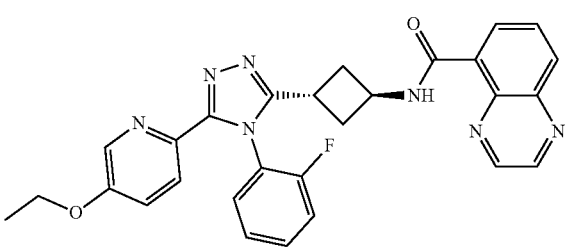 |

-continued
| Example No. (where applicable) | Structure |
|---|---|
| 155 | 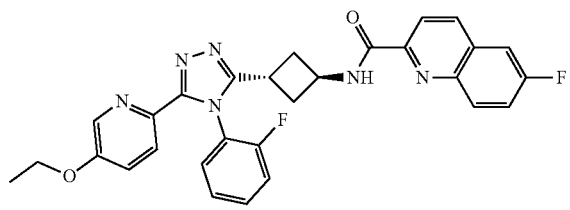 |
| 156 | 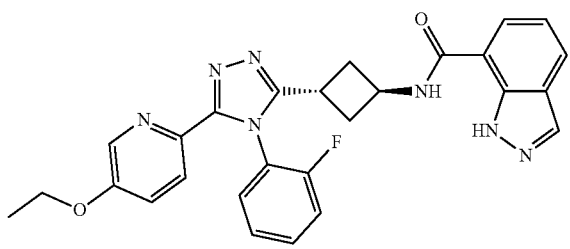 |
| 157 | 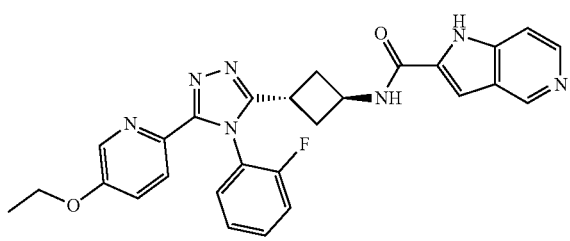 |
| 158 | 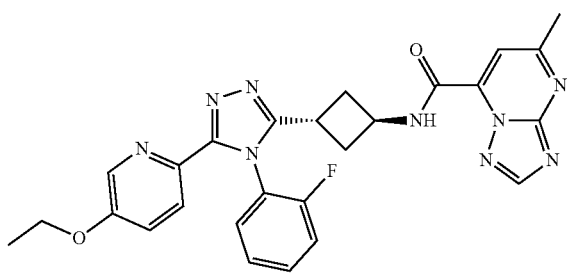 |
| 159 | 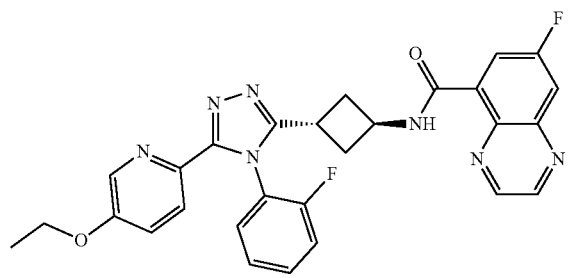 |
| 160 | 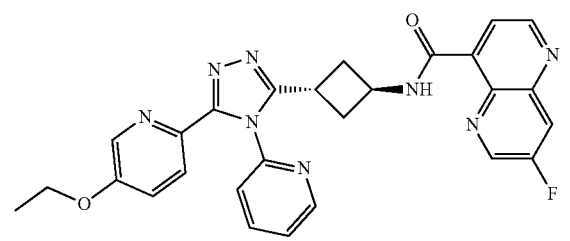 |

| Example No. (where applicable) | Structure |
|---|---|
| 162 | 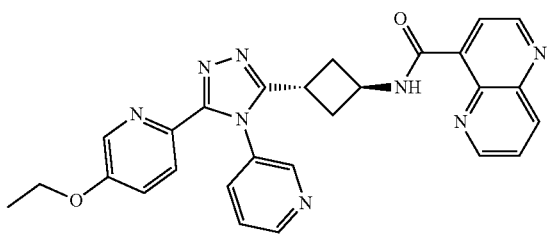 |
| 163 | 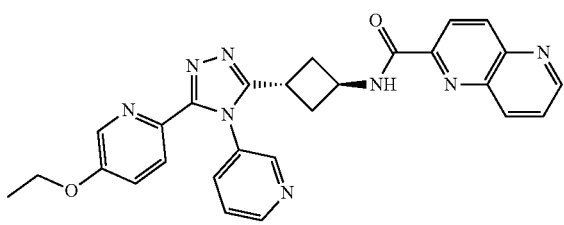 |
| 164 | 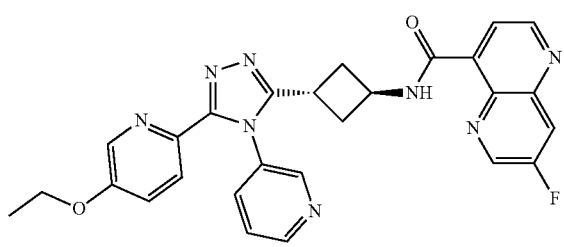 |
| 166 | 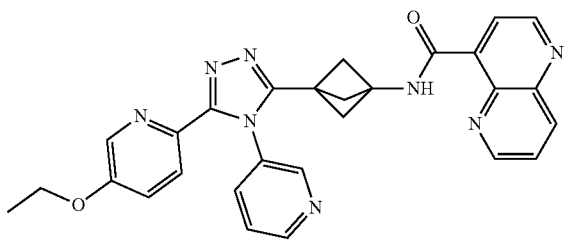 |
| 168 | 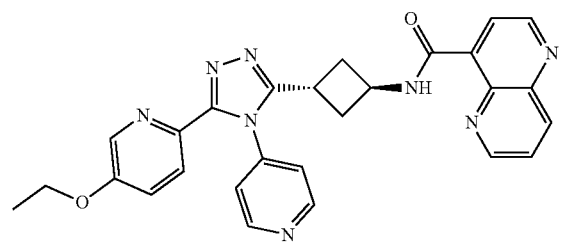 |
| 169 | 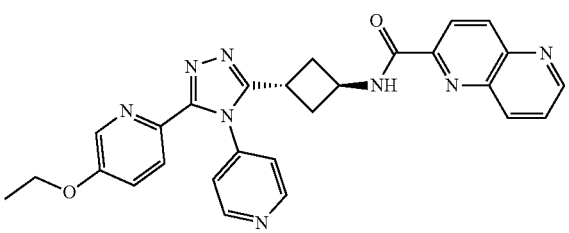 |

-continued
| Example No. (where applicable) | Structure |
|---|---|
| 170 | 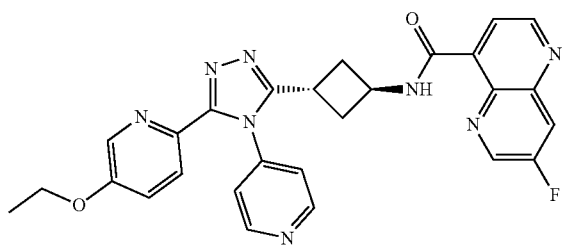 |
| 172 | 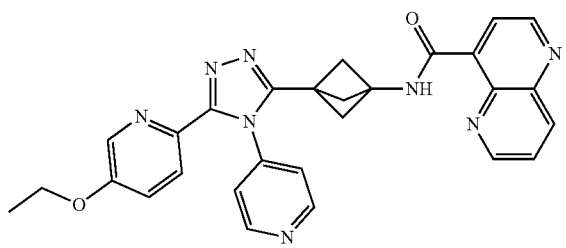 |
| 174 | 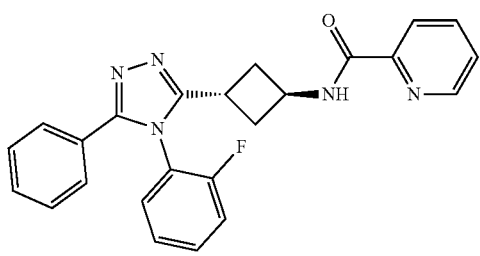 |
| 175 | 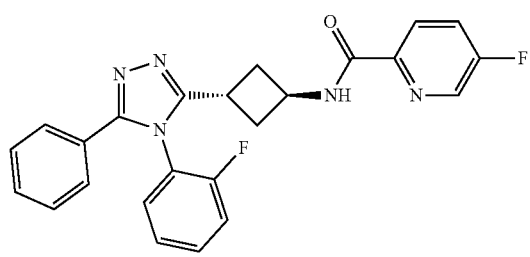 |
| 176 | 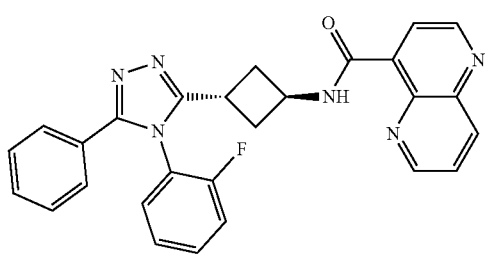 |
| 177 | 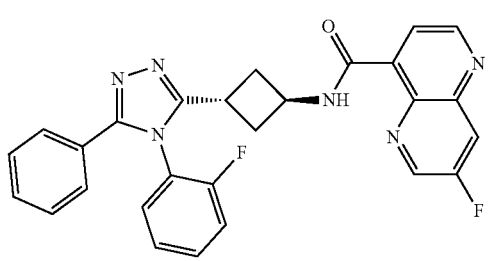 |

| Example No. (where applicable) | Structure |
|---|---|
| 178 | 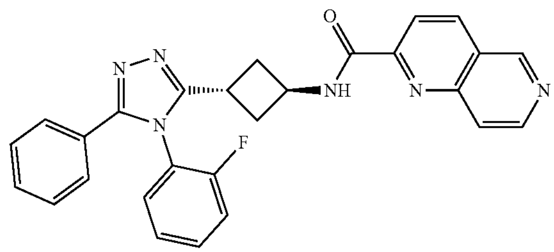 |
| 180 | 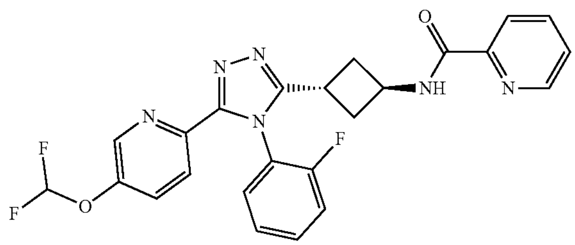 |
| 181 | 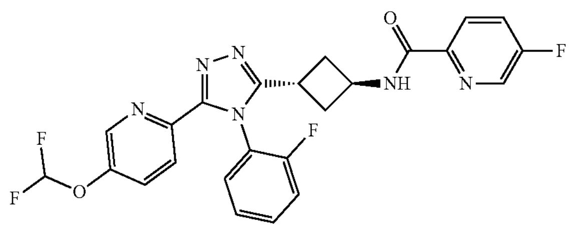 |
| 182 | 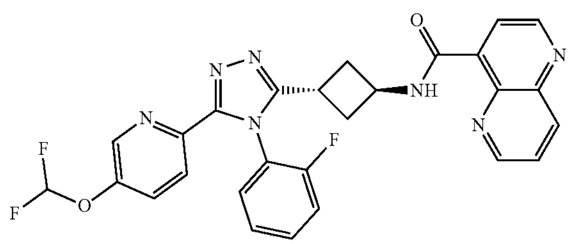 |
| 183 | 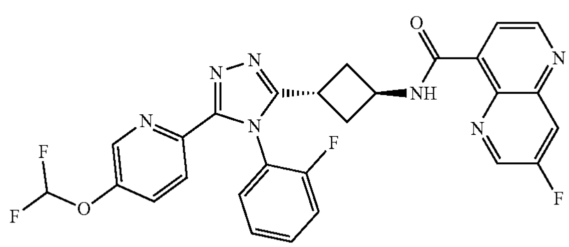 |
| 184 | 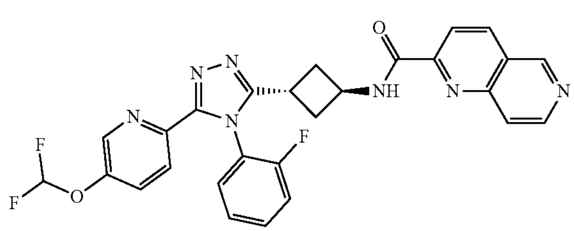 |

-continued
| Example No. (where applicable) | Structure |
|---|---|
| 185 | 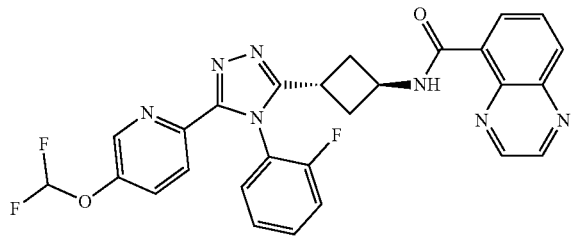 |
| 186 | 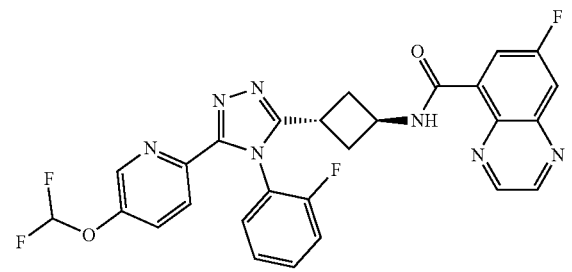 |
| 188 | 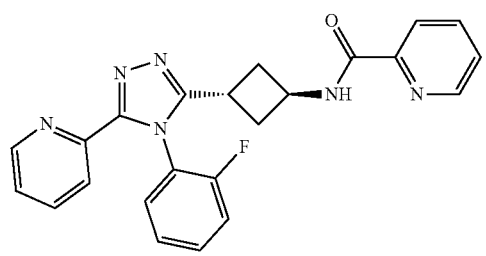 |
| 189 | 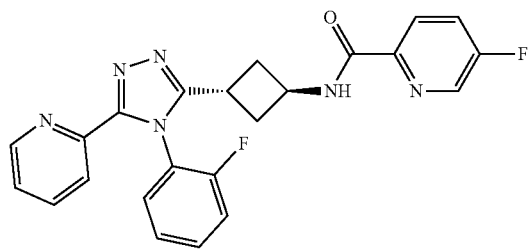 |
| 190 | 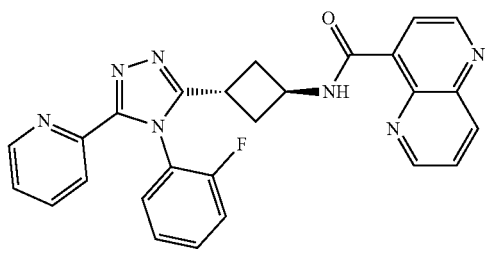 |
| 191 | 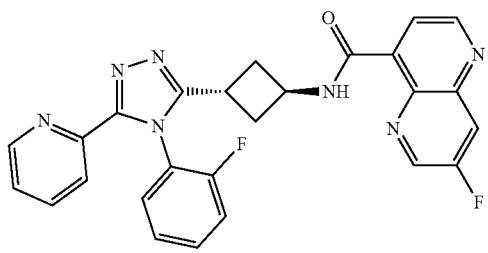 |

-continued
| Example No. (where applicable) | Structure |
|---|---|
| 192 | 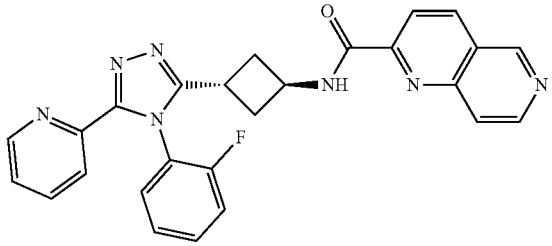 |
| 193 | 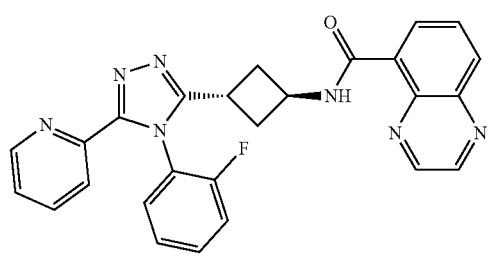 |
| 194 | 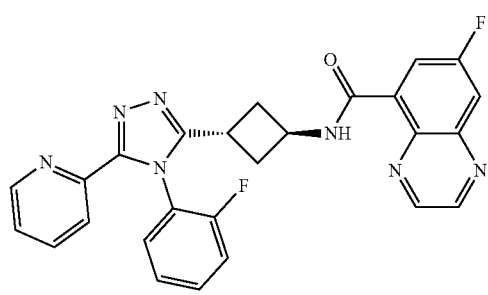 |
| 196 | 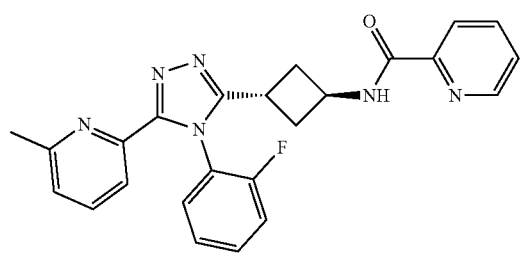 |
| 197 | 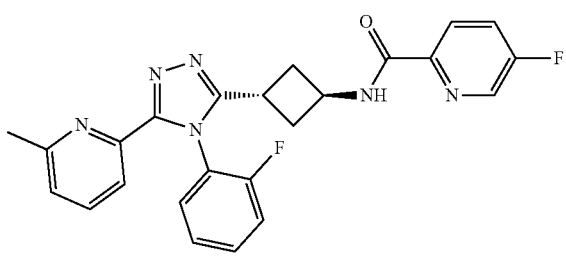 |
| 198 | 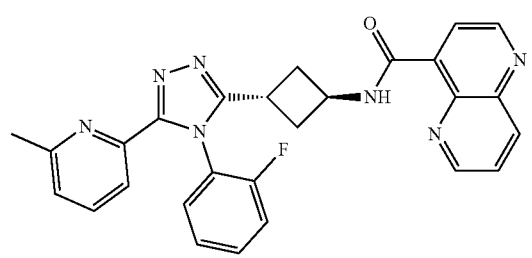 |

| Example No. (where applicable) | Structure |
|---|---|
| 199 | 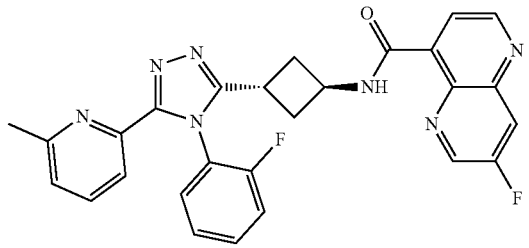 |
| 200 | 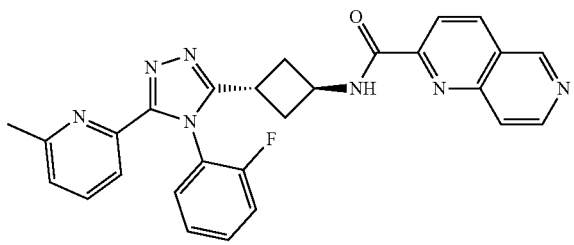 |
| 201 | 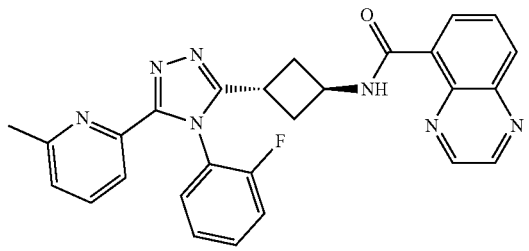 |
| 202 | 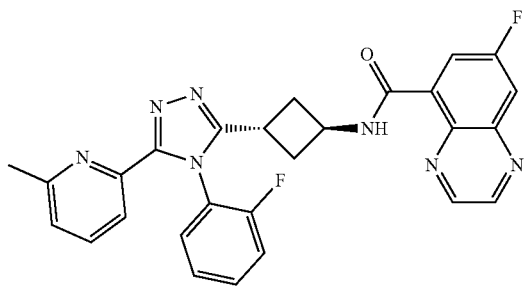 |

The compounds according to the invention may be prepared from readily available starting materials using synthetic methods known in the art. Preferably, the compounds are obtained in accordance with the following method which forms part of the invention:

(a) reacting a compound of general formula (II):

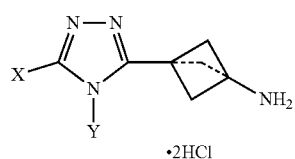

(II)

with a compound of general formula (III):

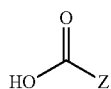

(III)

wherein in formulae (II) and (III), X, Y and Z are as herein defined;

(b) if desired, resolving a compound thus obtained into the stereoisomers thereof; and/or (c) if desired, converting a compound thus obtained into a salt thereof, particularly a pharmaceutically acceptable salt thereof.

Intermediate compound (II) also forms part of the invention.

The method described above may be used to prepare any compound of formula (I) as herein described.

The reaction of the compound of formula (II) with the compound of formula (III) is conveniently carried out in a solvent or mixture of solvents, such as for example a polar solvent such as acetonitrile, DMF, DCM, EtOAc, TBME, or THF or mixtures thereof. DMF is a preferred solvent. The reaction may suitably be carried out at room temperature, typically for a time from 1-5 hours (e.g. 1 hour, 2 hours or 3 hours).

In an embodiment, the compound of general formula (II) may be obtained by the following method which forms part of the invention:

(aa) reacting a compound of general formula (IV) with a compound of general formula (V) to form a compound of general formula (VI):

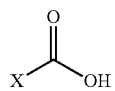
(IV)

(V)

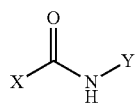
(VI)

(bb) reacting the compound of general formula (VI) with a thionylating agent to form a compound of general formula (VII):

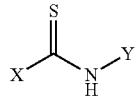
(VII)

(cc) methylating the compound of general formula (VII) to form a compound of general formula (VIII):

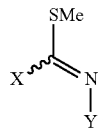
(VIII)

(dd) reacting the compound of general formula (VIII) with a compound of general formula (IX) to form a compound of general formula (X):

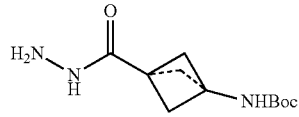
(IX)

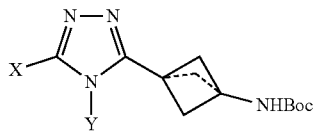
(X)

and (ee) deprotecting the Boc group of the compound of general formula (X) to form a compound of general formula (II):

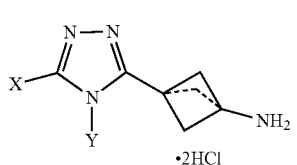
(II)

wherein in formulae (IV) to (X), X and Y are as herein defined.

Step (aa) may suitably be performed under conventional amide formation conditions known to those skilled in the art. For example, the compounds of formulae (V) and (IV) may be reacted in the presence of HATU and DIPEA in DMF at room temperature for a period of 1 to 24 hours (e.g. 2 hours), or the compounds of formulae (V) and (IV) may be dissolved in DCM and pyridine, the reaction cooled in an ice bath and $POCl_3$ added dropwise and the resulting mixture stirred at room temperature for a period of 1 to 18 hours.

Step (bb) may be performed using a conventional thionylating agent known to those skilled in the art such as Lawesson's reagent (2,4-bis(4-methoxyphenyl)-1,3,2,4-dithiadiphosphetane-2,4-dithione) in a suitable solvent such as toluene. Suitably, about 0.5 to about 1 molar equivalent of the thionating agent may be employed. The thionation reaction may suitably be performed at a temperature of up to 100° C. (e.g. 80° C.) for a period of 2 to 24 hours (e.g. 16 hours).

Step (cc) may be performed using a conventional methylation reaction known to those skilled in the art. For example, the compound of general formula (VII) may suitably be reacted with at least one molar equivalent of methyl iodide in the presence of a base such as sodium hydroxide, sodium carbonate, potassium hydroxide or potassium carbonate.

Step (dd) may be performed using conventional triazole cyclisation conditions known to those skilled in the art. For example, compounds of formulae (VIII) and (IX) may be combined together in the presence of a suitable solvent (e.g. 1-butanol) and reacted under microwave irradiation or heated in an oil bath. This reaction may suitably be performed at a temperature of from 100 to 140° C. for a period of 1 to 24 hours (e.g. 5 to 20 hours). Step (ee) may be performed using conventional Boc deprotection conditions known to those skilled in the art. For examples, compounds of formula (X) may be dissolved in a suitable solvent (e.g. EtOH or IPA) and HCl (e.g. 5 N in IPA) added. HCl (e.g. 5 N in IPA) is typically added in 10-40 equiv, and additional portions can be added if necessary. The reaction can be performed at room temperature or elevated temperatures (e.g. 50-60° C.) for a period of 1 to 24 hours (e.g. 2 to 18 hours).

In an embodiment, the compounds of formula (I) may be obtained by the following method which forms part of the invention:

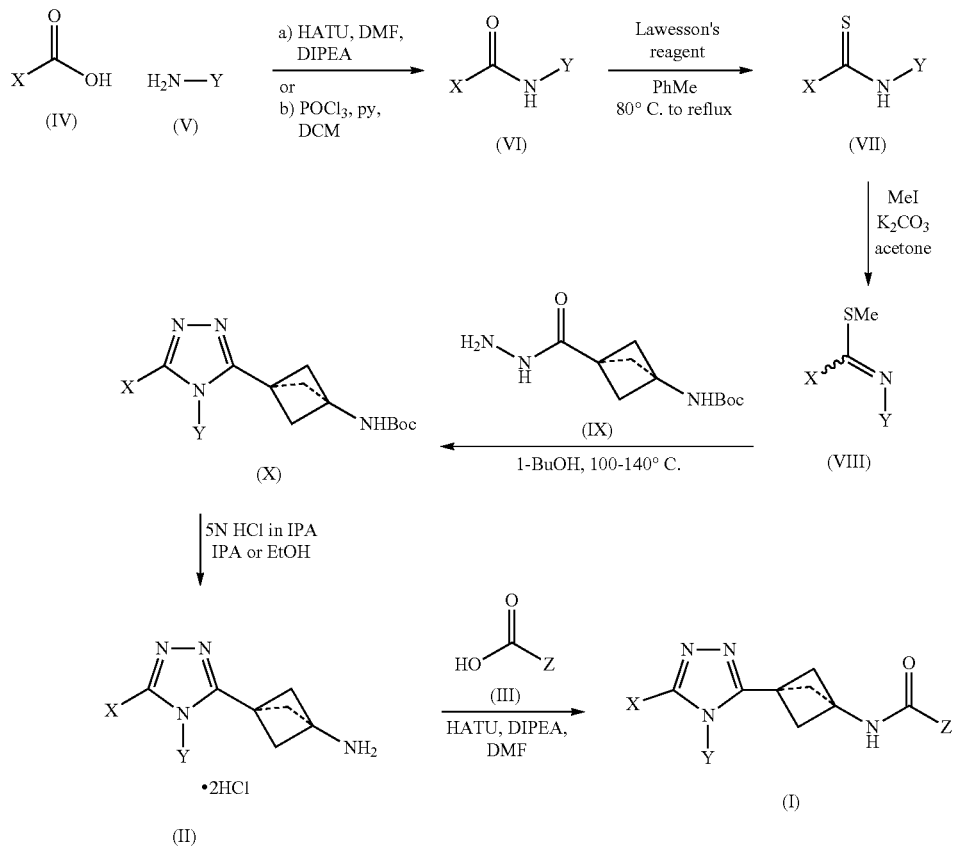

Any of the intermediate compounds produced during preparation of the compounds of formula (I) form further aspects of the invention, in particular compounds (VI), (VII), (VIII), (IX) and (X).

The compounds used as starting materials in the methods of preparation of compounds of formulae (I)-(X) are either known from the literature or may be commercially available. Alternatively, these may be obtained by methods known from the literature.

The compounds of general formulae (I) may be resolved into their enantiomers and/or diastereomers. For example, where these contain only one chiral centre or axis, these may be provided in the form of a racemate or may be provided as pure enantiomers, i.e. in the R- or S-form. Any of the compounds which occur as racemates may be separated into their enantiomers by methods known in the art, such as column separation on chiral phases or by recrystallisation from an optically active solvent. Those compounds with at least two asymmetric centres or axes may be resolved into their diastereomers on the basis of their physical-chemical differences using methods known per se, e.g. by chromatography and/or fractional crystallisation, and where these compounds are obtained in racemic limn, they may subsequently be resolved into the enantiomers.

The invention further extends to tautomers of any of the compounds herein disclosed. As will be appreciated, certain compounds according to the invention may exist in tautomeric forms, i.e. in forms which readily interconvert by way of a chemical reaction which may involve the migration of a proton accompanied by a switch of a single bond and adjacent double bond. For example, the compounds may undergo amide-imidic acid tautomerism. Dependent on the conditions, the compounds may predominantly exist in the amide or imidic acid form and the invention is not intended to be limited to the particular form shown in any of the structural formulae given herein.

The compounds according to the invention may be converted into a salt thereof; particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

In a further aspect there is provided pharmaceutical formulations comprising a compound of formula (I) as herein defined, or a tautomer, stereoisomer, pharmaceutically acceptable salt, or pro-drug thereof, together with one or more pharmaceutically acceptable carriers or excipients.

The compounds according to the invention and their pharmaceutically acceptable salts have valuable pharmacological properties, particularly an inhibitory effect on WNT/ß-catenin and hippo signalling through inhibition the adenosine binding site of the catalytic domain of tankyrase 1/2 and stabilization of the AXIN protein and AMOT proteins respectively. In view of their ability to inhibit signalling in the WNT and hippo signalling pathways, the compounds according to the invention and their pharmaceutically acceptable salts are suitable for the treatment and/or prevention of any condition or disease which may be affected by de-regulated signalling in the WNT and hippo signalling pathways, in particular those conditions or diseases which involve activation of ß-catenin or altered YAP/TAZ signalling. The compounds of the invention and their pharmaceutically acceptable salts also have valuable pharmacological properties through affecting other target proteins of tankyrase 1/2.

The WNT and hippo signalling pathways play a central role in the pathology of a variety of cancers. The compounds of the invention are thus particularly suitable for preventing and/or retarding proliferation and metastasis of tumor cells, in particular carcinomas such as adenocarcinomas. More specifically, the compounds are effective in treatment and/or prevention of tumors emerging from colorectal tissue, uterus, pancreas, skin, liver, thyroid, prostate, ovary, stomach, lung, lymphoid, bladder, cervix, thyroid, head and neck, brain, breast and kidney, and in the treatment of melanoma. Particularly preferably, the compounds herein described may be used in the treatment and/or prevention of colorectal cancer, non-small cell lung cancer and melanoma.

As used herein, the term "proliferation" refers to cells undergoing mitosis. The term "retarding proliferation" indicates that the compounds inhibit proliferation of a cancer cell. In preferred embodiments, "retarding proliferation" indicates that DNA replication is at least 10% less than that observed in untreated cells, more preferably at least 25% less, yet more preferably at least 50% less, e.g. 75%, 90% or 95% less than that observed in untreated cancer cells.

The term "carcinoma" refers to any malignant growth which arises from epithelial cells. Exemplary carcinomas include basal cell carcinoma, squamous cell carcinoma and adenocarcinoma. Adenocarcinomas are malignant tumors originating in the glandular epithelium and include colorectal, pancreatic, breast and prostate cancers.

The compounds of the invention also find use in cancer immunotherapy. They may, for example, be used in a combination therapy together with known immune checkpoint inhibitors, such as PD-1 and PD-L1.

As used herein, the term "immunotherapy" refers to the beneficial therapeutic enhancement of the interplay between the immune system and a tumor, infection, or other diseases. In particular, immunotherapy is a type of therapy that uses substances to stimulate or suppress the immune system to help the body fight cancer, infection, and other diseases. Some types of immunotherapy only target certain cells of the immune system. Others affect the immune system in a general way.

The compounds according to the invention and their pharmaceutically acceptable salts have valuable pharmacological properties that may also be used for treatment or prevention of non-cancer indications that are influenced by the activity of tankyrase 1/2, dependent or independent of its impact on WNT and/or hippo signalling. These include non-regenerative wound healing, viral infections such as Herpes Simplex Virus (HSV) infections, fibrosis such as pulmonary, dermal-, renal- and liver fibrosis, myocardial fibrosis, and metabolic conditions such as aberrant systemic glucose metabolism.

Viewed from a further aspect the invention thus provides a compound of formula (I) as herein defined, or a tautomer, stereoisomer, pharmaceutically acceptable salt, or pro-drug thereof, for use in therapy. Unless otherwise specified, the term "therapy" as used herein is intended to include both treatment and prevention.

In a still further aspect the invention provides a compound of formula (I) as herein defined, or a tautomer, stereoisomer, pharmaceutically acceptable salt, or pro-drug thereof; for use in the treatment or prevention of a tumor emerging from colorectal tissue, uterus, pancreas, skin, liver, thyroid, prostate, ovary, stomach, lung, lymphoid, bladder, cervix, thyroid, head and neck, brain, breast or kidney, in the treatment of melanoma, in the treatment of non-regenerative wound healing, or in the treatment or prevention of viral infections such as Herpes Simplex Virus infections, fibrosis such as pulmonary-, dermal-, renal- and liver fibrosis, myocardial fibrosis, or metabolic conditions such as aberrant systemic glucose metabolism.

In another aspect the invention provides the use of a compound of formula (I) as herein defined, or a tautomer, stereoisomer, pharmaceutically acceptable salt, or pro-drug thereof; in the manufacture of a medicament for use in a method of treatment or prevention of a tumour emerging from colorectal tissue, uterus, pancreas, skin, liver, thyroid, prostate, ovary, stomach, lung, lymphoid, bladder, cervix, thyroid, head and neck, brain, breast or kidney, in the treatment of melanoma, in the treatment of non-regenerative wound healing, or in the treatment or prevention of viral infections such as Herpes Simplex Virus infections, fibrosis such as pulmonary-, dermal-, renal- and liver fibrosis, myocardial fibrosis, or metabolic conditions such as aberrant systemic glucose metabolism.

Also provided is a method of treatment of a human or non-human animal body to treat or prevent a tumour emerging from colorectal tissue, uterus, pancreas, skin, liver, thyroid, prostate, ovary, stomach, lung, lymphoid, bladder, cervix, thyroid, head and neck, brain, breast or kidney, to treat melanoma, to treat non-regenerative wound healing, or to treat or prevent viral infections such as Herpes Simplex Virus infections, fibrosis such as pulmonary-, dermal-, renal- and liver fibrosis, myocardial fibrosis, or metabolic conditions such as aberrant systemic glucose metabolism, said method comprising the step of administering to said body an effective amount of a compound of formula (I) as herein defined, or a tautomer, stereoisomer, pharmaceutically acceptable salt, or pro-drug thereof.

Small molecules that selectively target the developmental pathways which control pattern formation during embryogenesis, including the WNT and hippo signalling pathways, are considered to be valuable for directing differentiation of pluripotent stem cells toward many desired tissue types (see Wang et al., ACS Chemical Biology, 16 Nov. 2010). As modulators of WNT signalling, the compounds herein described also have effects on the development of cellular differentiation. The compounds described herein therefore have valuable properties for use in regenerative medicine, for example in protocols for lineage specific in vitro differentiation of progenitor cells. By "progenitor cell" is meant a cell with the capacity to differentiate into another cell type, e.g. a stem cell.

According to this aspect, the present invention provides a method (e.g. an in vitro method) of promoting and/or directing cellular differentiation comprising contacting a progenitor cell with an effective amount of a compound of formula (I) as herein defined, or a tautomer, stereoisomer, pharmaceutically acceptable salt, or pro-drug thereof. In particular, the progenitor cell is contacted with said at least one compound under suitable conditions and for a sufficient time for the progenitor cell to differentiate into a new cell type. In a related aspect, the present invention provides the use of at least one compound as herein defined for promoting and/or directing cellular differentiation of a progenitor cell, especially in vitro.

Preferably, the progenitor cell is a totipotent or a pluripotent cell, especially a stem cell such as an embryonic stem cell. Preferred are mammalian progenitor cells such as mouse, rat and human cells, especially human cells. Such stem cells may be obtained from established cell cultures or may be derived directly from mammalian tissue by methods known in the art, including non tissue-destructive methods.

In a preferred embodiment, the progenitor cell is promoted and/or directed to differentiate into a new cell type which is a myocyte (e.g. a cardiomyocyte), a neuronal cell (e.g. a dopaminergic neuronal cell), an endocrine pancreatic cell or a hepatocyte or a cell type which may further differentiate into a myocyte, a neuronal cell, an endocrine pancreatic cell or a hepatocyte. Especially preferably, the progenitor cell is an embryonic stem cell and the new cell type is a cardiomyocyte, a dopaminergic neuronal cell, an endocrine pancreatic cell, a hepatocyte, or a cardiomyocyte.

The dosage required to achieve the desired activity of the compounds herein described will depend on the compound which is to be administered, the patient, the nature and severity of the condition, the method and frequency of administration and may be varied or adjusted according to choice. Typically, the dosage may be expected to be in the range from 1 to 100 mg, preferably 1 to 30 mg (when administered intravenously) and from 1 to 1000 mg, preferably from 1 to 200 mg (when administered orally).

The compounds of the invention may be formulated with one or more conventional carriers and/or excipients according to techniques well known in the art. Typically, the compositions will be adapted for oral or parenteral administration, for example by intradermal, subcutaneous, intraperitoneal or intravenous injection. Suitable pharmaceutical forms thus include plain or coated tablets, capsules, suspensions and solutions containing the active component optionally together with one or more conventional inert carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propylene glycol, stearylalcohol, carboxymethylcellulose or fatty substances such as hard fat or suitable mixtures of any of the above.

Alternatively, the compounds of the invention may be administered topically at or near the affected site. Topical compositions include gels, creams, ointments, sprays, lotions, salves, sticks, powders, pessaries, suppositories, aerosols, drops, solutions and any of the other conventional pharmaceutical forms in the art. Topical administration to inaccessible sites may be achieved by techniques known in the art, e.g. by use of catheters or other appropriate drug delivery systems.

Due to their enhanced solubility, the compounds may suitably be formulated in a form for parenteral administration, e.g. for intravenous injection. For this purpose, sterile solutions containing the active compounds may be employed.

The pharmacological properties of the compounds of the invention can be analysed using standard assays for functional activity. Detailed protocols for testing of the compounds of the invention are provided in the Examples.

The invention will now be described in more detail in the following non-limiting Examples:

EXAMPLES

General Procedures:

In the following general procedures A to F, groups X, Y and Z may represent any of the groups herein described.

Step A: Amide Preparation

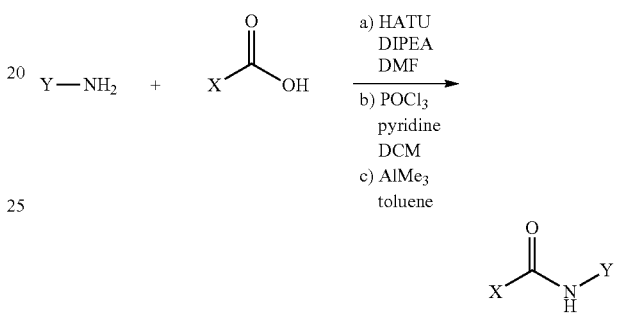

Method a):

To a solution of acid (1.0 equiv.) and DIPEA (1.2 equiv.) in dried DMF (0.2-0.5 M) was added HATU (1.1 equiv.) under an inert atmosphere. The reaction was stirred for 1 h before the amine (1.1 equiv.) was added. The stirring was continued for 2 to 24 hours and then evaporated to dryness. The residue was either first extracted (treated with a diluted aqueous sodium bicarbonate and DCM) or directly purified by flash column chromatography on silica gel (gradient of ethyl acetate in heptane, usually 10 to 100%) to afford the target amides.

Method b):

An equimolar mixture of the starting acid and amine were dissolved in a 5:1 mixture of DCM and pyridine (reaction molarity 0.2-0.5 M), the solution was cooled in an ice-bath and treated by a dropwise addition of 1.0-1.1 equiv. of phosphorous oxychloride. The cooling bath was removed and the mixture was stirred at ambient temperature for 1 to 18 hours. After an acidic extractive work-up, drying and chromatography, the desired amides were obtained.

Method c):

Under an atmosphere of nitrogen, appropriate aniline (1.2 equiv.) was dissolved in dry toluene (0.24 M) and the solution was treated by a dropwise addition of trimethylaluminium (2 M solution in toluene, 1.2 equiv.) observing quite some fuming. After 15-30 minutes, usually methyl or ethyl ester (1 equiv.) was added, a reflux condenser was fitted on the flask and the mixture was heated to 70-100° C. in a dry-syn. After 1-3 hours of reaction, the mixture was cooled down and quenched with 1N aqueous HCl to a slightly acidic pH. After dilution with water, the milky aqueous layer was extracted three times with DCM. The organic extracts were dried over sodium sulfate, filtered and evaporated to dryness leaving, in most cases, a crude amide of sufficient purity to be applied in the next step of the synthesis.

Step B: Thioamide Preparation

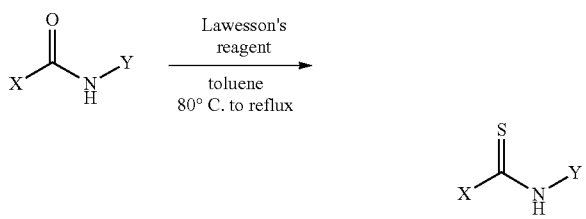

The amide (1.0 equiv.) was suspended under a nitrogen atmosphere in anhydrous toluene (0.10 to 0.25 M). Lawesson's reagent (1 equiv.) was added and the mixture was refluxed during 2 to 24 hours. After the reaction mixture was concentrated, the residue was extracted with DCM from aqueous phase or directly purified by flash column chromatography on silica gel (usually a gradient of ethyl acetate in heptane was used, sometimes a gradient of DCM in heptane) to afford a batch of desired thioamide.

Step C: Methylation of Thioamide

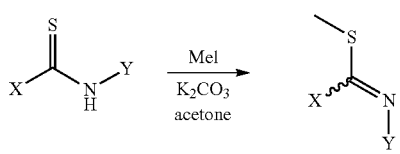

To a solution of thioamide (1.0 equiv.) and iodomethane (1.1-1.3 equiv.) in acetone (0.10 to 0.30 M) was added $K_2CO_3$ (1.3-1.5 equiv.). The suspension was stirred at room temperature till the reaction completion (2 hours to overnight). After solvent evaporation, the reaction mixture was either extracted from aqueous solution with DCM affording the crude product (as a mixture of E/Z isomers) that could be used without any purification in the next step. For better results in the next step, the crude product might be flashed over silica gel column eluted with a gradient of ethyl acetate (5 to 30%) in heptane.

Step D: Triazole Cyclisation

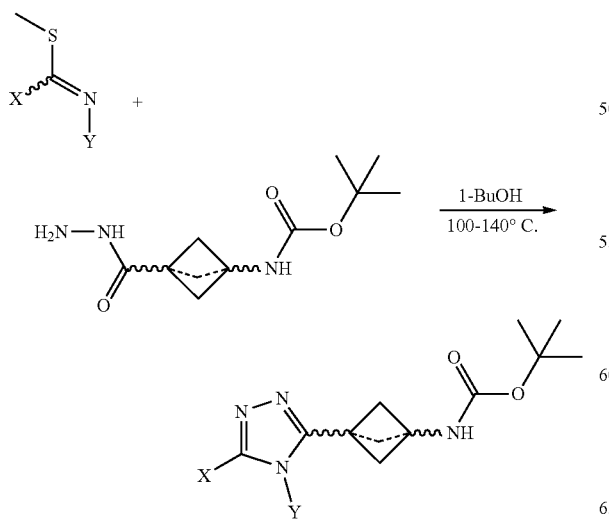

A suspension of carbimidothioate (1.0-1.1 equiv.) and an appropriate Boc-protected amino hydrazide (1.0-1.1 equiv.) in 1-butanol (0.10 to 0.30 M) was placed into a microwave vial and closed with a cap. The mixture was irradiated (or heated in an oil bath) at a temperature ranging from 100 to 140° C. until the completion of the reaction (typically 5 to 20 hours). After evaporating to dryness, the residue was purified by flash column chromatography on silica gel (gradient of ethyl acetate in heptane as eluent) to afford 1,2,4-triazole derivatives. Occasionally, a partial removal of Boc group was observed and the crude was flashed using a gradient of methanol in DCM to recover two products.

Step E: Boc Removal

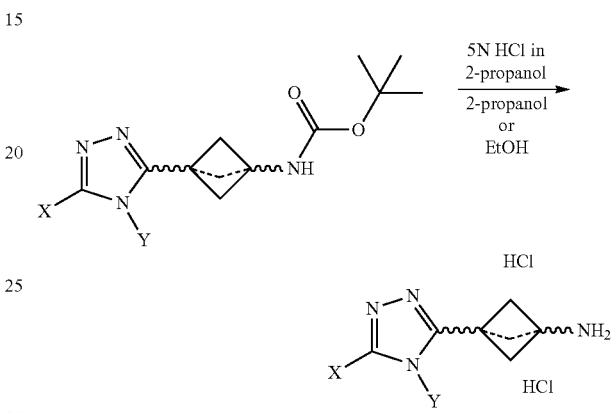

To a solution or suspension of the Boc-protected 1,2,4-triazole derivate (1.0 equiv.) in absolute ethanol or 2-propanol (0.05 to 0.25 M) was added hydrogen chloride as a 5N solution in 2-propanol (10-40 equiv.). The reaction was stirred at ambient or slightly elevated (50-60° C.) temperature during 2 to 18 hours. After reaction completion (if needed, extra portions of HCl were added) the solvents were removed in vacuo, sometimes stripping the residue with acetonitrile. The crude salt, most of the time a dihydrochloride, was used as such in the final step. Sometimes free amine was liberated by extraction from basic aqueous phase.

Step F: Amide Coupling Towards the Target Molecules

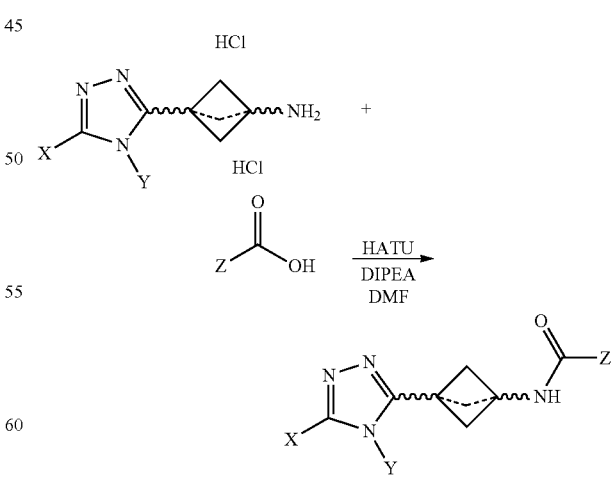

To a suspension or solution of the acid (1.1 equiv.) and HATU (1.2 equiv.) in anhydrous acetonitrile or N,N-dimethylformamide (0.02 to 0.10 M) was added DIPEA (2.0 equiv.) and the mixture was stirred from 30-60 minutes, preferably under an inert atmosphere before a suitable amine (1.0 equiv.) or its hydrochloride salt was added followed in the latter case by extra DIPEA (2.0 equiv.). The coupling was complete mostly within 1-3 hours, when the mixture was concentrated to dryness. The residue was submitted to purification by preparative SFC or by flash silica gel chromatography (0 via 5 to 10% gradient of methanol in DCM) followed by basic mode reversed-phase column (PoraPak Rxn RP, gradient acetonitrile in 10 nM aqueous ammonium bicarbonate). The final compound was obtained mostly as a white powder after lyophilisation from an acetonitrile/water mixture.

Preparation of Final Compounds and Intermediates

Example 1: Preparation of tert-butyl a 1r,3r)-3-(hydrazinecarbonyl)cyclobutyl)carbamate

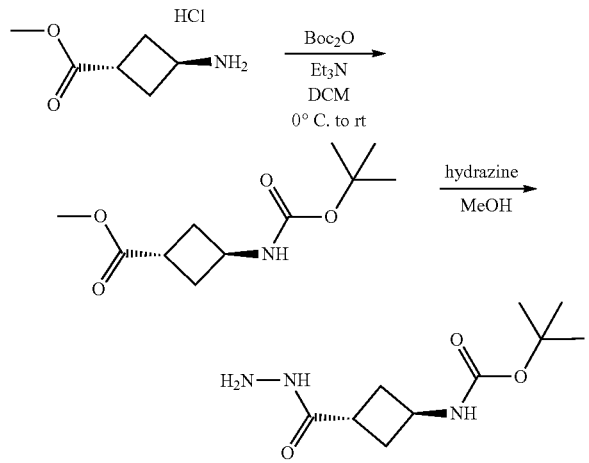

Step (a): Methyl trans-3-amino-cyclobutanecarboxylate hydrochloride (39.94 g, 241 mmol) was suspended in dichloromethane (400 ml). The solution was cooled to 0° C. before Et₃N (4 equiv., 134 ml, 965 mmol) and Boc anhydride (1.2 equiv., 63.2 g, 289 mmol) were added. The cooling bath was removed and the mixture was stirred while slowly allowing to warm up to room temperature. After 20 hours of stirring, the salts were filtered off and the filtrate was rinsed three times with water. The organic layer was dried over sodium sulfate, filtered and concentrated in vacuo. The residue was triturated in heptane, the solid was filtered off and dried in air flow to give methyl (1r,3r)-3-((tert-butoxycarbonyl)amino)cyclobutane-1-carboxylate as a white solid (46.3 gram, 80% yield).

LC/MS (ESI) m/z for C₁₁H₁₉NO₄ 229 (calcd), 215 ([M-Me]⁺, found).

¹H NMR (400 MHz, Chloroform-d) δ 4.73 (br s, 1H), 4.31 (br s, 1H), 3.70 (s, 3H), 3.01 (pseudo heptet, J=9.6, 1H), 2.62 (ddd, J=12.9, 7.8, 3.7 Hz, 2H), 2.27-2.10 (m, 2H), 1.44 (s, 9H).

Step (b): Methyl (1r,3r)-3-((tert-butoxycarbonyl)amino)cyclobutane-1-carboxylate (2.50 g, 8.72 mmol) was suspended in methanol (60 ml) and hydrazine hydrate (2.54 ml, 52.3 mmol) was added. The mixture was stirred at ambient temperature during 18 hours. The resulting suspension was filtered over a glass filter. The white solids were rinsed twice with water and twice with diethyl ether. The white solid was dried on air to yield the title compound as a white solid (4.75 gram, 95% yield).

LC/MS (ESI) m/z for C₁₀H₁₉N₃O₃ 229 (calcd), 174 ([M-t-Bu]⁺, found).

¹H NMR (400 MHz, DMSO-d₆) δ 8.88 (br s, 1H), 7.13 (d, J=8.1 Hz, 1H), 4.25-4.06 (m, 3H), 2.71 (tt, J=9.0, 3.7 Hz, 1H), 2.32-2.17 (m, 2H), 2.12-1.97 (m, 2H), 1.36 (s, 9H).

Example 2: Preparation of tert-butyl (3-(hydrazinecarbonyl)bicyclo[1.1.1]pentan-1-yl) carbamate

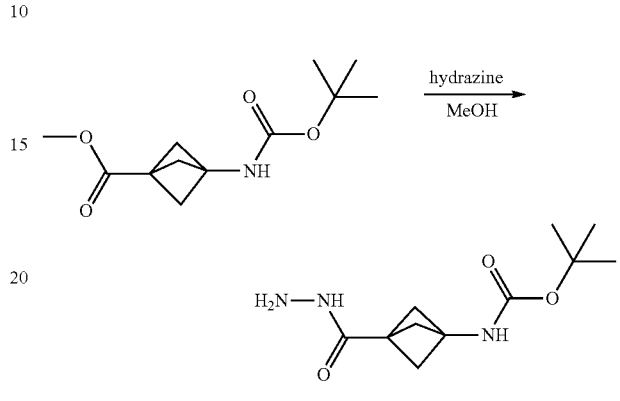

Methyl 3-((tert-butoxycarbonyl)amino)bicyclo[1.1.1]pentane-1-carboxylate (0.497 g, 2.00 mmol) was suspended in methanol (10 mL) and hydrazine hydrate (0.974 ml, 20.00 mmol) was added. The mixture was stirred at room temperature for 18 hours. After completion the mixture was evaporated to dryness, stripped twice with methanol and acetonitrile to give the title compound as an off-white solid (482 mg, 97% yield).

LC/MS (ESI) m/z for C₁₁H₁₉N₃O₃ 241 (calcd), 242 ([M+H]⁺, found).

¹H NMR (400 MHz, DMSO-do) δ 9.01 (s, 1H), 7.56 (br s, 1H), 4.18 (s, 2H), 2.02 (s, 6H), 1.37 (s, 9H).

Example 3: Preparation of amine building block A: (1S,3r)-3-(4-(2-chlorophenyl)-5-(pyrimidin-4-yl)-4H-1,2,4-triazol-3-yl)cyclobutan-1-amine

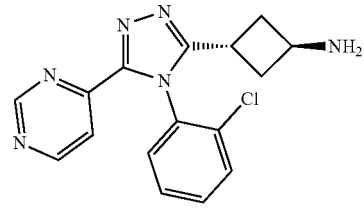

Step (a): N-(2-chlorophenyl)pyrimidine-4-carboxamide was prepared according to the general procedure A, method a) as a purple solid (16.4 g, 87% yield).

LC/MS (ESI) m/z for C₁₁H₈ClN₃O 233/235 (calcd) 234/236 ([M+H]⁺, found).

¹H NMR (400 MHz, DMSO-d₆) δ 10.59 (s, 1H), 9.46 (d, J=1.5 Hz, 1H), 9.19 (d, J=5.1 Hz, 1H), 8.26 (dd, J=8.0, 1.6 Hz, 1H), 8.18 (dd, J=5.1, 1.5 Hz, 1H), 7.60 (dd, J=8.0, 1.4 Hz, 1H), 7.45 (td, J=7.8, 1.5 Hz, 1H), 7.27 (td, J=7.7, 1.6 Hz, 1H).

Step (b) N-(2-chlorophenyl)pyrimidine-4-carbothioamide was prepared following the general procedure B and obtained as an orange solid (18.0 g, 99% yield).

LC/MS (ESI) m/z for C₁₁118 ClN₃S 249/251 (calcd) 250/252 ([M+H]⁺, found).

¹H NMR (400 MHz, Chloroform-d) δ 12.39 (s, 1H), 9.31 (s, 1H), 9.08 (dd, J=8.2, 1.5 Hz, 1H), 9.01 (d, J=5.3 Hz, 1H), 8.64 (dd, J=5.1, 1.3 Hz, 1H), 7.54 (dd, J=8.0, 1.5 Hz, 1H), 7.40 (td, J=7.8, 1.5 Hz, 1H), 7.27 (td, J=7.8, 1.6 Hz, 1H).

Step (c): methyl N-(2-chlorophenyl)pyrimidine-4-carbimidothioate was prepared according to the general procedure C as an orange oil (13.2 g, ~90% pure, 89% yield). LC/MS (ESI) m/z for C₁₂H₁₀ClN₃S 263/265 (calcd) 264/266 ([M+H]⁺, found).

¹H NMR (400 MHz, Chloroform-d, broadened signals) δ 9.29 (s, 1H), 8.77 (br s, 1H), 7.38 (br d, J=6.9 Hz, 1H), 7.15 (br s, 1H), 7.03 (br s, 2H), 6.78 (br s, 1H), 2.43 (br s, 3H).

Step (d): tert-butyl ((1S,3r)-3-(4-(2-chlorophenyl)-5-(pyrimidin-4-yl)-4H-1,2,4-triazol-3-yl)cyclobutyl)carbamate was prepared according to the general procedure D as an off-white solid (961 mg, 90% pure, 86% yield).

LC/MS (ESI) m/z for C₂₁H₂₃ClN₆O₂ 426/428 (calcd) 427/429 ([M+H]⁺, found).

¹H NMR (400 MHz, Chloroform-d) δ 8.80 (pseudo d, J=5.3 Hz, 2H), 8.26 (dd, J=5.2, 1.3 Hz, 1H), 7.54 (dd, J=7.9, 1.2 Hz, 1H), 7.49 (td, J=7.3, 1.4 Hz, 1H), 7.42 (td, J=7.6, 1.4 Hz, 1H), 7.27 (dd, J=7.7, 1.5 Hz, 1H), 4.75 (br s, 1H), 4.35 (h, J=6.8 Hz, 1H), 3.32-3.20 (m, 1H), 2.94-2.82 (m, 2H), 2.26 (br s, 2H), 1.42 (s, 9H).

Step (e): the title compound was prepared similarly to the general procedure E, but employing HCl in dioxane and methanol as main solvent. The free amine was liberated after re-dissolving the HCl salt in water and basification with aqueous potassium carbonate. After extraction with DCM, the organic layer was dried over sodium sulfate, filtered and evaporated to dryness giving the title compound as an orange oil (623 mg, 92% pure, 87% yield). This material was re-dissolved in acetonitrile and used as a 0.20 molar solution in the final step.

LC/MS (ESI) m/z for C₁₆H₁₅ClN₆ 326/328 (calcd) 327/328 ([M+H]⁺, found).

¹H NMR (400 MHz, Chloroform-d) δ 8.84-8.76 (m, 2H), 8.26 (dd, J=5.3, 1.3 Hz, 1H), 7.53 (dd, J=8.0, 1.6 Hz, 1H), 7.48 (td, J=7.7, 1.6 Hz, 1H), 7.42 (td, J=7.6, 1.6 Hz, 1H), 7.31-7.23 (m, 1H), 3.92 (p, J=6.4 Hz, 1H), 3.27 (tt, J=9.4, 5.0 Hz, 1H), 2.87-2.73 (m, 2H), 2.06-1.88 (m, 2H), 1.45 (br s, 2H).

Example 4: Preparation of N-((1S,3r)-3-(4-(2-chlorophenyl)-5-(pyrimidin-4-yl)-4H-1,2,4-triazol-3-yl)cyclobutyl)quinoline-8-carboxamide

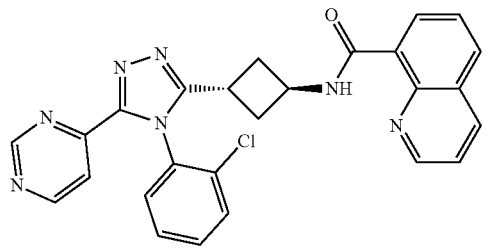

The title compound was prepared according to the general procedure F and obtained as a white solid (32.4 mg, 64% yield).

LC/MS (ESI) m/z for C₂₆H₂₀ClN₇O 481/483 (calcd.) 482/484 ([M+H]⁺, found).

¹H NMR (400 MHz, Chloroform-d) b 11.57 (d, J=5.4 Hz, 1H), 8.91 (dd, J=4.2, 1.7 Hz, 1H), 8.86-8.78 (m, 3H), 8.32-8.25 (m, 2H), 7.96 (dd, J=8.1, 1.3 Hz, 1H), 7.67 (t, J=7.7 Hz, 1H), 7.56-7.44 (m, 3H), 7.41 (td, J=7.6, 1.5 Hz, 1H), 7.32 (dd, J=7.7, 1.5 Hz, 1H), 4.84 (h, J=6.4 Hz, 1H), 3.51 (tt, J=9.7, 5.6 Hz, 1H), 3.17-3.03 (m, 2H), 2.60-2.49 (m, 2H).

Example 5: Preparation of N-((1S,3r)-3-(4-(2-chlorophenyl)-5-(pyrimidin-4-yl)-4H-1,2,4-triazol-3-yl)cyclobutyl)-1,5-naphthyridine-4-carboxamide

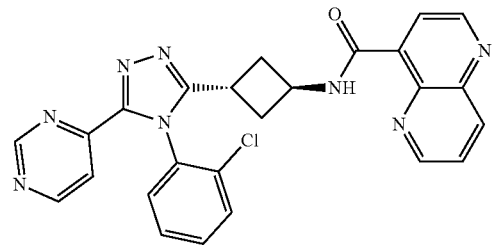

The title compound was prepared according to the general procedure F and obtained as a white solid (12.7 mg, 26% yield). LC/MS (ESI) m/z for C₂₅H₁₉C₁₁N₈O 482/484 (calcd.) 483/485 ([M+H]⁺, found).

¹H NMR (400 MHz, Chloroform-d) δ 11.32 (d, J=5.8 Hz, 1H), 9.15 (d, J=4.4 Hz, 1H), 8.98 (dd, J=4.2, 1.7 Hz, 1H), 8.85-8.79 (m, 2H), 8.60-8.52 (m, 2H), 8.29 (dd, J=5.3, 1.3 Hz, 1H), 7.75 (dd, J=8.5, 4.2 Hz, 1H), 7.54 (dd, J=7.9, 1.5 Hz, 1H), 7.48 (td, J=7.7, 1.6 Hz, 1H), 7.42 (td, J=7.6, 1.6 Hz, 1H), 7.32 (dd, J=7.8, 1.5 Hz, 1H), 4.88 (h, J=7.2 Hz, 1H), 3.49 (tt, J=9.7, 5.4 Hz, 1H), 3.17-3.04 (m, 2H), 2.65-2.50 (m, 2H).

Example 6: Preparation of N-((1S,3r)-3-(4-(2-chlorophenyl)-5-(pyrimidin-4-yl)-4H-1,2,4-triazol-3-yl)cyclobutyl)quinoline-4-carboxamide

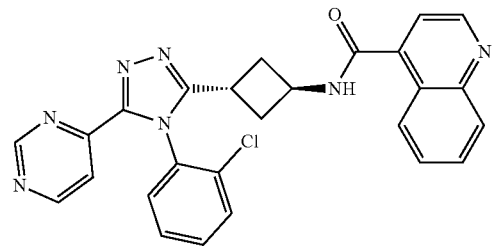

The title compound was prepared according to the general procedure F and obtained as a white solid (25.7 mg, 50% yield).

LC/MS (ESI) m/z for C₂₆H₂₀ClN₇O 481/483 (calcd) 482/484 ([M+14]⁺, found).

¹H NMR (400 MHz, Chloroform-d) δ 8.96-8.90 (m, 1H), 8.85-8.78 (m, 2H), 8.28 (dd, J=5.3, 1.5 Hz, 1H), 8.18 (d, J=8.4 Hz, 1H), 8.13 (d, J=8.5 Hz, 1H), 7.76 (ddd, J=8.4, 6.9, 1.4 Hz, 1H), 7.60 (ddd, J=8.3, 6.8, 1.2 Hz, 1H), 7.56 (dd, J=8.0, 1.6 Hz, 1H), 7.50 (td, J=7.7, 1.7 Hz, 1H), 7.44 (td, J=7.7, 1.7 Hz, 1H), 7.41 (dd, J=4.5, 1.9 Hz, 1H), 7.31 (dd, J=7.8, 1.7 Hz, 1H), 6.30 (s, 1H), 4.93 (h, J=7.2 Hz, 1H), 3.44-3.34 (m, 1H), 3.15-3.05 (m, 2H), 2.57-2.41 (m, 2H).

Example 7: Preparation of N-((1S,3r)-3-(4-(2-chlorophenyl)-5-(pyrimidin-4-yl)-4H-1,2,4-triazol-3-yl)cyclobutyl)quinoline-5-carboxamide

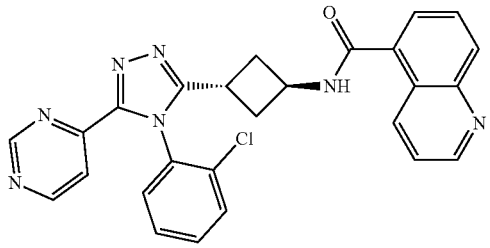

The title compound was prepared according to the general procedure F and obtained as a white solid (44.4 mg, 90% yield).

LC/MS (ESI) m/z for $C_{26}H_{20}ClN_7O$ 481/483 (calcd) 482/484 ([M+H]$^+$, found).

$^1$H NMR (400 MHz, Chloroform-d) δ 8.95 (dd, J=4.1, 1.4 Hz, 1H), 8.82 (s, 1H), 8.81 (d, J=3.8 Hz, 1H), 8.73 (d, J=8.6 Hz, 1H), 8.28 (dd, J=5.3, 1.2 Hz, 1H), 8.18 (dd, J=6.7, 2.9 Hz, 1H), 7.70-7.62 (m, 2H), 7.55 (dd, J=8.0, 1.4 Hz, 1H), 7.50 (td, J=7.4, 1.5 Hz, 1H), 7.48-7.40 (m, 2H), 7.31 (dd, J=7.7, 1.4 Hz, 1H), 6.31 (d, J=6.6 Hz, 1H), 4.90 (h, J=7.3 Hz, 1H), 3.40 (tt, J=9.7, 5.1 Hz, 1H), 3.09 (tt, J=8.2, 4.0 Hz, 2H), 2.55-2.39 (m, 2H).

Example 8: Preparation of N-((1S,3r)-3-(4-(2-chlorophenyl)-5-(pyrimidin-4-yl)-4H-1,2,4-triazol-3-yl)cyclobutyl)isonicotinamide

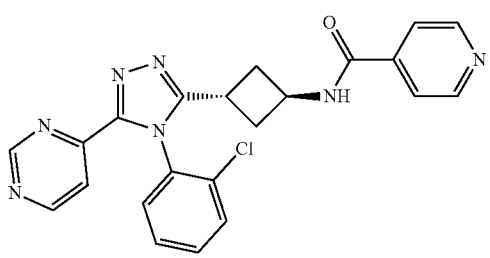

The title compound was prepared according to the general procedure F and obtained as a white solid (33.4 mg, 74% yield).

LC/MS (ESI) m/z for $C_{22}H_{18}ClN_7O$ 431/433 (calcd) 432/434 ([M+H]$^+$, found).

$^1$H NMR (400 MHz, Chloroform-d) δ 8.82 (dd, J=3.4, 1.9 Hz, 2H), 8.74 (d, J=5.1 Hz, 2H), 8.27 (dd, J=5.3, 1.4 Hz, 1H), 7.61-7.57 (m, 2H), 7.55 (dd, J=8.0, 1.7 Hz, 1H), 7.50 (td, J=7.7, 1.7 Hz, 1H), 7.43 (td, J=7.6, 1.7 Hz, 1H), 7.30 (dd, J=7.8, 1.6 Hz, 1H), 6.41 (d, J=6.3 Hz, 1H), 4.79 (h, J=7.1 Hz, 1H), 3.39 (tt, J=9.6, 5.0 Hz, 1H), 3.11-2.98 (m, 2H), 2.52-2.38 (m, 2H).

Example 9: Preparation of N-((1S,3r)-3-(4-(2-chlorophenyl)-5-(pyrimidin-4-yl)-4H-1,2,4-triazol-3-yl)cyclobutyl)nicotinamide

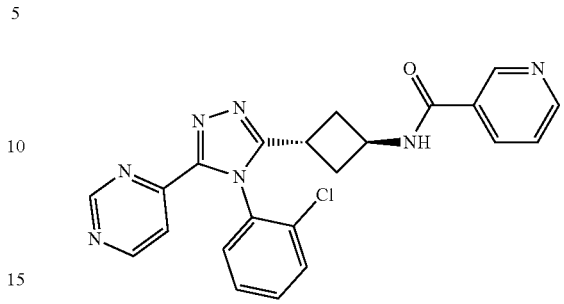

The title compound was prepared according to the general procedure F and obtained as a white solid (28.2 mg, 65% yield).

LC/MS (ESI) m/z for $C_{22}H_{18}ClN_7O$ 431/433 (calcd) 432/434 ([M+H]$^+$, found).

$^1$H NMR (400 MHz, Chloroform-d) δ 8.94 (s, 1H), 8.85-8.78 (m, 2H), 8.73 (d, J=3.0 Hz, 1H), 8.27 (dd, J=5.3, 1.2 Hz, 1H), 8.10 (dt, J=8.0, 1.6 Hz, 1H), 7.55 (dd, J=8.0, 1.5 Hz, 1H), 7.50 (td, J=7.7, 1.6 Hz, 1H), 7.43 (td, J=7.6, 1.6 Hz, 1H), 7.39 (dd, J=7.8, 4.8 Hz, 1H), 7.30 (dd, J=7.8, 1.5 Hz, 1H), 6.38 (d, J=5.9 Hz, 1H), 4.80 (h, J=7.1 Hz, 1H), 3.40 (tt, J=9.8, 5.6 Hz, 1H), 3.11-3.00 (m, 2H), 2.52-2.37 (m, 2H).

Example 10: Preparation of N-((1S,3r)-3-(4-(2-chlorophenyl)-5-(pyrimidin-4-yl)-4H-1,2,4-triazol-3-yl)cyclobutyl)picolinamide

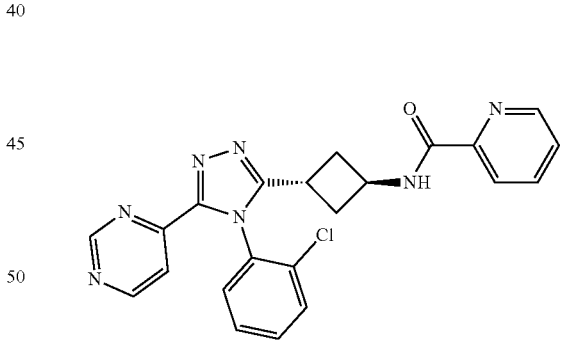

The title compound was prepared according to the general procedure F and obtained as a white solid (41.1 mg, 94% yield).

LC/MS (ESI) m/z for $C_{22}H_{18}ClN_7O$ 431/433 (calcd) 432/434 ([M+H]$^+$, found).

$^1$H NMR (400 MHz, Chloroform-d) δ 8.82 (s, 1H), 8.81 (d, J=3.3 Hz, 1H), 8.53 (qd, J=4.8, 0.6 Hz, 1H), 8.28 (dd, J=5.3, 1.3 Hz, 1H), 8.23 (d, J=6.6 Hz, 1H), 8.17 (d, J=7.8 Hz, 1H), 7.84 (td, J=7.7, 1.7 Hz, 1H), 7.54 (dd, J=8.0, 1.5 Hz, 1H), 7.49 (td, J=7.7, 1.6 Hz, 1H), 7.46-7.38 (m, 2H), 7.30 (dd, J=7.8, 1.5 Hz, 1H), 4.86-4.72 (m, 1H), 3.49-3.36 (m, 1H), 3.11-3.00 (m, 2H), 2.53-2.38 (m, 2H).

Example 11: Preparation of N-((1S,3r)-3-(4-(2-chlorophenyl)-5-(pyrimidin-4-yl)-4H-1,2,4-triazol-3-yl)cyclobutyl)pyrimidine-4-carboxamide

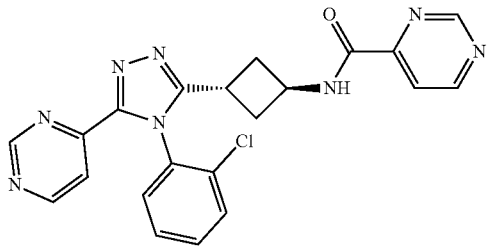

The title compound was prepared according to the general procedure F and obtained as a white solid (22.8 mg, 52% yield).

LC/MS (ESI) m/z for $C_{21}H_{17}ClN_8O$ 432/434 (calcd) 433/435 ([M+H]$^+$, found).

$^1$H NMR (400 MHz, Chloroform-d) δ 9.22 (d, J=1.3 Hz, 1H), 8.97 (d, J=5.0 Hz, 1H), 8.82 (dd, J=3.3, 1.9 Hz, 2H), 8.28 (dd, J=5.3, 1.3 Hz, 1H), 8.17 (br d, J=6.7 Hz, 1H), 8.09 (dd, J=5.0, 1.3 Hz, 1H), 7.55 (dd, J=8.0, 1.5 Hz, 1H), 7.50 (td, J=7.7, 1.6 Hz, 1H), 7.43 (td, J=7.6, 1.6 Hz, 1H), 7.30 (dd, J=7.8, 1.5 Hz, 1H), 4.83 (h, J=7.1 Hz, 1H), 3.41 (tt, J=9.6, 5.4 Hz, 1H), 3.11-3.00 (m, 2H), 2.55-2.39 (m, 2H).

Example 12: Preparation of N-((1S,3r)-3-(4-(2-chlorophenyl)-5-(pyrimidin-4-yl)-4H-1,2,4-triazol-3-yl)cyclobutyl)benzamide

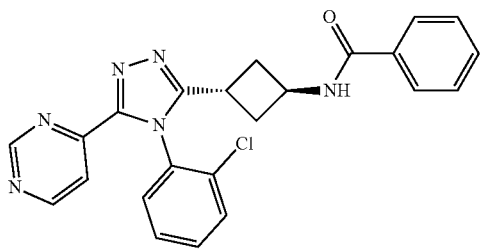

The title compound was prepared according to the general procedure F and obtained as a white solid (28.6 mg, 47% yield).

LC/MS (ESI) m/z for $C_{23}H_{19}ClN_6O$ 430/432 (calcd) 431/433 ([M+H]$^+$, found).

$^1$H NMR (400 MHz, Chloroform-d) δ 8.82 (s, 1H), 8.80 (d, J=3.3 Hz, 1H), 8.27 (dd, J=5.2, 0.9 Hz, 1H), 7.74 (pseudo d, J=7.2 Hz, 2H), 7.54 (dd, J=8.0, 1.5 Hz, 1H), 7.52-7.45 (m, 2H), 7.42 (pseudo t, J=7.4 Hz, 3H), 7.30 (dd, J=7.8, 1.4 Hz, 1H), 6.32 (br d, J=5.8 Hz, 1H), 4.75 (h, J=6.5 Hz, 1H), 3.40 (tt, J=10.0, 5.5 Hz, 1H), 3.11-2.97 (m, 2H), 2.49-2.34 (m, 2H).

Example 13: Preparation of N-((1S,3r)-3-(4-(2-chlorophenyl)-5-(pyrimidin-4-yl)-4H-1,2,4-triazol-3-yl)cyclobutyl)-2-fluorobenzamide

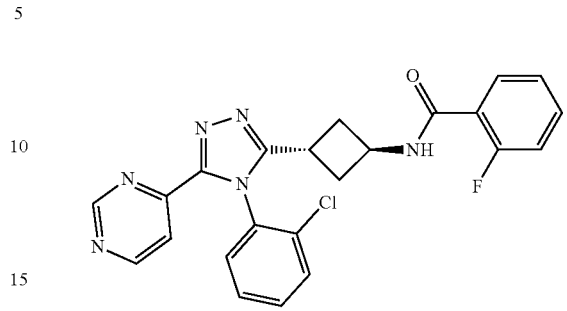

The title compound was prepared according to the general procedure F and obtained as a white solid (35.4 mg, 79% yield).

LC/MS (ESI) m/z for $C_{23}H_{18}ClFN_6O$ 448/450 (calcd) 449/451 ([M-FH]$^+$, found).

$^1$H NMR (400 MHz, Chloroform-d) δ 8.82 (s, 1H), 8.81 (d, J=3.2 Hz, 1H), 8.28 (dd, J=5.3, 1.4 Hz, 1H), 8.07 (td, J=8.0, 1.9 Hz, 1H), 7.54 (dd, J=8.0, 1.7 Hz, 1H), 7.48 (tdd, J=7.7, 5.5, 2.1 Hz, 2H), 7.42 (td, J=7.6, 1.6 Hz, 1H), 7.33-7.27 (m, 1H), 7.24 (dd, J=7.4, 1.1 Hz, 1H), 7.11 (ddd, J=12.2, 8.3, 1.1 Hz, 1H), 6.93 (dd, J=13.6, 6.0 Hz, 1H), 4.79 (h, J=8.1 Hz, 1H), 3.45-3.34 (m, 1H), 3.11-2.99 (m, 2H), 2.48-2.32 (m, 2H).

Example 14: Preparation of N-((1S,3r)-3-(4-(2-chlorophenyl)-5-(pyrimidin-4-yl)-4H-1,2,4-triazol-3-yl)cyclobutyl)-3-fluorobenzamide

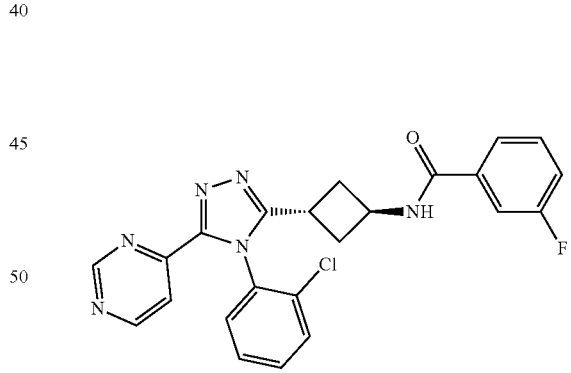

The title compound was prepared according to the general procedure F and obtained as a white solid (37.3 mg, 82% yield).

LC/MS (ESI) m/z for $C_{23}H_{18}ClFN_6O$ 448/450 (calcd) 449/451 ([M+H]$^+$, found).

$^1$H NMR (400 MHz, Chloroform-d) δ 8.82 (s, 1H), 8.81 (d, J=3.1 Hz, 1H), 8.27 (dd, J=5.3, 1.4 Hz, 1H), 7.54 (dd, J=8.0, 1.7 Hz, 1H), 7.53-7.35 (m, 5H), 7.30 (dd, J=7.8, 1.7 Hz, 1H), 7.19 (tdd, J=8.2, 2.6, 1.0 Hz, 1H), 6.30 (br d, J=6.3 Hz, 1H), 4.75 (pseudo h, J=7.1 Hz, 1H), 3.39 (ttd, J=9.6, 5.4, 1.1 Hz, 1H), 3.11-2.97 (m, 2H), 2.50-2.34 (m, 2H).

Example 15: Preparation of N-((1S,3r)-3-(4-(2-chlorophenyl)-5-(pyrimidin-4-yl)-4H-1,2,4-triazol-3-yl)cyclobutyl)-4-fluorobenzamide

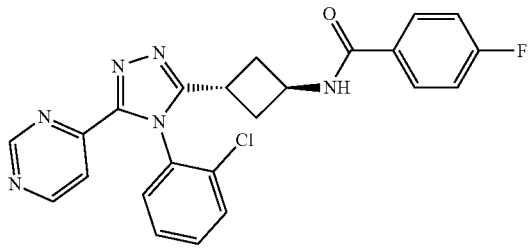

The title compound was prepared according to the general procedure F and obtained as a white solid (16.0 mg, 35% yield).

LC/MS (ESI) m/z for $C_{23}H_{18}ClFN_6O$ 448/450 (calcd) 449/451 ([M+H]$^+$, found).

$^1$H NMR (400 MHz, Chloroform-d) δ 8.82 (s, 1H), 8.81 (d, J=3.2 Hz, 1H), 8.27 (dd, J=5.3, 1.4 Hz, 1H), 7.80-7.71 (m, 2H), 7.54 (dd, J=8.0, 1.7 Hz, 1H), 7.49 (td, J=7.7, 1.6 Hz, 1H), 7.42 (td, J=7.6, 1.7 Hz, 1H), 7.30 (dd, J=7.8, 1.6 Hz, 1H), 7.14-7.05 (m, 2H), 6.25 (br d, J=6.2 Hz, 1H), 4.75 (h, J=7.0 Hz, 1H), 3.39 (tt, J=9.8, 5.3 Hz, 1H), 3.11-2.97 (m, 2H), 2.49-2.34 (m, 2H).

Example 16: Preparation of N-((1S,3r)-3-(4-(2-chlorophenyl)-5-(pyrimidin-4-yl)-4H-1,2,4-triazol-3-yl)cyclobutyl)-2,6-difluorobenzamide

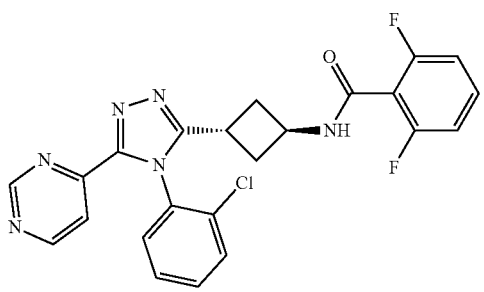

The title compound was prepared according to the general procedure F and obtained as a white solid (38.6 mg, 82% yield).

LC/MS (ESI) m/z for $C_{23}H_{17}ClF_2N_6O$ 466/468 (calcd) 467/469 ([M+H]$^+$, found).

$^1$H NMR (400 MHz, Chloroform-d) δ 8.82 (s, 1H), 8.81 (d, J=3.7 Hz, 1H), 8.27 (dd, J=5.2, 1.4 Hz, 1H), 7.55 (dd, J=8.0, 1.7 Hz, 1H), 7.49 (td, J=7.7, 1.7 Hz, 1H), 7.43 (td, J=7.6, 1.7 Hz, 1H), 7.35 (tt, J=8.4, 6.3 Hz, 1H), 7.30 (dd, J=7.7, 1.6 Hz, 1H), 6.93 (t, J=8.1 Hz, 2H), 6.18 (br d, J=6.2 Hz, 1H), 4.77 (h, J=7.1 Hz, 1H), 3.43-3.33 (m, 1H), 3.10-2.98 (m, 2H), 2.51-2.34 (m, 2H).

Example 17: Preparation of N-((1S,3r)-3-(4-(2-chlorophenyl)-5-(pyrimidin-4-yl)-4H-1,2,4-triazol-3-yl)cyclobutyl)-5-fluoropicolinamide

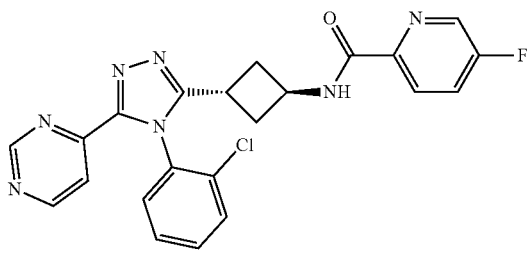

The title compound was prepared according to the general procedure F and obtained as a white solid (35.8 mg, 78% yield).

LC/MS (ESI) in/z for $C_{22}H_{17}ClFN_7O$ 449/451 (calcd) 450/452 ([M+H]$^+$, found).

$^1$H NMR (400 MHz, Chloroform-d) δ 8.82 (s, 1H), 8.81 (d, J=3.2 Hz, 1H), 8.36 (d, J=2.8 Hz, 1H), 8.28 (dd, J=5.3, 1.4 Hz, 1H), 8.20 (dd, J=8.7, 4.6 Hz, 1H), 8.05 (br d, J=7.1 Hz, 1H), 7.57-7.46 (m, 3H), 7.42 (td, J=7.5, 1.7 Hz, 1H), 7.30 (dd, J=7.8, 1.7 Hz, 1H), 4.79 (h, J=6.9 Hz, 1H), 3.46-3.35 (m, 1H), 3.10-2.99 (m, 2H), 2.52-2.35 (m, 2H).

Example 18: Preparation of N-((1S,3r)-3-(4-(2-chlorophenyl)-5-(pyrimidin-4-yl)-4H-1,2,4-triazol-3-yl)cyclobutyl)-3-fluoropicolinamide

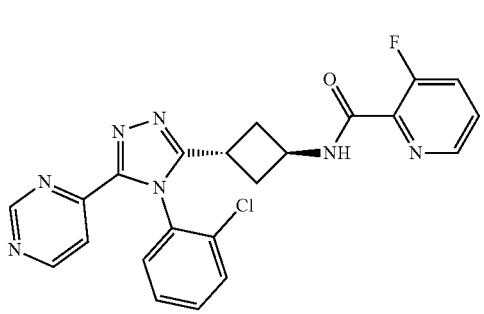

The title compound was prepared according to the general procedure F and obtained as a white solid (24.0 mg, 52% yield).

LC/MS (ESI) m/z for $C_{22}H_{17}ClFN_7O$ 449/451 (calcd) 450/452 ([M+H]$^+$ found). 1H NMR (400 MHz, Chloroform-d) δ 8.82 (s, 1H), 8.81 (d, J=3.3 Hz, 1H), 8.36 (dt, J=4.3, 1.4 Hz, 1H), 8.28 (dd, J=5.3, 1.4 Hz, 1H), 8.04 (br d, J=6.6 Hz, 1H), 7.58-7.51 (m, 2H), 7.51-7.45 (m, 2H), 7.42 (td, J=7.6, 1.7 Hz, 1H), 7.29 (dd, J=7.8, 1.6 Hz, 1H), 4.74 (h, J=7.1 Hz, 1H), 3.48-3.38 (m, 1H), 3.10-2.98 (m, 2H), 2.56-2.40 (m, 2H).

Example 19: Preparation of N-((1S,3r)-3-(4-(2-chlorophenyl)-5-(pyrimidin-4-yl)-4H-1,2,4-triazol-3-yl)cyclobutyl)-6-fluoropicolinamide

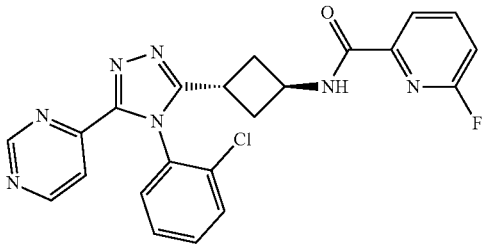

The title compound was prepared according to the general procedure F and obtained as a white solid (25.4 mg, 56% yield).

LC/MS (ESI) m/z for $C_{22}H_{17}ClFN_7O$ 449/451 (calcd) 450/452 ([M+H]$^+$ found).

$^1$H NMR (400 MHz, Chloroform-d) δ 8.82 (s, 1H), 8.81 (d, J=3.3 Hz, 1H), 8.28 (dd, J=5.2, 1.4 Hz, 1H), 8.07 (dd, J=7.5, 2.2 Hz, 1H), 7.95 (q, J=7.8 Hz, 1H), 7.89 (br d, J=7.1 Hz, 1H), 7.55 (dd, J=7.9, 1.7 Hz, 1H), 7.50 (td, J=7.7, 1.7 Hz, 1H), 7.43 (td, J=7.6, 1.7 Hz, 1H), 7.30 (dd, J=7.8, 1.6 Hz, 1H), 7.09 (dd, J=8.1, 2.5 Hz, 1H), 4.80 (h, J=7.2 Hz, 1H), 3.47-3.35 (m, 1H), 3.11-2.99 (m, 2H), 2.52-2.36 (m, 2H).

Example 20: Preparation of amine building block B: 3-(4-(2-chlorophenyl)-5-(pyrimidin-4-yl)-4H-1,2,4-triazol-3-yl)bicyclo[1.1.1]pentan-1-amine trihydrochloride Step (a): Tert-butyl (3-(4-(2-chlorophenyl)-5-(pyrimidin-4-yl)-4H-1,2,4-triazol-3-yl)bicyclo[1.1.1]pentan-1-yl)carbamate was prepared from 124 mg (0.50 mmol) of tert-butyl (3-(hydrazinecarbonyl)bicyclo[1.1.1]pentan-1-yl)carbamate (Example 2) and 153 mg (0.55 mmol) of methyl N-(2-chlorophenyl)pyrimidine-4-carbimidothioate (Example 3, step c) according to the general procedure D as a yellow glass (167 mg, 75% yield). LC/MS (ESI) m/z for $C_{22}H_{23}ClN_6O_2$ 438/440 (calcd) 439/441 ([M+H]$^+$ found).

$^1$H NMR (400 MHz, Chloroform-d) δ 8.81 (d, J=1.2 Hz, 1H), 8.79 (d, J=5.3 Hz, 1H), 8.24 (dd, J=5.2, 1.2 Hz, 1H), 7.58-7.47 (m, 2H), 7.43 (td, J=7.5, 1.7 Hz, 1H), 7.34 (dd, J=7.8, 1.2 Hz, 1H), 4.94 (s, 1H), 2.22 (br d, J=3.9 Hz, 6H), 1.40 (s, 9H).

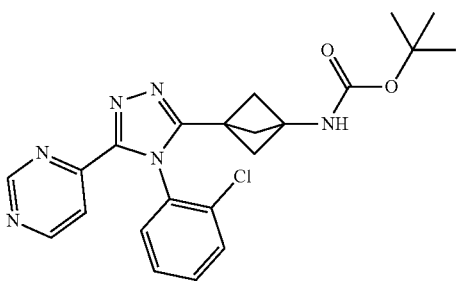

Step (b): The crude title compound was prepared according to the general procedure E as a yellow glass (189 mg, 92% yield) of a presumed trichloride adduct based on mass balance.

LC/MS (ESI) m/z for $C_{17}H_{15}ClN_6$ 338/340 (calcd) 339/341 ([M+H]$^+$ found)

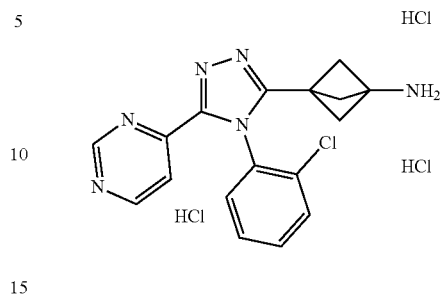

Example 21: Preparation of N-(3-(4-(2-chlorophenyl)-5-(pyrimidin-4-yl)-4H-1,2,4-triazol-3-yl)bicyclo[1.1.1]pentan-1-yl)-1,5-naphthyridine-4-carboxamide

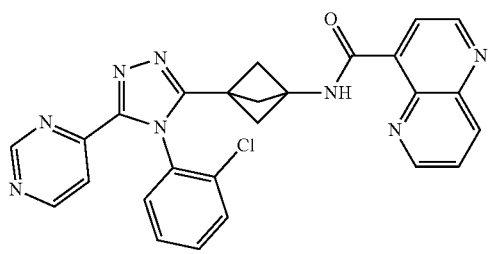

The title compound was prepared according to the general procedure F as a white solid (10.4 mg, 42% yield).

LC/MS (ESI) m/z for $C_{26}H_{19}ClN_8O$ 494/496 (calcd) 495/497 ([M+H]$^+$ found).

$^1$H NMR (400 MHz, Chloroform-d) δ 11.48 (s, 1H), 9.14 (d, J=4.4 Hz, 1H), 8.99 (dd, J 4.2, 1.7 Hz, 1H), 8.84 (d, J=1.2 Hz, 1H), 8.81 (d, J=5.3 Hz, 1H), 8.56 (dd, J=8.5, 1.6 Hz, 1H), 8.49 (d, J=4.4 Hz, 1H), 8.27 (dd, J=5.2, 1.3 Hz, 1H), 7.75 (dd, J=8.5, 4.3 Hz, 1H), 7.57 (dd, J=8.0, 1.6 Hz, 1H), 7.53 (td, J=8.1, 7.6, 1.6 Hz, 1H), 7.46 (td, J=7.5, 1.7 Hz, 1H), 7.41 (dd, J=7.8, 1.5 Hz, 1H), 2.50 (pseudo dd, J=9.1, 6.3 Hz, 6H).

Example 22: Preparation of N-(3-(4-(2-chlorophenyl)-5-(pyrimidin-4-yl)-4H-1,2,4-triazol-3-yl)bicyclo[1.1.1]pentan-1-yl)picolinamide

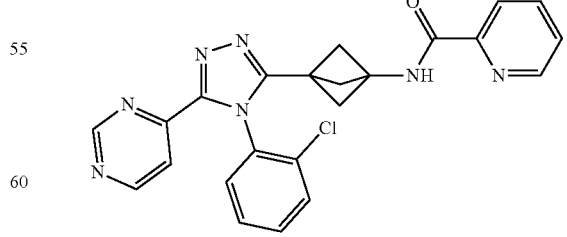

The title compound was prepared according to the general procedure F as a white solid (15.2 mg, 67% yield).

LC/MS (ESI) m/z for $C_{23}H_{18}ClN_7O$ 443/445 (calcd) 444/446 ([M+H]$^+$, found). 1H NMR (400 MHz, Chloroform-d) δ 8.83 (d, J=1.3 Hz, 1H), 8.80 (d, J=5.3 Hz, 1H), 8.51 (dq, J=4.9, 0.8 Hz, 1H), 8.41 (br s, 1H), 8.26 (dd, J=5.3, 1.3 Hz, 1H), 8.11 (d, J=7.8 Hz, 1H), 7.84 (td, J=7.7, 1.7 Hz, 1H), 7.56 (dd, J=8.0, 1.6 Hz, 1H), 7.52 (td, J=8.1, 7.6, 1.6 Hz, 1H), 7.48-7.40 (m, 2H), 7.38 (dd, J=7.8, 1.4 Hz, 1H), 2.48-2.37 (m, 6H).

Example 23: Preparation of N-(3-(4-(2-chlorophenyl)-5-(pyrimidin-4-yl)-4H-1,2,4-triazol-3-yl)bicyclo[1.1.1]pentan-1-yl)benzamide

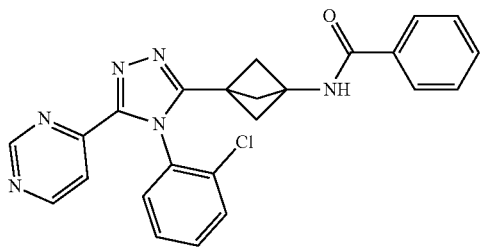

The title compound was prepared according to the general procedure F and obtained as a white solid (20.1 mg, 90% yield).

LC/MS (ESI) m/z for $C_{24}H_{19}ClN_6O$ 442/444 (calcd) 443/445 ([M+H]$^+$, found.

$^1$H NMR (400 MHz, Chloroform-d) δ 8.83 (d, J=1.3 Hz, 1H), 8.80 (d, J=5.3 Hz, 1H), 8.25 (dd, J=5.3, 1.4 Hz, 1H), 7.73-7.66 (m, 2H), 7.59-7.47 (m, 3H), 7.47-7.34 (m, 4H), 6.53 (br s, 1H), 2.47-2.35 (m, 6H).

Example 24: Preparation of amine building block C: (1S,3r)-3-(4-(2-fluorophenyl)-5-(thiazol-2-yl)-4H-1,2,4-triazol-3-yl)cyclobutan-1-amine dihydrochloride

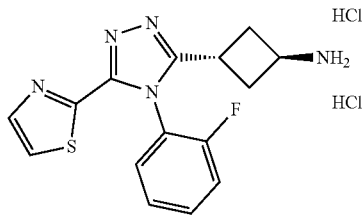

Step (a): N-(2-fluorophenyl)thiazole-2-carboxamide was prepared according to the general procedure A, method b) as an off-white solid (1.80 g, 79% yield).

LC/MS (ESI) m/z for $C_{10}H_7FN_2OS$ 222 (calcd) 223 ([M+H]$^+$, found).

Step (b): N-(2-fluorophenyl)thiazole-2-carbothioamide was prepared according to the general procedure B as a yellow solid (1.63 g, 86% yield).

LC/MS (ESI) m/z for $C_{10}H_7FN_2S_2$ 238 (calcd) 239 ([M+H]$^+$, found).

Step (c): methyl N-(2-fluorophenyl)thiazole-2-carbimidothioate was prepared according to the general procedure C as a yellow oil (1.65 g, 95% pure, 91% yield) solidifying upon standing.

LC/MS (ESI) m/z for $C_{11}H_9FN_2S_2$: 252 (calcd) 253 ([M+H]$^+$, found).

$^1$H NMR (400 MHz, Chloroform-d, all signals very broad) δ 7.91 (pseudo d, J=32.8 Hz, 1H), 7.47 (pseudo d, J=40.9 Hz, 1H), 7.17-7.06 (m, 3H), 6.95 (pseudo d, J=55.5 Hz, 1H), 2.52 (pseudo d, J=36.5 Hz, 3H).

Step (d): tert-butyl ((1S,3r)-3-(4-(2-fluorophenyl)-5-(thiazol-2-yl)-4H-1,2,4-triazol-3-yl)cyclobutyl)carbamate was prepared according to the general procedure D as a white solid (102 mg, 48% yield).

LC/MS (ESI) m/z for $C_{20}H_{22}FN_5O_2S$ 415 (calcd) 416 ([M+H]$^+$, found).

$^1$H NMR (400 MHz, Chloroform-d) δ 7.63 (d, J=3.2 Hz, 1H), 7.54 (tdd, J=7.5, 5.0, 2.0 Hz, 1H), 7.36 (d, J=3.2 Hz, 1H), 7.33-7.21 (m, 3H), 4.75 (br s, 1H), 4.40-4.11 (m, 1H), 3.32 (br s, 1H), 2.95-2.85 (m, 1H), 2.83 (br s, 1H), 2.28 (br s, 2H), 1.42 (s, 9H).

Step (e): the title salt was prepared following the general procedure E and obtained as an off-white solid (97 mg, 100% yield).

LC/MS (ESI) m/z for $C_{15}H_{14}FN_5S$ 315 (calcd) 316 ([M+H]$^+$, found).

Example 25: Preparation of N-((1S,3r)-3-(4-(2-fluorophenyl)-5-(thiazol-2-yl)-4H-1,2,4-triazol-3-yl)cyclobutyl)picolinamide

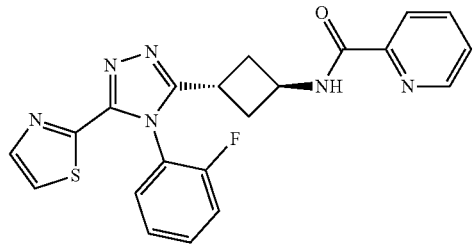

The title compound was prepared according to the general procedure F as a white solid (21.3 mg, 84% yield).

LC/MS (ESI) m/z for $C_{21}H_{17}FN_6OS$ 420 (calcd) 421 ([M+H]$^+$, found).

$^1$H NMR (400 MHz, Chloroform-d) δ 8.53 (dq, J=4.5, 0.9 Hz, 1H), 8.23 (br d, J=7.0 Hz, 1H), 8.17 (dt, J=7.8, 1.1 Hz, 1H), 7.84 (td, J=7.7, 1.7 Hz, 1H), 7.64 (d, J=3.2 Hz, 1H), 7.57-7.49 (m, 1H), 7.43 (ddd, J=7.8, 4.7, 1.3 Hz, 1H), 7.37 (d, J=3.2 Hz, 1H), 7.33-7.27 (m, 2H), 7.26-7.21 (m, 1H), 4.78 (h, J=7.0 Hz, 1H), 3.54-3.43 (m, 1H), 3.11-2.96 (m, 2H), 2.56-2.39 (m, 2H).

Example 26: Preparation of N-((1S,3r)-3-(4-(2-fluorophenyl)-5-(thiazol-2-yl)-4H-1,2,4-triazol-3-yl)cyclobutyl)-1,5-naphthyridine-4-carboxamide

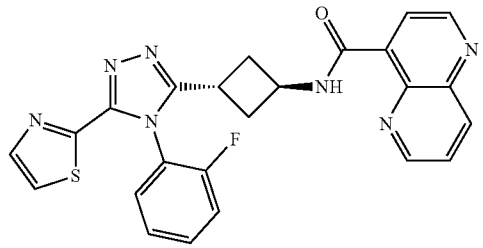

The title compound was prepared according to the general procedure F as a white solid (6.6 mg, 23% yield).

LC/MS (ESI) m/z for $C_{24}H_{18}FN_7OS$ 471 (calcd) 472 ([M+H]$^+$, found).

$^1$H NMR (400 MHz, Chloroform-d) δ 11.33 (d, J=6.0 Hz, 1H), 9.15 (d, J=4.5 Hz, 1H), 8.98 (dd, J=4.2, 1.8 Hz, 1H), 8.59-8.52 (m, 2H), 7.75 (dd, J=8.5, 4.2 Hz, 1H), 7.65 (d, J=3.2 Hz, 1H), 7.57-7.47 (m, 1H), 7.37 (d, J=3.2 Hz, 1H), 7.34-7.22 (m, 3H), 4.92-4.80 (m, 1H), 3.60-3.49 (m, 1H), 3.15-3.02 (m, 2H), 2.68-2.51 (m, 2H).

Example 27: Preparation of N-((1S,3r)-3-(4-(2-fluorophenyl)-5-(thiazol-2-yl)-4H-1,2,4-triazol-3-yl)cyclobutyl)benzamide

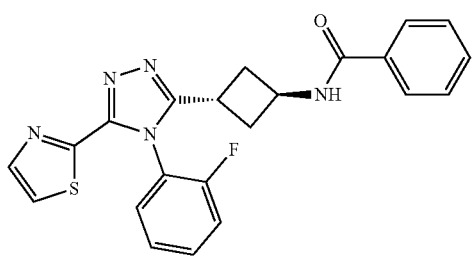

The title compound was prepared according to the general procedure F as a white solid (23.0 mg, 90% yield).

LC/MS (ESI) m/z for $C_{22}H_{18}FN_5OS$ 419 (calcd) 420 ([M+H]$^+$, found).

$^1$H NMR (400 MHz, Chloroform-d) δ 7.78-7.70 (m, 2H), 7.64 (d, J=3.2 Hz, 1H), 7.57-7.46 (m, 2H), 7.46-7.39 (m, 2H), 7.37 (d, J=3.2 Hz, 1H), 7.33-7.27 (m, 2H), 7.26-7.20 (m, 1H), 6.33 (br d, J=6.2 Hz, 1H), 4.73 (h, J=6.8 Hz, 1H), 3.46 (tt, J=10.0, 5.6 Hz, 1H), 3.09-2.95 (m, 2H), 2.52-2.36 (m, 2H).

Example 28: Preparation of 4-fluoro-N-((1S,3r)-3-(4-(2-fluorophenyl)-5-(thiazol-2-yl)-4H-1,2,4-triazol-3-yl)cyclobutyl)benzamide

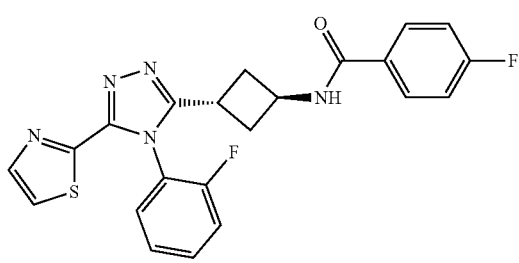

The title compound was prepared according to the general procedure F as a white solid (25.2 mg, 95% yield).

LC/MS (ESI) m/z for $C_{22}H_{17}F_2N_5OS$ 419 (calcd) 420 ([M+H]$^+$, found).

$^1$H NMR (400 MHz, Chloroform-d) δ 7.80-7.71 (m, 2H), 7.64 (d, J=3.2 Hz, 1H), 7.58-7.49 (m, 1H), 7.37 (d, J=3.2 Hz, 1H), 7.33-7.27 (m, 2H), 7.26-7.21 (m, 1H), 7.14-7.05 (m, 2H), 6.27 (br d, J=6.2 Hz, 1H), 4.73 (ht, J=7.3, 1.5 Hz, 1H), 3.45 (tt, J=9.9, 5.3 Hz, 1H), 3.08-2.94 (m, 2H), 2.52-2.36 (m, 2H).

Example 29: Preparation of 7-fluoro-N-((1S,3r)-3-(4-(2-fluorophenyl)-5-(thiazol-2-yl)-4H-1,2,4-triazol-3-yl)cyclobutyl)-1,5-naphthyridine-4-carboxamide

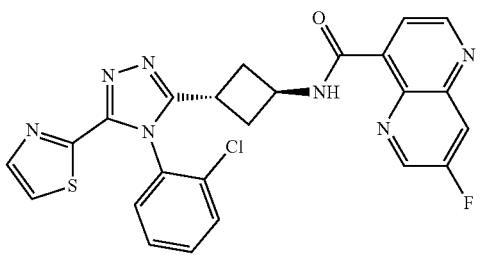

The title compound was prepared according to the general procedure F as a white solid (15.8 mg, 64% yield).

LC/MS (ESI) m/z for $C_{24}H_{17}F_2N_7OS$ 489 (calcd) 490 ([M+H]$^+$, found).

$^1$H NMR (400 MHz, Chloroform-d) δ 10.84 (br d, J=6.0 Hz, 1H), 9.16 (d, J=4.5 Hz, 1H), 8.91 (d, J=2.8 Hz, 1H), 8.52 (d, J=4.5 Hz, 1H), 8.20 (dd, J=8.6, 2.9 Hz, 1H), 7.65 (d, J=3.2 Hz, 1H), 7.58-7.48 (m, 1H), 7.37 (d, J=3.2 Hz, 1H), 7.34-7.28 (m, 2H), 7.25 (d, J=8.4 Hz, 1H), 4.87 (ht, J=7.1, 1.5 Hz, 1H), 3.58-3.47 (m, 1H), 3.15-3.01 (m, 2H), 2.66-2.50 (m, 2H).

Example 30: Preparation of 5-ethoxy-N-((1S,3r)-3-(4-(2-fluorophenyl)-5-(thiazol-2-yl)-4H-1,2,4-triazol-3-yl)cyclobutyl)picolinamide

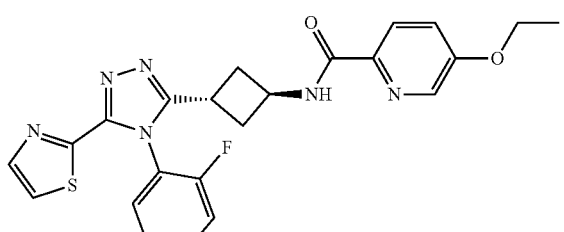

The title compound was prepared according to the general procedure F as a white solid (12 mg, 51% yield).

LC/MS (ESI) m/z for $C_{23}H_{21}FN_6O_2S$ 464 (calcd) 465 ([M+H]$^+$, found).

$^1$H NMR (400 MHz, Chloroform-d) δ 8.16 (d, J=2.7 Hz, 1H), 8.09 (d, J=8.7 Hz, 1H), 8.03 (br d, J=7.0 Hz, 1H), 7.64 (d, J=3.2 Hz, 1H), 7.57-7.49 (m, 1H), 7.36 (d, J=3.2 Hz, 1H), 7.32-7.20 (m, 4H), 4.80-4.68 (m, 1H), 4.12 (q, J=7.0 Hz, 2H), 3.54-3.41 (m, 1H), 3.09-2.95 (m, 2H), 2.54-2.37 (m, 2H), 1.46 (t, J=7.0 Hz, 3H).

Example 31: Preparation of amine building block D: (1r,3r)-3-(4-phenyl-5-(thiazol-2-yl)-4H-1,2,4-triazol-3-yl)cyclobutan-1-amine dihydrochloride

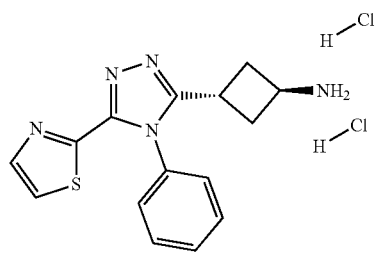

Step (a): N-phenylthiazole-2-carboxamide was prepared according to the general procedure A, method b) as a yellow oil (1.43 g, 69% yield) solidifying upon standing.

LC/MS (ESI) m/z for $C_{10}H_8N_2OS$ 204 (calcd) 205 ([M+H]$^+$, found).

Step (b): N-phenylthiazole-2-carbothioamide was prepared following the general procedure B as an orange oil (1.36 g, 89% yield).

LC/MS (ESI) m/z for $C_{10}H_8N_2S_2$ 220 (calcd) 221 ([M+H]$^+$, found).

Step (c): methyl N-phenylthiazole-2-carbimidothioate was prepared according to the general procedure C as a yellow oil (0.92 g, 85% pure, 54% yield, compound prone to hydrolysis).

LC/MS (ESI) m/z for $C_{11}H_{10}N_2S_2$ 234 (calcd) 235 ([M+H]$^+$, found).

$^1$H NMR (400 MHz, Chloroform-d, all signals very broad) δ 7.95 (s, ~0.5H), 7.84 (s, ~0.5H), 7.49 (s, ~0.5H), 7.37 (pseudo t, J=7.7 Hz, ~2.5H), 7.16 (pseudo t, J=7.4 Hz, 1H), 7.02 (s, 1H), 6.80 (s, 1H), 2.54 (s, ~1.5H), 2.39 (s, ~1.5H).

Step (d): tert-butyl ((1r,3r)-3-(4-phenyl-5-(thiazol-2-yl)-4H-1,2,4-triazol-3-yl)cyclobutyl)carbamate was prepared according to the general procedure D as a white solid (185 mg, 44% yield).

LC/MS (ESI) m/z for $C_{20}H_{23}N_5O_2S$ 397 (calcd) 398 ([M+H]$^+$ found).

$^1$H NMR (400 MHz, Chloroform-d) δ 7.66 (d, J=3.2 Hz, 1H), 7.57-7.46 (m, 3H), 7.34 (d, J=3.2 Hz, 1H), 7.24-7.18 (m, 2H), 4.73 (br s, 1H), 4.39-4.27 (m, 1H), 3.33 (br s, 1H), 2.86 (br dt, J=12.3, 7.2 Hz, 2H), 2.26 (br s, 2H). 1.42 (s, 9H).

Step (e): the title compound was prepared according to the general procedure E as a white solid (106 mg, 100% yield).

LC/MS (ESI) m/z for $C_{15}H_{15}N_5S$ 297 (calcd) 298 ([M+H]$^+$, found).

Example 32: Preparation of N-((1r,3r)-3-(4-phenyl-5-(thiazol-2-yl)-4H-1,2,4-triazol-3-yl)cyclobutyl)picolinamide

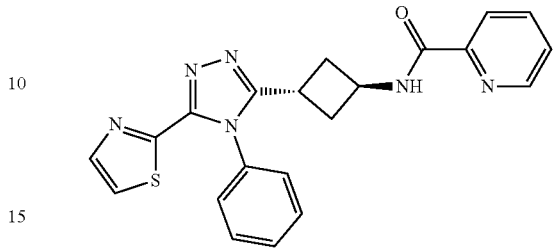

The title compound was prepared according to the general procedure F as a white solid (24.9 mg, 87% yield).

LC/MS (ESI) m/z for $C_{21}H_{18}N_6OS$ 402 (calcd) 403 ([M+H]$^+$, found).

$^1$H NMR (400 MHz, Chloroform-d) δ 8.53 (dq, J=4.8, 1.0 Hz, 1H), 8.22 (d, J=7.0 Hz, 1H), 8.16 (dd, J=7.8, 1.1 Hz, 1H), 7.84 (td, J=7.7, 1.7 Hz, 1H), 7.67 (d, J=3.2 Hz, 1H), 7.57-7.47 (m, 3H), 7.42 (ddd, J=7.7, 4.8, 1.2 Hz, 1H), 7.35 (d, J=3.2 Hz, 1H), 7.26-7.21 (m, 2H), 4.84-4.72 (m, 1H), 3.49 (ttd, J=9.6, 5.6, 1.2 Hz, 1H), 3.03 (dtd, J=13.5, 5.6, 2.5 Hz, 2H), 2.45 (ddd, J=12.8, 9.5, 6.2 Hz, 2H).

Example 33: Preparation of N-((1r,3r)-3-(4-phenyl-5-(thiazol-2-yl)-4H-1,2,4-triazol-3-yl)cyclobutyl)-1,5-naphthyridine-4-carboxamide

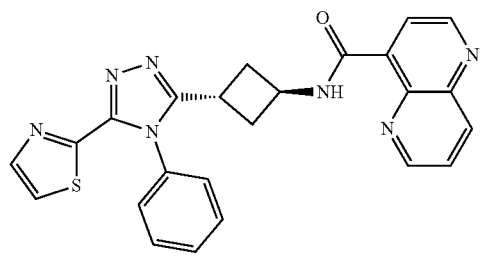

The title compound was prepared according to the general procedure F as a pale yellow solid (13.7 mg, 42% yield).

LC/MS (ESI) m/z for $C_{24}H_{19}N_7OS$ 453 (calcd) 454 ([M+H]$^+$, found).

$^1$H NMR (400 MHz, Chloroform-d) δ 11.31 (d, J=6.0 Hz, 1H), 9.15 (d, J=4.5 Hz, 1H), 8.97 (dd, J=4.2, 1.8 Hz, 1H), 8.59-8.52 (m, 2H), 7.74 (dd, J=8.6, 4.2 Hz, 1H), 7.67 (d, J=3.2 Hz, 1H), 7.56-7.46 (m, 3H), 7.36 (d, J=3.2 Hz, 1H), 7.30-7.22 (m, 2H), 4.92-4.80 (m, 1H), 3.55 (ttd, J=9.5, 5.5, 1.3 Hz, 1H), 3.08 (pseudo ddd, J=13.4, 8.2, 5.4 Hz, 2H), 2.56 (dtd, J=12.8, 6.3, 2.6 Hz, 2H).

Example 34: Preparation of N-((1r,3r)-3-(4-phenyl-5-(thiazol-2-yl)-4H-1,2,4-triazol-3-yl)cyclobutyl)benzamide

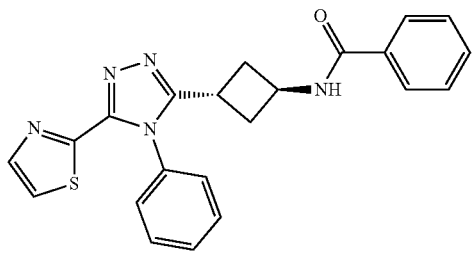

The title compound was prepared according to the general procedure F as a white solid (25.6 mg, 90% yield).

LC/MS (ESI) m/z for $C_{22}H_{19}N_5OS$ 401 (calcd) 402 ([M+H]$^+$, found).

$^1$H NMR (400 MHz, Chloroform-d) δ 7.77-7.70 (m, 2H), 7.67 (d, J=3.2 Hz, 1H), 7.57-7.46 (m, 4H), 7.46-7.38 (m, 2H), 7.35 (d, J=3.2 Hz, 1H), 7.26-7.20 (m, 2H), 6.30 (br d, J=6.2 Hz, 1H), 4.74 (ht, J=7.0, 1.5 Hz, 1H), 3.52-3.39 (m, 1H), 3.07-2.97 (m, 2H), 2.46-2.35 (m, 2H).

Example 35: Preparation of 4-fluoro-N-((1r,3r)-3-(4-phenyl-5-(thiazol-2-yl)-4H-1,2,4-triazol-3-yl)cyclobutyl)benzamide

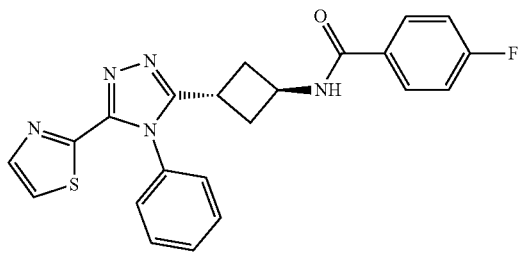

The title compound was prepared according to the general procedure F a white solid (27.1 mg, 92% yield).

LC/MS (ESI) m/z for $C_{22}H_{18}FN_5OS$ 419 (calcd) 420 ([M+H]$^+$, found).

$^1$H NMR (400 MHz, Chloroform-d) δ 7.79-7.71 (m, 2H), 7.66 (d, J=3.2 Hz, 1H), 7.57-7.47 (m, 3H), 7.35 (d, J=3.2 Hz, 1H), 7.26-7.20 (m, 2H), 7.14-7.04 (m, 2H), 6.28 (br d, J=6.1 Hz, 1H), 4.79-4.67 (m, 1H), 3.50-3.40 (m, 1H), 3.07-2.96 (m, 2H), 2.47-2.35 (m, 2H).

Example 36: Preparation of amine building block E: (1r,3r)-3-(4-phenyl-5-(thiazol-2-yl)-4H-1,2,4-triazol-3-yl)cyclobutan-1-amine dihydrochloride

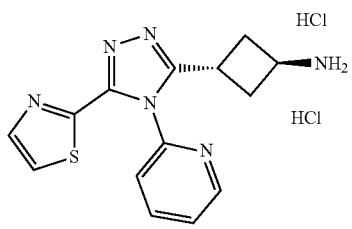

Step (a): N-(pyridin-2-yl)thiazole-2-carboxamide was prepared according to the general procedure A, method a) as a white solid (373 mg, 60% yield).

LC/MS (ESI) m/z for $C_9H_7N_3OS$ 205 (calcd) 206 ([M+H]$^+$, found).

$^1$H NMR (400 MHz, Chloroform-d) δ 9.68 (br s, 1H), 8.37 (ddd, J=4.8, 2.0, 0.9 Hz, 1H), 8.33 (d, J=8.3 Hz, 1H), 7.96 (d, J=3.1 Hz, 1H), 7.77 (td, J=8.4, 7.4, 2.0 Hz, 1H), 7.66 (d, J=3.0 Hz, 1H), 7.11 (ddd, J=7.4, 4.8, 1.0 Hz, 1H).

Step (b): N-(pyridin-2-yl)thiazole-2-carbothioamide was prepared according to the general procedure B as an orange semisolid (80 mg, 88% pure, 18% yield).

LC/MS (ESI) m/z for $C_9H_7N_3S_2$ 221 (calcd) 222 ([M+H]$^+$, found).

Step (c): methyl N-(pyridin-2-yl)thiazole-2-carbimidothioate was synthesised according to the general procedure C as a yellow oil (45 mg, 62% yield).

LC/MS (ESI) m/z for $C_{10}H_9N_3S_2$ 235 (calcd) 236 ([M+H]$^+$, found).

$^1$H NMR (400 MHz, Chloroform-d) δ 8.46 (d, J=5.1 Hz, 1H), 7.88 (s, 1H), 7.69 (td, J=7.8, 1.9 Hz, 1H), 7.45 (s, 1H), 7.07 (dd, J=7.3, 4.9 Hz, 1H), 6.92 (br s, 1H), 2.49 (br s, 3H).

Step (d): tert-butyl a 1r,3r)-3-(4-(pyridin-2-yl)-5-(thiazol-2-yl)-4H-1,2,4-triazol-3-yl)cyclobutyl)carbamate was prepared according to the general procedure D as a white solid (75 mg, 97% yield).

LC/MS (ESI) m/z for $C_{19}H_{22}N_6O_2S$ 398 (calcd) 399 ([M+H]$^+$ found).

$^1$H NMR (400 MHz, Chloroform-d) δ 8.61 (dd, J=4.8, 1.8 Hz, 1H), 7.89 (td, J=7.8, 2.0 Hz, 1H), 7.61 (d, J=3.3 Hz, 1H), 7.47 (dd, J=7.5, 4.8 Hz, 1H), 7.35 (d, J=3.2 Hz, 1H), 7.32 (d, J=7.9 Hz, 1H), 4.73 (br s, 1H), 4.29 (pseudo h, J=7.0 Hz, 1H), 3.47 (br s, 1H), 2.85 (tt, J=8.0, 5.3 Hz, 2H), 2.24 (br s, 2H), 1.42 (s, 9H).

Step (e): the title compound was obtained according to the general procedure E as a white solid (69 mg, 100% yield).

LC/MS (ESI) m/z for $C_{15}H_{15}N_5S$ 298 (calcd) 299 ([M+H]$^+$, found).

$^1$H NMR (400 MHz, DMSO-d6) δ 8.62 (dd, J=4.6, 1.5 Hz, 1H), 8.24 (br s, ~2H), 8.08 (td, J=7.7, 1.9 Hz, 1H), 7.87 (s, 1H), 7.75 (d, J=3.2 Hz, 1H), 7.67 (d, J=7.9 Hz, 1H), 7.64 (dd, J=7.7, 5.0 Hz, 1H), 3.91-3.75 (m, 1H), 3.58 (tt, J=10.0, 5.6 Hz, 1H), 2.68 (ddd, J=13.4, 8.0, 5.4 Hz, 2H), 2.33 (ddd, J=12.8, 9.5, 5.7 Hz, 2H).

Example 37: Preparation of N-((1r,3r)-3-(4-(pyridin-2-yl)-5-(thiazol-2-yl)-4H-1,2,4-triazol-3-yl)cyclobutyl)-1,5-naphthyridine-4-carboxamide

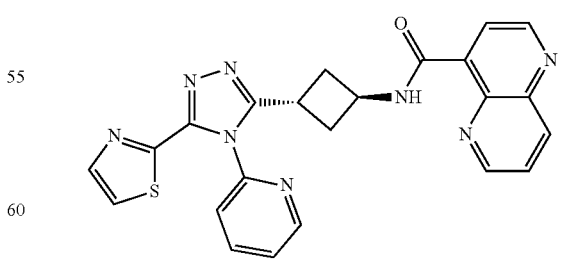

The title compound was prepared according to the general procedure F as a white solid (9.9 mg, 43% yield).

LC/MS (ESI) m/z for $C_{23}H_{18}N_8OS$ 454 (calcd) 455 ([M+H]$^+$ found).

¹H NMR (400 MHz, Chloroform-d) δ 11.30 (br d, J=6.0 Hz, 1H), 9.14 (d, J=4.5 Hz, 1H), 8.99 (dd, J=4.3, 1.8 Hz, 1H), 8.61 (ddd, J=4.8, 1.9, 0.8 Hz, 1H), 8.59-8.51 (m, 2H), 7.88 (td, J=7.8, 1.9 Hz, 1H), 7.74 (dd, J=8.6, 4.3 Hz, 1H), 7.63 (d, J=3.2 Hz, 1H), 7.46 (ddd, J=7.6, 4.9, 1.0 Hz, 11-1), 7.39-7.33 (m, 2H), 4.88-4.74 (m, 1H), 3.78-3.66 (m, 1H), 3.06 (tt, J=8.2, 5.4 Hz, 2H), 2.55 (ddd, J=12.8, 9.5, 6.3 Hz, 2H).

Example 38: Preparation of N-((1r,3r)-3-(4-(pyridin-2-yl)-5-(thiazol-2-yl)-4H-1,2,4-triazol-3-yl)cyclobutyl)quinoline-8-carboxamide

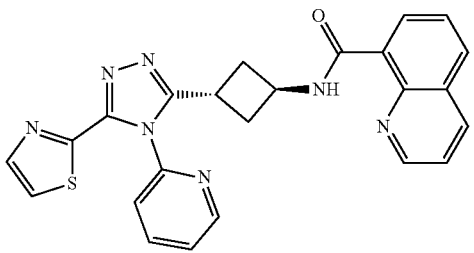

The title compound was prepared according to the general procedure F as a white solid (21.6 mg, 93% yield).

LC/MS (ESI) m/z for $C_{24}H_{19}N_7OS$ 453 (calcd) 454 ([M+H]$^+$ found).

¹H NMR (400 MHz, Chloroform-d) δ 11.55 (br d, J=5.7 Hz, 1H), 8.92 (dd, J=4.3, 1.9 Hz, 1H), 8.82 (dd, J=7.4, 1.6 Hz, 1H), 8.60 (dq, J=4.9, 0.8 Hz, 1H), 8.28 (dd, J=8.3, 1.8 Hz, 1H), 7.96 (dd, J=8.1, 1.6 Hz, 1H), 7.87 (td, J=7.8, 1.9 Hz, 1H), 7.66 (t, J=7.8 Hz, 1H), 7.62 (d, J=3.2 Hz, 1H), 7.50 (dd, J=8.3, 4.3 Hz, 1H), 7.45 (ddd, J=7.6, 5.0, 1.0 Hz, 1H), 7.37 (s, 1H), 7.36-7.32 (m, 1H), 4.83-4.72 (m, 1H), 3.80-3.68 (m, 1H), 3.11-3.00 (m, 2H), 2.59-2.47 (m, 2H).

Example 39: Preparation of 7-fluoro-N-((1r,3r)-3-(4-(pyridin-2-yl)-5-(thiazol-2-yl)-4H-1,2,4-triazol-3-yl)cyclobutyl)-1,5-naphthyridine-4-carboxamide

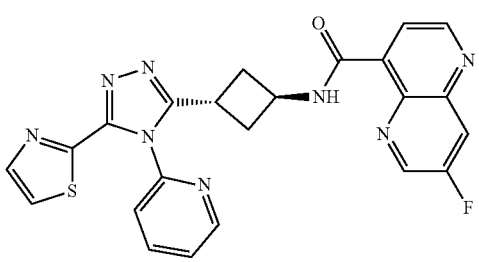

The title compound was prepared following the general procedure F as a white solid (22.3 mg, 92% yield).

LC/MS (ESI) m/z for $C_{23}H_{17}FN_8OS$ 472 (calcd) 473 ([M+H]$^+$ found).

¹H NMR (400 MHz, Chloroform-d) δ 10.82 (br d, J=6.0 Hz, 1H), 9.15 (d, J=4.4 Hz, 1H), 8.92 (d, J=2.8 Hz, 1H), 8.62 (dq, J=4.8, 1.0 Hz, 1H), 8.51 (d, J=4.4 Hz, 1H), 8.20 (dd, J=8.7, 2.9 Hz, 1H), 7.89 (td, J=7.8, 1.9 Hz, 1H), 7.63 (d, J=3.2 Hz, 1H), 7.46 (ddd, J=7.6, 4.9, 1.0 Hz, 1H), 7.40-7.33 (m, 2H), 4.82 (ht, J=7.1, 1.6 Hz, 1H), 3.75-3.64 (m, 1H), 3.12-3.01 (m, 2H), 2.59-2.48 (m, 2H).

Example 40: Preparation of amine building block E: (1S,3r)-3-(4-(2-chlorophenyl)-5-(thiazol-2-yl)-4H-1,2,4-triazol-3-yl)cyclobutan-1-amine

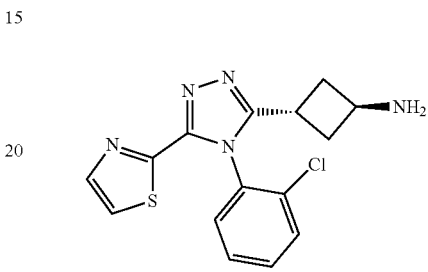

Step (a): N-(2-chlorophenyl)thiazole-2-carboxamide was prepared according to the general procedure A, method b) as a yellow solid (1.49 g, 95% pure, 80% yield).

LC/MS (ESI) m/z for $C_{10}H_7ClN_2OS$ 238/240 (calcd) 239/241 ([M+H]$^+$, found).

Step (b): N-(2-chlorophenyl)thiazole-2-carbothioamide was prepared according to the general procedure B as a yellow solid (1.10 g, 73% yield).

LC/MS (ESI) m/z for $C_{10}H_7ClN_2S_2$ 254/256 (calcd) 255/257 ([M+H]$^+$, found).

¹H NMR (400 MHz, Chloroform-d) δ 11.31 (br s, 1H), 8.97 (dd, J=8.2, 1.5 Hz, 1H), 7.97 (d, J=3.2 Hz, 1H), 7.62 (d, J=3.2 Hz, 1H), 7.51 (dd, J=7.9, 1.5 Hz, 1H), 7.38 (ddd, J=8.6, 7.6, 1.5 Hz, 1H), 7.23 (ddd, J=7.8, 7.3, 1.6 Hz, 1H).

Step (c): methyl N-(2-chlorophenyl)thiazole-2-carbimidothioate was synthesised according to the general procedure C as a yellow oil (1.12 g, 96% yield).

LC/MS (ESI) m/z for $C_{11}H_9ClN_2S_2$ 268/270 (calcd) 269/271 ([M+1.1]$^+$, found).

¹H NMR (400 MHz, Chloroform-d) δ 7.90 (br s, 1H), 7.46 (br s, 1H), 7.43 (dd, J=8.0, 1.4 Hz, 1H), 7.27 (td, J=7.7, 1.4 Hz, 1H), 7.10 (td, J=7.7, 1.6 Hz, 1H), 6.87 (very br s, 1H), 2.54 (very br s, 3H).

Step (d): the title compound was prepared according to the general procedure D, whereby the reaction mixture was heated in a microwave oven at 180° C. during 2-3 days recovering directly the deprotected amine as a colourless semisolid (178 mg, 21% yield) from a complex mixture.

LC/MS (ESI) m/z for $C_{15}H_{14}ClN_5S$ 331/333 (calcd) 332/334 ([M+II]$^+$, found).

¹H NMR (400 MHz, Chloroform-d) δ 7.62 (d, J=3.2 Hz, 1H), 7.55 (dd, J=8.0, 1.7 Hz, 1H), 7.50 (td, J=7.7, 1.7 Hz, 1H), 7.43 (td, J=7.5, 1.7 Hz, 1H), 7.34 (d, J=3.2 Hz, 1H), 7.31 (dd, J=7.7, 1.7 Hz, 1H), 3.91 (p, J=6.2 Hz, 1H), 3.26 (apparent tt, J=9.8, 5.2 Hz, 1H), 2.87-2.71 (m, 2H), 1.97 (apparent dddd, J=21.9, 12.8, 9.2, 5.9 Hz, 2H), 1.56 (br s, 2H, $NH_2+H_2O$).

Example 41: Preparation of N-((1S,3r)-3-(4-(2-chlorophenyl)-5-(thiazol-2-yl)-4H-1,2,4-triazol-3-yl)cyclobutyl)-1,5-naphthyridine-4-carboxamide

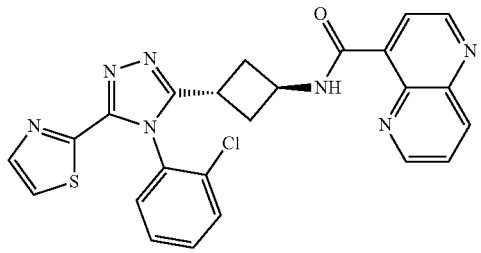

The title compound was prepared according to the general procedure F as a white solid (13.4 mg, 57% yield).

LC/MS (ESI) m/z for $C_{24}H_{18}ClN_7OS$ 487/489 (calcd) 488/490 ([M+H]$^+$, found).

$^1$H NMR (400 MHz, Chloroform-d) δ 11.32 (d, J=5.6 Hz, 1H), 9.15 (d, J=4.4 Hz, 1H), 8.98 (dd, J=4.2, 1.7 Hz, 1H), 8.57 (dd, J=8.5, 1.7 Hz, 1H), 8.55 (d, J=4.6 Hz, 1H), 7.75 (dd, J=8.5, 4.2 Hz, 1H), 7.63 (d, J=3.2 Hz, 1H), 7.55 (dd, J=8.0, 1.5 Hz, 1H), 7.49 (td, J=7.7, 1.7 Hz, 1H), 7.43 (td, J=7.6, 1.6 Hz, 1H), 7.39-7.32 (m, 2H), 4.85 (apparent h, J=7.1 Hz, 1H), 3.49 (tt, J=9.8, 5.5 Hz, 1H), 3.17-3.02 (m, 2H), 2.63-2.50 (m, 2H).

Example 42: Preparation of N-((1S,3r)-3-(4-(2-chlorophenyl)-5-(thiazol-2-yl)-4H-1,2,4-triazol-3-yl)cyclobutyl)picolinamide

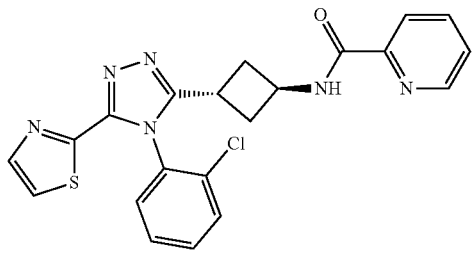

The title compound was prepared according to the general procedure F as an off-white solid (17.5 mg, 79% yield).

LC/MS (ESI) m/z for $C_{21}H_{17}ClN_6OS$ 436/438 (calcd) 437/439 ([M+H]$^+$, found).

$^1$H NMR (400 MHz, Chloroform-d) δ 8.53 (dq, J=4.8, 1.1 Hz, 1H), 8.22 (br d, J=7.0 Hz, 1H), 8.16 (dt, J=7.8, 1.1 Hz, 1H), 7.84 (td, J=7.7, 1.7 Hz, 1H), 7.63 (d, J=3.2 Hz, 1H), 7.56 (dd, J=8.0, 1.6 Hz, 1H), 7.50 (td, J=7.7, 1.7 Hz, 1H), 7.47-7.39 (m, 2H), 7.38-7.30 (m, 2H), 4.77 (hd, J=7.1, 1.0 Hz, 1H), 3.43 (ttd, J=9.6, 5.8, 1.2 Hz, 1H), 3.12-2.99 (m, 2H), 2.52-2.38 (m, 2H).

Example 43: Preparation of N-((1S,3r)-3-(4-(2-chlorophenyl)-5-(thiazol-2-yl)-4H-1,2,4-triazol-3-yl)cyclobutyl)benzamide

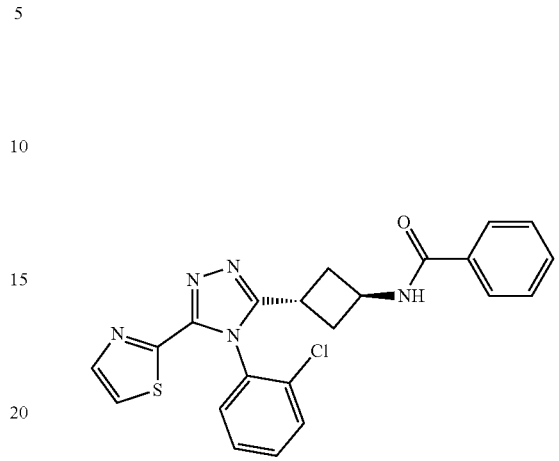

The title compound was prepared following the general procedure F as a white solid (17.9 mg, 81% yield).

LC/MS (ESI) m/z for $C_{22}H_{18}ClN_5OS$ 435/437 (calcd) 436/438 ([M+H]$^+$, found).

$^1$H NMR (400 MHz, Chloroform-d) δ 7.77-7.70 (m, 2H), 7.62 (d, J=3.2 Hz, 1H), 7.56 (dd, J=8.0, 1.6 Hz, 1H), 7.53-7.46 (m, 2H), 7.46-7.38 (m, 3H), 7.38-7.30 (m, 2H), 6.31 (br d, J=6.2 Hz, 1H), 4.73 (pseudo h, J=6.8 Hz, 1H), 3.46-3.34 (m, 1H), 3.12-2.96 (m, 2H), 2.47-2.34 (m, 2H).

Example 44: Preparation of N-((1S,3r)-3-(4-(2-chlorophenyl)-5-(thiazol-2-yl)-4H-1,2,4-triazol-3-yl)cyclobutyl)-4-fluorobenzamide

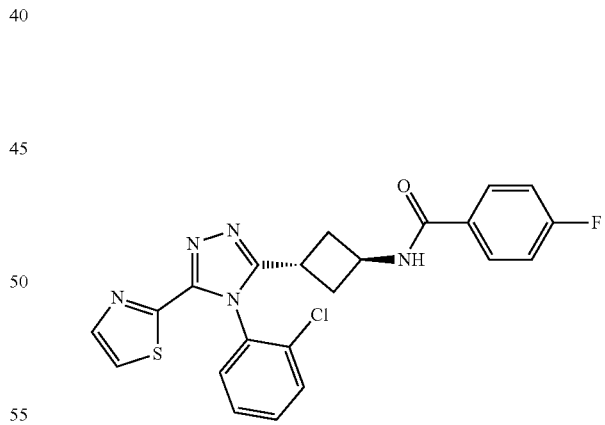

The title compound was prepared according to the general procedure F as a white solid (18.9 mg, 82% yield).

LC/MS (ESI) m/z for $C_{22}H_{17}ClFN_5OS$ 453/455 (calcd) 454/456 ([M+H]$^+$, found).

$^1$H NMR (400 MHz, Chloroform-d) δ 7.79-7.71 (m, 2H), 7.62 (d, J=3.2 Hz, 1H), 7.56 (dd, J=8.0, 1.6 Hz, 1H), 7.50 (td, J=7.6, 1.7 Hz, 1H), 7.44 (td, J=7.5, 1.6 Hz, 1H), 7.38-7.30 (m, 2H), 7.14-7.05 (m, 2H), 6.27 (d, J=6.1 Hz, 1H), 4.78-4.66 (m, 1H), 3.44-3.33 (m, 1H), 3.11-2.95 (m, 2H), 2.47-2.34 (m, 2H).

Example 45: Preparation of amine building block F: 3-(4-(2-fluorophenyl)-5-(thiazol-2-yl)-4H-1,2,4-triazol-3-yl)bicyclo[1.1.1]pentan-1-amine dihydrochloride

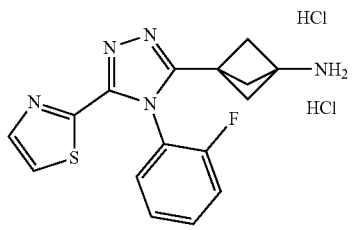

Step (a): tert-butyl (3-(4-(2-fluorophenyl)-5-(thiazol-2-yl)-4H-1,2,4-triazol-3-yl)bicyclo[1.1.1]pentan-1-yl)carbamate was prepared from 121 mg (0.50 mmol) of tert-butyl (3-(hydrazinecarbonyl)bicyclo[1.1.1]pentan-1-yl)carbamate (Example 2) and 133 mg (0.50 mmol, 95% pure) of methyl N-(2-fluorophenyl)thiazole-2-carbimidothioate (Example 24c) according to the general procedure D as an off-white glass (131 mg, 91% pure, 56% yield).

LC/MS (ESI) m/z for $C_{21}H_{22}FN_5O_2S$ 427 (calcd) 428 ([M+H]$^+$ found).

$^1$H NMR (400 MHz, Chloroform-d) δ 7.63 (d, J=3.3 Hz, 1H), 7.60-7.50 (m, 1H), 7.35 (d, J=3.2 Hz, 1H), 7.33-7.28 (m, 2H), 7.28-7.22 (m, 1H, coinciding with chloroform signal), 4.91 (br s, 1H), 2.23 (distorted s, 6H), 1.40 (s, 9H).

Step (b): the title compound was obtained according to the general procedure E as a white solid (121 mg, 99% yield).

LC/MS (ESI) m/z for $C_{16}H_{14}FN_5S$ 327 (calcd) 328 ([M+H]$^+$, found).

Example 46: Preparation of N-(3-(4-(2-fluorophenyl)-5-(thiazol-2-yl)-4H-1,2,4-triazol-3-yl)bicyclo[1.1.1]pentan-1-yl)-1,5-naphthyridine-4-carboxamide

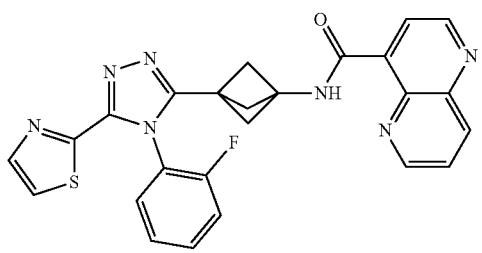

The title compound was prepared according to the general procedure F as a white solid (12.5 mg, 51% yield).

LC/MS (ESI) m/z for $C_{25}H_{18}FN_7OS$ 483 (calcd) 484 ([M+H]$^+$, found).

$^1$H NMR (400 MHz, Chloroform-d) δ 11.48 (s, 1H), 9.14 (d, J=4.5 Hz, 1H), 9.00 (dd, J=4.3, 1.7 Hz, 1H), 8.56 (dd, J=8.6, 1.8 Hz, 1H), 8.50 (d, J=4.4 Hz, 1H), 7.75 (dd, J=8.6, 4.3 Hz, 1H), 7.65 (d, J=3.2 Hz, 1H), 7.63-7.54 (m, 1H), 7.41-7.27 (m, 4H), 2.57-2.47 (m, 6H).

Example 47: Preparation of amine building block G: (1S,3r)-3-(4-(2-fluorophenyl)-5-(5-(methylsulfonyl)pyridin-2-yl)-4H-1,2,4-triazol-3-yl)cyclobutan-1-amine dihydro chloride

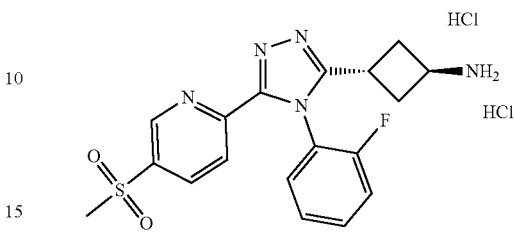

Step (a): N-(2-fluorophenyl)-5-(methylsulfonyl)picolinamide was prepared following the general procedure A, method b) as a white solid (347 mg, 55% yield).

LC/MS (ESI) m/z for $C_{13}H_{11}FN_2O_3S$ 294 (calcd) 295 ([M+H]$^+$, found).

Step (b): N-(2-fluorophenyl)-5-(methylsulfonyl)pyridine-2-carbothioamide was prepared according to the general procedure B as an orange solid (270 mg, 78% yield).

LC/MS (ESI) m/z for $C_{13}H_{11}FN_2O_2S_2$ 310 (calcd) 311 ([M+H]$^+$, found).

$^1$H NMR (400 MHz, Chloroform-d) δ 12.10 (br s, 1H), 9.13 (dd, J=2.2, 0.8 Hz, 1H), 9.02 (td, J=8.1, 2.1 Hz, 1H), 8.97 (dd, J=8.4, 0.9 Hz, 1H), 8.41 (dd, J=8.4, 2.3 Hz, 1H), 7.34-7.20 (m, 3H), 3.16 (s, 3H).

Step (c): methyl N-(2-fluorophenyl)-5-(methylsulfonyl)pyridine-2-carbimidothioate was prepared according to the general procedure C as a yellow glassy solid (282 mg, 98% yield).

LC/MS (ESI) m/z for $C_{14}H_{13}FN_2O_2S_2$ 324 (calcd) 325 ([M+H]$^+$, found).

$^1$H NMR (400 MHz, Chloroform-d) δ 9.15 (br s, 1H), 8.17 (very br s, 2H), 7.04 (very br s, 4H), 3.12 (s, 3H), 2.44 (very br d, 3H).

Step (d): tert-butyl ((1S,3r)-3-(4-(2-fluorophenyl)-5-(5-(methylsulfonyl)pyridin-2-yl)-4H-1,2,4-triazol-3-yl)cyclobutyl)carbamate was prepared according to the general procedure D as a white solid (343 mg, 81% yield).

LC/MS (ESI) m/z for $C_{23}H_{26}FN_5O_4S$ 487 (calcd) 488 ([M+H]$^+$, found).

$^1$H NMR (400 MHz, Chloroform-d) δ 8.71 (d, J=2.2 Hz, 1H), 8.53 (dd, J=8.4, 0.8 Hz, 1H), 8.27 (dd, J=8.4, 2.4 Hz, 1H), 7.56-7.47 (m, 1H), 7.29-7.14 (m, 3H), 4.73 (br s, 1H), 4.35 (h, J=7.1 Hz, 1H), 3.38-3.26 (m, 1H), 3.07 (s, 3H), 2.97-2.87 (m, 1H), 2.83 (br s, 1H), 2.29 (apparent br d, J=30.5 Hz, 2H), 1.42 (s, 9H).

Step (e): the crude title compound was obtained according to the general procedure E as a white solid (319 mg, 100% yield).

LC/MS (ESI) m/z for $C_{18}H_{18}FN_5O_2S$ 387 (calcd) 388 ([M+H]$^+$, found).

$^1$H NMR (400 MHz, DMSO-d6) δ 8.71 (s, 1H), 8.44 (d, J=2.3 Hz, 2H), 8.32 (br s, 3H, NH2+HCl), 7.68-7.61 (m, 1H), 7.59 (td, J=7.8, 1.5 Hz, 1H), 7.49 (dd, J=9.9, 8.5 Hz, 1H), 7.38 (t, J=7.6 Hz, 1H), 3.87 (apparent h, J=6.3 Hz, 1H), 3.56 (apparent tt, J=9.9, 5.8 Hz, 1H), 3.33 (s, 3H), 2.86-2.75 (m, 1H), 2.66-2.55 (m, 1H), 2.45-2.28 (m, 2H).

Example 48: Preparation of N-((1S,3r)-3-(4-(2-fluorophenyl)-5-(5-(methylsulfonyepyridin-2-yl)-4H-1,2,4-triazol-3-yl)cyclobutyl)quinoline-8-carboxamide

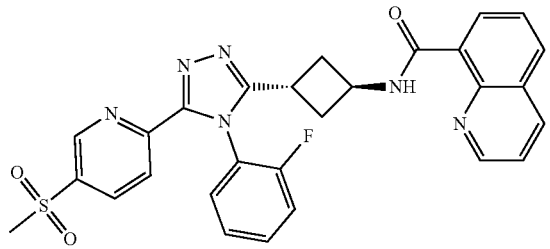

The title compound was prepared according to the general procedure F as a white solid (24.9 mg, 91% yield).

LC/MS (ESI) m/z for $C_{28}H_{23}FN_6O_3S$ 542 (calcd) 543 ([M+H]$^+$ found).

$^1$H NMR (400 MHz, Chloroform-d) δ 11.56 (d, J=5.8 Hz, 1H), 8.91 (dd, J=4.3, 1.8 Hz, 1H), 8.83 (dd, J=7.4, 1.6 Hz, 1H), 8.73 (d, J=2.3 Hz, 1H), 8.56 (d, J=8.4 Hz, 1H), 8.28 (dt, J=8.4, 2.5 Hz, 2H), 7.96 (dd, J=8.1, 1.6 Hz, 1H), 7.67 (t, J=7.7 Hz, 1H), 7.49 (dt, J=8.3, 5.0 Hz, 2H), 7.26-7.18 (m, 3H), 4.85 (apparent dq, J=13.4, 6.8 Hz, 1H), 3.57 (apparent tt, J=10.1, 5.8 Hz, 1H), 3.16-3.01 (m, 2H), 3.08 (s, 3H), 2.67-2.50 (m, 2H).

Example 49: Preparation of N-((1S,3r)-3-(4-(2-fluorophenyl)-5-(5-(methylsulfonyl)pyridin-2-yl)-4H-1,2,4-triazol-3-yl)cyclobutyl)-1,5-naphthyridine-4-carboxamide

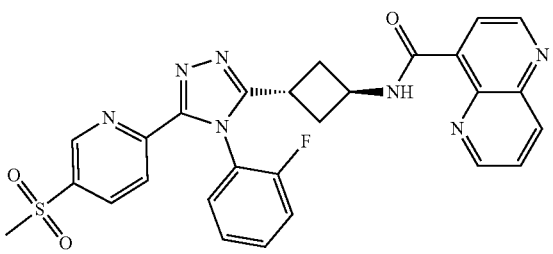

The title compound was prepared according to the general procedure F as a white solid (14.8 mg, 53% yield).

LC/MS (ESI) m/z for $C_{27}H_{22}FN_7O_3S$ 543 (calcd) 544 ([M+H]$^+$ found).

$^1$H NMR (400 MHz, Chloroform-d) δ 11.31 (br d, J=6.1 Hz, 1H), 9.15 (d, J=4.5 Hz, 1H), 8.97 (dd, J=4.2, 1.8 Hz, 1H), 8.73 (dd, J=2.5, 0.8 Hz, 1H), 8.57 (pseudo d, J=1.6 Hz, 1H), 8.55 (pseudo d, J=4.2 Hz, 2H), 8.29 (dd, J=8.3, 2.3 Hz, 1H), 7.74 (dd, J=8.5, 4.2 Hz, 1H), 7.55-7.46 (m, 1H), 7.30-7.19 (m, 3H), 4.89 (h, J=7.1 Hz, 1H), 3.55 (tt, J=10.0, 5.5 Hz, 1H), 3.17-3.02 (m, 2H), 3.08 (s, 3H), 2.69-2.52 (m, 2H).

Example 50: Preparation of 7-fluoro-N-((1S,3r)-3-(4-(2-fluorophenyl)-5-(5-(methylsulfonyl)pyridin-2-yl)-4H-1,2,4-triazol-3-yl)cyclobutyl)-1,5-naphthyridine-4-carboxamide

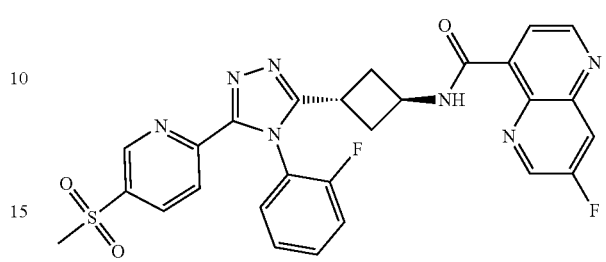

The title compound was prepared according to the general procedure F as a white solid (13.8 mg, 81% yield).

LC/MS (ESI) m/z for $C_{27}H_{21}F_2N_7O_3S$ 561 (calcd) 562 ([M+H]$^+$ found).

$^1$H NMR (400 MHz, Chloroform-d) δ 10.83 (d, J=6.1 Hz, 1H), 9.16 (d, J=4.5 Hz, 1H), 8.91 (d, J=2.8 Hz, 1H), 8.73 (dd, J=2.3, 0.8 Hz, 1H), 8.56 (dd, J=8.4, 0.8 Hz, 1H), 8.52 (d, J=4.4 Hz, 1H), 8.29 (dd, J=8.4, 2.3 Hz, 1H), 8.20 (dd, J=8.7, 2.9 Hz, 1H), 7.56-7.46 (m, 1H), 7.30-7.19 (m, 3H), 4.89 (apparent h, J=7.1 Hz, 1H), 3.53 (tt, J=9.5, 5.1 Hz, 1H), 3.17-3.01 (m, 2H), 3.08 (s, 3H), 2.67-2.50 (m, 2H).

Example 51: Preparation of amine building block H: (1S,3r)-3-(5-(5-ethoxypyridin-2-yl)-4-(2-fluorophenyl)-4H-1,2,4-triazol-3-yl)cyclobutan-1-amine dihydrochloride

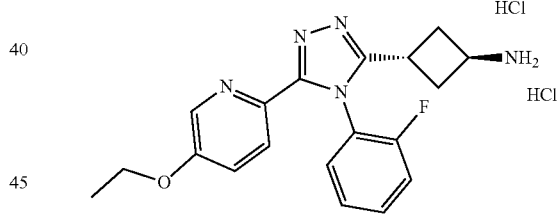

Step (a): 5-ethoxy-N-(2-fluorophenyl)picolinamide was prepared according to the general procedure A, method a) as an off-white solid (747 mg, 80% yield).

LC/MS (ESI) m/z for $C_{14}H_{13}FN_2O_2$ 260 (calcd) 261 ([M+H]$^+$, found).

$^1$H NMR (400 MHz, Chloroform-d) δ 10.15 (s, 1H), 8.57 (td, J=8.1, 1.6 Hz, 1H), 8.28 (d, J=2.8 Hz, 1H), 8.22 (d, J=8.7 Hz, 1H), 7.32 (dd, J=8.7, 2.8 Hz, 1H), 7.23-7.08 (m, 2H), 7.10-7.03 (m, 1H), 4.17 (q, J=7.0 Hz, 2H), 1.49 (t, J=7.0 Hz, 3H).

Step (b): 5-ethoxy-N-(2-fluorophenyl)pyridine-2-carbothioamide was prepared following the general procedure B as a yellow solid (546 mg, 100% yield).

LC/MS (ESI) m/z for $C_{14}H_{13}FN_2OS$ 276 (calcd) 277 ([M+H]$^+$, found).

$^1$H NMR (400 MHz, Chloroform-d) δ 12.02 (s, 1H), 9.04-8.97 (m, 1H), 8.73 (d, J=8.8 Hz, 1H), 8.21 (d, J=2.8 Hz, 1H), 7.30 (dd, J=8.9, 2.9 Hz, 1H), 7.25-7.17 (m, 3H), 4.17 (q, J=6.9 Hz, 2H), 1.49 (t, J=7.0 Hz, 3H).

Step (c): methyl 5-ethoxy-N-(2-fluorophenyl)pyridine-2-carbimidothioate was prepared according to the to the general procedure C as a yellow oil (222 mg, 91% yield).

LC/MS (ESI) m/z for $C_{15}H_{15}FN_2OS$ 290 (calcd) 291 ([M+H]$^+$, found).

$^1$H NMR (400 MHz, Chloroform-d) δ 8.30 (s, 1H), 7.20-6.63 (br m, 6H), 4.08 (br s, 2H), 2.49 (very br s, 3H), 1.43 (t, J=6.8 Hz, 3H).

Step (d): tert-butyl ((1S,3r)-3-(5-(5-ethoxypyridin-2-yl)-4-(2-fluorophenyl)-4H-1,2,4-triazol-3-yl)cyclobutyl)carbamate was prepared according to the general procedure D as a yellow foam (258 mg, 73% yield).

LC/MS (ESI) m/z for $C_{24}H_{28}FN_5O_3$ 453 (calcd) 454 ([M+H]$^+$, found).

Step (e): the title compound was prepared crude according to the general procedure E as a purple glass (121 mg, 100% yield).

LC/MS (ESI) m/z for $C_{19}H_{20}FN_5O$·353 (calcd) 354 ([M+H]$^+$, found).

Example 52: Preparation of N-((1S,3r)-3-(5-(5-ethoxypyridin-2-yl)-4-(2-fluorophenyl)-4H-1,2,4-triazol-3-yl)cyclobutyl)benzamide

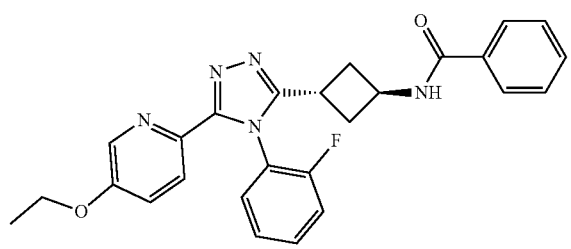

The title compound was prepared according to the general procedure F as a white solid (13.1 mg, 33% yield).

LC/MS (ESI) m/z for $C_{26}H_{24}FN_5O_2$ 457 (calcd) 458 ([M+H]$^+$, found).

$^1$H NMR (400 MHz, Chloroform-d) δ 8.15 (d, J=8.7 Hz, 1H), 7.88 (d, J=2.9 Hz, 1H), 7.76-7.71 (m, 2H), 7.55-7.39 (m, 4H), 7.26-7.15 (m, 4H), 6.28 (d, J=6.2 Hz, 1H), 4.72 (h, J=6.7 Hz, 1H), 4.04 (q, J=7.0 Hz, 2H), 3.51-3.36 (m, 1H), 3.09-2.96 (m, 2H), 2.48-2.32 (m, 2H), 1.40 (t, J=7.0 Hz, 3H).

Example 53: Preparation of 6-cyano-N-((1S,3r)-3-(5-(5-ethoxypyridin-2-yl)-4-(2-fluorophenyl)-4H-1,2,4-triazol-3-yl)cyclobutyl)picolinamide

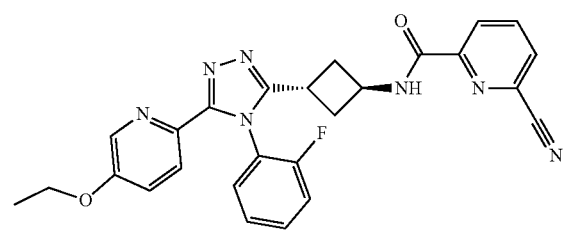

The title compound was prepared according to the general procedure F as a white solid (14.5 mg, 73% yield).

LC/MS (ESI) m/z for $C_{26}H_{22}FN_7O_2$ 483 (calcd) 484 ([M+H]$^+$, found).

$^1$H NMR (400 MHz, Chloroform-d) δ 8.39 (dd, J=7.9, 1.2 Hz, 1H), 8.16 (d, J=8.7 Hz, 1H), 8.05-7.97 (m, 2H), 7.88 (d, J=1.5 Hz, 1H), 7.82 (dd, J=7.7, 1.2 Hz, 1H), 7.50-7.42 (m, 1H), 7.33-7.16 (m, 4H), 4.83 (h, J=7.2 Hz, 1H), 4.04 (q, J=6.9 Hz, 2H), 3.47 (tt, J=9.9, 5.3 Hz, 1H), 3.15-2.95 (m, 2H), 2.55-2.35 (m, 2H), 1.40 (t, J=7.0 Hz, 3H).

Example 54: Preparation of N-((1S,3r)-3-(5-(5-ethoxypyridin-2-yl)-4-(2-fluorophenyl)-4H-1,2,4-triazol-3-yl)cyclobutyl)picolinamide

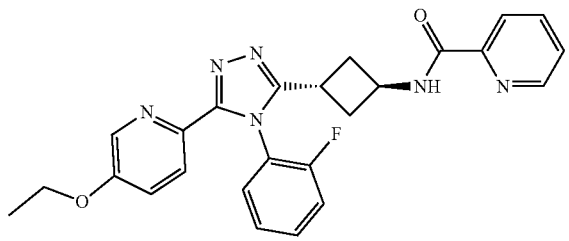

The title compound was prepared according to the general procedure F as a white solid (16.8 mg, 46% yield).

LC/MS (ESI) m/z for $C_{25}H_{23}FN_6O_2$ 458 (calcd) 459 ([M+H]$^+$, found).

$^1$H NMR (400 MHz, Chloroform-d) δ 8.53 (dt, J=4.7, 1.3 Hz, 1H), 8.21 (d, J=7.0 Hz, 1H), 8.19-8.12 (m, 2H), 7.88 (d, J=2.8 Hz, 1H), 7.83 (td, J=7.7, 1.7 Hz, 1H), 7.48-7.38 (m, 2H), 7.24-7.15 (m, 4H), 4.76 (h, J=7.0 Hz, 1H), 4.04 (q, J=6.9 Hz, 2H), 3.47 (tt, J=10.0, 5.1 Hz, 1H), 3.09-2.97 (m, 2H), 2.52-2.36 (m, 2H), 1.40 (t, J=7.0 Hz, 3H).

Example 55: Preparation of N-((1S,3r)-3-(5-(5-ethoxypyridin-2-yl)-4-(2-fluorophenyl)-4H-1,2,4-triazol-3-yl)cyclobutyl)-1,5-naphthyridine-4-carboxamide

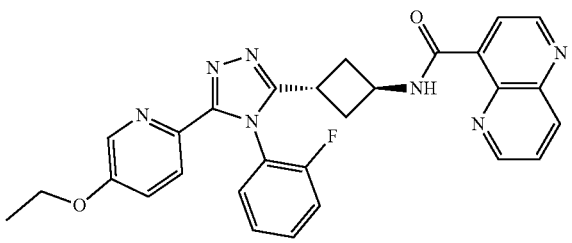

The title compound was prepared according to the general procedure F as a white solid (21.4 mg, 38% yield).

LC/MS (ESI) m/z for $C_{28}H_{24}FN_7O_2$ 509 (calcd) 510 ([M+H]$^+$, found).

$^1$H NMR (400 MHz, Chloroform-d) δ 11.31 (d, J=5.9 Hz, 1H), 9.14 (d, J=4.4 Hz, 1H), 8.98 (dd, J=4.2, 1.8 Hz, 1H), 8.58-8.52 (m, 2H), 8.17 (d, J=8.8 Hz, 1H), 7.88 (d, J=2.9 Hz, 1H), 7.74 (dd, J=8.6, 4.2 Hz, 1H), 7.48-7.40 (m, 1H), 7.26-7.14 (m, 4H), 4.84 (h, J=6.9 Hz, 1H), 4.04 (q, J=7.0 Hz, 2H), 3.53 (tt, J=10.3, 5.6 Hz, 1H), 3.14-3.02 (m, 2H), 2.62-2.48 (m, 2H), 1.40 (t, J=7.0 Hz, 3H).

Example 56: Preparation of N-((1S,3r)-3-(5-(5-ethoxypyridin-2-yl)-4-(2-fluorophenyl)-4H-1,2,4-triazol-3-yl)cyclobutyl)-4-fluorobenzamide

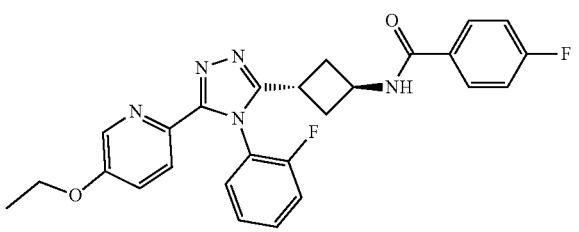

The title compound was prepared according to the general procedure F as a white solid (11.0 mg, 27% yield).
LC/MS (ESI) m/z for $C_{26}H_{23}F_2N_5O_2$ 475 (calcd) 476 ([M+11]$^+$, found).
$^1$H NMR (400 MHz, Chloroform-d) δ 8.15 (d, J=8.7 Hz, 1H), 7.88 (s, 1H), 7.75 (dd, J=8.8, 5.4 Hz, 2H), 7.49-7.41 (m, 1H), 7.25-7.15 (m, 4H), 7.09 (t, J=8.6 Hz, 2H), 6.24 (d, J=9.0 Hz, 1H), 4.72 (h, J=7.4 Hz, 1H), 4.04 (q, J=7.0 Hz, 2H), 3.44 (tt, J=9.0, 5.5 Hz, 1H), 3.11-2.94 (m, 2H), 2.48-2.30 (m, 2H), 1.40 (t, J=7.0 Hz, 3H).

Example 57: Preparation of N-((1S,3r)-3-(5-(5-ethoxypyridin-2-yl)-4-(2-fluorophenyl)-4H-1,2,4-triazol-3-yl)cyclobutyl)-7-fluoro-1,5-naphthyridine-4-carboxamide

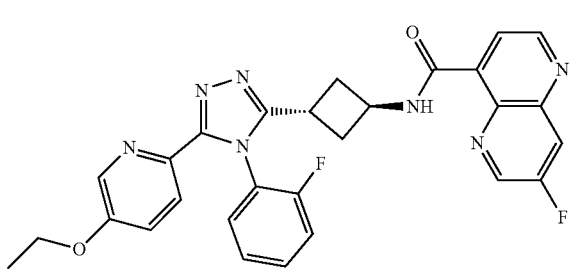

The title compound was prepared according to the general procedure F as a white solid (14.0 mg, 33% yield).
LC/MS (ESI) m/z for $C_{28}H_{23}F_2N_7O_2$ 527 (calcd) 528 ([M+H]$^+$ found).
$^1$H NMR (400 MHz, Chloroform-d) δ 10.83 (d, J=6.0 Hz, 1H), 9.15 (d, J=4.4 Hz, 1H), 8.91 (d, 0.1=2.9 Hz, 1H), 8.52 (d, J=4.4 Hz, 1H), 8.20 (dd, J=8.7, 2.9 Hz, 1H), 8.17 (d, J=9.0 Hz, 1H), 7.88 (d, J=2.9 Hz, 1H), 7.49-7.40 (m, 1H), 7.25-7.14 (m, 4H), 4.85 (h, J=7.1 Hz, 1H), 4.04 (q, J=7.0 Hz, 2H), 3.52 (tt, J=9.6, 5.2 Hz, 1H), 3.14-3.01 (m, 2H), 2.62-2.46 (m, 2H), 1.40 (t, J=7.0 Hz, 3H).

Example 58: Preparation of 5-ethoxy-N-((1S,3r)-3-(5-(5-ethoxypyridin-2-yl)-4-(2-fluorophenyl)-4H-1,2,4-triazol-3-yl)cyclobutyl)picolinamide

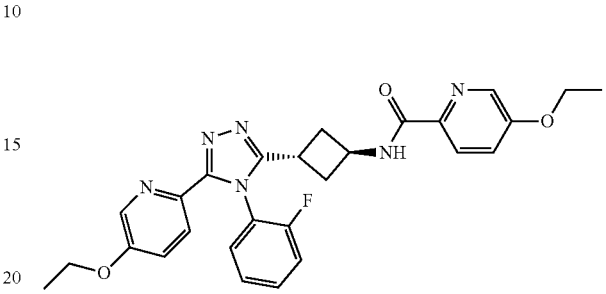

The title compound was prepared according to the general procedure F as a white solid (44.1 mg, 96% yield).
LC/MS (ESI) m/z for $C_{27}H_{27}FN_6O_3$ 502 (calcd) 503 ([M+1-1]$^+$ found).
$^1$H NMR (400 MHz, Chloroform-d) δ 8.16 (s, 1H), 8.15 (d, J=6.7 Hz, 1H), 8.09 (d, J=8.7 Hz, 1H), 8.02 (d, J=7.0 Hz, 1H), 7.88 (d, J=2.9 Hz, 1H), 7.48-7.40 (m, 1H), 7.26-7.14 (m, 5H), 4.73 (h, J=6.8 Hz, 1H), 4.11 (q, J=6.9 Hz, 2H), 4.04 (q, J=7.0 Hz, 2H), 3.47 (tt, J=9.9, 5.8 Hz, 1H), 3.10-2.95 (m, 2H), 2.50-2.32 (m, 2H), 1.46 (t, J=7.0 Hz, 3H), 1.40 (t, J=7.0 Hz, 3H).

Example 59: Preparation of N-((1S,3r)-3-(5-(5-ethoxypyridin-2-yl)-4-(2-fluorophenyl)-4H-1,2,4-triazol-3-yl)cyclobutyl)-5-fluoropicolinamide

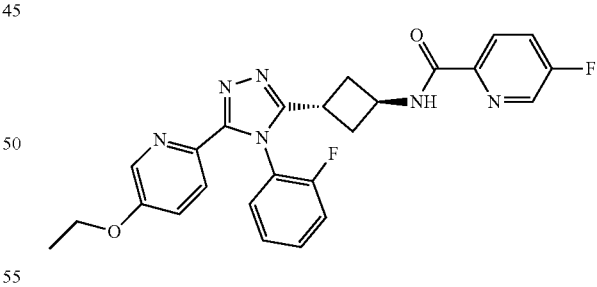

The title compound was prepared according to the general procedure F as a white solid (17.3 mg, 52% yield).
LC/MS (ESI) m/z for $C_{25}H_{22}F_2N_6O_2$ 476 (calcd) 477 ([M+H]$^+$ found).
$^1$H NMR (400 MHz, Chloroform-d) δ 8.36 (d, J=2.7 Hz, 1H), 8.20 (dd, J=8.7, 4.6 Hz, 1H), 8.16 (d, J=8.7 Hz, 1H), 8.03 (d, J=6.9 Hz, 1H), 7.88 (d, J=2.8 Hz, 1H), 7.51 (td, J=8.3, 2.8 Hz, 1H), 7.48-7.39 (m, 1H), 7.24-7.14 (m, 4H), 4.76 (h, J=6.9 Hz, 1H), 4.04 (q, J=7.0 Hz, 2H), 3.45 (tt, J=9.9, 5.5 Hz, 1H), 3.10-2.94 (m, 2H), 2.51-2.33 (m, 2H), 1.40 (t, J=7.0 Hz, 3H).

Example 60: Preparation of N-((1S,3r)-3-(5-(5-ethoxypyridin-2-yl)-4-(2-fluorophenyl)-4H-1,2,4-triazol-3-yl)cyclobutyl)quinoline-8-carboxamide

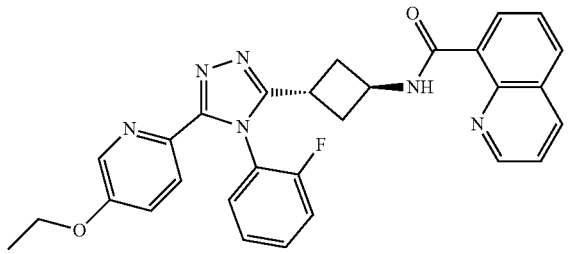

The title compound was prepared according to the general procedure F as a white solid (18.7 mg, 63% yield).

LC/MS (ESI) m/z for $C_{29}H_{25}FN_6O_2$ 508 (calcd) 509 ([M+H]$^+$ found).

$^1$H NMR (400 MHz, Chloroform-d) δ 11.54 (d, J=5.7 Hz, 1H), 8.91 (dd, J=4.3, 1.8 Hz, 1H), 8.83 (dd, J=7.3, 1.7 Hz, 1H), 8.28 (dd, J=8.3, 1.9 Hz, 1H), 8.16 (d, J=8.7 Hz, 1H), 7.95 (dd, J=8.1, 1.6 Hz, 1H), 7.88 (d, J=3.0 Hz, 1H), 7.66 (t, J=7.7 Hz, 1H), 7.49 (dd, J=8.3, 4.3 Hz, 1H), 7.47-7.38 (m, 1H), 7.25-7.13 (m, 4H), 4.81 (h, J=6.5 Hz, 1H), 4.04 (q, J=7.0 Hz, 2H), 3.56 (tt, J=9.7, 5.5 Hz, 1H), 3.14-3.03 (m, 2H), 2.61-2.46 (m, 2H), 1.40 (t, J=7.0 Hz, 3H).

Example 61: Preparation of amine building block I: 3-(5-(5-ethoxypyridin-2-yl)-4-(2-fluorophenyl)-4H-1,2,4-triazol-3-yl)bicyclo[1.1.1]pentan-1-amine dihydrochloride

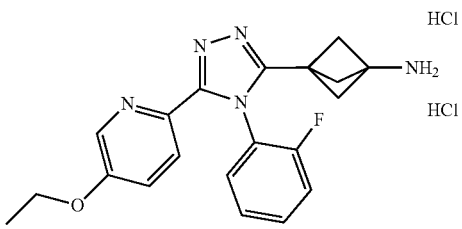

Step (a): Tert-butyl (3-(5-(5-ethoxypyridin-2-yl)-4-(2-fluorophenyl)-4H-1,2,4-triazol-3-yl)bicyclo[1.1.1]pentan-1-yl)carbamate was prepared from tert-butyl (3-(hydrazinecarbonyl)bicyclo[1.1.1]pentan-1-yl)carbamate (133 mg, Example 2) and methyl 5-ethoxy-N-(2-fluorophenyl)pyridine-2-carbimidothioate (160 mg, Example 51, step c) following the general procedure D as a brown oil (148 mg, 56% yield).

LC/MS (ESI) m/z for $C_{25}H_{28}FN_5O_3$ 465 (calcd) 466 ([M+H]$^+$, found).

Step (b): The title compound was prepared crude according to the general procedure E as a purple glass (139 mg, 96% yield).

LC/MS (ESI) m/z for $C_{20}H_{20}FN_5O$·365 (calcd) 366 ([M+H]$^+$, found).

Example 62: Preparation of N-(3-(5-(5-ethoxypyridin-2-yl)-4-(2-fluorophenyl)-4H-1,2,4-triazol-3-yl)bicyclo[1.1.1]pentan-1-yl)-1,5-naphthyridine-4-carboxamide

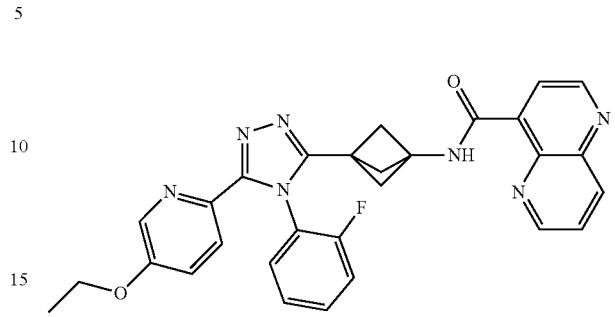

The title compound was prepared according to the general procedure F as a white solid (9.0 mg, 24% yield).

LC/MS (ESI) m/z for $C_{29}H_{24}FN_7O_2$ 521 (calcd) 522 ([M+H]$^+$ found).

$^1$H NMR (400 MHz, Chloroform-d) δ 11.43 (s, 1H), 9.14 (d, J=4.4 Hz, 1H), 8.99 (dd, J=4.4, 1.7 Hz, 1H), 8.55 (dd, J=8.6, 1.8 Hz, 1H), 8.50 (d, J=4.4 Hz, 1H), 8.13 (d, J=8.7 Hz, 1H), 7.89 (s, 1H), 7.74 (dd, J=8.4, 4.3 Hz, 1H), 7.51-7.45 (m, 1H), 7.36-7.18 (m, 3H), 4.04 (q, J=6.9 Hz, 2H), 2.49 (distorted td, J=11.2, 1.6 Hz, 6H), 1.40 (t, J=7.0 Hz, 3H).

Example 63: Preparation of amine building block J: 3-(5-(5-ethoxypyridin-2-yl)-4-phenyl-4H-1,2,4-triazol-3-yl)bicyclo[1.1.1]pentan-1-amine dihydrochloride

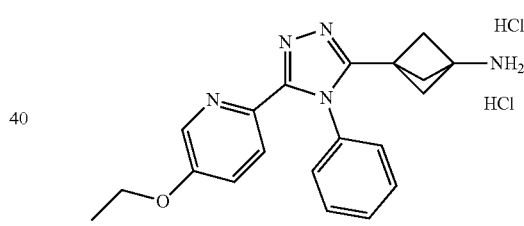

Step (a): 5-ethoxy-N-phenylpicolinamide was prepared according to the general procedure A, method a) as an off-white solid (560 mg, 77% yield).

LC/MS (ESI) m/z for $C_{14}H_{14}N_2O_2$ 242 (calcd) 243 ([M+H]$^+$, found).

$^1$H NMR (400 MHz, Chloroform-d) δ 9.84 (s, 1H), 8.25 (d, J=3.0 Hz, 1H), 8.24 (d, J=8.8 Hz, 1H), 7.77 (dd, J=8.5, 1.3 Hz, 2H), 7.38 (dd, J=8.5, 7.3 Hz, 2H), 7.32 (dd, J=8.7, 2.8 Hz, 1H), 7.13 (tt, J=7.4, 1.0 Hz, 1H), 4.16 (q, J=7.0 Hz, 2H), 1.49 (t, J=7.0 Hz, 3H).

Step (b): 5-ethoxy-N-phenylpyridine-2-carbothioamide was prepared according to the general procedure B as a yellow solid (455 mg, 76% yield).

LC/MS (ESI) m/z for $C_{14}H_{14}N_2OS$ 258 (calcd) 259 ([M+H]$^+$, found).

$^1$H NMR (400 MHz, Chloroform-d) δ 11.81 (s, 1H), 8.76 (d, J=8.9 Hz, 1H), 8.18 (d, J=2.8 Hz, 1H), 8.04 (d, J=7.4 Hz, 2H), 7.45 (t, J=7.9 Hz, 2H), 7.33-7.27 (m, 2H), 4.17 (q, J=7.0 Hz, 2H), 1.49 (t, J=7.0 Hz, 3H).

Step (c): methyl 5-ethoxy-N-phenylpyridine-2-carbimidothioate was prepared according to the general procedure C as a yellow oil (449 mg, 88% yield).

LC/MS (ESI) m/z for C$_{15}$H$_{16}$N$_2$OS 272 (calcd) 273 ([M+H]$^+$, found).

$^1$H NMR (400 MHz, Chloroform-d) δ 8.31 (s, 1H), 7.37-6.58 (br m, 7H), 4.08 (s, 2H), 2.44 (very br s, 3H), 1.43 (t, J=7.1 Hz, 3H).

Step (d): tert-butyl (3-(5-(5-ethoxypyridin-2-yl)-4-phenyl-4H-1,2,4-triazol-3-yl)bicyclo[1.1.1]pentan-1-yl)carbamate was prepared according to the general procedure D as a brown oil (94 mg, 48% yield).

LC/MS (ESI) m/z for C$_{25}$H$_{29}$N$_5$O$_3$ 447 (calcd) 448 ([M+H]$^+$, found).

Step (e): the title compound was prepared according to the general procedure E as a white solid (77 mg, 100% yield).

LC/MS (ESI) m/z for C$_{20}$H$_{21}$N$_5$O 347 (calcd) 348 ([M+H]$^+$, found).

Example 64: Preparation of N-(3-(5-(5-ethoxypyridin-2-yl)-4-phenyl-4H-1,2,4-triazol-3-yl)bicyclo[1.1.1]pentan-1-yl)-1,5-naphthyridine-4-carboxamide

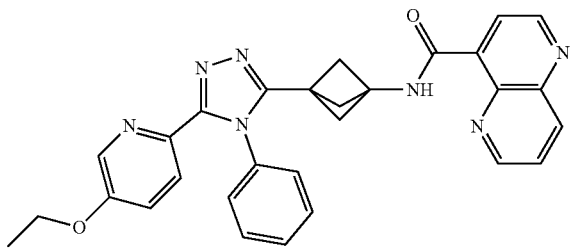

The title compound was prepared according to the general procedure F as a white solid (6.2 mg, 19% yield).

LC/MS (ESI) m/z for C$_{29}$H$_{25}$N$_7$O$_2$ 503 (calcd) 504 ([M+H]$^+$, found).

$^1$H NMR (400 MHz, Chloroform-d) δ 11.41 (s, 1H), 9.13 (d, J=4.4 Hz, 1H), 8.98 (dd, J=4.3, 1.7 Hz, 1H), 8.54 (dd, J=8.6, 1.8 Hz, 1H), 8.50 (d, J=4.4 Hz, 1H), 7.99 (d, J=8.7 Hz, 1H), 7.94 (d, J=2.8 Hz, 1H), 7.73 (dd, J=8.6, 4.3 Hz, 1H), 7.53-7.43 (m, 4H), 7.31-7.28 (m, 1H), 7.20-7.14 (m, 1H), 4.03 (q, J=7.0 Hz, 2H), 2.47 (s, 6H), 1.39 (t, J=7.0 Hz, 3H).

Example 65: Preparation of N-(3-(5-(5-ethoxypyridin-2-yl)-4-phenyl-4H-1,2,4-triazol-3-yl)bicyclo[1.1.1]pentan-1-yl)-7-fluoro-1,5-naphthyridine-4-carboxamide

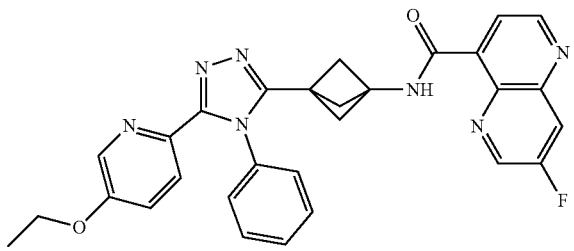

The title compound was prepared according to the general procedure F as a white solid (13.1 mg, 37% yield).

LC/MS (ESI) m/z for C$_{29}$H$_{24}$FN$_7$O$_2$ 521 (calcd) 522 ([M+H]$^+$, found).

$^1$H NMR (400 MHz, Chloroform-d) δ 10.93 (s, 1H), 9.14 (d, J=4.5 Hz, 1H), 8.92 (d, J=2.9 Hz, 1H), 8.47 (d, J=4.5 Hz, 1H), 8.18 (dd, J=8.6, 2.9 Hz, 1H), 7.99 (d, J=8.8 Hz, 1H), 7.94 (d, J=2.8 Hz, 1H), 7.50-7.43 (m, 3H), 7.31-7.27 (m, 2H), 7.18 (dd, J=8.7, 2.9 Hz, 1H), 4.03 (q, J=7.0 Hz, 2H), 2.46 (s, 6H), 1.39 (t, J=7.0 Hz, 3H).

Example 66: Preparation of N-(3-(5-(5-ethoxypyridin-2-yl)-4-phenyl-4H-1,2,4-triazol-3-yl)bicyclo[1.1.1]pentan-1-yl)picolinamide

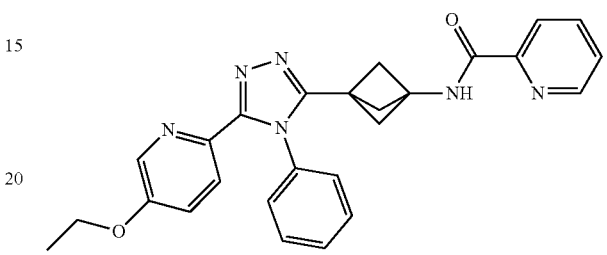

The title compound was prepared according to the general procedure F as a white solid (13.2 mg, 44% yield).

LC/MS (ESI) m/z for C$_{26}$H$_{24}$N$_6$O$_2$ 452 (calcd) 453 ([M+H]$^+$, found).

$^1$H NMR (400 MHz, Chloroform-d) δ 8.50 (dq, J=4.7, 0.8 Hz, 1H), 8.38 (s, 1H), 8.11 (dt, J=7.8, 1.2 Hz, 1H), 7.98 (d, J=8.8 Hz, 1H), 7.93 (d, J=2.9 Hz, 1H), 7.82 (td, J=7.7, 1.7 Hz, 1H), 7.49-7.43 (m, 3H), 7.41 (ddd, J=7.4, 4.8, 1.2 Hz, 1H), 7.25-7.21 (m, 2H), 7.17 (dd, J=8.7, 2.9 Hz, 1H), 4.03 (q, J=6.9 Hz, 2H), 2.39 (s, 6H), 1.39 (t, J=7.0 Hz, 3H).

Example 67: Preparation of amine building block K: (1r,3r)-3-(5-(5-ethoxypyridin-2-yl)-4-phenyl-4H-1,2,4-triazol-3-yl)cyclobutan-1-amine dihydrochloride

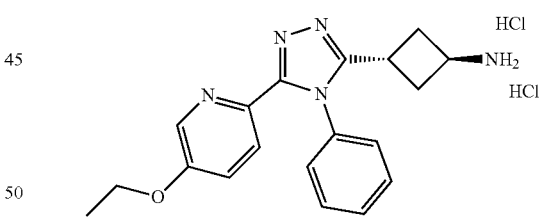

Step (a): tert-butyl ((1r,3r)-3-(5-(5-ethoxypyridin-2-yl)-4-phenyl-4H-1,2,4-triazol-3-yl)cyclobutyl)carbamate was prepared from tert-butyl ((1r,3r)-3-(hydrazinecarbonyl)cyclobutyl)carbamate (449 mg, Example 1) and methyl 5-ethoxy-N-phenylpyridine-2-carbimidothioate (533 mg, Example 63c) according to the general procedure D as a yellow foam (595 mg, 76% pure, 53% yield).

LC/MS (ESI) m/z for C$_{24}$H$_{29}$N$_5$O$_3$ 435 (calcd) 436 ([M+H]$^+$, found).

Step (b): the title compound was prepared according to the general procedure E as a yellow solid (462 mg, 92% yield).

LC/MS (ESI) m/z for C$_{19}$H$_{21}$N$_5$O 335 (calcd) 336 ([M+H]$^+$, found).

Example 68: Preparation of N-((1r,3r)-3-(5-(5-ethoxypyridin-2-yl)-4-phenyl-4H-1,2,4-triazol-3-yl)cyclobutyl)picolinamide

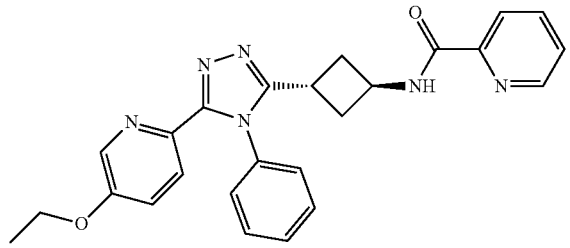

The title compound was prepared according to the general procedure F as a white solid (30.3 mg, 52% yield).

LC/MS (ESI) m/z for $C_{25}H_{24}N_6O_2$ 440 (calcd) 441 ([M+1-1]$^+$, found).

$^1$H NMR (400 MHz, Chloroform-d) δ 8.53 (dq, J=4.8, 1.1 Hz, 1H), 8.21 (d, J=7.0 Hz, 1H), 8.16 (dt, J=7.8, 1.2 Hz, 1H), 8.01 (d, J=8.8 Hz, 1H), 7.94 (d, J=2.9 Hz, 1H), 7.84 (td, J=7.7, 1.7 Hz, 1H), 7.46-7.38 (m, 4H), 7.21 (dd, J=8.7, 2.9 Hz, 1H), 7.17-7.12 (m, 2H), 4.76 (h, J=6.5 Hz, 1H), 4.04 (q, J=7.0 Hz, 2H), 3.50 (dddd, J=10.4, 8.9, 6.2, 5.0 Hz, 1H), 3.09-2.98 (m, 2H), 2.47-2.37 (m, 2H), 1.40 (t, J=7.0 Hz, 3H).

Example 69: Preparation of N-((1r,3r)-3-(5-(5-ethoxypyridin-2-yl)-4-phenyl-4H-1,2,4-triazol-3-yl)cyclobutyl)-1,5-naphthyridine-4-carboxamide The title compound was prepared according to the general procedure F as a white solid (19.9 mg, 31% yield).

LC/MS (ESI) m/z for $C_{28}H_{25}N_7O_2$ 491 (calcd) 492 ([M+H]$^+$, found).

$^1$H NMR (400 MHz, Chloroform-d) δ 11.31 (d, J=6.0 Hz, 1H), 9.14 (d, J=4.3 Hz, 1H), 8.97 (dd, J=4.2, 1.9 Hz, 1H), 8.58-8.52 (m, 2H), 8.02 (d, J=8.7 Hz, 1H), 7.94 (d, J=2.8 Hz, 1H), 7.74 (dd, J=8.6, 4.2 Hz, 1H), 7.43 (t, J=3.1 Hz, 3H), 7.21 (dd, J=8.7, 2.9 Hz, 1H), 7.19-7.15 (m, 2H), 4.85 (h, J=7.2 Hz, 1H), 4.04 (q, J=6.9 Hz, 2H), 3.56 (tt, J=9.8, 5.4 Hz, 1H), 3.08 (ddd, J=13.2, 8.2, 5.5 Hz, 2H), 2.54 (ddd, J=12.7, 9.4, 6.1 Hz, 2H), 1.40 (t, J=7.0 Hz, 3H).

Example 70: Preparation of N-((1r,3r)-3-(5-(5-ethoxypyridin-2-yl)-4-phenyl-4H-1,2,4-triazol-3-yl)cyclobutyl)-4-fluorobenzamide

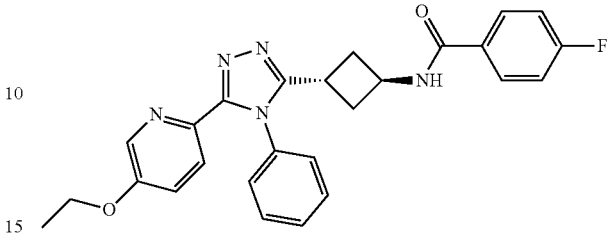

The title compound was prepared according to the general procedure F as a white solid (32.7 mg, 57% yield).

LC/MS (ESI) m/z for $C_{26}H_{24}FN_5O_2$ 457 (calcd) 458 ([M+H]$^+$, found).

$^1$H NMR (400 MHz, Chloroform-d) δ 8.01 (d, J=8.7 Hz, 1H), 7.94 (s, 1H), 7.75 (dd, J=8.8, 5.2 Hz, 2H), 7.46-7.38 (m, 3H), 7.20 (dd, J=8.7, 2.9 Hz, 1H), 7.15 (dd, J=6.8, 2.8 Hz, 2H), 7.12-7.05 (m, 2H), 6.23 (d, J=6.2 Hz, 1H), 4.72 (h, J=6.9 Hz, 1H), 4.04 (q, J=7.0 Hz, 2H), 3.46 (tt, J=9.9, 5.3 Hz, 1H), 3.02 (ddd, J=13.3, 8.1, 5.5 Hz, 2H), 2.37 (ddd, J=12.6, 9.4, 6.2 Hz, 2H), 1.40 (t, J=7.0 Hz, 3H).

Example 71: Preparation of N-((1r,3r)-3-(5-(5-ethoxypyridin-2-yl)-4-phenyl-4H-1,2,4-triazol-3-yl)cyclobutyl)quinoline-8-carboxamide

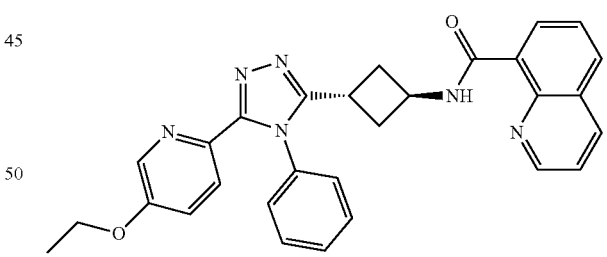

The title compound was prepared according to the general procedure F as a white solid (15.0 mg, 52% yield).

LC/MS (ESI) m/z for $C_{29}H_{26}N_6O_2$ 490 (calcd) 491 ([M+H]$^+$, found).

$^1$H NMR (400 MHz, Chloroform-d) δ 11.53 (d, J=5.7 Hz, 1H), 8.90 (dd, J=4.3, 1.9 Hz, 1H), 8.83 (dd, J=7.4, 1.6 Hz, 1H), 8.28 (dd, J=8.3, 1.8 Hz, 1H), 8.02 (d, J=8.7 Hz, 1H), 7.95 (dd, J=8.2, 1.8 Hz, 2H), 7.66 (t, J=7.7 Hz, 1H), 7.49 (dd, J=8.3, 4.3 Hz, 1H), 7.41 (distorted t, J=3.3 Hz, 3H), 7.23-7.14 (m, 3H), 4.82 (h, J=6.5 Hz, 1H), 4.04 (q, J=6.9 Hz, 2H), 3.64-3.50 (m, 1H), 3.08 (ddd, J=13.4, 8.1, 5.7 Hz, 2H), 2.52 (ddd, J=12.4, 9.5, 5.8 Hz, 2H), 1.40 (t, J=7.0 Hz, 3H).

Example 72: Preparation of N-((1r,3r)-3-(5-(5-ethoxypyridin-2-yl)-4-phenyl-4H-1,2,4-triazol-3-yl)cyclobutyl)benzamide

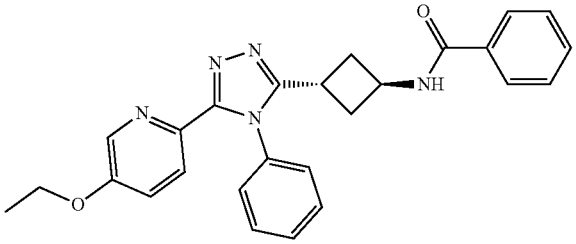

The title compound was prepared according to the general procedure, method a) as a white solid (28.2 mg, 45% yield).

LC/MS (ESI) m/z for $C_{26}H_{25}N_5O_2$ 439 (calcd) 440 ([M+H]$^+$, found).

$^1$H NMR (400 MHz, Chloroform-d) δ 8.01 (d, J=8.8 Hz, 1H), 7.94 (d, J=2.9 Hz, 1H), 7.74 (dt, J=7.0, 1.4 Hz, 2H), 7.53-7.46 (m, 1H), 7.46-7.38 (m, 5H), 7.21 (dd, J=8.7, 2.9 Hz, 1H), 7.19-7.11 (m, 2H), 6.29 (d, J=6.1 Hz, 1H), 4.73 (h, J=6.6 Hz, 1H), 4.04 (q, J=6.9 Hz, 2H), 3.47 (tt, J=9.4, 5.2 Hz, 1H), 3.02 (ddd, J=13.2, 8.0, 5.3 Hz, 2H), 2.37 (ddd, J=12.6, 9.3, 5.9 Hz, 2H), 1.40 (t, J=7.0 Hz, 3H).

Example 73: Preparation of N-((1r,3r)-3-(5-(5-ethoxypyridin-2-yl)-4-phenyl-4H-1,2,4-triazol-3-yl)cyclobutyl)-1H-benzo[d]imidazole-2-carboxamide

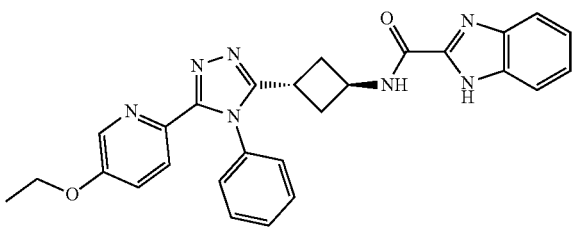

The title compound was prepared according to the general procedure F as a white solid (10.2 mg, 37% yield).

LC/MS (ESI) m/z for $C_{27}H_{25}N_7O_2$ 479 (calcd) 480 ([M+H]$^+$, found).

$^1$H NMR (400 MHz, Chloroform-d) δ 10.41 (s, 1H), 8.02 (d, J=8.8 Hz, 1H), 7.94 (d, J=2.8 Hz, 1H), 7.77 (d, J=7.8 Hz, 1H), 7.69 (d, J=7.2 Hz, 1H), 7.54 (d, J=8.0 Hz, 1H), 7.47-7.41 (m, 3H), 7.41-7.29 (m, 2H), 7.20 (dd, J=8.7, 2.9 Hz, 1H), 7.18-7.12 (m, 2H), 4.86 (dq, J=13.5, 6.7 Hz, 1H), 4.04 (q, J=7.0 Hz, 2H), 3.49 (tt, J=10.1, 5.8 Hz, 1H), 3.05 (ddd, J=13.3, 8.0, 5.5 Hz, 2H), 2.42 (ddd, J=12.7, 9.3, 6.0 Hz, 2H), 1.40 (t, J=7.0 Hz, 3H).

Example 74: Preparation of amine building block L: (1r,3r)-3-(4-(5-chlorothiophen-2-yl)-5-(5-ethoxypyridin-2-yl)-4H-1,2,4-triazol-3-yl)cyclobutan-1-amine dihydrochloride

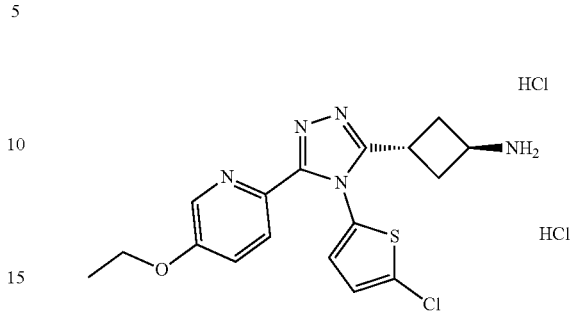

Step (a): N-(5-chlorothiophen-2-yl)-5-ethoxypicolinamide was prepared according to the general procedure A, method a) as a brown solid (516 mg, 79% pure, 79% yield).

LC/MS (ESI) m/z for $C_{12}H_{11}ClN_2O_2S$ 282/284 (calcd) 283/285 ([M+H]$^+$, found).

Step (b): N-(5-chlorothiophen-2-yl)-5-ethoxypyridine-2-carbothioamide was prepared according to the general procedure B as a yellow solid (135 mg, 77% pure, 24% yield).

LC/MS (ESI) m/z for $C_{12}H_{11}ClN_2OS_2$ 298/300 (calcd) 299/301 ([M+H]$^+$, found).

Step (c): methyl N-(5-chlorothiophen-2-yl)-5-ethoxypyridine-2-carbimidothioate was prepared according to the general procedure C as a yellow oil (98 mg, 90% yield).

LC/MS (ESI) m/z for $C_{13}H_{13}ClN_2OS_2$ 312/314 (calcd) 313/315 ([M+H]$^+$, found).

Step (d): tert-butyl ((1r,3r)-3-(4-(5-chlorothiophen-2-yl)-5-(5-ethoxypyridin-2-yl)-4H-1,2,4-triazol-3-yl)cyclobutyl)carbamate was prepared according to the general procedure D as a brown oil (97 mg, 74% pure, 48% yield).

LC/MS (ESI) m/z for $C_{22}H_{26}ClN_5O_3S$ 475/477 (calcd) 476/478 ([M+H]$^+$, found).

Step (e): the title compound was prepared according to the general procedure E as a brown glass (67 mg, only 40% pure due to alcoholysis, 40% yield).

LC/MS (ESI) m/z for $C_{17}H_{18}ClN_5OS$ 375/377 (calcd) 376/378 ([M+H]$^+$, found).

Example 75: Preparation of N-((1r,3r)-3-(4-(5-chlorothiophen-2-yl)-5-(5-ethoxypyridin-2-yl)-4H-1,2,4-triazol-3-yl)cyclobutyl)picolinamide

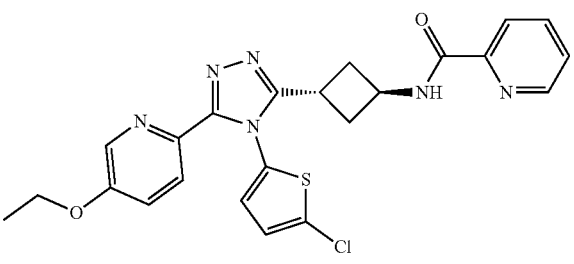

The title compound was prepared according to the general procedure F as a white solid (14.9 mg, 97% yield).

LC/MS (ESI) m/z for $C_{23}H_{21}ClN_6O_2S$ 480/482 (calcd) 481/483 ([M+H]$^+$, found).

$^1$H NMR (400 MHz, Chloroform-d) δ 8.55 (dt, J=4.7, 1.4 Hz, 1H), 8.26 (d, J=6.9 Hz, 1H), 8.18 (dt, J=7.9, 1.2 Hz, 1H), 8.09 (d, J=2.9 Hz, 1H), 8.06 (d, J=8.7 Hz, 1H), 7.85 (td, J=7.7, 1.7 Hz, 1H), 7.43 (ddd, J=7.8, 4.8, 1.3 Hz, 1H), 7.24 (dd, J=8.7, 2.8 Hz, 1H), 6.82 (d, J=4.0 Hz, 1H), 6.72 (d, J=4.0 Hz, 1H), 4.79 (h, J=7.3 Hz, 1H), 4.09 (q, J=6.9 Hz, 2H), 3.66-3.54 (m, 1H), 3.11-3.01 (m, 2H), 2.54 (ddd, J=12.6, 9.4, 6.1 Hz, 2H), 1.43 (t, J=7.0 Hz, 3H).

Example 76: Preparation of N-((1r,3r)-3-(4-(5-chlorothiophen-2-yl)-5-(5-ethoxypyridin-2-yl)-4H-1,2,4-triazol-3-yl)cyclobutyl)-1,5-naphthyridine-4-carboxamide

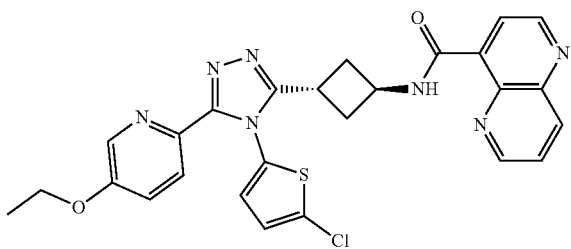

The title compound was prepared according to the general procedure F as a white solid (5.5 mg, 25% yield).

LC/MS (ESI) m/z for $C_{26}H_{22}ClN_7O_2S$ 531/533 (calcd) 532/534 ([M+11]$^+$, found).

$^1$H NMR (400 MHz, Chloroform-d) δ 11.34 (d, J=6.1 Hz, 1H), 9.16 (d, J=4.4 Hz, 1H), 9.01 (dd, J=4.3, 1.8 Hz, 1H), 8.57 (dd, J=7.0, 2.6 Hz, 2H), 8.10 (d, J=2.8 Hz, 1H), 8.07 (d, J=8.8 Hz, 1H), 7.75 (dd, J=8.5, 4.2 Hz, 1H), 7.24-7.21 (m, 1H, coinciding with chloroform peak), 6.82 (d, J=4.0 Hz, 1H), 6.73 (d, J=4.0 Hz, 1H), 4.87 (dq, J=14.0, 7.5 Hz, 1H), 4.09 (q, J=7.0 Hz, 2H), 3.66 (apparent hept, J=5.2 Hz, 1H), 3.16-3.06 (m, 2H), 2.65 (ddd, J=12.8, 9.5, 6.5 Hz, 2H), 1.44 (t, J=7.0 Hz, 3H).

Example 77: Preparation of amine building block M: (1r,3r)-3-(4-(5-chlorothiophen-2-yl)-5-(thiazol-2-yl)-4H-1,2,4-triazol-3-yl)cyclobutan-1-amine

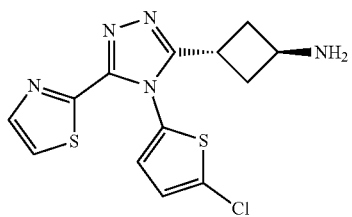

Step (a): N-(5-chlorothiophen-2-yl)thiazole-2-carboxamide was prepared according to the general procedure A, method b) as a peach-coloured solid (140 mg, 31% yield).

LC/MS (ESI) m/z for $C_8H_5ClN_2OS_2$ 244/246 (calcd) 245/247 ([M+H]$^+$, found).

$^1$H NMR (400 MHz, Chloroform-d) δ 9.59 (br s, 1H), 7.95 (d, J=3.0 Hz, 1H), 7.68 (d, J=3.0 Hz, 1H), 6.75 (d, J=4.2 Hz, 1H), 6.59 (d, J=4.2 Hz, 1H).

Step (b): N-(5-chlorothiophen-2-yl)thiazole-2-carbothioamide was prepared according to the general procedure B as a yellow solid (119 mg, 81 yield).

LC/MS (ESI) m/z for $C_8H_5ClN_2S_3$ 260/262 (calcd) 261/263 ([M+H]$^+$, found).

$^1$H NMR (400 MHz, Chloroform-d) δ 11.30 (br s, 1H), 7.92 (d, J=3.1 Hz, 1H), 7.61 (d, J=3.1 Hz, 1H), 6.91 (d, J=4.2 Hz, 1H), 6.85 (d, J=4.2 Hz, 1H).

Step (c): methyl N-(5-chlorothiophen-2-yl)thiazole-2-carbimidothioate was prepared according to the general procedure C as a yellow solid (98 mg, 79% yield).

LC/MS (ESI) m/z for $C_9H_7ClN_2S_3$ 274/276 (calcd) 275/277 ([M+H]$^+$, found).

Step (d): the title compound was obtained following the general procedure D at 150° C. resulting partially in direct deprotection as a brown semisolid (25 mg, 20% yield).

LC/MS (ESI) m/z for $C_{13}H_{12}ClN_5S_2$ 337/339 (calcd) 338/340 ([M+H]$^+$, found).

Example 78: Preparation of N-((1r,3r)-3-(4-(5-chlorothiophen-2-yl)-5-(thiazol-2-yl)-4H-1,2,4-triazol-3-yl)cyclobutyl)-1,5-naphthridine-4-carboxamide

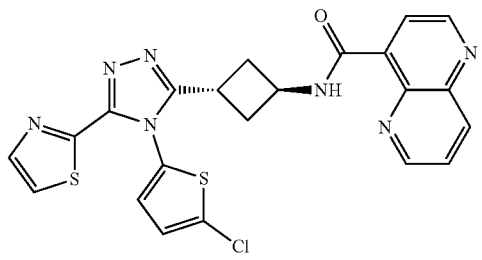

The title compound was prepared according to the general procedure F as a white solid (9.1 mg, 50% yield).

LC/MS (ESI) m/z for $C_{22}H_{16}ClN_7OS_2$ 493/495 (calcd) 494/496 ([M-FH]$^+$, found).

$^1$H NMR (400 MHz, Chloroform-d) δ 11.37 (d, J=6.1 Hz, 1H), 9.16 (d, J=4.4 Hz, 1H), 9.01 (dd, J=4.3, 1.8 Hz, 1H), 8.61-8.53 (m, 2H), 7.81 (d, J=3.2 Hz, 1H), 7.76 (dd, J=8.6, 4.3 Hz, 1H), 7.44 (d, J=3.3 Hz, 1H), 6.91 (d, J=4.0 Hz, 1H), 6.86 (d, J=4.0 Hz, 1H), 4.89 (h, J=6.9 Hz, 1H), 3.67 (tdd, J=9.8, 5.5, 4.3 Hz, 1H), 3.17-3.03 (m, 2H), 2.75-2.62 (m, 2H).

Example 79: Preparation of N-((1r,3r)-3-(4-(5-chlorothiophen-2-yl)-5-(thiazol-2-yl)-4H-1,2,4-triazol-3-yl)cyclobutyl)picolinamide

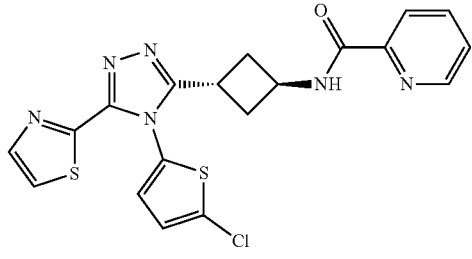

The title compound was prepared according to the general procedure F as a white solid (7.8 mg, 49% yield).

LC/MS (ESI) m/z for $C_{19}H_{15}ClN_6OS_2$ 442/444 (calcd) 443/445 ([M+H]$^+$, found).

$^1$H NMR (400 MHz, Chloroform-d) δ 8.56 (dt, J=4.8, 1.2 Hz, 1H), 8.27 (d, J=7.0 Hz, 1H), 8.18 (dt, J=7.9, 1.1 Hz, 1H), 7.86 (td, J=7.7, 1.7 Hz, 1H), 7.80 (d, J=3.2 Hz, 1H), 7.48-7.40 (m, 2H), 6.91 (d, J=4.0 Hz, 1H), 6.84 (d, J=4.0 Hz, 1H), 4.86-4.75 (m, 1H), 3.61 (ttd, J=9.5, 5.4, 1.2 Hz, 1H), 3.11-3.00 (m, 2H), 2.57 (ddd, J=12.8, 9.5, 6.3 Hz, 2H).

Example 80: Preparation of amine building block N: (1r,3r)-3-(5-(5-ethoxypyridin-2-yl)-4-(5-methyl-thiophen-2-yl)-4H-1,2,4-triazol-3-yl)cyclobutan-1-amine dihydrochloride

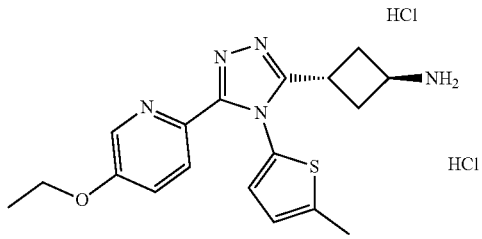

Step (a): 5-ethoxy-N-(5-methylthiophen-2-yl)picolinamide was prepared according to the general procedure A, method a) as a beige solid (273 mg, 77% yield).

LC/MS (ESI) m/z for $C_{13}H_{14}N_2O_2S$ 262 (calcd) 263 ([M+H]$^+$, found).

$^1$H NMR (400 MHz, Chloroform-d) δ 10.18 (s, 1H), 8.24 (d, J=2.8 Hz, 1H), 8.21 (d, J=8.7 Hz, 1H), 7.31 (dd, J=8.7, 2.7 Hz, 1H), 6.62 (d, J=3.6 Hz, 1H), 6.54 (dd, J=3.4, 1.2 Hz, 1H), 4.15 (q, J=6.9 Hz, 2H), 2.45 (d, J=1.2 Hz, 3H), 1.48 (t, J=6.9 Hz, 3H).

Step (b): 5-ethoxy-N-(5-methylthiophen-2-yl)pyridine-2-carbothioamide was prepared according to the general procedure B as a yellow solid (176 mg, 58% yield).

LC/MS (ESI) m/z for $C_{13}H_{14}N_2OS_2$ 278 (calcd) 279 ([M+H]$^+$, found).

$^1$H NMR (400 MHz, Chloroform-d) δ 12.30 (s, 1H), 8.65 (d, J=8.8 Hz, 1H), 8.17 (d, J=2.9 Hz, 1H), 7.29 (dd, J=8.8, 2.9 Hz, 1H), 6.98 (d, J=3.8 Hz, 1H), 6.64 (dd, J=3.8, 1.2 Hz, 1H), 4.16 (q, J=7.0 Hz, 2H), 2.47 (d, J=1.1 Hz, 3H), 1.49 (t, J=7.0 Hz, 3H).

Step (c): methyl 5-ethoxy-N-(5-methylthiophen-2-yl)pyridine-2-carbimidothioate was prepared according to the general procedure C as a yellow oil (191 mg, 99% yield).

LC/MS (ESI) m/z for $C_{14}H_{16}N_2OS_2$ 292 (calcd) 293 ([M+H]$^+$, found).

$^1$H NMR (400 MHz, Chloroform-d) δ δ 8.36 (d, J=2.8 Hz, 1H), 7.84 (br s, 1H), 7.24 (br s, 1H), 7.04 (br s, 1H), 6.68 (br s, 1H), 4.14 (q, J=7.0 Hz, 2H), 2.49 (br s, 3H), 2.45 (br s, 3H), 1.47 (t, J=7.0 Hz, 3H).

Step (d): tert-butyl a 1r,3r)-3-(5-(5-ethoxypyridin-2-yl)-4-(5-methylthiophen-2-yl)-4H-1,2,4-triazol-3-yl)cyclobutyl)carbamate was prepared according to the general procedure D as a brown oil (188 mg, 79% pure, 53% yield).

LC/MS (ESI) m/z for $C_{23}H_{29}N_5O_3S$ 455 (calcd) 456 ([M+11]$^+$, found).

Step (e): the title compound was prepared according to the general procedure E as a brown solid (153 mg, 72% pure, 79% yield).

LC/MS (ESI) m/z for $C_{18}H_{21}N_5OS$ 355 (calcd) 356 ([M+H]$^+$, found).

Example 81: Preparation of N-((1r,3r)-3-(5-(5-ethoxypyridin-2-yl)-4-(5-methylthiophen-2-yl)-4H-1,2,4-triazol-3-yl)cyclobutyl)picolinamide

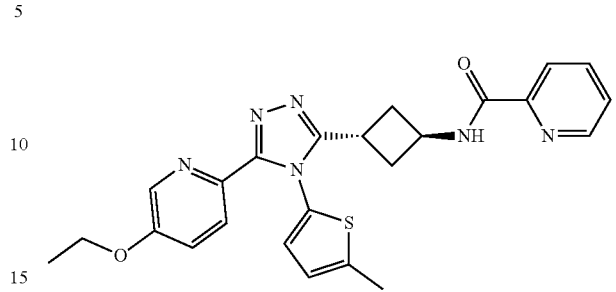

The title compound was prepared according to the general procedure F as a yellow solid (19 mg, 85% yield).

LC/MS (ESI) m/z for $C_{24}H_{24}N_6O_2S$ 460 (calcd) 461 (M$^+$+H) found.

$^1$H NMR (400 MHz, Chloroform-d) δ 8.55 (dt, J=4.7, 1.4 Hz, 1H), 8.25 (d, J=7.1 Hz, 1H), 8.18 (dt, J=7.8, 1.1 Hz, 1H), 8.12 (d, J=2.9 Hz, 1H), 7.95 (d, J=8.7 Hz, 1H), 7.85 (td, J=7.7, 1.7 Hz, 1H), 7.43 (ddd, J=7.7, 4.7, 1.2 Hz, 1H), 7.22 (dd, J=8.7, 3.0 Hz, 1H), 6.70 (d, J=3.6 Hz, 1H), 6.62 (dd, J=3.6, 1.3 Hz, 1H), 4.78 (h, J=7.1 Hz, 1H), 4.08 (q, J=6.9 Hz, 2H), 3.61 (tt, J=10.1, 5.5 Hz, 1H), 3.06 (ddd, J=13.4, 8.1, 5.5 Hz, 2H), 2.56-2.48 (m, 2H), 2.47 (d, J=1.1 Hz, 3H), 1.43 (t, J=7.0 Hz, 3H).

Example 82: Preparation of N-((1r,3r)-3-(5-(5-ethoxypyridin-2-yl)-4-(5-methylthiophen-2-yl)-4H-1,2,4-triazol-3-yl)cyclobutyl)-1,5-naphthyridine-4-carboxamide

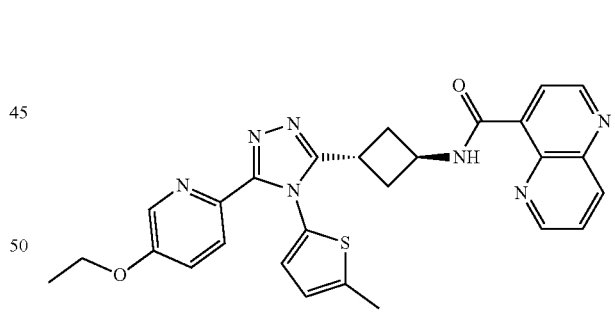

The title compound was prepared according to the general procedure F as a white solid (8.4 mg, 34% yield).

LC/MS (ESI) m/z for $C_{27}H_{25}N_7O_2S$ 511 (calcd) 512 ([M+H]$^+$ found).

$^1$H NMR (400 MHz, Chloroform-d) δ 11.31 (d, J=6.0 Hz, 1H), 9.15 (d, J=4.4 Hz, 1H), 9.00 (dd, J=4.3, 1.8 Hz, 1H), 8.59-8.53 (m, 2H), 8.12 (d, J=2.8 Hz, 1H), 7.97 (d, J=8.7 Hz, 1H), 7.75 (dd, J=8.5, 4.2 Hz, 1H), 7.22 (dd, J=8.8, 3.0 Hz, 1H), 6.72 (d, J=3.7 Hz, 1H), 6.61 (dd, J=3.7, 1.4 Hz, 1H), 4.86 (h, J=6.6 Hz, 1H), 4.08 (q, J=7.0 Hz, 2H), 3.67 (ddd, J=14.1, 9.2, 5.2 Hz, 1H), 3.11 (ddd, J=13.6, 7.9, 5.4 Hz, 2H), 2.63 (ddd, J=12.6, 9.2, 6.6 Hz, 2H), 2.47 (s, 3H), 1.43 (t, J=7.0 Hz, 3H).

Example 83: Preparation of N-((1r,3r)-3-(5-(5-ethoxypyridin-2-yl)-4-(5-methylthiophen-2-yl)-4H-1,2,4-triazol-3-yl)cyclobutyl)quinoline-8-carboxamide

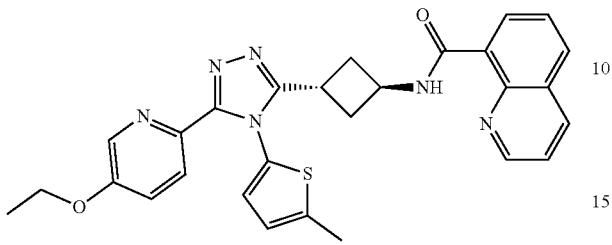

The title compound was prepared according to the general procedure F as a white solid (12 mg, 42% yield).

LC/MS (ESI) m/z for $C_{28}H_{26}N_6O_2S$ 510 (calcd) 511 ([M+H]$^+$ found).

$^1$H NMR (400 MHz, Chloroform-d) δ 11.57 (d, J=5.8 Hz, 1H), 8.94 (dd, J=4.2, 1.9 Hz, 1H), 8.85 (dd, J=7.4, 1.6 Hz, 1H), 8.29 (dd, J=8.3, 1.8 Hz, 1H), 8.12 (d, J=2.8 Hz, 1H), 7.96 (dd, J=8.3, 1.6 Hz, 2H), 7.68 (t, J=7.7 Hz, 1H), 7.54-7.46 (m, 1H), 7.22 (dd, J=8.7, 3.0 Hz, 1H), 6.72 (d, J=3.7 Hz, 1H), 6.60 (dd, J=3.6, 1.4 Hz, 1H), 4.83 (h, J=6.0 Hz, 1H), 4.08 (q, J=6.9 Hz, 2H), 3.69 (tt, J=10.1, 5.6 Hz, 1H), 3.17-3.05 (m, 2H), 2.62 (ddd, J=12.4, 9.3, 6.0 Hz, 2H), 2.46 (s, 3H), 1.43 (t, J=6.9 Hz, 3H).

Example 84: Preparation of N-((1r,3r)-3-(5-(5-ethoxypyridin-2-yl)-4-(5-methylthiophen-2-yl)-4H-1,2,4-triazol-3-yl)cyclobutyl)-7-fluoro-1,5-naphthyridine-4-carboxamide

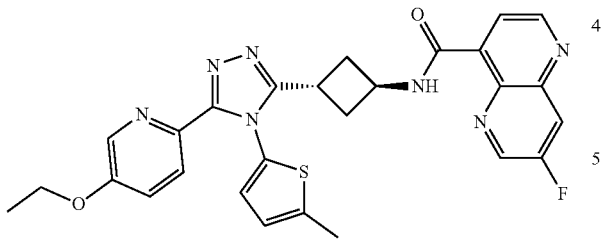

The title compound was prepared according to the general procedure F as a white solid (13 mg, 43% yield).

LC/MS (ESI) m/z for $C_{27}H_{24}FN_7O_2S$ 529 (calcd) 530 ([M+H]$^+$ found).

$^1$H NMR (400 MHz, Chloroform-d) δ 10.84 (d, J=6.0 Hz, 1H), 9.16 (d, J=4.4 Hz, 1H), 8.93 (d, J=2.9 Hz, 1H), 8.54 (d, J=4.4 Hz, 1H), 8.20 (dd, J=8.7, 2.9 Hz, 1H), 8.12 (d, J=2.9 Hz, 1H), 7.97 (d, J=8.8 Hz, 1H), 7.22 (dd, J=8.9, 2.8 Hz, 1H), 6.72 (d, J=3.7 Hz, 1H), 6.62 (d, J=3.4 Hz, 1H), 4.87 (dq, J=14.2, 7.1 Hz, 1H), 4.08 (q, J=7.0 Hz, 2H), 3.66 (dq, J=15.0, 5.0 Hz, 1H), 3.17-3.05 (m, 2H), 2.61 (ddd, J=12.6, 9.7, 6.6 Hz, 2H), 2.47 (s, 3H), 1.43 (t, J=7.0 Hz, 3H).

Example 85: Preparation of amine building block O: 3-(5-(5-ethoxypyridin-2-yl)-4-(5-methylthiophen-2-yl)-4H-1,2,4-triazol-3-yl)bicyclo[1.1.1]pentan-1-amine dihydrochloride

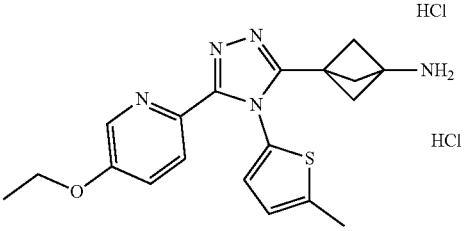

Step (a): tert-butyl (3-(5-(5-ethoxypyridin-2-yl)-4-(5-methylthiophen-2-yl)-4H-1,2,4-triazol-3-yl)bicyclo[1.1.1]pentan-1-yl)carbamate was prepared from tert-butyl (3-(hydrazinecarbonyl)bicyclo[1.1.1]pentan-1-yl)carbamate (21 mg, Example 2) and methyl 5-ethoxy-N-(5-methylthiophen-2-yl)pyridine-2-carbimidothioate (35 mg, Example 80, step c) according to the general procedure D as a brown oil (28 mg, 87% pure, 60% yield).

LC/MS (ESI) m/z for $C_{24}H_{29}N_5O_3S$ 467 (calcd) 468 ([M+H]$^+$, found).

Step (b): the title compound was prepared according to the general procedure E as a brown solid (21 mg, 90% pure, 83% yield).

LC/MS (ESI) m/z for $C_{19}H_{21}N_5OS$ 367 (calcd) 368 ([M+H]$^+$, found.

Example 86: Preparation of N-(3-(5-(5-ethoxypyridin-2-yl)-4-(5-methylthiophen-2-yl)-4H-1,2,4-triazol-3-yl)bicyclo[1.1.1]pentan-1-yl)-7-fluoro-1,5-naphthyridine-4-carboxamide

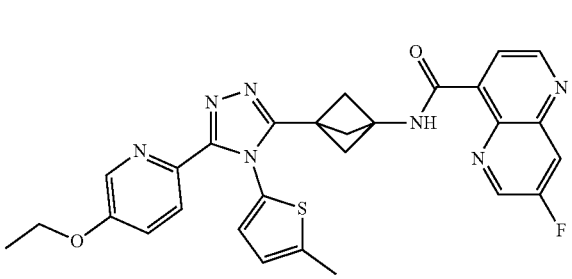

The title compound was prepared according to the general procedure F as a white solid (21.8 mg, 74% yield).

LC/MS (ESI) m/z for $C_{28}H_{24}FN_7O_2S$ 541 (calcd) 542 ([M+H]$^+$ found).

$^1$H NMR (400 MHz, Chloroform-d) δ 10.99 (s, 1H), 9.16 (d, J=4.5 Hz, 1H), 8.95 (d, J=2.9 Hz, 1H), 8.50 (d, J=4.5 Hz, 1H), 8.20 (dd, J=8.6, 2.9 Hz, 1H), 8.12 (d, J=2.8 Hz, 1H), 7.93 (d, J=8.7 Hz, 1H), 7.20 (dd, J=8.7, 2.9 Hz, 1H), 6.84 (d, J=3.7 Hz, 1H), 6.66 (d, J=2.9 Hz, 1H), 4.08 (q, J=7.0 Hz, 2H), 2.58 (s, 6H), 2.51 (s, 3H), 1.42 (t, J=7.0 Hz, 3H).

Example 87: Preparation of amine building block P: (1r,3r)-3-(4-(5-methylthiophen-2-yl)-5-(thiazol-2-yl)-4H-1,2,4-triazol-3-yl)cyclobutan-1-amine dihydrochloride

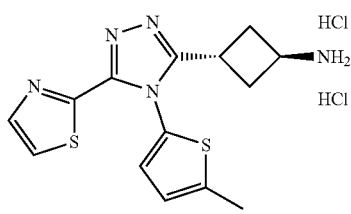

Step (a): N-(5-methylthiophen-2-yl)thiazole-2-carboxamide was prepared according to the general procedure A, method b) as a white solid (161 mg, 35% yield).
LC/MS (ESI) m/z for $C_9H_8N_2OS_2$ 224 (calcd) 225 ([M+H]$^+$, found).
$^1$H NMR (400 MHz, Chloroform-d) δ 9.50 (br s, 1H), 7.93 (d, J=3.0 Hz, 1H), 7.65 (d, J=3.1 Hz, 1H), 6.66 (d, J=3.7 Hz, 1H), 6.56 (dq, J=3.6, 1.2 Hz, 1H), 2.46 (d, J=1.2 Hz, 3H).

Step (b): N-(5-methylthiophen-2-yl)thiazole-2-carbothioamide was prepared according to the general procedure B as a yellow solid (193 mg, 88% yield).
LC/MS (ESI) m/z for $C_9H_8N_2S_3$ 240 (calcd) 241 ([M+H]$^+$, found).

Step (c): methyl N-(5-methylthiophen-2-yl)thiazole-2-carbimidothioate was prepared according to the general procedure C as a yellow oil (196 mg, 98% yield).
LC/MS (ESI) m/z for $C_{10}H_{10}N_2S_3$ 254 (calcd) 255 ([M+H]$^+$, found).

Step (d): tert-butyl ((1r,3r)-3-(4-(5-methylthiophen-2-yl)-5-(thiazol-2-yl)-4H-1,2,4-triazol-3-yl)cyclobutyl)carbamate was prepared according to the general procedure D as an off-white solid (22 mg, 14% yield).
LC/MS (ESI) m/z for $C_{19}H_{23}N_5O_2S_2$ 417 (calcd) 418 ([M+H]$^+$, found).

Step (e): the title compound was prepared according to the general procedure E as an off-white solid (21 mg, 100% yield).
LC/MS (ESI) m/z for $C_{14}H_{15}N_5S_2$ 317 (calcd) 318 ([M+H]$^+$, found).

Example 88: Preparation of N-((1r,3r)-3-(4-(5-methylthiophen-2-yl)-5-(thiazol-2-yl)-4H-1,2,4-triazol-3-yl)cyclobutyl)picolinamide

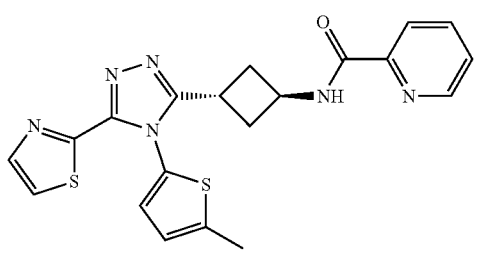

The title compound was prepared according to the general procedure F as an off-white solid (7.6 mg, 68% yield).
LC/MS (ESI) m/z for $C_{20}H_{18}N_6OS_2$ 422 (calcd) 423 ([M+H]$^+$, found).
$^1$H NMR (400 MHz, Chloroform-d) δ 8.55 (dt, J=4.7, 1.4 Hz, 1H), 8.26 (br d, J=7.0 Hz, 1H), 8.18 (dt, J=7.8, 1.1 Hz, 1H), 7.85 (td, J=7.7, 1.7 Hz, 1H), 7.81 (d, J=3.2 Hz, 1H), 7.44 (ddd, J=7.6, 4.8, 1.2 Hz, 1H), 7.40 (d, J=3.2 Hz, 1H), 6.82 (d, J=3.7 Hz, 1H), 6.74-6.68 (m, 1H), 4.79 (h, J=7.1 Hz, 1H), 3.68-3.55 (m, 1H), 3.11-3.01 (m, 2H), 2.60-2.48 (m, 2H), 2.53 (d, J=1.1 Hz, 3H).

Example 89: Preparation of N-((1r,3r)-3-(4-(5-methylthiophen-2-yl)-5-(thiazol-2-yl)-4H-1,2,4-triazol-3-yl)cyclobutyl)-1,5-naphthyridine-4-carboxamide

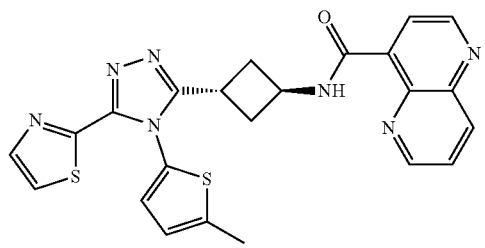

The title compound was prepared according to the general procedure F as a white solid (6.7 mg, 52% yield).
LC/MS (ESI) m/z for $C_{23}H_{19}N_7OS_2$ 473 (calcd) 474 ([M+H]$^+$, found).
$^1$H NMR (400 MHz, Chloroform-d) δ 11.35 (d, J=6.0 Hz, 1H), 9.16 (d, J=4.4 Hz, 1H), 9.00 (dd, J=4.2, 1.8 Hz, 1H), 8.60-8.54 (m, 2H), 7.82 (d, J=3.2 Hz, 1H), 7.76 (dd, J=8.5, 4.2 Hz, 1H), 7.41 (d, J=3.2 Hz, 1H), 6.84 (d, J=3.6 Hz, 1H), 6.71 (dq, J=3.4, 1.1, 1H), 4.88 (h, J=7.2 Hz, 1H), 3.67 (tdd, J=9.9, 5.8, 4.5 Hz, 1H), 3.16-3.06 (m, 2H), 2.72-2.61 (m, 2H), 2.52 (d, J=1.1 Hz, 3H).

Example 90: Preparation of amine building block P: (1S,3r)-3-(4-(2-fluorophenyl)-5-(pyrazin-2-yl)-4H-1,2,4-triazol-3-yl)cyclobutan-1-amine dihydrochloride

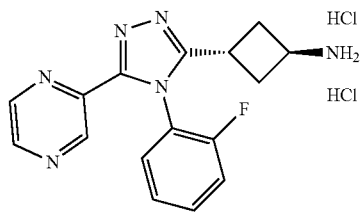

Step (a): N-(2-fluorophenyl)pyrazine-2-carboxamide was prepared according to the general procedure A, method a) as an off-white solid (812 mg, 88% yield).
LC/MS (ESI) m/z for $C_{11}H_8FN_3O$ 217 (calcd) 218 ([M+H]$^+$, found).

Step (b): N-(2-fluorophenyl)pyrazine-2-carbothioamide was prepared according to the general procedure B as a yellow solid (333 mg, 38% yield). LC/MS (ESI) m/z for $C_{11}H_8FN_3S$ 233 (calcd) 234 ([M+H]$^+$, found).

Step (c): methyl N-(2-fluorophenyl)pyrazine-2-carbimidothioate was prepared according to the general procedure C as a yellow oil (333 mg, 92% yield).

LC/MS (ESI) m/z for C$_{12}$H$_{10}$FN$_3$S 247 (calcd) 248 ([M+H]$^+$, found).

Step (d): tert-butyl ((1S,3r)-3-(4-(2-fluorophenyl)-5-(pyrazin-2-yl)-4H-1,2,4-triazol-3-yl)cyclobutyl)carbamate was prepared according to the general procedure D as a brown oil (141 mg, 68% pure, 34% yield).

LC/MS (ESI) m/z for C$_{21}$H$_{23}$FN$_6$O$_2$ 410 (calcd) 411 ([M+H]$^+$, found).

Step (e): the title compound was prepared according to the general procedure E as a purple glass (113 mg, 88% pure, 100% yield).

LC/MS (ESI) m/z for C$_{16}$H$_{15}$FN$_6$·310 (calcd) 311 ([M+H]$^+$, found).

Example 91: Preparation of N-((1S,3r)-3-(4-(2-fluorophenyl)-5-(pyrazin-2-yl)-4H-1,2,4-triazol-3-yl)cyclobutyl)picolinamide

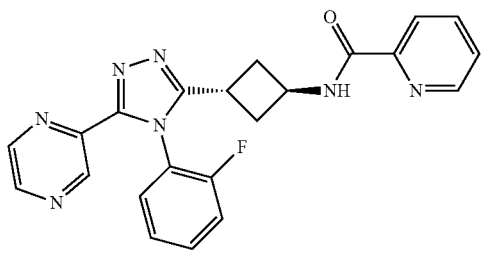

The title compound was prepared according to the general procedure F as a white solid (7.9 mg, 22% yield).

LC/MS (ESI) m/z for C$_{22}$H$_{18}$FN$_7$O 415 (calcd) 416 ([M+H]$^+$ found).

$^1$H NMR (400 MHz, Chloroform-d) δ 9.52 (d, J=1.8 Hz, 1H), 8.53 (dt, J=4.5, 1.3 Hz, 1H), 8.49 (dd, J=4.3, 2.5 Hz, 1H), 8.22 (br d, J=6.9 Hz, 1H), 8.19 (dd, J=2.6, 1.5 Hz, 1H), 8.17 (dt, J=7.8, 1.1 Hz, 1H), 7.84 (td, J=7.7, 1.7 Hz, 1H), 7.51-7.45 (m, 1H), 7.42 (ddd, J 7.6, 4.8, 1.2 Hz, 1H), 7.24-7.17 (m, 3H), 4.79 (h, J=6.8 Hz, 1H), 3.49 (tt, J=10.0, 5.6 Hz, 1H), 3.14-2.96 (m, 2H), 2.58-2.40 (m, 2H).

Example 92: Preparation of amine building block R: (1S,3r)-3-(5-(5-(ethoxy-d5)pyridin-2-yl)-4-(2-fluorophenyl)-4H-1,2,4-triazol-3-yl)cyclobutan-1-amine dihydrochloride

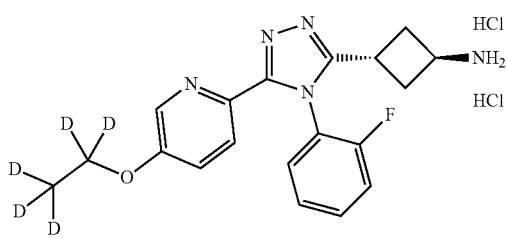

Step (a): 5-(ethoxy-d5)-N-(2-fluorophenyl)picolinamide was prepared according to the general procedure A, method a) as a brown solid (398 mg, 64% yield).

LC/MS (ESI) m/z for C$_{14}$H$_8$D$_5$FN$_2$O$_2$ 265 (calcd) 266 ([M+H]$^+$, found). $^1$H NMR (400 MHz, Chloroform-d) δ 10.14 (s, 1H), 8.56 (td, J=8.1, 1.7 Hz, 1H), 8.28 (d, J=2.7 Hz, 1H), 8.22 (d, J=8.7 Hz, 1H), 7.31 (dd, J=8.7, 2.8 Hz, 1H), 7.22-7.10 (m, 2H), 7.10-7.02 (m, 1H).

Step (b): 5-(ethoxy-d5)-N-(2-fluorophenyl)pyridine-2-carbothioamide was prepared according to the general procedure B as a yellow oil (386 mg, 91% yield).

LC/MS (ESI) m/z for C$_{14}$H$_8$D$_5$FN$_2$OS 281 (calcd) 282 ([M+H]$^+$, found).

$^1$H NMR (400 MHz, Chloroform-d) δ 12.01 (br s, 1H), 9.03-8.95 (m, 1H), 8.72 (d, J=8.9 Hz, 1H), 8.20 (d, J=2.8 Hz, 1H), 7.29 (dd, J=8.8, 2.8 Hz, 1H), 7.25-7.16 (m, 3H).

Step (c): methyl 5-(ethoxy-d5)-N-(2-fluorophenyl)pyridine-2-carbimidothioate was prepared according to the general procedure C as a yellow oil (369 mg, 91% yield).

LC/MS (ESI) m/z for C$_{15}$H$_{10}$D$_5$FN$_2$OS 295 (calcd) 296 ([M+H]$^+$, found).

Step (d): tert-butyl ((1S,3r)-3-(5-(5-(ethoxy-d5)pyridin-2-yl)-4-(2-fluorophenyl)-4H-1,2,4-triazol-3-yl)cyclobutyl)carbamate was prepared according to the general procedure D as a brown solid (416 mg, 71% yield).

LC/MS (ESI) m/z for C$_{24}$H$_{23}$D$_5$FN$_5$O$_3$ 458 (calcd) 459 ([M+H]$^+$, found).

$^1$H NMR (400 MHz, Chloroform-d) δ 8.13 (d, J=8.7 Hz, 1H), 7.87 (d, J=2.9 Hz, 1H), 7.49-7.40 (m, 1H), 7.25-7.13 (m, 4H), 4.73 (br s, 1H), 4.32 (h, J=7.1 Hz, 1H), 3.31 (br s, 1H), 2.94-2.84 (m, 1H), 2.83 (br s, 1H), 2.25 (br s, 2H), 1.42 (s, 9H).

Step (e): the title compound was prepared according to the general procedure E as a green solid (392 mg, 100% yield).

LC/MS (ESI) m/z for C$_{19}$H$_{15}$D$_5$FN$_5$O 358 (calcd) 359 ([M+H]$^+$, found).

$^1$H NMR (400 MHz, DMSO-d6) δ 8.34 (br d, J=5.5 Hz, 3H, NH$_2$+HCl), 8.03 (d, J=8.7 Hz, 1H), 7.93 (d, J=2.9 Hz, 1H), 7.59 (tdd, J=7.6, 5.1, 1.7 Hz, 1H), 7.55-7.47 (m, 2H), 7.44 (ddd, J=9.9, 8.3, 1.3 Hz, 1H), 7.34 (td, J=7.7, 1.3 Hz, 1H), 3.85 (h, J=6.5 Hz, 1H), 3.52 (tt, J=9.8, 5.7 Hz, 1H), 2.82-2.72 (m, 1H), 2.64-2.53 (m, 1H), 2.43-2.26 (m, 2H).

Example 93: Preparation of N-((1S,3r)-3-(5-(5-(ethoxy-d5)pyridin-2-yl)-4-(2-fluorophenyl)-4H-1,2,4-triazol-3-yl)cyclobutyl)picolinamide

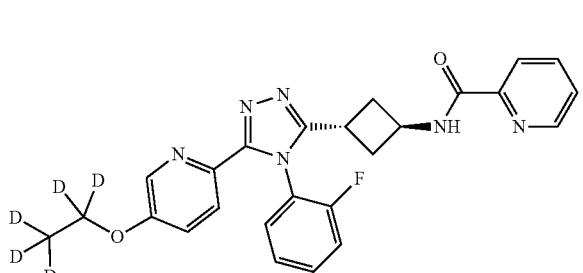

The title compound was prepared according to the general procedure F as a white solid (30.5 mg, 87% yield).

LC/MS (ESI) m/z for C$_{25}$H$_{18}$D$_5$FN$_6$O$_2$ 463 (calcd) 464 ([M+H]$^+$, found).

$^1$H NMR (400 MHz, Chloroform-d) δ 8.53 (dt, J=4.7, 1.3 Hz, 1H), 8.21 (d, J=6.9 Hz, 1H), 8.16 (dd, J=8.8, 3.2 Hz, 2H), 7.87 (d, J=2.9 Hz, 1H), 7.83 (td, J=7.7, 1.7 Hz, 2H), 7.49-7.38 (m, 2H), 7.24-7.14 (m, 4H), 4.76 (h, J=7.2 Hz, 1H), 3.52-3.42 (m, 1H), 3.10-2.96 (m, 2H), 2.52-2.35 (m, 2H).

Example 94: Preparation of N-((1S,3r)-3-(5-(5-(ethoxy-d5)pyridin-2-yl)-4-(2-fluorophenyl)-4H-1,2,4-triazol-3-yl)cyclobutyl)-7-fluoro-1,5-naphthyridine-4-carboxamide

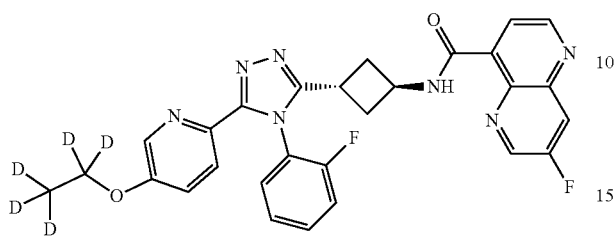

The title compound was prepared according to the general procedure F as a white solid (10.6 mg, 65% yield).

LC/MS (ESI) m/z for $C_{28}H_{18}D_5F_2N_7O_2$ 532 (calcd) 533 ([M+H]$^+$, found).

$^1$H NMR (400 MHz, Chloroform-d) δ 10.81 (d, J=6.0 Hz, 1H), 9.15 (d, J=4.5 Hz, 1H), 8.91 (d, J=2.9 Hz, 1H), 8.52 (d, J=4.4 Hz, 1H), 8.19 (dd, J=8.7, 2.7 Hz, 1H), 8.17 (d, J=8.9 Hz, 1H), 7.88 (d, J=2.8 Hz, 1H), 7.48-7.40 (m, 1H), 7.25-7.14 (m, 4H), 4.85 (h, J=6.9 Hz, 1H), 3.51 (tt, J=9.9, 5.3 Hz, 1H), 3.15-3.01 (m, 2H), 2.61-2.46 (m, 2H).

Example 95: Preparation of N-((1S,3r)-3-(5-(5-(ethoxy-d5)pyridin-2-yl)-4-(2-fluorophenyl)-4H-1,2,4-triazol-3-yl)cyclobutyl)quinoline-8-carboxamide

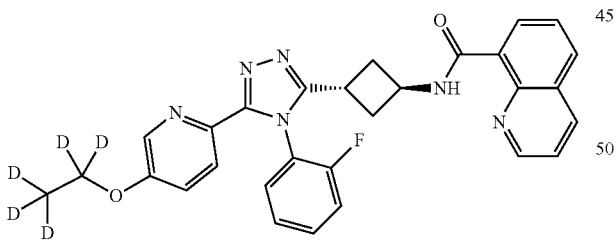

The title compound was prepared according to the general procedure F as a white solid (20.2 mg, 77% yield).

LC/MS (ESI) m/z for $C_{29}H_{20}D_5FN_6O_2$ 513 (calcd) 514 ([M+H]$^+$, found).

$^1$H NMR (400 MHz, Chloroform-d) δ 11.54 (d, J=5.7 Hz, 1H), 8.91 (dd, J=4.3, 1.8 Hz, 1H), 8.83 (dd, J=7.4, 1.6 Hz, 1H), 8.28 (dd, J=8.3, 1.9 Hz, 1H), 8.17 (br d, J=6.8 Hz, 1H), 7.95 (dd, J=8.1, 1.6 Hz, 1H), 7.88 (br s, 1H), 7.66 (t, J=7.7 Hz, 1H), 7.49 (dd, J=8.3, 4.3 Hz, 1H), 7.46-7.38 (m, 1H), 7.24-7.12 (m, 4H), 4.81 (h, J=6.8 Hz, 1H), 3.63-3.50 (m, 1H), 3.13-3.02 (m, 2H), 2.61-2.46 (m, 2H).

Example 96: Preparation of N-((1S,3r)-3-(5-(5-ethoxypyridin-2-yl)-4-(2-fluorophenyl)-4H-1,2,4-triazol-3-yl)cyclobutyl)-1,5-naphthyridine-2-carboxamide The title compound was prepared according to the general procedure F as a white solid (17.0 mg, 66% yield).

LC/MS (ESI) m/z for $C_{23}H_{24}FN_7O_2$ 509 (calcd) 510 ([M+H]$^+$ found).

$^1$H NMR (400 MHz, Chloroform-d) δ 9.06 (dd, J=4.2, 1.7 Hz, 1H), 8.57-8.48 (m, 2H), 8.41 (dd, J=8.4, 1.7 Hz, 1H), 8.35 (d, J=6.9 Hz, 1H), 8.17 (d, J=8.7 Hz, 1H), 7.89 (d, J=2.9 Hz, 1H), 7.71 (dd, J=8.6, 4.2 Hz, 1H), 7.49-7.41 (m, 1H), 7.25-7.15 (m, 4H), 4.84 (h, J=7.1 Hz, 1H), 4.04 (q, J=7.0 Hz, 2H), 3.51 (tt, J=9.8, 5.1 Hz, 1H), 3.14-3.01 (m, 2H), 2.62-2.46 (m, 2H), 1.40 (t, J=7.0 Hz, 3H).

Example 97: Preparation of N-((1S,3r)-3-(5-(5-ethoxypyridin-2-yl)-4-(2-fluorophenyl)-4H-1,2,4-triazol-3-yl)cyclobutyl)-1,6-naphthyridine-2-carboxamide The title compound was prepared according to the general procedure F as a white solid (12.7 mg, 49% yield).

LC/MS (ESI) m/z for $C_{28}H_{24}FN_7O_2$ 509 (calcd) 510 ([M+H]$^+$ found).

$^1$H NMR (400 MHz, Chloroform-d) δ 9.36 (s, 1H), 8.82 (d, J=5.9 Hz, 1H), 8.49-8.40 (m, 2H), 8.38 (d, J=6.8 Hz, 1H), 8.17 (d, J=8.7 Hz, 1H), 7.92 (d, J=5.9 Hz, 1H), 7.89 (s, 1H), 7.50-7.40 (m, 1H), 7.25-7.15 (m, 4H), 4.86 (h, J=7.3 Hz, 1H), 4.04 (q, J=6.9 Hz, 2H), 3.50 (tt, J=9.7, 5.2 Hz, 1H), 3.17-3.00 (m, 2H), 2.62-2.46 (m, 2H), 1.40 (t, J=6.9 Hz, 3H).

Example 98: Preparation of N-((1S,3r)-3-(5-(5-ethoxypyridin-2-yl)-4-(2-fluorophenyl)-4H-1,2,4-triazol-3-yl)cyclobutyl)-1H-pyrrolo[2,3-b]pyridine-6-carboxamide

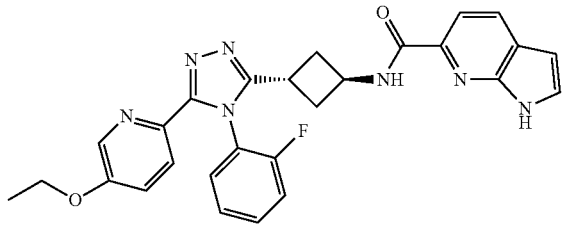

The title compound was prepared according to the general procedure F as a white solid (17.7 mg, 70% yield).

LC/MS (ESI) m/z for $C_{27}H_{24}FN_7O_2$ 497 (calcd) 498 ([M+H]$^+$ found).

$^1$H NMR (400 MHz, Chloroform-d) δ 9.20 (s, 1H), 8.19-8.11 (m, 2H), 8.05-7.96 (m, 2H), 7.88 (d, J=2.8 Hz, 1H), 7.47 (dd, J=3.6, 2.4 Hz, 1H), 7.45-7.38 (m, 1H), 7.24-7.12 (m, 4H), 6.55 (dd, J=3.5, 1.9 Hz, 1H), 4.76 (h, J=7.1 Hz, 1H), 4.04 (q, J=7.0 Hz, 2H), 3.49 (tt, J=10.0, 5.5 Hz, 1H), 3.02 (tt, J=8.2, 5.5 Hz, 2H), 2.58-2.42 (m, 2H), 1.40 (t, J=7.0 Hz, 3H).

Example 99: Preparation of N-((1S,3r)-3-(5-(5-ethoxypyridin-2-yl)-4-(2-fluorophenyl)-4H-1,2,4-triazol-3-yl)cyclobutyl)isoquinoline-3-carboxamide

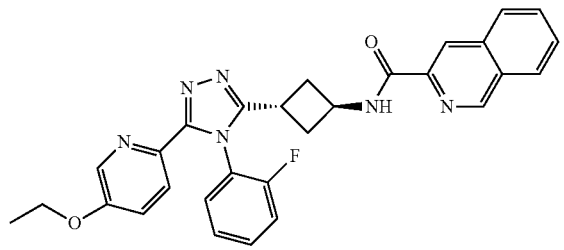

The title compound was prepared according to the general procedure F as a white solid (15.4 mg, 60% yield).

LC/MS (ESI) m/z for $C_{29}H_{25}FN_6O_2$ 508 (calcd) 509 ([M+H]$^+$ found).

$^1$H NMR (400 MHz, Chloroform-d) δ 9.14 (s, 1H), 8.58 (s, 1H), 8.41 (d, J=6.9 Hz, 1H), 8.17 (br s, 1H), 8.03 (d, J=8.1 Hz, 1H), 7.98 (d, J=8.0 Hz, 1H), 7.88 (br s, 1H), 7.77 (ddd, J=8.1, 6.8, 1.3 Hz, 1H), 7.70 (ddd, J=8.3, 7.0, 1.3 Hz, 1H), 7.49-7.40 (m, 1H), 7.25-7.14 (m, 4H), 4.83 (h, J=7.1 Hz, 1H), 4.04 (q, J=7.0 Hz, 2H), 3.51 (tt, J=9.5, 5.7 Hz, 1H), 3.14-3.00 (m, 2H), 2.56-2.40 (m, 2H), 1.40 (t, J=7.0 Hz, 3H).

Example 100: Preparation of rac-N-((1R,3r)-3-(5-(5-ethoxypyridin-2-yl)-4-(2-fluorophenyl)-4H-1,2,4-triazol-3-yl)cyclobutyl)-5-(1-hydroxyethyl)picolinamide

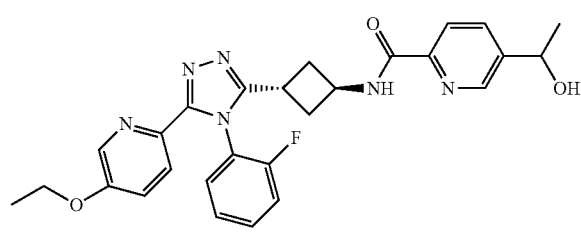

The title compound was prepared employing the crude potassium salt of the acid according to the general procedure F as a white solid (8.5 mg, 33% yield).

LC/MS (ESI) m/z for $C_{27}H_{27}FN_6O_3$ 502 (calcd) 503 ([M+H]$^+$, found).

$^1$H NMR (400 MHz, Chloroform-d) δ 8.53 (d, J=2.2 Hz, 1H), 8.18 (d, J=7.3 Hz, 1H), 8.14 (t, J=7.8 Hz, 2H), 7.88 (d, J=2.9 Hz, 1H), 7.84 (dd, J=8.1, 2.3 Hz, 1H), 7.48-7.40 (m, 1H), 7.24-7.14 (m, 4H), 5.03 (q, J=6.4 Hz, 1H), 4.75 (h, J=6.9 Hz, 1H), 4.04 (q, J=7.0 Hz, 2H), 3.45 (hept, J=5.1 Hz, 1H), 3.08-2.94 (sym. m, 2H), 2.51-2.34 (sym. m, 2H), 2.15 (br s, 1H), 1.54 (d, J=6.6 Hz, 3H), 1.40 (t, J=7.0 Hz, 3H).

Example 101: Preparation of N-((1S,3r)-3-(5-(5-ethoxypyridin-2-yl)-4-(2-fluorophenyl)-4H-1,2,4-triazol-3-yl)cyclobutyl)-5-(2-hydroxypropan-2-yl)picolinamide

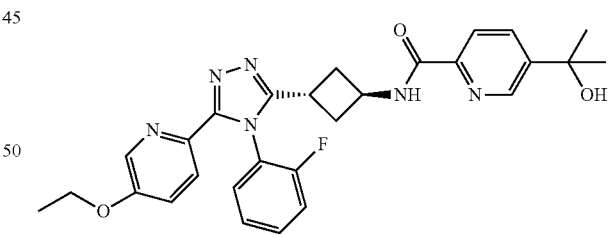

The title compound was prepared employing the crude potassium salt of the acid according to the general procedure F as a white solid (9.2 mg, 35% yield).

LC/MS (ESI) m/z for $C_{28}H_{29}FN_6O_3$ 516 (calcd) 517 ([M+H]$^+$, found).

$^1$H NMR (400 MHz, Chloroform-d) δ 8.67 (d, J=2.3 Hz, 1H), 8.17 (dd, J=12.1, 8.0 Hz, 2H), 8.11 (d, J=8.2 Hz, 1H), 7.92 (dd, J=8.1, 2.3 Hz, 1H), 7.88 (s, 1H), 7.48-7.40 (m, 1H), 7.25-7.14 (m, 4H), 4.76 (h, J=6.5 Hz, 1H), 4.04 (q, J=6.9 Hz, 2H), 3.46 (tt, J=9.9, 5.7 Hz, 1H), 3.10-2.95 (sym. m, 2H), 2.51-2.35 (sym. m, 2H), 1.89 (br s, 1H), 1.62 (s, 6H), 1.40 (t, J=7.0 Hz, 3H).

Example 102: Preparation of N-((1S,3r)-3-(5-(5-ethoxypyridin-2-yl)-4-(2-fluorophenyl)-4H-1,2,4-triazol-3-yl)cyclobutyl)-3-methylpicolinamide

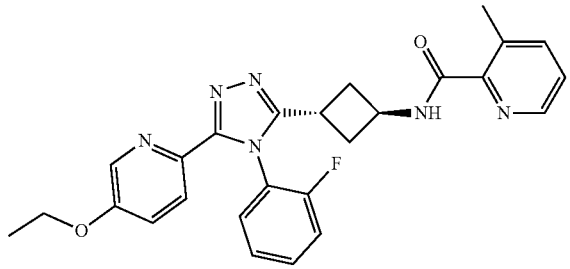

The title compound was prepared according to the general procedure F as a white solid (13.6 mg, 57% yield).

LC/MS (ESI) m/z for $C_{26}H_{25}FN_6O_2$ 472 (calcd) 473 ([M+H]$^+$, found).

$^1$H NMR (400 MHz, Chloroform-d) δ 8.36 (dd, J=4.6, 1.6 Hz, 1H), 8.33 (d, J=6.7 Hz, 1H), 8.16 (br s, 1H), 7.88 (br s, 1H), 7.57 (dd, J=7.7, 1.6 Hz, 1H), 7.48-7.40 (m, 1H), 7.29 (dd, J=7.7, 4.6 Hz, 1H), 7.25-7.13 (m, 4H), 4.69 (h, J=6.7 Hz, 1H), 4.04 (q, J=6.9 Hz, 2H), 3.48 (tt, J=9.6, 5.9 Hz, 1H), 3.10-2.96 (sym. m, 2H), 2.71 (s, 3H), 2.50-2.33 (sym. m, 2H), 1.40 (t, J=7.0 Hz, 3H).

Example 103: Preparation of N-((1S,3r)-3-(5-(5-ethoxypyridin-2-yl)-4-(2-fluorophenyl)-4H-1,2,4-triazol-3-yl)cyclobutyl)-4-methylpicolinamide

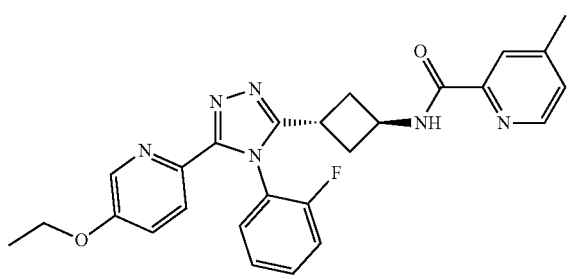

The title compound was prepared according to the general procedure F as a white powder (8.0 mg, 33% yield).

LC/MS (ESI) m/z for $C_{26}H_{25}FN_6O_2$ 472 (calcd) 473 ([M+H]$^+$, found).

$^1$H NMR (400 MHz, Chloroform-d) δ 8.37 (d, J=4.9 Hz, 1H), 8.20 (d, J=6.9 Hz, 1H), 8.16 (d, J=8.8 Hz, 1H), 7.99 (s, 1H), 7.88 (br s, 1H), 7.48-7.40 (m, 1H), 7.25-7.14 (m, 5H), 4.75 (h, J=7.1 Hz, 1H), 4.04 (q, J=7.0 Hz, 2H), 3.52-3.41 (sym. m, 1H), 3.10-2.96 (sym. m, 2H), 2.50-2.34 (sym. m, 2H), 2.41 (s, 3H), 1.40 (t, J=7.0 Hz, 3H).

Example 104: Preparation of N-((1S,3r)-3-(5-(5-ethoxypyridin-2-yl)-4-(2-fluorophenyl)-4H-1,2,4-triazol-3-yl)cyclobutyl)quinoline-2-carboxamide

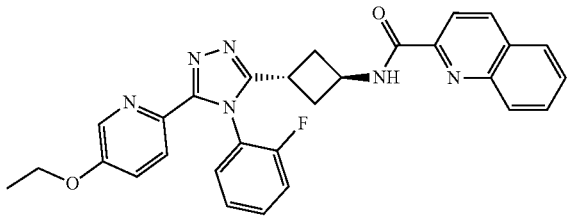

The title compound was prepared according to the general procedure F as a white powder (15.2 mg, 59% yield).

LC/MS (ESI) m/z for $C_{29}H_{25}FN_6O_2$ 508 (calcd) 509 ([M+H]$^+$, found).

$^1$H NMR (400 MHz, Chloroform-d) δ 8.43 (d, J=6.8 Hz, 1H), 8.33-8.24 (sym. m, 2H), 8.17 (br s, 1H), 8.10 (d, J=8.4 Hz, 1H), 7.88 (dd, J=8.1, 1.4 Hz, 2H), 7.77 (ddd, J=8.5, 6.9, 1.5 Hz, 1H), 7.62 (ddd, J=8.0, 6.9, 1.1 Hz, 1H), 7.49-7.40 (m, 1H), 7.25-7.15 (m, 4H), 4.83 (h, J=7.1 Hz, 1H), 4.04 (q, J=6.9 Hz, 2H), 3.60-3.46 (sym. m, 1H), 3.14-3.00 (sym. m, 2H), 2.62-2.45 (sym. m, 2H), 1.40 (t, J=7.0 Hz, 3H).

Example 105: Preparation of amine building block S: (1S,3r)-3-(5-(5-cyclopropoxypyridin-2-yl)-4-(2-fluorophenyl)-4H-1,2,4-triazol-3-yl)cyclobutan-1-amine dihydrochloride

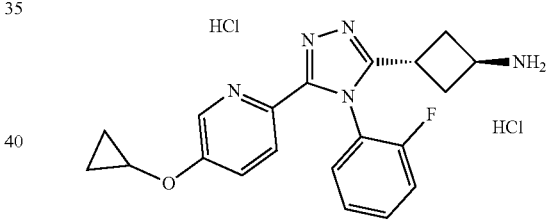

Step (a): 5-cyclopropoxy-N-(2-fluorophenyl)picolinamide was prepared according to the general procedure A, method c) as an orange solid (36 mg, 64% yield).

LC/MS (ESI) m/z for $C_{15}H_{13}FN_2O_2$ 272 (calcd) 273 ([M+H]$^+$, found).

$^1$H NMR (400 MHz, Chloroform-d) δ 10.15 (br s, 1H), 8.57 (td, J=8.1, 1.7 Hz, 1H), 8.38 (d, J=2.7 Hz, 1H), 8.24 (d, J=8.7 Hz, 1H), 7.53 (dd, J=8.6, 2.8 Hz, 1H), 7.22-7.10 (m, 2H), 7.07 (dddd, J=8.4, 7.1, 5.2, 1.8 Hz, 1H), 3.87 (tt, J=6.1, 3.2 Hz, 1H), 0.94-0.80 (m, 4H).

Step (b): 5-cyclopropoxy-N-(2-fluorophenyl)pyridine-2-carbothioamide was prepared following the general procedure B as a yellow solid (34.6 mg, 92% yield).

LC/MS (ESI) m/z for $C_{15}H_{13}FN_2OS$ 288 (calcd) 289 ([M+H]$^+$, found).

Step (c): methyl 5-cyclopropoxy-N-(2-fluorophenyl)pyridine-2-carbimidothioate was prepared according to the to the general procedure C as a pale yellow semi-solid (29 mg, 80% yield).

LC/MS (ESI) m/z for $C_{16}H_{15}FN_2OS$ 302 (calcd) 303 ([M+H]$^+$, found).

Step (d): tert-butyl ((1S,3r)-3-(5-(5-cyclopropoxypyridin-2-yl)-4-(2-fluorophenyl)-4H-1,2,4-triazol-3-yl)cyclobutyl)

carbamate was prepared according to the general procedure D as a pale ochre semisolid (34 mg, ~93% purity, 71% yield).

LC/MS (ESI) m/z for $C_{25}H_{28}FN_5O_3$ 465 (calcd) 466 ([M+H]$^+$, found).

$^1$H NMR (400 MHz, Chloroform-d) δ 8.16 (d, J=8.8 Hz, 1H), 7.98 (d, J=2.8 Hz, 1H), 7.49-7.42 (m, 1H), 7.40 (dd, J=8.8, 2.8 Hz, 1H), 7.25-7.14 (m, 3H), 4.75 (br s, 1H), 4.32 (h, J=7.0 Hz, 1H), 3.73 (tt, J=5.8, 3.2 Hz, 1H), 3.31 (br s, 1H), 2.94-2.85 (m, 1H), 2.83 (br s, 1H), 2.22 (br s, 2H), 1.42 (s, 9H), 0.82-0.72 (m, 4H).

Step (e): the crude title compound was prepared according to the general procedure E as a pale yellow glass (36 mg, ~83% purity, ~100% yield).

LC/MS (ESI) m/z for $C_{20}H_{20}FN_5O$·365 (calcd) 366 ([M+H]$^+$, found).

Example 106: Preparation of N-((1S,3r)-3-(5-(5-cyclopropoxypyridin-2-yl)-4-(2-fluorophenyl)-4H-1,2,4-triazol-3-yl)cyclobutyl)picolinamide

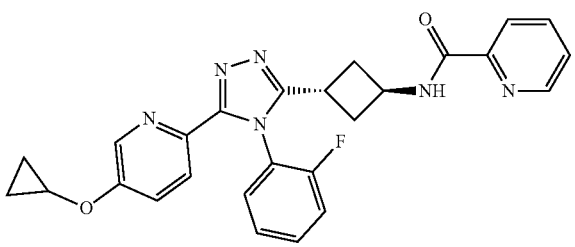

The title compound was prepared according to the general procedure F as a white solid (24.3 mg, 75% yield).

LC/MS (ESI) m/z for $C_{26}H_{23}FN_6O_2$ 470 (calcd) 471 ([M+H]$^+$, found).

$^1$H NMR (400 MHz, Chloroform-d) δ 8.53 (dt, J=4.8, 1.3 Hz, 1H), 8.26-8.13 (m, 3H), 7.99 (s, 1H), 7.83 (td, J=7.7, 1.7 Hz, 1H), 7.50-7.37 (m, 3H), 7.24-7.14 (m, 3H), 4.77 (h, J=7.0 Hz, 1H), 3.74 (tt, J=6.1, 3.1 Hz, 1H), 3.47 (tt, J=10.0, 5.4 Hz, 1H), 3.11-2.96 (sym. m, 2H), 2.52-2.35 (sym. m, 2H), 0.84-0.71 (m, 4H).

Example 107: Preparation of 5-fluoro-N-((1S,3r)-3-(4-(2-fluorophenyl)-5-(5-(methylsulfonyl)pyridin-2-yl)-4H-1,2,4-triazol-3-yl)cyclobutyl) picolinamide

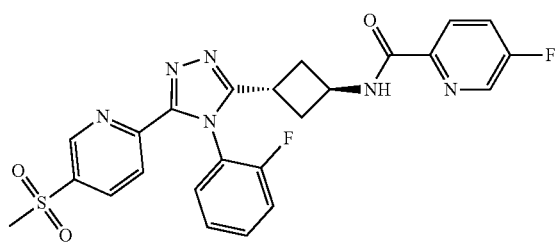

The title compound was prepared according to the general procedure F as a white solid (15.5 mg, 75% yield).

LC/MS (ESI) m/z for $C_{24}H_{20}F_2N_6O_3S$ 510 (calcd) 511 ([M+H]$^+$ found).

$^1$H NMR (400 MHz, Chloroform-d) δ 8.72 (dd, J=2.5, 0.8 Hz, 1H), 8.55 (dd, J=8.4, 0.8 Hz, 1H), 8.36 (d, J=2.7 Hz, 1H), 8.28 (dd, J=8.4, 2.3 Hz, 1H), 8.20 (dd, J=8.7, 4.6 Hz, 1H), 8.05 (d, J=7.1 Hz, 1H), 7.57-7.47 (m, 2H), 7.30-7.17 (m, 3H), 4.86-4.74 (m, 1H), 3.47 (tdd, J=9.9, 5.7, 4.5 Hz, 1H), 3.13-3.03 (m, 1H), 3.08 (s, 3H), 3.03-2.95 (m, 1H), 2.57-2.39 (m, 2H).

Example 108: Preparation of amine building block T: (1r,3r)-3-(4-(pyridin-3-yl)-5-(thiazol-2-yl)-4H-1,2,4-triazol-3-yl)cyclobutan-1-amine trihydrochloride

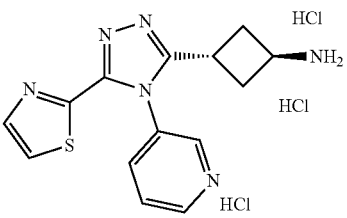

Step (a): N-(pyridin-3-yl)thiazole-2-carboxamide was prepared according to the general procedure A, method a) as a yellow semisolid (423 mg, 67% yield).

LC/MS (ESI) m/z for $C_9H_7N_3OS$ 205 (calcd) 206 ([M+H]$^+$, found).

1H NMR (400 MHz, Chloroform-d) δ 9.15 (br s, 1H), 8.79 (d, J=2.7 Hz, 1H), 8.43 (dd, J=4.8, 1.5 Hz, 1H), 8.31 (ddd, J=8.3, 2.6, 1.5 Hz, 1H), 7.95 (d, J=3.0 Hz, 1H), 7.68 (d, J=3.0 Hz, 1H), 7.35 (dd, J=8.3, 4.7 Hz, 1H).

Step (b): N-(pyridin-3-yl)thiazole-2-carbothioamide was prepared in a crude form following the general procedure 13 as a yellow solid (760 mg, just 40% pure, ~69% yield).

LC/MS (ESI) m/z for $C_9H_7N_3S_2$ 221 (calcd) 222 ([M+H]$^+$, found).

Step (c): methyl N-(pyridin-3-yl)thiazole-2-carbimidothioate was prepared according to the to the general procedure C as a yellow oil (265 mg, 81% yield).

LC/MS (ESI) m/z for $C_{10}H_9N_3S_2$ 235 (calcd) 236 ([M+H]$^+$, found).

Step (d): tert-butyl ((1r,3r)-3-(4-(pyridin-3-yl)-5-(thiazol-2-yl)-4H-1,2,4-triazol-3-yl)cyclobutyl)carbamate was prepared according to the general procedure D as a white foam (397 mg, 95% purity, 80% yield).

LC/MS (ESI) m/z for $C_{19}H_{22}N_6O_2S$ 398 (calcd) 399 ([M+H]$^+$, found).

$^1$H NMR (400 MHz, Chloroform-d) δ 8.77 (dd, J=4.8, 1.5 Hz, 1H), 8.51 (d, J=2.6 Hz, 1H), 7.65-7.58 (m, 2H), 7.48 (dd, J=8.1, 4.8 Hz, 1H), 7.37 (d, J=3.2 Hz, 1H), 4.74 (br s, 1H), 4.36 (apparent h, J=7.3 Hz, 1H), 3.37-3.25 (m, 1H), 2.92-2.80 (symmetrical m, 2H), 2.30 (br s, 2H), 1.42 (s, 9H).

Step (e): the crude title compound was prepared according to the general procedure E as a white powder (373 mg, ~95% purity, 99% yield).

LC/MS (ESI) m/z for $C_{14}H_{14}N_6S$·298 (calcd) 299 ([M+H]$^+$, found).

$^1$H NMR (400 MHz, DMSO-d6) δ 8.84-8.77 (m, 2H), 8.38 (br s, 3H), 8.12 (ddd, J=8.0, 2.5, 1.5 Hz, 1H), 7.88 (d, J=3.2 Hz, 1H), 7.76 (d, J=3.2 Hz, 1H), 7.71 (dd, J=8.1, 4.9 Hz, 1H), 3.84 (apparent h, J=6.4 Hz, 1H), 3.63-3.51 (m, 1H), 2.73 (ddd, J=13.3, 7.9, 5.4 Hz, 2H), 2.34 (ddd, J=12.7, 9.4, 5.6 Hz, 2H).

Example 109: Preparation of N-((1r,3r)-3-(4-(pyridin-3-yl)-5-(thiazol-2-yl)-4H-1,2,4-triazol-3-yl)cyclobutyl)picolinamide

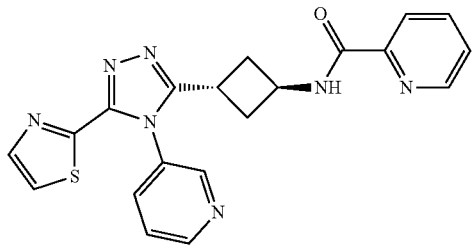

The title compound was prepared according to the general procedure F as a white powder (11.0 mg, 67% yield).

LC/MS (ESI) m/z for $C_{20}H_{17}N_7OS$ 403 (calcd) 404 ([M+H]$^+$, found).

$^1$H NMR (400 MHz, Chloroform-d) δ 8.77 (dd, J=4.9, 1.6 Hz, 1H), 8.56-8.51 (m, 2H), 8.23 (br d, J=6.9 Hz, 1H), 8.16 (dt, J=7.9, 1.1 Hz, 1H), 7.84 (td, J=7.7, 1.7 Hz, 1H), 7.65 (ddd, J=8.1, 2.5, 1.5 Hz, 1H), 7.63 (d, J=3.2 Hz, 1H), 7.48 (dd, J=8.1, 4.8 Hz, 1H), 7.43 (ddd, J=7.7, 4.8, 1.2 Hz, 1H), 7.38 (d, J=3.2 Hz, 1H), 4.87-4.73 (sym. m, 1H), 3.47 (ttd, J=9.5, 5.5, 1.2 Hz, 1H), 3.03 (ddd, J=13.4, 8.2, 5.5 Hz, 2H), 2.54-2.44 (sym. m, 2H).

Example 110: Preparation of amine building block U: (1S,3r)-3-(4-(2-fluorophenyl)-5-(5-isopropoxypyridin-2-yl)-4H-1,2,4-triazol-3-yl)cyclobutan-1-amine dihydrochloride

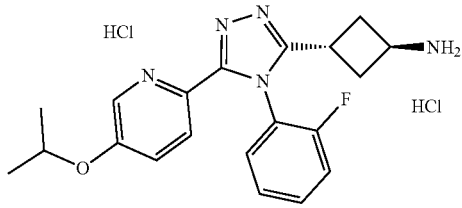

Step (a): N-(2-fluorophenyl)-5-isopropoxypicolinamide was prepared crude according to the general procedure A, method c) as an orange oil solidifying upon standing (564 mg, 95% purity, 98% yield).

LC/MS (ESI) m/z for $C_{15}H_{15}FN_2O_2$ 274 (calcd) 275 ([M+H]$^+$, found).

$^1$H NMR (400 MHz, Chloroform-d) δ 10.13 (br s, 1H), 8.56 (td, J=8.1, 1.7 Hz, 1H), 8.25 (d, J=2.8 Hz, 1H), 8.21 (d, J=8.6 Hz, 1H), 7.30 (dd, J=8.7, 2.8 Hz, 1H), 7.21-7.10 (m, 2H), 7.06 (dddd, J=8.3, 7.1, 5.3, 1.7 Hz, 1H), 4.68 (hept, J=6.1 Hz, 1H), 1.41 (d, J=6.1 Hz, 6H).

Step (b): N-(2-fluorophenyl)-5-isopropoxypyridine-2-carbothioamide was prepared in a crude form following the general procedure B as a yellow solid (460 mg, 80% yield).

LC/MS (ESI) m/z for $C_{15}H_{15}FN_2OS$ 290 (calcd) 291 ([M+H]$^+$, found).

Step (c): methyl N-(2-fluorophenyl)-5-isopropoxypyridine-2-carbimidothioate was prepared according to the general procedure C as a yellow oil (461 mg, 96% yield).

LC/MS (ESI) m/z for $C_{16}H_{17}FN_2OS$ 304 (calcd) 305 ([M+H]$^+$, found).

Step (d): tert-butyl ((1S,3r)-3-(4-(2-fluorophenyl)-5-(5-isopropoxypyridin-2-yl)-4H-1,2,4-triazol-3-yl)cyclobutyl)carbamate was prepared according to the general procedure D as a brown semisolid (345 mg, 89% pure, 66% yield).

LC/MS (ESI) m/z for $C_{25}H_{30}FN_5O_3$ 467 (calcd) 468 ([M+H]$^+$, found).

$^1$H NMR (400 MHz, Chloroform-d) δ 8.12 (d, J=8.7 Hz, 1H), 7.84 (d, J=2.8 Hz, 1H), 7.45 (tdd, J=7.6, 4.9, 2.1 Hz, 1H), 7.25-7.13 (m, 4H), 4.74 (very br s, 1H), 4.53 (hept, J=6.1 Hz, 1H), 4.38-4.24 (sym. m, 1H), 3.31 (very br s, 1H), 2.94-2.77 (m+very br s, 2H), 2.22 (very br s, 2H), 1.42 (s, 9H), 1.31 (d, J=6.1 Hz, 6H).

Step (e): the crude title compound was prepared according to the general procedure E as a brown glass (300 mg, ≈95% purity, 100% yield).

LC/MS (ESI) m/z for $C_{20}H_{22}FN_5O$·367 (calcd) 368 ([M+H]$^+$, found).

Example 111: Preparation of N-((1S,3r)-3-(4-(2-fluorophenyl)-5-(5-isopropoxypyridin-2-yl)-4H-1,2,4-triazol-3-yl)cyclobutyl)picolinamide

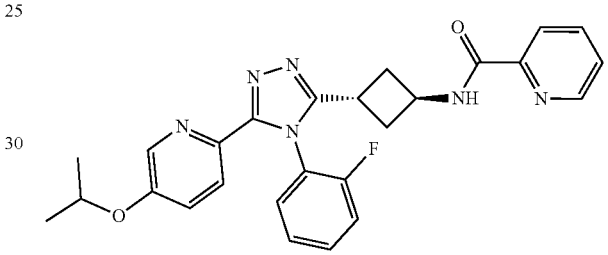

The title compound was prepared according to the general procedure F as a white powder (18.3 mg, 77% yield).

LC/MS (ESI) m/z for $C_{26}H_{25}FN_6O_2$ 472 (calcd) 473 ([M+H]$^+$, found).

$^1$H NMR (400 MHz, Chloroform-d) δ 8.53 (dt, J=4.7, 1.4 Hz, 1H), 8.21 (d, J=6.9 Hz, 1H), 8.18-8.08 (m, 2H), 7.84 (br s, 1H), 7.83 (td, J=7.8, 1.8 Hz, 1H), 7.48-7.38 (m, 2H), 7.25-7.14 (m, 4H), 4.76 (h, J=7.2 Hz, 1H), 4.54 (hept, J=6.0 Hz, 1H), 3.47 (tt, J=10.1, 5.8 Hz, 11-1), 3.11-2.97 (sym. m, 2H), 2.52-2.36 (sym. m, 2H), 1.32 (d, J=6.0 Hz, 6H).

Example 112: Preparation of amine building block V: (1S,3r)-3-(4-(2-fluorophenyl)-5-(5-(methoxy-d3)pyridin-2-yl)-4H-1,2,4-triazol-3-yl)cyclobutan-1-amine dihydro chloride

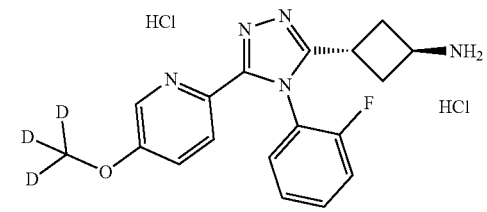

Step (a): N-(2-fluorophenyl)-5-(methoxy-d3)picolinamide was prepared crude according to the general procedure A, method c) as an orange solid (330 mg, 98% purity, 100% yield).

LC/MS (ESI) m/z for $C_{13}H_8D_3FN_2O_2$ 249 (calcd) 250 ([M+H]$^+$, found).

Step (b): N-(2-fluorophenyl)-5-(methoxy-d3)pyridine-2-carbothioamide was prepared following the general procedure B as a yellow solid (260 mg, 75% yield).

LC/MS (ESI) m/z for $C_{13}H_8D_3FN_2OS$ 265 (calcd) 266 ([M+H]$^+$, found).

Step (c): methyl N-(2-fluorophenyl)-5-(methoxy-d3)pyridine-2-carbimidothioate was prepared according to the to the general procedure C as a yellow oil (295 mg, 96% yield).

LC/MS (ESI) m/z for $C_{14}H_{10}D_3FN_2OS$ 279 (calcd) 280 ([M+H]$^+$, found).

Step (d): tert-butyl a 1S,3r)-3-(4-(2-fluorophenyl)-5-(5-(methoxy-d3)pyri din-2-yl)-4H-1,2,4-triazol-3-yl)cyclobutyl)carbamate was prepared according to the general procedure D as a brown foam (354 mg, 75% yield).

LC/MS (ESI) m/z for $C_{23}H_{23}D_3FN_5O_3$ 442 (calcd) 443 ([M+H]$^+$, found).

$^1$H NMR (400 MHz, Chloroform-d) δ 8.16 (d, J=8.7 Hz, 1H), 7.89 (d, J=2.9 Hz, 1H), 7.46 (tdd, J=7.6, 4.9, 1.9 Hz, 1H), 7.25-7.13 (m, 4H), 4.73 (very br s, 1H), 4.39-4.25 (m, 1H), 3.31 (very br s, 1H), 2.94-2.85 (m, 1H), 2.83 (very br s, 1H), 2.24 (very br s, 2H), 1.42 (s, 9H).

Step (e): the crude title compound was prepared according to the general procedure E as a brown glass (336 mg, ~96% purity, 100% yield).

LC/MS (ESI) m/z for $C_{18}H_{15}D_3FN_5O$·342 (calcd) 343 ([M+H]$^+$, found).

Example 113: Preparation of N-((1S,3r)-3-(4-(2-fluorophenyl)-5-(5-(methoxy-d3)pyridin-2-yl)-4H-1,2,4-triazol-3-yl)cyclobutyl)picolinamide Example 114: Preparation of N-((1r,3r)-3-(4-(pyridin-3-yl)-5-(thiazol-2-yl)-4H-1,2,4-triazol-3-yl)cyclobutyl)quinoline-8-carboxamide

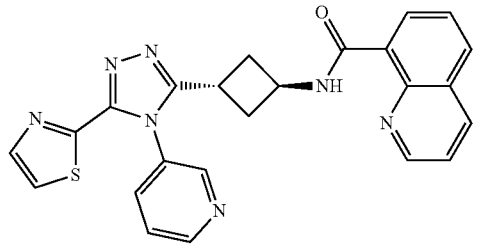

The title compound was prepared according to the general procedure F as a white solid (20.0 mg, 87% yield).

LC/MS (ESI) m/z for $C_{24}H_{19}N_7OS$ 453 (calcd) 454 ([M+H]$^+$, found).

$^1$H NMR (400 MHz, Chloroform-d) δ 11.57 (d, J=5.8 Hz, 1H), 8.91 (dd, J=4.3, 1.9 Hz, 1H), 8.82 (dd, J=7.4, 1.6 Hz, 1H), 8.76 (dd, J=4.8, 1.5 Hz, 1H), 8.56 (d, J=2.5 Hz, 1H), 8.28 (dd, J=8.3, 1.8 Hz, 1H), 7.96 (dd, J=8.1, 1.6 Hz, 1H), 7.71-7.64 (m, 2H), 7.63 (d, J=3.2 Hz, 1H), 7.48 (ddd, J=9.7, 8.2, 4.6 Hz, 2H), 7.37 (d, J=3.2 Hz, 1H), 4.91-4.79 (sym. m, 1H), 3.56 (ttd, J=9.4, 5.7, 1.3 Hz, 1H), 3.09 (ddd, J=13.5, 8.4, 5.6 Hz, 2H), 2.59 (ddd, J=12.9, 9.4, 6.0 Hz, 2H).

Example 115: Preparation of N-((1S,3r)-3-(5-(5-ethoxypyridin-2-yl)-4-(2-fluorophenyl)-4H-1,2,4-triazol-3-yl)cyclobutyl)-1H-indole-7-carboxamide

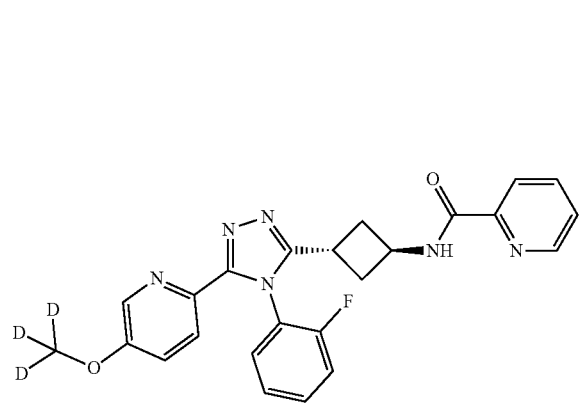

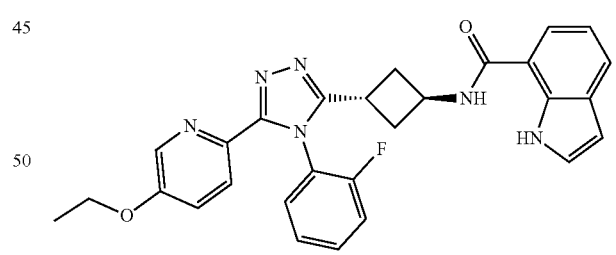

The title compound was prepared according to the general procedure F as a white solid (17.5 mg, 77% yield).

LC/MS (ESI) m/z for $C_{24}H_8D_3FN_6O_2$ 447 (calcd) 448 ([M+H]$^+$, found).

$^1$H NMR (400 MHz, Chloroform-d) δ 8.53 (dt, J=4.7, 1.3 Hz, 1H), 8.21 (d, J=6.9 Hz, 1H), 8.20-8.13 (m, 2H), 7.89 (br d, J=2.9 Hz, 1H), 7.83 (td, J=7.7, 1.7 Hz, 1H), 7.49-7.38 (m, 2H), 7.26-7.14 (m, 4H), 4.76 (apparent h, J=6.8 Hz, 1H), 3.52-3.41 (sym. m, 1H), 3.11-2.96 (sym. m, 2H), 2.52-2.35 (sym. m, 2H).

The title compound was prepared according to the general procedure F as a white powder (21.4 mg, 85% yield).

LC/MS (ESI) m/z for $C_{28}H_{25}FN_6O_2$ 496 (calcd) 497 ([M+H]$^+$, found).

$^1$H NMR (400 MHz, Chloroform-d) δ 10.27 (br s, 1H), 8.21 (very br s, 1H), 7.79 (d, J=7.7 Hz, 1H), 7.49-7.40 (m, 1H), 7.34 (d, J=7.4 Hz, 1H), 7.30 (t, J=2.8 Hz, 1H), 7.26-7.15 (m, 5H), 7.09 (t, J=7.6 Hz, 1H), 6.55 (dd, J=3.1, 2.1 Hz, 1H), 6.52 (d, J=5.8 Hz, 1H), 4.79 (h, J=6.4 Hz, 1H), 4.04 (q, J=7.0 Hz, 2H), 3.49 (br s, 1H), 3.13-2.98 (sym. m, 2H), 2.50-2.33 (sym. m, 2H), 1.40 (t, J=6.9 Hz, 3H).

Example 116: Preparation of N-((1S,3r)-3-(5-(5-ethoxypyridin-2-yl)-4-(2-fluorophenyl)-4H-1,2,4-triazol-3-yl)cyclobutyl)-2,3-dihydrobenzo[b][1,4]dioxine-5-carboxamide

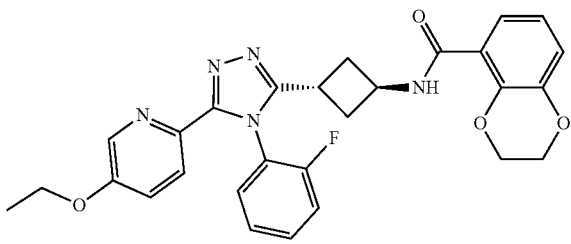

The title compound was prepared according to the general procedure F as a white powder (23.1 mg, 89% yield).

LC/MS (ESI) m/z for $C_{28}H_{26}FN_5O_4$ 515 (calcd) 516 ([M+H]$^+$, found).

$^1$H NMR (400 MHz, Chloroform-d) δ 8.16 (very br s, 1H), 7.88 (very br s, 1H), 7.77 (d, J 5.7 Hz, 1H), 7.68 (dd, J=7.8, 1.9 Hz, 1H), 7.48-7.39 (m, 1H), 7.25-7.13 (m, 4H), 6.98 (dd, J=8.0, 1.9 Hz, 1H), 6.91 (t, J=7.9 Hz, 1H), 4.66 (h, J=6.7 Hz, 1H), 4.44-4.37 (m, 2H), 4.33-4.27 (m, 2H), 4.04 (q, J=7.0 Hz, 2H), 3.52-3.38 (sym. m, 1H), 3.05-2.94 (sym. m, 2H), 2.48-2.32 (sym. m, 2H), 1.40 (t, J=6.9 Hz, 3H).

Example 117: Preparation of N-((1S,3r)-3-(5-(5-ethoxypyridin-2-yl)-4-(2-fluorophenyl)-4H-1,2,4-triazol-3-yl)cyclobutyl)-1-methyl-1H-imidazole-4-carboxamide

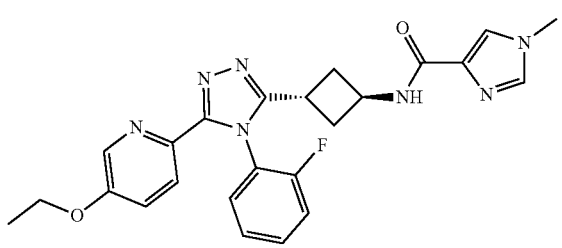

The title compound was prepared according to the general procedure F as a white powder (19.0 mg, 82% yield).

LC/MS (ESI) m/z for $C_{24}H_{24}FN_7O_2$ 461 (calcd) 462 ([M+H]$^+$, found).

$^1$H NMR (400 MHz, Chloroform-d) δ 8.14 (d, J=8.7 Hz, 1H), 7.87 (d, J=3.0 Hz, 1H), 7.48 (d, J=1.2 Hz, 1H), 7.47-7.40 (m, 1H), 7.33 (d, J=1.5 Hz, 1H), 7.24-7.13 (m, 5H), 4.70 (hd, J=7.0, 1.1 Hz, 1H), 4.03 (q, J=7.0 Hz, 2H), 3.71 (s, 3H), 3.50-3.38 (sym. m, 1H), 3.06-2.92 (sym. m, 2H), 2.43-2.26 (sym. m, 2H), 1.39 (t, J=7.0 Hz, 3H).

Example 118: Preparation of N-((1S,3r)-3-(5-(5-ethoxypyridin-2-yl)-4-(2-fluorophenyl)-4H-1,2,4-triazol-3-yl)cyclobutyl)imidazo[1,2-a]pyridine-2-carboxamide The title compound was prepared according to the general procedure F as a white solid (14.2 mg, 56% yield).

LC/MS (ESI) m/z for $C_{27}H_{24}FN_7O_2$ 497 (calcd) 498 ([M+H]$^+$, found).

$^1$H NMR (400 MHz, Chloroform-d) δ 8.18-8.12 (m, 2H), 8.11 (s, 1H), 7.88 (d, J=2.9 Hz, 1H), 7.58-7.49 (m, 2H), 7.49-7.40 (m, 1H), 7.26-7.14 (m, 5H), 6.85 (td, J=6.8, 1.2 Hz, 1H), 4.77 (hd, J=7.1, 1.0 Hz, 1H), 4.04 (q, J=7.0 Hz, 2H), 3.53-3.43 (sym. m, 1H), 3.11-2.97 (sym. m, 2H), 2.50-2.34 (sym. m, 2H), 1.40 (t, J=7.0 Hz, 3H).

Example 119: Preparation of N-((1S,3r)-3-(5-(5-ethoxypyridin-2-yl)-4-(2-fluorophenyl)-4H-1,2,4-triazol-3-yl)cyclobutyl)-6-methylpicolinamide

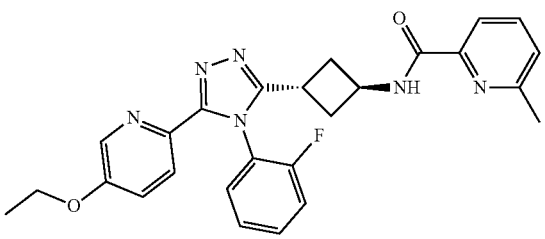

The title compound was prepared according to the general procedure F as a white solid (18.4 mg, 77% yield).

LC/MS (ESI) m/z for $C_{26}H_{25}FN_6O_2$ 472 (calcd) 473 ([M+11]$^+$, found).

$^1$H NMR (400 MHz, Chloroform-d) δ 8.26 (d, J=6.9 Hz, 1H), 8.16 (d, J=8.7 Hz, 1H), 7.96 (d, J=7.7 Hz, 1H), 7.88 (br s, 1H), 7.70 (t, J=7.7 Hz, 1H), 7.48-7.40 (m, 1H), 7.26-7.13 (m, 5H), 4.75 (h, J=7.2 Hz, 1H), 4.04 (q, J=6.9 Hz, 2H), 3.48 (tt, J=9.7, 5.4 Hz, 1H), 3.09-2.96 (sym. m, 2H), 2.56 (s, 3H), 2.55-2.39 (sym. m, 2H), 1.40 (t, J=7.0 Hz, 3H).

Example 120: Preparation of N-((1S,3r)-3-(5-(5-ethoxypyridin-2-yl)-4-(2-fluorophenyl)-4H-1,2,4-triazol-3-yl)cyclobutyl)-1-methyl-1H-pyrazole-3-carboxamide

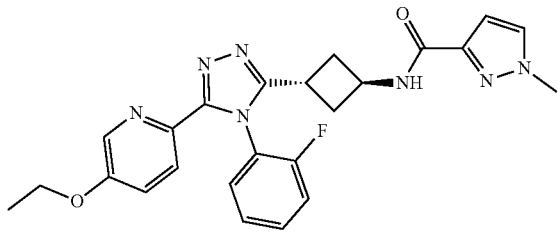

The title compound was prepared according to the general procedure F as a white solid (10.9 mg, 47% yield).

LC/MS (ESI) m/z for $C_{24}H_{24}FN_7O_2$ 461 (calcd) 462 ([M+H]$^+$, found).

$^1$H NMR (400 MHz, Chloroform-d) δ 8.15 (d, J=8.8 Hz, 1H), 7.88 (d, J=2.8 Hz, 1H), 7.48-7.40 (m, 1H), 7.34 (d, J=2.3 Hz, 1H), 7.24-7.14 (m, 4H), 7.00 (d, J=6.7 Hz, 1H), 6.76 (d, J=2.3 Hz, 1H), 4.69 (h, J=6.9 Hz, 1H), 4.04 (q, J=7.0 Hz, 2H), 3.91 (s, 3H), 3.45 (tt, J=9.9, 5.7 Hz, 1H), 3.06-2.93 (sym. m, 2H), 2.46-2.30 (sym. m, 2H), 1.40 (t, J=7.0 Hz, 3H).

Example 121: Preparation of amine building block W: 3-(5-(5-ethoxypyridin-2-yl)-4-(pyridin-2-yl)-4H-1,2,4-triazol-3-yl)bicyclo[1.1.1]pentan-1-amine trihydrochloride

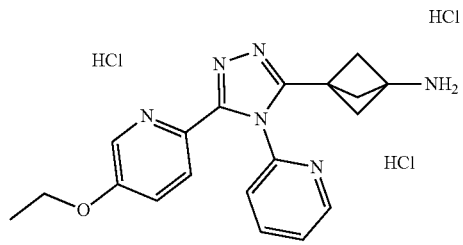

Step (a): tert-butyl (3-(5-(5-ethoxypyridin-2-yl)-4-(pyridin-2-yl)-4H-1,2,4-triazol-3-yl)bicyclo[1.1.1]pentan-1-yl)carbamate was prepared according to the general procedure D as a colourless glass (116 mg, 93% purity, 83% yield) from methyl 5-ethoxy-N-(pyridin-2-yl)pyridine-2-carbimidothioate and tert-butyl (3-(hydrazinecarbonyl)bicyclo[1.1.1]pentan-1-yl)carbamate (Example 2).

LC/MS (ESI) m/z for $C_{24}H_{28}N_6O_3$ 448 (calcd) 449 ([M+H]$^+$, found).

$^1$H NMR (400 MHz, Chloroform-d) δ 8.59 (dd, J=4.8, 1.9 Hz, 1H), 8.13 (d, J=8.8 Hz, 1H), 7.88-7.78 (m, 2H), 7.43 (dd, J=7.4, 4.7 Hz, 1H), 7.28 (d, J=7.5 Hz, 1H), 7.20 (dd, J=8.8, 2.9 Hz, 1H), 4.90 (very br s, 1H), 4.02 (q, J=7.0 Hz, 2H), 2.19 (s, 6H), 1.40 (s, 9H), 1.39 (t, J=7.0 Hz, 3H).

Step (b): the crude title compound was prepared according to the general procedure E as a white, yellow-tinted solid (108 mg, 97% yield).

LC/MS (ESI) m/z for $C_{19}H_{20}N_6O$·348 (calcd) 349 ([M+H]$^+$, found).

Example 122: Preparation of N-(3-(5-(5-ethoxypyridin-2-yl)-4-(pyridin-2-yl)-4H-1,2,4-triazol-3-yl)bicyclo[1.1.1]pentan-1-yl)-1,5-naphthyridine-4-carboxamide

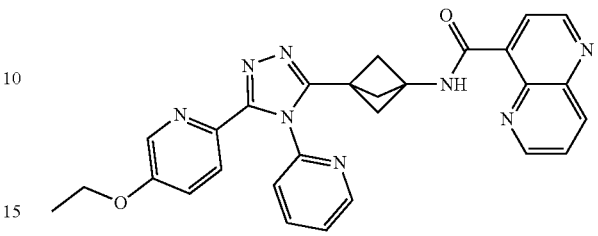

The title compound was prepared according to the general procedure F as a white powder (12.1 mg, 48% yield).

LC/MS (ESI) m/z for $C_{28}H_{24}N_8O_2$ 504 (calcd) 505 ([M+H]$^+$, found).

$^1$H NMR (400 MHz, Chloroform-d) δ 11.46 (br s, 1H), 9.14 (d, J=4.5 Hz, 1H), 9.00 (dd, J=4.3, 1.7 Hz, 1H), 8.63 (dd, J=5.1, 1.8 Hz, 1H), 8.55 (dd, J=8.6, 1.7 Hz, 1H), 8.50 (d, J=4.4 Hz, 1H), 8.15 (d, J=8.8 Hz, 1H), 7.87 (td, J=7.7, 1.9 Hz, 1H), 7.84 (d, J=3.0 Hz, 1H), 7.75 (dd, J=8.6, 4.3 Hz, 1H), 7.46 (ddd, J=7.6, 4.8, 1.0 Hz, 1H), 7.34 (d, J=7.9 Hz, 1H), 7.21 (dd, J=8.7, 2.9 Hz, 1H), 4.03 (q, J=7.0 Hz, 2H), 2.48 (s, 6H), 1.40 (t, J=7.0 Hz, 3H).

Example 123: Preparation of amine building block X: (1r,3r)-3-(5-(5-ethoxypyridin-2-yl)-4-(pyridin-2-yl)-4H-1,2,4-triazol-3-yl)cyclobutan-1-amine trihydrochloride

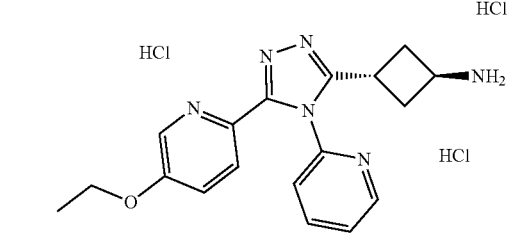

Step (a): 5-ethoxy-N-(pyridin-2-yl)picolinamide was prepared according to the general procedure A, method c) as a white solid with an orange tint (737 mg, 99% yield).

LC/MS (ESI) m/z for $C_{13}H_{13}N_3O_2$ 243 (calcd) 244 ([M+H]$^+$, found).

$^1$H NMR (400 MHz, Chloroform-d) δ 10.38 (ln s, 1H), 8.41 (dt, J=8.3, 1.0 Hz, 1H), 8.35 (ddd, J=4.9, 2.0, 0.9 Hz, 1H), 8.27 (d, J=2.8 Hz, 1H), 8.22 (d, J=8.7 Hz, 1H), 7.75 (ddd, J=8.8, 7.3, 2.0 Hz, 1H), 7.31 (dd, J=8.7, 2.9 Hz, 1H), 7.05 (ddd, J=7.2, 4.8, 1.0 Hz, 1H), 4.16 (q, J=7.0 Hz, 2H), 1.48 (t, J=7.0 Hz, 3H).

Step (b): 5-ethoxy-N-(pyridin-2-yl)pyridine-2-carbothioamide was prepared following the general procedure B as a yellow solid (449 mg, 58% yield).

LC/MS (ESI) m/z for $C_{13}H_{13}N_3OS$ 259 (calcd) 260 ([M+H]$^+$, found).

Step (c): methyl 5-ethoxy-N-(pyridin-2-yl)pyridine-2-carbimidothioate was prepared according to the to the general procedure C as a pale yellow oil (175 mg, 90% purity, 32% yield).

LC/MS (ESI) m/z for C₁₄H₁₅N₃OS 273 (calcd) 274 ([M+H]⁺, found).

¹H NMR (400 MHz, Chloroform-d) δ 8.38 (d, J=4.7 Hz, 1H), 8.26 (d, J=2.9 Hz, 1H), 7.54 (t, J=7.3 Hz, 1H), 7.35-7.20 (br m, 1H), 7.03 (distorted d, J=8.6 Hz, 1H), 6.94 (dd, J=7.4, 4.9 Hz, 1H), 6.71 (br s, 1H), 4.07 (q, J=7.0 Hz, 2H), 2.43 (br s, 3H), 1.42 (t, J=7.0 Hz, 3H).

Step (d): tert-butyl ((1r,3r)-3-(5-(5-ethoxypyridin-2-yl)-4-(pyridin-2-yl)-4H-1,2,4-triazol-3-yl)cyclobutyl)carbamate was prepared according to the general procedure D as a colourless glass (134 mg, 92% purity, 97% yield).

LC/MS (ESI) m/z for C₂₃H₂₈N₆O₃ 436 (calcd) 437 ([M+H]⁺, found).

¹H NMR (400 MHz, Chloroform-d) δ 8.55 (dd, J=4.7, 2.0 Hz, 1H), 8.13 (d, J=8.8 Hz, 1H), 7.85 (d, J=2.8 Hz, 1H), 7.79 (td, J=7.8, 2.0 Hz, 1H), 7.38 (dd, J=7.5, 4.8 Hz, 1H), 7.23 (dd, J=8.7, 2.9 Hz, 1H), 7.15 (d, J=7.9 Hz, 1H), 4.74 (very br s, 1H), 4.28 (apparent h, J=7.2 Hz, 1H), 4.03 (q, J=6.9 Hz, 2H), 3.48 (br s, 1H), 2.85 (ddd, J=13.1, 8.1, 5.4 Hz, 2H), 2.21 (br s, 2H), 1.42 (s, 9H), 1.39 (t, J=7.0 Hz, 3H).

Step (e): the crude title compound was prepared according to the general procedure E as a white, orange-tinted solid (125 mg, ~95% purity, 95% yield).

LC/MS (ESI) m/z for C₁₈H₂₀N₆O·336 (calcd) 337 ([M+H]⁺, found).

Example 124: Preparation of N-((1r,3r)-3-(5-(5-ethoxypridin-2-yl)-4-(pyridin-2-yl)-4H-1,2,4-triazol-3-yl)cyclobutyl)-1,5-naphthyridine-4-carboxamide

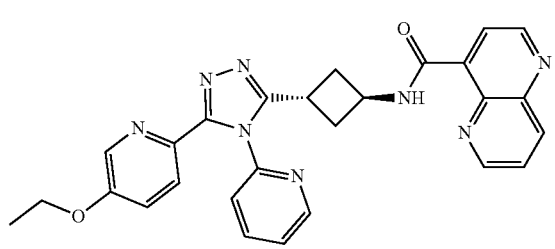

The title compound was prepared according to the general procedure F as a white powder (13.7 mg, 55% yield).

LC/MS (ESI) m/z for C₂₇H₂₄N₈O₂ 492 (calcd) 493 ([M+H]⁺, found).

¹H NMR (400 MHz, Chloroform-d) δ 11.32 (d, J=6.0 Hz, 1H), 9.14 (d, J=4.4 Hz, 1H), 8.99 (dd, J=4.3, 1.8 Hz, 1H), 8.59-8.52 (m, 3H), 8.17 (d, J=8.8 Hz, 1H), 7.87 (d, J=2.9 Hz, 1H), 7.79 (td, J=7.7, 1.9 Hz, 1H), 7.75 (dd, J=8.5, 4.2 Hz, 1H), 7.37 (ddd, J=7.5, 4.9, 1.0 Hz, 1H), 7.24 (dd, J=8.9, 2.9 Hz, 1H), 7.18 (dt, J=7.9, 1.0 Hz, 1H), 4.79 (h, J=6.9 Hz, 1H), 4.05 (q, J=6.9 Hz, 2H), 3.74 (ttd, J=9.5, 5.8, 0.9 Hz, 1H), 3.06 (ddd, J=13.2, 8.0, 5.4 Hz, 2H), 2.52 (ddd, J=12.7, 9.4, 6.0 Hz, 2H), 1.41 (t, J=7.0 Hz, 3H).

Example 125: Preparation of N-((1S,3r)-3-(5-(5-ethoxypyridin-2-yl)-4-(2-fluorophenyl)-4H-1,2,4-triazol-3-yl)cyclobutyl)-6-(trifluoromethyl)picolinamide

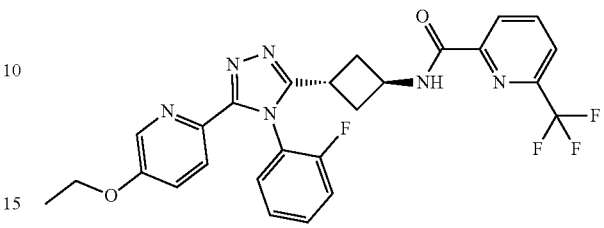

The title compound was prepared according to the general procedure F as a white solid (14.3 mg, 54% yield).

LC/MS (ESI) m/z for C₂₆H₂₂F₄N₆O₂ 526 (calcd) 527 ([M+H]⁺, found).

¹H NMR (400 MHz, Chloroform-d) δ 8.37 (d, J=7.8 Hz, 1H), 8.16 (d, J=8.7 Hz, 1H), 8.09-8.00 (m, 2H), 7.88 (br s, 1H), 7.80 (dd, J=7.8, 1.1 Hz, 1H), 7.49-7.40 (m, 1H), 7.25-7.14 (m, 4H), 4.83 (h, J=7.3 Hz, 1H), 4.04 (q, J=7.0 Hz, 2H), 3.46 (tt, J=10.4, 5.0 Hz, 1H), 3.12-2.95 (sym. m, 2H), 2.57-2.40 (sym. m, 2H), 1.40 (t, J=7.0 Hz, 3H).

Example 126: Preparation of N-((1S,3r)-3-(5-(5-ethoxypyridin-2-yl)-4-(2-fluorophenyl)-4H-1,2,4-triazol-3-yl)cyclobutyl)-1H-pyrrolo[2,3-c]pyridine-2-carboxamide

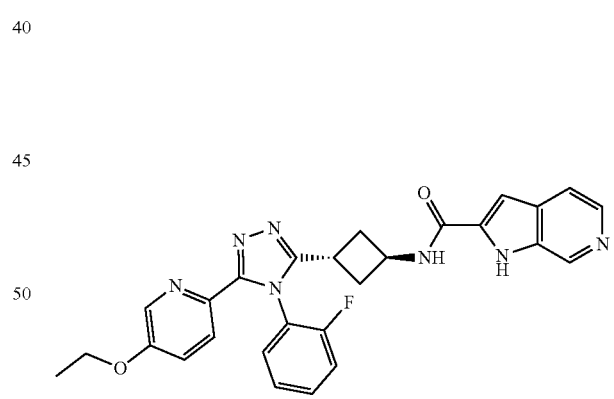

The title compound was prepared according to the general procedure F as a white solid (12.8 mg, 51% yield).

LC/MS (ESI) m/z for C₂₇H₂₄FN₇O₂ 497 (calcd) 498 ([M+H]⁺, found).

¹H NMR (400 MHz, Chloroform-d) δ 9.94 (very br s, 1H), 8.87 (br s, 1H), 8.28 (br s, 1H), 8.11 (d, J=8.7 Hz, 1H), 7.89 (s, 1H), 7.53 (br s, 1H), 7.49-7.37 (m, 1H), 7.24-7.12 (m, 4H), 6.90 (d, J=6.4 Hz, 1H), 6.88 (s, 1H), 4.88-4.74 (m, 1H), 4.03 (q, J=6.9 Hz, 2H), 3.44 (tt, J=9.5, 4.8 Hz, 1H), 3.08-2.90 (sym. m, 2H), 2.61-2.44 (sym. m, 2H), 1.40 (t, J=7.0 Hz, 3H).

Example 127: Preparation of N-((1S,3r)-3-(5-(5-ethoxypyridin-2-yl)-4-(2-fluorophenyl)-4H-1,2,4-triazol-3-yl)cyclobutyl)-5-methoxy-1H-pyrrolo[2,3-c]pyridine-2-carboxamide

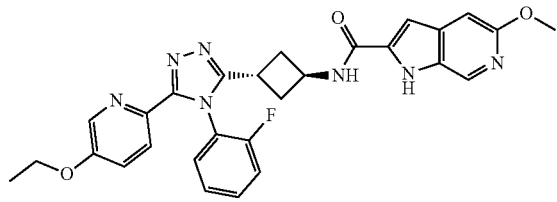

The title compound was prepared according to the general procedure F as a white solid (16 mg, 58% yield).

LC/MS (ESI) m/z for $C_{28}H_{26}FN_7O_3$ 527 (calcd) 528 ([M-FH]$^+$, found).

$^1$H NMR (400 MHz, Chloroform-d) δ 9.27 (br s, 1H), 8.46 (s, 1H), 8.13 (d, J=8.7 Hz, 1H), 7.88 (d, J=2.8 Hz, 1H), 7.50-7.41 (m, 1H), 7.24-7.15 (m, 4H), 6.89 (s, 1H), 6.70 (s, 1H), 6.58 (d, J=6.4 Hz, 1H), 4.80 (h, J=7.3 Hz, 1H), 4.04 (q, J=7.0 Hz, 2H), 3.96 (s, 3H), 3.44 (tt, J=9.4, 5.3 Hz, 1H), 3.09-2.92 (sym. m, 2H), 2.57-2.40 (sym. m, 2H), 1.40 (t, J=7.0 Hz, 3H).

Example 128: Preparation of N-((1R,3r)-3-(5-(5-ethoxypyridin-2-yl)-4-(2-fluorophenyl)-4H-1,2,4-triazol-3-yl)cyclobutyl)-6-(1-hydroxyethyl)picolinamide

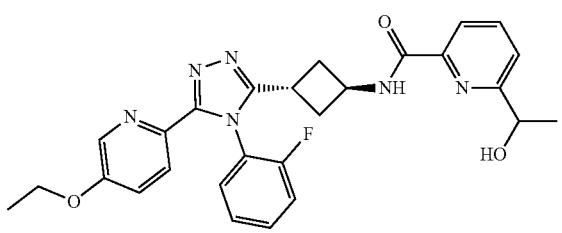

The title compound was prepared employing the crude potassium salt of the acid according to the general procedure F as a white, hygroscopic solid (15.1 mg, 54% yield).

LC/MS (ESI) m/z for $C_{27}H_{27}FN_6O_3$ 502 (calcd) 503 ([M+H]$^+$, found).

$^1$H NMR (400 MHz, Chloroform-d) δ 8.16 (d, J=8.8 Hz, 1H), 8.08 (dd, J=7.7, 1.1 Hz, 1H), 8.02 (d, J=6.9 Hz, 1H), 7.88 (d, J=2.8 Hz, 1H), 7.85 (t, J=7.7 Hz, 1H), 7.48 (d, J=7.8 Hz, 1H), 7.47-7.40 (m, 1H), 7.24-7.14 (m, 4H), 5.01-4.91 (sym. m, 1H), 4.78 (h, J=7.5 Hz, 1H), 4.04 (q, J=7.0 Hz, 2H), 3.46 (tt, J=10.0, 5.1 Hz, 1H), 3.22 (d, J=4.7 Hz, 1H), 3.11-2.95 (sym. m, 2H), 2.56-2.39 (sym. m, 2H), 1.54 (d, J=6.5 Hz, 3H), 1.40 (t, J=7.0 Hz, 3H).

Example 129: Preparation of N-((1S,3r)-3-(5-(5-ethoxypyridin-2-yl)-4-(2-fluorophenyl)-4H-1,2,4-triazol-3-yl)cyclobutyl)-6-(2-hydroxypropan-2-yl)picolinamide

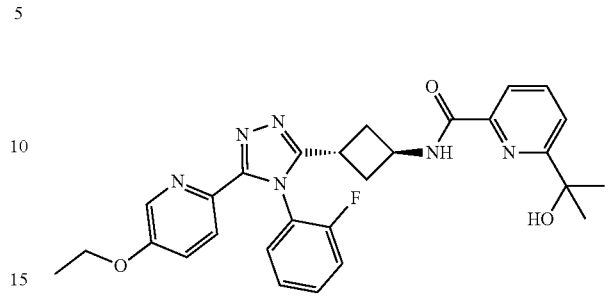

The title compound was prepared employing the crude potassium salt of the acid according to the general procedure F as a white solid (19.6 mg, 74% yield).

LC/MS (ESI) m/z for $C_{28}H_{29}FN_6O_3$ 516 (calcd) 517 ([M+H]$^+$, found).

$^1$H NMR (400 MHz, Chloroform-d) δ 8.16 (d, J=8.7 Hz, 1H), 8.08 (dd, J=7.6, 1.0 Hz, 1H), 7.93 (d, J=6.9 Hz, 1H), 7.90-7.82 (m, 2H), 7.58 (dd, J=7.9, 1.0 Hz, 1H), 7.49-7.40 (m, 1H), 7.25-7.14 (m, 4H), 4.79 (h, J=7.3 Hz, 1H), 4.04 (q, J=7.0 Hz, 2H), 3.84 (br s, 1H), 3.46 (tt, J=10.3, 5.3 Hz, 1H), 3.11-2.95 (sym. m, 2H), 2.56-2.39 (sym. m, 2H), 1.57 (s, 6H), 1.40 (t, J=7.0 Hz, 3H).

Example 130: Preparation of N-((1R,3r)-3-(4-(2-chlorophenyl)-5-(pyrimidin-4-yl)-4H-1,2,4-triazol-3-yl)cyclobutyl)-5-ethoxypicolinamide

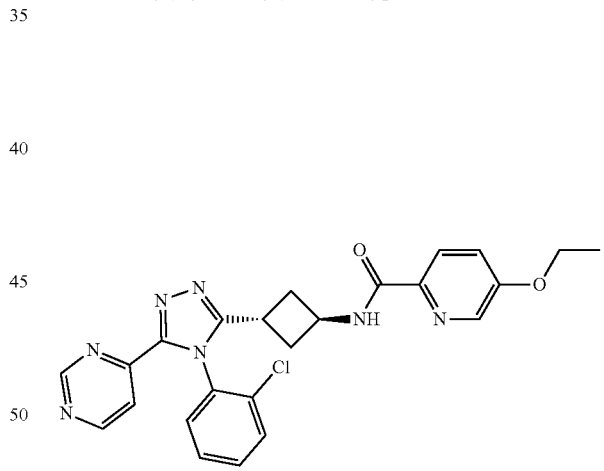

The title compound was prepared according to the general procedure F as a white solid (19.0 mg, 79% yield).

LC/MS (ESI) m/z for $C_{24}H_{22}ClN_7O_2$ 475/477 (calcd) 476/478 ([M+H]$^+$ found).

$^1$H NMR (400 MHz, Chloroform-d) δ 8.82 (s, 1H), 8.81 (d, J=3.5 Hz, 1H), 8.28 (dd, J=5.3, 1.4 Hz, 1H), 8.16 (d, J=2.8 Hz, 1H), 8.09 (d, J=8.6 Hz, 1H), 8.02 (d, J=7.0 Hz, 1H), 7.53 (dd, J=8.0, 1.6 Hz, 1H), 7.48 (td, J=7.7, 1.7 Hz, 1H), 7.42 (td, J=7.6, 1.7 Hz, 1H), 7.29 (dd, J=7.8, 1.7 Hz, 1H), 7.24 (dd, J=8.9, 2.9 Hz, 1H), 4.76 (h, J=7.4, 6.9 Hz, 1H), 4.12 (q, J=6.9 Hz, 2H), 3.42 (ttd, J=9.4, 5.6, 1.1 Hz, 1H), 3.10-2.98 (m, 2H), 2.50-2.35 (m, 2H), 1.46 (t, J=7.0 Hz, 3H).

Example 131: Preparation of N-((1R,3r)-3-(4-(2-chlorophenyl)-5-(pyrimidin-4-yl)-4H-1,2,4-triazol-3-yl)cyclobutyl)-5-methoxypicolinamide

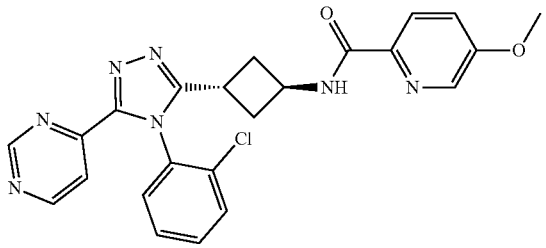

The title compound was prepared according to the general procedure F as a white solid (9.5 mg, 41% yield).

LC/MS (ESI) m/z for $C_{23}H_{20}ClN_7O_2$ 461/463 (calcd) 462/464 ([M+H]$^+$ found).

$^1$H NMR (400 MHz, Chloroform-d) δ 8.82 (s, 1H), 8.81 (d, J=3.5 Hz, 1H), 8.28 (dd, J=5.2, 1.4 Hz, 1H), 8.18 (d, J=2.8 Hz, 1H), 8.11 (d, J=8.7 Hz, 1H), 8.03 (d, J=7.0 Hz, 1H), 7.54 (dd, J=8.0, 1.7 Hz, 1H), 7.48 (td, J=7.7, 1.7 Hz, 1H), 7.42 (td, J=7.6, 1.7 Hz, 1H), 7.32-7.25 (m, 2H), 4.83-4.70 (m, 1H), 3.90 (s, 3H), 3.47-3.36 (m, 1H), 3.10-2.99 (m, 2H), 2.51-2.35 (m, 2H).

Example 132: Preparation of N-((1R,3r)-3-(4-(2-chlorophenyl)-5-(pyrimidin-4-yl)-4H-1,2,4-triazol-3-yl)cyclobutyl)-3-cyanobenzamide

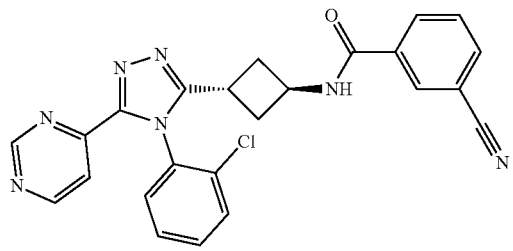

The title compound was prepared according to the general procedure F as a white solid (17.5 mg, 76% yield).

LC/MS (ESI) m/z for $C_{24}H_{18}ClN_7O$ 455/457 (calcd) 456/458 ([M+H]$^+$ found).

$^1$H NMR (400 MHz, Chloroform-d) δ 8.82 (s, 1H), 8.81 (d, J=3.3 Hz, 1H), 8.26 (dd, J=5.3, 1.5 Hz, 1H), 8.04 (t, J=1.8 Hz, 1H), 8.01 (dt, J=7.9, 1.5 Hz, 1H), 7.78 (dt, J=7.8, 1.4 Hz, 1H), 7.61-7.52 (m, 2H), 7.50 (td, J=7.7, 1.7 Hz, 1H), 7.43 (td, J=7.5, 1.7 Hz, 1H), 7.31 (dd, J=7.7, 1.6 Hz, 1H), 6.47 (d, J=6.3 Hz, 1H), 4.85-4.73 (m, 1H), 3.45-3.34 (m, 1H), 3.10-2.98 (m, 2H), 2.52-2.38 (m, 2H).

Example 133: Preparation of amine building block Y: (1S,3r)-3-(4-(2-chlorophenyl)-5-(5-ethoxypyridin-2-yl)-4H-1,2,4-triazol-3-yl)cyclobutan-1-amine trihydrochloride

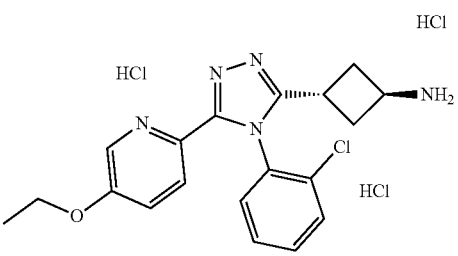

Step (a): N-(2-chlorophenyl)-5-ethoxypicolinamide was prepared according to the general procedure A, method a) as an off-white solid (596 mg, 72% yield).

GC/MS (EI) m/z for $C_{14}H_{13}ClN_2O_2$ 276/278 (calcd) 276/278 ([M]$^+$, found).

$^1$H NMR (400 MHz, Chloroform-d) δ 10.53 (br s, 1H), 8.64 (dd, J=8.3, 1.5 Hz, 1H), 8.30 (d, J=2.8 Hz, 1H), 8.23 (d, J=8.6 Hz, 1H), 7.42 (dd, J=8.0, 1.5 Hz, 1H), 7.36-7.29 (m, 2H), 7.06 (td, J=7.7, 1.5 Hz, 1H), 4.17 (q, J=7.0 Hz, 2H), 1.49 (t, J=7.0 Hz, 3H).

Step (b): N-(2-chlorophenyl)-5-ethoxypyridine-2-carbothioamide was prepared following the general procedure B as a yellow solid (447 mg, 95% pure, 80% yield).

$^1$H NMR (400 MHz, Chloroform-d) δ 12.25 (br s, 1H), 9.00 (dd, J=8.3, 1.5 Hz, 1H), 8.74 (d, J=8.8 Hz, 1H), 8.23 (d, J=2.8 Hz, 1H), 7.50 (dd, J=8.0, 1.5 Hz, 1H), 7.37 (td, J=7.8, 1.5 Hz, 1H), 7.31 (dd, J=8.9, 2.9 Hz, 1H), 7.21 (td, J=7.7, 1.6 Hz, 1H), 4.18 (q, J=7.0 Hz, 2H), 1.49 (t, J=7.0 Hz, 3H).

Step (c): methyl N-(2-chlorophenyl)-5-ethoxypyridine-2-carbimidothioate was prepared according to the to the general procedure C as a yellow oil (401 mg, 85% yield).

LC/MS (ESI) m/z for $C_{15}H_{15}ClN_2OS$ 306/308 (calcd) 307/309 ([M+H]$^+$, found). 1H NMR (400 MHz, Chloroform-d) δ 8.31 (d, J=2.8 Hz, 1H), 7.37 (d, J=8.4 Hz, 1H), 7.18-7.02 (br m, 3H), 6.98 (t, J=8.0 Hz, 1H), 6.75 (br s, 1H), 4.08 (q, J=7.0 Hz, 2H), 2.41 (br s, 3H), 1.44 (t, J=6.9 Hz, 3H).

Step (d): tert-butyl ((1S,3r)-3-(4-(2-chlorophenyl)-5-(5-ethoxypyridin-2-yl)-4H-1,2,4-triazol-3-yl)cyclobutyl)carbamate was prepared according to the general procedure D as a yellow oil (145 mg, 95% pure, 86% yield).

LC/MS (ESI) m/z for $C_{24}H_{28}ClN_5O_3$ 469/471 (calcd) 470/472 ([M+H]$^+$, found).

Step (e): the title compound was prepared crude according to the general procedure E as a yellow glass (147 mg, 94% pure, 93% yield).

LC/MS (ESI) m/z for $C_{19}H_{20}ClN_5O$·369/371 (calcd) 370/372 ([M+H]$^+$, found).

Example 134: Preparation of N-((1S,3r)-3-(4-(2-chlorophenyl)-5-(5-ethoxypyridin-2-yl)-4H-1,2,4-triazol-3-yl)cyclobutyl)picolinamide

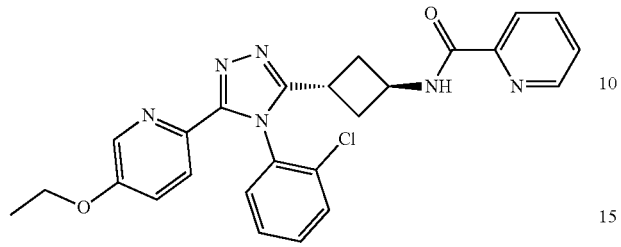

The title compound was prepared according to the general procedure F as a white solid (16.8 mg, 45% yield).

LC/MS (ESI) m/z for $C_{25}H_{23}ClN_6O_2$ 474/476 (calcd) 475/477 ([M+H]$^+$, found).

$^1$H NMR (400 MHz, Chloroform-d) δ 8.53 (d, J=4.5 Hz, 1H), 8.21 (d, J=7.0 Hz, 1H), 8.16 (br s+d, J=7.8 Hz, 2H), 7.84 (br s+td, J=7.7, 1.7 Hz, 2H), 7.48 (dd, J=7.8, 1.8 Hz, 1H), 7.45-7.33 (m, 3H), 7.30 (dd, J=7.5, 1.9 Hz, 1H), 7.22 (d, J=8.6 Hz, 1H), 4.76 (h, J=6.6 Hz, 1H), 4.03 (q, J=7.0 Hz, 2H), 3.50-3.33 (sym. m, 1H), 3.11-2.98 (sym. m, 2H), 2.48-2.33 (sym. m, 2H), 1.40 (t, J=6.9 Hz, 3H).

Example 135: Preparation of N-((1S,3r)-3-(4-(2-chlorophenyl)-5-(5-ethoxypyridin-2-yl)-4H-1,2,4-triazol-3-yl)cyclobutyl)-1,5-naphthyridine-4-carboxamide

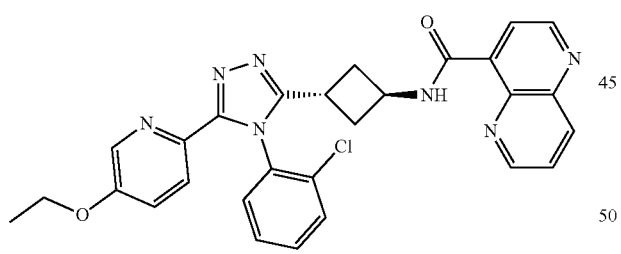

The title compound was prepared according to the general procedure F as a white solid (11.9 mg, 29% yield).

LC/MS (ESI) m/z for $C_{25}H_{24}ClN_7O_2$ 525/527 (calcd) 526/528 ([M+H]$^+$, found).

$^1$H NMR (400 MHz, Chloroform-d) δ 11.31 (d, J=5.9 Hz, 1H), 9.14 (d, J=4.5 Hz, 1H), 8.98 (dd, J=4.2, 1.8 Hz, 1H), 8.58-8.53 (m, 2H), 8.17 (d, J=8.8 Hz, 1H), 7.86 (d, J=2.8 Hz, 1H), 7.74 (dd, J=8.5, 4.2 Hz, 1H), 7.48 (dd, J=7.6, 1.9 Hz, 1H), 7.39 (dtd, J=14.9, 7.3, 1.8 Hz, 2H), 7.32 (dd, J=7.5, 2.0 Hz, 1H), 7.22 (dd, J=8.8, 2.9 Hz, 1H), 4.84 (h, J=7.2 Hz, 1H), 4.04 (q, J=7.0 Hz, 2H), 3.47 (apparent tt, J=9.5, 5.5 Hz, 1H), 3.18-2.99 (sym. m, 2H), 2.58-2.45 (sym. m, 2H), 1.40 (t, J=7.0 Hz, 3H).

Example 136: Preparation of N-((1S,3r)-3-(4-(2-chlorophenyl)-5-(5-ethoxypyridin-2-yl)-4H-1,2,4-triazol-3-yl)cyclobutyl)benzamide

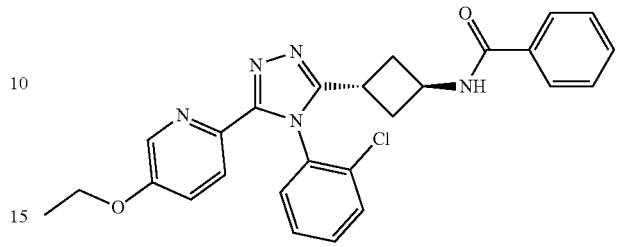

The title compound was prepared according to the general procedure F as a white solid (24.5 mg, 66% yield).

LC/MS (ESI) m/z for $C_{26}H_{24}ClN_5O_2$ 473/475 (calcd) 474/476 ([M+H]$^+$, found).

$^1$H NMR (400 MHz, Chloroform-d) δ 8.16 (d, J=8.7 Hz, 1H), 7.85 (d, J=3.0 Hz, 1H), 7.76-7.71 (m, 2H), 7.52-7.46 (m, 2H), 7.45-7.35 (m, 4H), 7.29 (dd, J=7.6, 1.9 Hz, 1H), 7.22 (dd, J=8.8, 2.9 Hz, 1H), 6.28 (d, J=6.1 Hz, 1H), 4.72 (h, J=6.8 Hz, 1H), 4.03 (q, J=7.0 Hz, 2H), 3.44-3.33 (sym. m, 1H), 3.12-2.95 (sym. m, 2H), 2.42-2.29 (sym. m, 2H), 1.40 (t, J=7.0 Hz, 3H).

Example 137: Preparation of N-((1S,3r)-3-(4-(2-chlorophenyl)-5-(5-ethoxypyridin-2-yl)-4H-1,2,4-triazol-3-yl)cyclobutyl)-4-fluorobenzamide

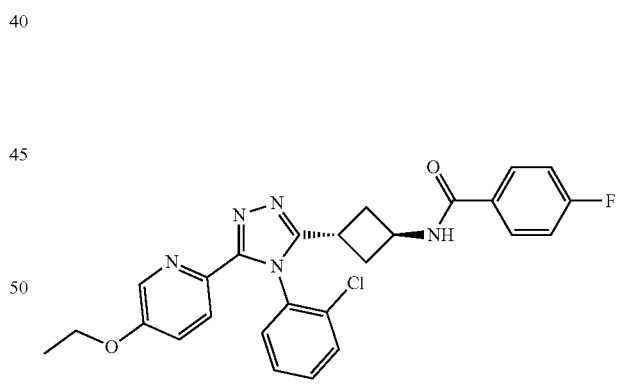

The title compound was prepared according to the general procedure F as a white solid (32 mg, 83% yield).

LC/MS (ESI) m/z for $C_{26}H_{23}ClFN_5O_2$ 491/493 (calcd) 492/494 ([M+H]$^+$, found).

$^1$H NMR (400 MHz, Chloroform-d) δ 8.15 (d, J=8.8 Hz, 1H), 7.85 (s, 1H), 7.79-7.71 (sym. m, 2H), 7.48 (dd, J=7.8, 1.7 Hz, 1H), 7.46-7.33 (m, 2H), 7.29 (dd, J=7.6, 1.8 Hz, 1H), 7.22 (dd, J=8.7, 2.4 Hz, 1H), 7.09 (t, J=8.6 Hz, 2H), 6.24 (d, J=6.1 Hz, 1H), 4.71 (h, J=7.0 Hz, 1H), 4.03 (q, J=7.0 Hz, 2H), 3.42-3.32 (sym. m, 1H), 3.12-2.93 (sym. m, 2H), 2.43-2.29 (sym. m, 2H), 1.40 (t, J=6.9 Hz, 3H).

Example 138: Preparation of amine building block Z: (1r,3r)-3-(4-(3-chlorophenyl)-5-(5-ethoxypyridin-2-yl)-4H-1,2,4-triazol-3-yl)cyclobutan-1-amine dihydrochloride

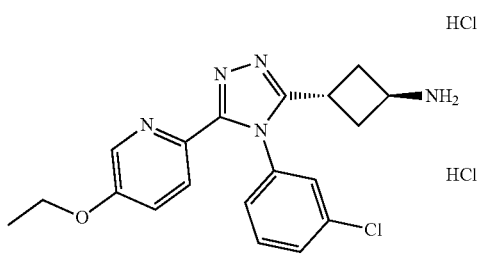

Step (a): N-(3-chlorophenyl)-5-ethoxypicolinamide was prepared according to the general procedure A, method a) as a white, crystalline solid (106 mg, 82% yield).

LC/MS (ESI) m/z for $C_{14}H_{13}ClN_2O_2$ 276/278 (calcd) 277/279 ([M+H]$^E$, found).

$^1$H NMR (400 MHz, Chloroform-d) δ 9.86 (s, 1H), 8.24 (d, J=2.8 Hz, 1H), 8.22 (d, J=8.6 Hz, 1H), 7.90 (t, J=2.0 Hz, 1H), 7.60 (ddd, J=8.2, 2.2, 0.9 Hz, 1H), 7.32 (dd, J=8.1, 2.2 Hz, 1H), 7.29 (t, J=7.4 Hz, 1H), 7.10 (ddd, J=8.1, 2.0, 1.0 Hz, 1H), 4.16 (q, J=7.0 Hz, 2H), 1.49 (t, J=7.0 Hz, 3H).

Step (b): N-(3-chlorophenyl)-5-ethoxypyridine-2-carbothioamide was prepared following the general procedure B as a yellow solid (95 mg, 85% yield).

LC/MS (ESI) m/z for $C_{14}H_{13}ClN_2OS$ 292/294 (calcd) 293/295 ([M+H]$^+$, found).

Step (c): methyl N-(3-chlorophenyl)-5-ethoxypyridine-2-carbimidothioate was prepared according to the to the general procedure C as a yellow solid (92 mg, 93% yield).

LC/MS (ESI) m/z for $C_{15}H_{15}ClN_2OS$ 306/308 (calcd) 307/309 ([M+H]$^+$, found).

Step (d): tert-butyl ((1r,3 r)-3-(4-(3-chlorophenyl)-5-(5-ethoxypyridin-2-yl)-4H-1,2,4-triazol-3-yl)cyclobutyl)carbamate was prepared according to the general procedure D as a white foam (130 mg, 90% yield).

LC/MS (ESI) m/z for $C_{24}H_{25}ClN_5O_3$ 469/471 (calcd) 470/472 ([M+H]$^+$, found).

$^1$H NMR (400 MHz, Chloroform-d) δ 8.07 (d, J=8.8 Hz, 1H), 7.92 (d, J=2.8 Hz, 1H), 7.43 (dt, J=8.2, 1.3 Hz, 1H), 7.36 (t, J=8.0 Hz, 1H), 7.22 (dd, J=8.7, 2.9 Hz, 1H), 7.16 (t, J=2.0 Hz, 1H), 7.03 (ddd, J=7.9, 2.0, 1.3 Hz, 1H), 4.73 (s, 1H), 4.39-4.27 (symmetrical m, 1H), 4.05 (q, J=7.0 Hz, 2H), 3.39-3.25 (broad m, 1H), 2.86 (apparent ddd, J=12.6, 7.7, 5.0 Hz, 2H), 2.35-2.18 (broad m, 2H), 1.42 (s, 9H), 1.40 (t, J=7.0 Hz, 3H).

Step (e): the title compound was prepared crude according to the general procedure E as a white powder (131 mg, ~91% purity, 100% yield).

LC/MS (ESI) m/z for $C_{19}H_{20}ClN_5O$·369/371 (calcd) 370/372 ([M+14]$^+$, found).

$^1$H NMR (400 MHz, DMSO-d6) δ 8.27 (broad d, J=3.8 Hz, 3H), 8.01 (d, J=2.9 Hz, 1H), 7.95 (d, J=8.8 Hz, 1H), 7.64-7.57 (m, 2H), 7.57-7.46 (m, 2H), 7.35 (dt, J=7.7, 1.6 Hz, 1H), 4.11 (q, J=7.0 Hz, 2H), 3.56 (apparent tt, J=9.7, 5.7 Hz, 1H), 2.73 (apparent ddd, J=13.4, 8.0, 5.6 Hz, 21-1), 2.31 (apparent ddd, J=13.0, 9.4, 5.6 Hz, 2H), 1.31 (t, J=7.0 Hz, 3H).

Example 139: Preparation of N-((1r,3r)-3-(4-(3-chlorophenyl)-5-(5-ethoxypyridin-2-yl)-4H-1,2,4-triazol-3-yl)cyclobutyl)quinoline-8-carboxamide

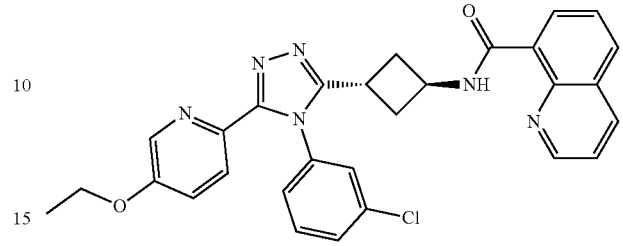

The title compound was prepared according to the general procedure F as a white solid (17.4 mg, 84% yield).

LC/MS (ESI) m/z for $C_{29}H_{25}ClN_6O_2$ 524/526 (calcd) 525/527 ([M+H]$^+$, found).

$^1$H NMR (400 MHz, Chloroform-d) δ 11.56 (d, J=5.7 Hz, 1H), 8.92 (dd, J=4.3, 1.8 Hz, 1H), 8.83 (dd, J=7.3, 1.6 Hz, 1H), 8.28 (dd, J=8.3, 1.9 Hz, 1H), 8.10 (d, J=8.6 Hz, 1H), 8.00-7.90 (m, 2H), 7.67 (t, J=7.8 Hz, 1H), 7.49 (dd, J=8.3, 4.3 Hz, 1H), 7.41 (dt, J=8.4, 1.5 Hz, 1H), 7.35 (t, J=8.0 Hz, 1H), 7.23 (dd, J=8.7, 2.9 Hz, 1H), 7.21 (t, J=2.0 Hz, 1H), 7.08 (dt, J=7.7, 1.6 Hz, 1H), 4.90-4.76 (m, 1H), 4.06 (q, J=7.0 Hz, 2H), 3.62-3.50 (m, 1H), 3.14-3.02 (m, 2H), 2.55 (ddd, J=12.7, 9.5, 6.0 Hz, 2H), 1.41 (t, J=7.0 Hz, 3H).

Example 140: Preparation of N-((1r,3r)-3-(4-(3-chlorophenyl)-5-(5-ethoxypyridin-2-yl)-4H-1,2,4-triazol-3-yl)cyclobutyl)picolinamide

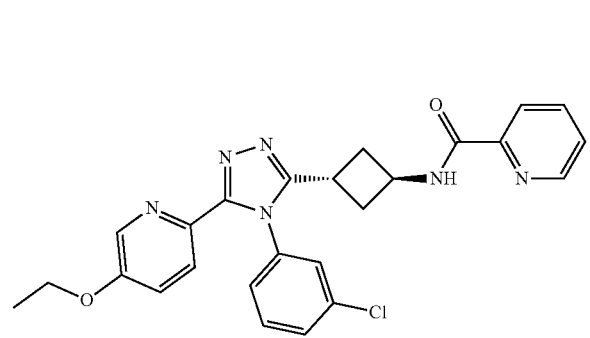

The title compound was prepared according to the general procedure F as a white solid (14.3 mg, 75% yield).

LC/MS (ESI) m/z for $C_{25}H_{23}ClN_6O_2$ 474/476 (calcd) 475/477 ([M+H]$^+$, found).

$^1$H NMR (400 MHz, Chloroform-d) δ 8.53 (dt, J=4.7, 1.3 Hz, 1H), 8.22 (d, J=7.0 Hz, 1H), 8.17 (dt, J=7.7, 1.0 Hz, 1H), 8.10 (d, J=8.7 Hz, 1H), 7.93 (br s, 1H), 7.84 (td, J=7.7, 1.7 Hz, 1H), 7.46-7.40 (m, 2H), 7.36 (t, J=8.0 Hz, 1H), 7.23 (dd, J=8.7, 2.7 Hz, 1H), 7.18 (t, J=2.0 Hz, 1H), 7.07 (dt, J=8.0, 1.4 Hz, 1H), 4.78 (h, J=7.0 Hz, 1H), 4.05 (q, J=7.0 Hz, 2H), 3.48 (tt, J=9.8, 5.3 Hz, 1H), 3.09-2.97 (m, 2H), 2.45 (ddd, J=12.8, 9.5, 6.2 Hz, 2H), 1.41 (t, J=7.0 Hz, 3H).

Example 141: Preparation of N-((1S,3r)-3-(5-(5-(ethoxy-d5)pyridin-2-yl)-4-(2-fluorophenyl)-4H-1,2,4-triazol-3-yl)cyclobutyl)-3-fluoroquinoline-8-carboxamide

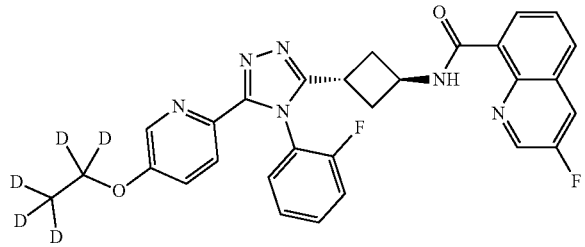

The title compound was prepared according to the general procedure F as a white solid (22.9 mg, 85% yield).

LC/MS (ESI) m/z for $C_{29}H_{19}D_5F_2N_6O_2$ 531 (calcd) 532 ([M+H]$^+$ found).

$^1$H NMR (400 MHz, Chloroform-d) δ 11.04 (d, J=5.8 Hz, 1H), 8.82 (d, J=3.0 Hz, 1H), 8.79 (dd, J=7.4, 1.6 Hz, 1H), 8.16 (d, J=8.7 Hz, 1H), 7.96-7.89 (m, 2H), 7.88 (br d, J=2.9 Hz, 1H), 7.70 (t, J=7.8 Hz, 1H), 7.48-7.39 (m, 1H), 7.24-7.13 (m, 4H), 4.87-4.76 (m, 1H), 3.54 (apparent tt, J=9.7, 5.9 Hz, 1H), 3.14-3.02 (m, 2H), 2.60-2.44 (m, 2H).

Example 142: Preparation of N-((1S,3r)-3-(5-(5-(ethoxy-d5)pyridin-2-yl)-4-(2-fluorophenyl)-4H-1,2,4-triazol-3-yl)cyclobutyl)pyrazolo[1,5-a]pyridine-3-carboxamide

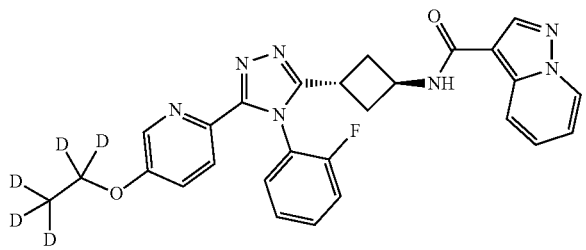

The title compound was prepared according to the general procedure F as a white solid (20.4 mg, 80% yield).

LC/MS (ESI) m/z for $C_{27}H_{19}D_5FN_7O_2$ 502 (calcd) 503 ([M+H]$^+$ found).

$^1$H NMR (400 MHz, Chloroform-d) δ 8.47 (dt, J=6.8, 1.1 Hz, 1H), 8.28 (dt, J=8.8, 1.2 Hz, 1H), 8.15 (d, J=8.5 Hz, 1H), 8.13 (s, 1H), 7.87 (br s, 1H), 7.48-7.40 (m, 1H), 7.34 (ddd, J=8.9, 6.9, 1.1 Hz, 1H), 7.25-7.13 (m, 4H), 6.91 (td, J=6.9, 1.4 Hz, 1H), 6.09 (d, J=6.1 Hz, 1H), 4.74 (apparent h, J=6.9 Hz, 1H), 3.47 (tt, J=10.2, 6.0 Hz, 1H), 3.10-2.93 (m, 2H), 2.52-2.35 (m, 2H).

Example 143: Preparation of N-((1r,3r)-3-(5-(5-ethoxypyridin-2-yl)-4-(5-methylthiophen-2-yl)-4H-1,2,4-triazol-3-yl)cyclobutyl)-1H-benzo[d]imidazole-2-carboxamide

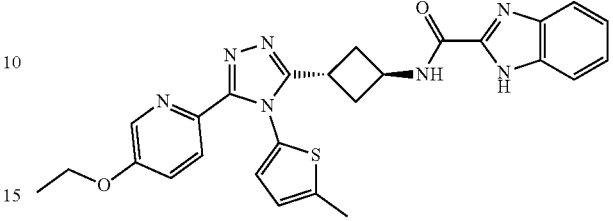

The title compound was prepared according to the general procedure F as a white solid (9.9 mg, 36% yield).

LC/MS (ESI) m/z for $C_{26}H_{25}N_7O_2S$ 499 (calcd) 500 ([M+H]$^+$ found).

$^1$H NMR (400 MHz, Chloroform-d) δ 10.78 (s, 1H), 8.12 (s, 1H), 7.96 (d, J=8.6 Hz, 1H), 7.78 (t, J=8.1 Hz, 2H), 7.56 (d, J=8.1 Hz, 1H), 7.39 (td, J=7.2, 1.1 Hz, 1H), 7.35 (td, J=8.0, 1.3 Hz, 1H), 7.22 (dd, J=8.8, 2.2 Hz, 1H), 6.71 (d, J=3.6 Hz, 1H), 6.63 (dd, J=3.8, 1.2 Hz, 1H), 4.88 (h, J=7.0 Hz, 1H), 4.08 (q, J=6.9 Hz, 2H), 3.68-3.56 (m, 1H), 3.09 (ddd, J=13.3, 7.9, 5.5 Hz, 2H), 2.57-2.49 (m, 2H), 2.49 (d, J=1.2 Hz, 3H), 1.43 (t, J=7.0 Hz, 3H).

Example 144: Preparation of N-((1S,3r)-3-(4-(2-fluorophenyl)-5-(5-(methylsulfonyl)pyridin-2-yl)-4H-1,2,4-triazol-3-yl)cyclobutyl)picolinamide

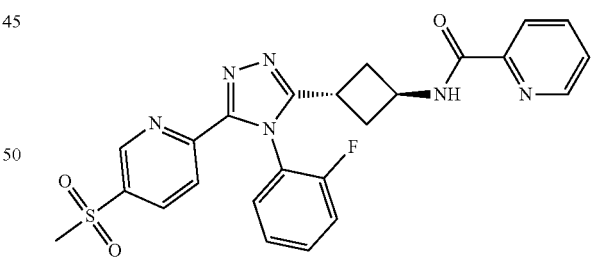

The title compound was prepared according to the general procedure F as a white solid (6.1 mg, 40% yield).

LC/MS (ESI) m/z for $C_{24}H_{21}FN_6O_3S$ 492 (calcd) 493 ([M+H]$^+$ found).

$^1$H NMR (400 MHz, Chloroform-d) δ 8.72 (d, J=2.3 Hz, 1H), 8.58-8.51 (m, 2H), 8.28 (dd, J=8.4, 2.3 Hz, 1H), 8.23 (br d, J=7.0 Hz, 1H), 8.17 (dt, J=7.7, 1.1 Hz, 1H), 7.84 (td, J=7.7, 1.7 Hz, 1H), 7.55-7.47 (m, 1H), 7.43 (ddd, J=7.6, 4.8, 1.2 Hz, 1H), 7.29-7.17 (m, 3H), 4.80 (h, J=7.1 Hz, 1H), 3.53-3.44 (m, 1H), 3.07 (s, 3H), 3.14-2.97 (m, 2H), 2.57-2.40 (m, 2H).

Example 145: Preparation of amine building block AA: (1r,3r)-3-(4-(pyridin-4-yl)-5-(thiazol-2-yl)-4H-1,2,4-triazol-3-yl)cyclobutan-1-amine dihydrochloride

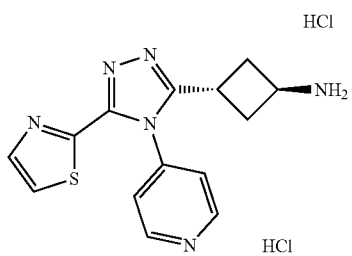

Step (a): N-(pyridin-4-yl)thiazole-2-carboxamide was prepared according to the general procedure A, method a) as a yellowish solid (407 mg, 95% purity, 63% yield).

LC/MS (ESI) m/z for $C_9H_7N_3OS$ 205 (calcd) 206 ([M+H]$^+$, found).

$^1$H NMR (400 MHz, Chloroform-d) δ 9.22 (br s, 1H), 8.59 (d, J=5.3 Hz, 2H), 7.96 (d, J=3.1 Hz, 1H), 7.70 (d, J=3.1 Hz, 1H), 7.67-7.60 (sym. m, 2H).

Step (b): N-(pyridin-4-yl)thiazole-2-carbothioamide was prepared following the general procedure B as a brown glass (118 mg, 95% pure, 27% yield).

LC/MS (ESI) m/z for $C_9H_7N_3S_2$ 221 (calcd) 222 ([M+H]$^+$, found).

$^1$H NMR (400 MHz, Chloroform-d) δ 10.90 (br s, 1H), 8.73-8.61 (sym. m, 2H), 8.08-8.00 (sym. m, 2H), 7.94 (d, J=3.1 Hz, 1H), 7.64 (d, J=3.2 Hz, 1H).

Step (c): ethyl N-(pyridin-4-yl)thiazole-2-carbimidothioate was prepared as a brownish semisolid (92 mg, ~95% purity, 70% yield) according to the to the general procedure C using iodoethane instead of iodomethane.

LC/MS (ESI) m/z for $C_{11}H_{11}N_3S_2$ 249 (calcd) 250 ([M+H]$^+$, found).

$^1$H NMR (400 MHz, Chloroform-d) δ 8.59-8.48 (sym. m, 2H), 7.90 (d, J=3.1 Hz, 1H), 7.49 (d, J=3.1 Hz, 1H), 6.81 (d, J=5.8 Hz, 2H), 3.12 (q, J=7.4 Hz, 2H), 1.29 (t, J=7.5 Hz, 3H).

Step (d): tert-butyl ((1r,3r)-3-(4-(pyridin-4-yl)-5-(thiazol-2-yl)-4H-1,2,4-triazol-3-yl)cyclobutyl)carbamate was prepared according to the general procedure D as a pale yellow solid (84 mg, 91% purity, 55% yield).

LC/MS (ESI) m/z for $C_{19}H_{22}N_6O_2S$ 398 (calcd) 399 ([M+H]$^+$, found).

$^1$H NMR (400 MHz, Chloroform-d) δ 8.81 (d, J=4.5 Hz, 2H), 7.63 (d, J=3.2 Hz, 1H), 7.39 (d, J=3.2 Hz, 1H), 7.23-7.16 (m, 2H), 4.74 (s, 1H), 4.36 (ht, J=7.0, 1.5 Hz, 1H), 3.30 (apparent hept, J=4.6 Hz, 1H), 2.92-2.80 (sym. m, 2H), 2.30 (br s, 2H), 1.42 (s, 9H).

Step (e): the crude title compound was prepared according to the general procedure E as a peachy-coloured solid (82 mg, ~86% purity, 100% yield).

LC/MS (ESI) m/z for $C_{14}H_{14}N_6S$·298 (calcd) 299 ([M+H]$^+$, found).

Example 146: Preparation of N-((1r,3r)-3-(4-(pyridin-4-yl)-5-(thiazol-2-yl)-4H-1,2,4-triazol-3-yl)cyclobutyl)quinoline-8-carboxamide

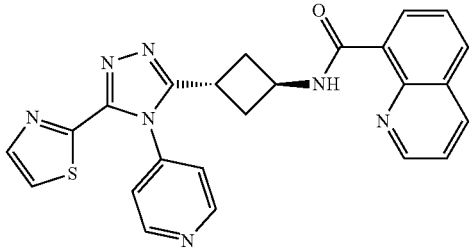

The title compound was prepared according to the general procedure F as a white solid (18.0 mg, 79% yield).

LC/MS (ESI) m/z for $C_{24}H_{19}N_7OS$ 453 (calcd) 454 ([M+H]$^+$, found).

$^1$H NMR (400 MHz, Chloroform-d) δ 11.57 (d, J=5.8 Hz, 1H), 8.91 (dd, J=4.3, 1.8 Hz, 1H), 8.83 (dd, J=7.4, 1.6 Hz, 1H), 8.81-8.76 (sym. m, 2H), 8.29 (dd, J=8.3, 1.8 Hz, 1H), 7.96 (dd, J=8.1, 1.6 Hz, 1H), 7.67 (t, J=7.7 Hz, 1H), 7.64 (d, J=3.2 Hz, 1H), 7.50 (dd, J=8.3, 4.3 Hz, 1H), 7.39 (d, J=3.2 Hz, 1H), 7.25-7.20 (sym. m, 2H), 4.85 (ht, J=6.9, 1.4 Hz, 1H), 3.59-3.50 (sym. m, 1H), 3.14-3.04 (sym. m, 2H), 2.60 (ddd, J=12.6, 9.4, 6.0 Hz, 2H).

Example 147: Preparation of N-((1S,3r)-3-(5-(5-ethoxypyridin-2-yl)-4-(2-fluorophenyl)-4H-1,2,4-triazol-3-yl)cyclobutyl)-1,8-naphthyridine-2-carboxamide

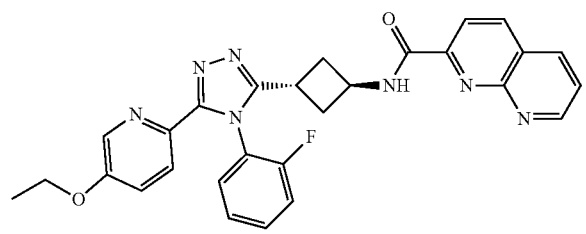

The title compound was prepared according to the general procedure F as a white powder (16.4 mg, 64% yield).

LC/MS (ESI) m/z for $C_{28}H_{24}FN_7O_2$ 509 (calcd) 510 ([M+11]$^+$, found).

$^1$H NMR (400 MHz, Chloroform-d) δ 9.19 (dd, J=4.2, 2.0 Hz, 1H), 8.58 (d, J=7.3 Hz, 1H), 8.46-8.35 (sym. m, 2H), 8.29 (dd, J=8.1, 2.0 Hz, 1H), 8.17 (s, 1H), 7.89 (d, J=1.6 Hz, 1H), 7.60 (dd, J=8.1, 4.2 Hz, 1H), 7.51-7.42 (m, 1H), 7.25-7.16 (m, 4H), 4.86 (h, J=6.9 Hz, 1H), 4.04 (q, J=7.0 Hz, 2H), 3.51 (ddd, J=15.6, 9.7, 6.0 Hz, 1H), 3.17-2.99 (sym. m, 2H), 2.54-2.37 (sym. m, 2H), 1.40 (t, J=7.0 Hz, 3H).

Example 148: Preparation of N-((1S,3r)-3-(5-(5-ethoxypyridin-2-yl)-4-(2-fluorophenyl)-4H-1,2,4-triazol-3-yl)cyclobutyl)-1H-pyrrolo[3,2-b]pyridine-2-carboxamide

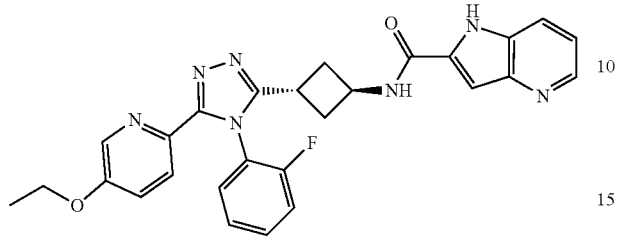

The title compound was prepared according to the general procedure F as a white solid (13.3 mg, 52% yield).

LC/MS (ESI) m/z for $C_{27}H_{24}FN_{7}O_{2}$ 497 (calcd) 498 ([M+H]$^+$, found).

$^1$H NMR (400 MHz, DMSO-d6, one NH signal not observed) δ 11.82 (s, 1H), 8.88 (d, J=7.4 Hz, 1H), 8.38 (dd, J=4.5, 1.5 Hz, 1H), 8.05 (d, J=8.8 Hz, 1H), 7.94 (d, J=2.9 Hz, 1H), 7.76 (d, J=8.1 Hz, 1H), 7.61-7.52 (m, 2H), 7.50 (dd, J=8.8, 3.0 Hz, 1H), 7.43 (ddd, J=9.8, 8.4, 1.3 Hz, 1H), 7.33 (td, J=7.7, 1.4 Hz, 1H), 7.26 (s, 1H), 7.18 (dd, J=8.3, 4.5 Hz, 1H), 4.71 (h, J=7.4 Hz, 1H), 4.10 (q, J=6.9 Hz, 2H), 2.85-2.74 (sym. m, 1H), 2.66-2.56 (sym. m, 1H), 2.45-2.30 (sym. m, 2H), 1.31 (t, J=7.0 Hz, 3H).

Example 149: Preparation of N-((1S,3r)-3-(5-(5-ethoxypyridin-2-yl)-4-(2-fluorophenyl)-4H-1,2,4-triazol-3-yl)cyclobutyl)-4H-thieno[3,2-b]pyrrole-5-carboxamide

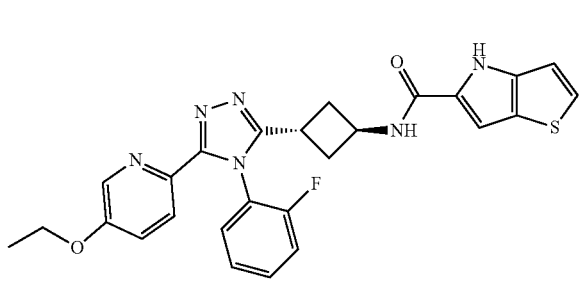

The title compound was prepared according to the general procedure F as a white powder (15.2 mg, 60% yield).

LC/MS (ESI) m/z for $C_{26}H_{23}FN_{6}O_{2}S$ 502 (calcd) 503 ([M+H]$^+$, found).

$^1$H NMR (400 MHz, Chloroform-d) δ 9.49 (s, 1H), 8.14 (d, J=8.7 Hz, 1H), 7.88 (d, J=2.9 Hz, 1H), 7.49-7.41 (m, 1H), 7.25-7.14 (m, 5H), 6.95 (d, J=5.4 Hz, 1H), 6.77 (d, J=1.7 Hz, 1H), 6.22 (d, J=6.2 Hz, 1H), 4.76 (h, J=6.7 Hz, 1H), 4.04 (q, J=7.0 Hz, 2H), 3.43 (tt, J=9.9, 5.3 Hz, 1H), 3.08-2.93 (sym. m, 2H), 2.52-2.31 (sym. m, 2H), 1.40 (t, J=7.0 Hz, 3H).

Example 150: Preparation of N-((1S,3r)-3-(5-(5-ethoxypyridin-2-yl)-4-(2-fluorophenyl)-4H-1,2,4-triazol-3-yl)cyclobutyl)-2-methyl-4H-thieno[3,2-b]pyrrole-5-carboxamide

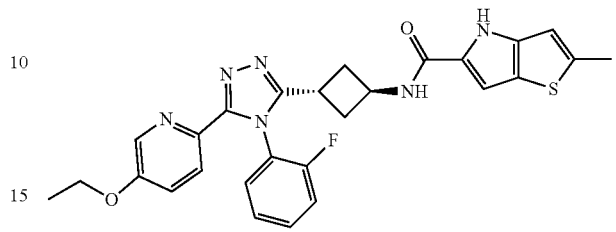

The title compound was prepared according to the general procedure F as a white solid (14.2 mg, 54% yield).

LC/MS (ESI) m/z for $C_{27}H_{25}FN_{6}O_{2}S$ 516 (calcd) 517 ([M+H]$^+$, found).

$^1$H NMR (400 MHz, Chloroform-d) δ 9.26 (s, 1H), 8.14 (d, J=8.6 Hz, 1H), 7.88 (d, J=3.0 Hz, 1H), 7.49-7.40 (m, 1H), 7.25-7.14 (m, 4H), 6.67 (d, J=1.3 Hz, 1H), 6.64 (s, 1H), 6.10 (d, J=6.4 Hz, 1H), 4.74 (h, J=6.9 Hz, 1H), 4.04 (q, J=7.0 Hz, 2H), 3.42 (tt, J=9.8, 5.3 Hz, 1H), 3.07-2.93 (sym. m, 2H), 2.53 (s, 3H), 2.47-2.29 (sym. m, 2H), 1.40 (t, J=7.0 Hz, 3H).

Example 151: Preparation of N-((1S,3r)-3-(5-(5-ethoxypyridin-2-yl)-4-(2-fluorophenyl)-4H-1,2,4-triazol-3-yl)cyclobutyl)-4H-furo[3,2-13]pyrrole-5-carboxamide

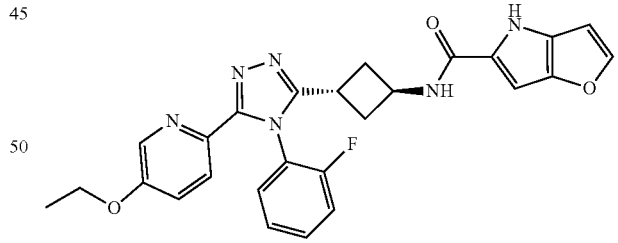

The title compound was prepared according to the general procedure F as a white solid (10.4 mg, 41% yield).

LC/MS (ESI) m/z for $C_{26}H_{23}FN_{6}O_{3}$ 486 (calcd) 487 ([M+H]$^+$, found).

$^1$H NMR (400 MHz, Chloroform-d) δ 8.95 (s, 1H), 8.15 (d, J=8.8 Hz, 1H), 7.88 (d, J=2.9 Hz, 1H), 7.46 (d, J=2.2 Hz, 1H), 7.48-7.41 (m, 1H), 7.25-7.15 (m, 4H), 6.46 (d, J=2.2 Hz, 1H), 6.44 (s, 1H), 6.03 (d, J=6.5 Hz, 1H), 4.74 (h, J=7.3 Hz, 1H), 4.04 (q, J=7.0 Hz, 2H), 3.43 (tt, J=9.9, 5.5 Hz, 1H), 3.07-2.92 (sym. m, 2H), 2.47-2.31 (sym. m, 2H), 1.40 (t, J=7.0 Hz, 3H).

Example 152: Preparation of N-((1S,3r)-3-(5-(5-ethoxypyridin-2-yl)-4-(2-fluorophenyl)-4H-1,2,4-triazol-3-yl)cyclobutyl)-1H-pyrrolo[2,3-b]pyridine-2-carboxamide

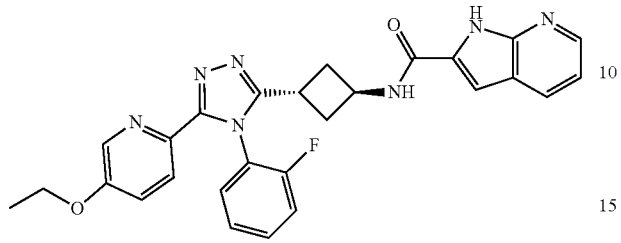

The title compound was prepared according to the general procedure F as a white solid (13.3 mg, 53% yield).

LC/MS (ESI) m/z for $C_{27}H_{24}FN_7O_2$ 497 (calcd) 498 ([M+H]$^+$, found).

$^1$H NMR (400 MHz, Chloroform-d) δ 10.60 (s, 1H), 8.51 (dd, J=4.7, 1.6 Hz, 1H), 8.15 (d, J=8.7 Hz, 1H), 7.97 (dd, J=7.9, 1.6 Hz, 1H), 7.88 (d, J=2.8 Hz, 1H), 7.49-7.41 (m, 1H), 7.25-7.16 (m, 4H), 7.13 (dd, J=8.0, 4.7 Hz, 1H), 6.81 (s, 1H), 6.55 (d, J=6.4 Hz, 1H), 4.79 (h, J=7.0 Hz, 1H), 4.03 (q, J=6.9 Hz, 2H), 3.46 (tt, J=9.6, 5.1 Hz, 1H), 3.10-2.95 (sym. m, 2H), 2.56-2.40 (sym. m, 2H), 1.40 (t, J=7.0 Hz, 3H).

Example 153: Preparation of N-((1S,3r)-3-(5-(5-ethoxypyridin-2-yl)-4-(2-fluorophenyl)-4H-1,2,4-triazol-3-yl)cyclobutyl)-1-methyl-1H-indazole-3-carboxamide

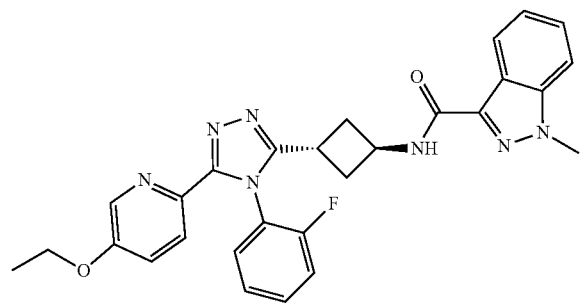

The title compound was prepared according to the general procedure F as a whitish solid (19.7 mg, 76% yield).

LC/MS (ESI) m/z for $C_{28}H_{26}FN_7O_2$ 511 (calcd) 512 ([M+H]$^+$, found).

$^1$H NMR (400 MHz, Chloroform-d) δ 8.34 (dt, J=8.1, 1.1 Hz, 1H), 8.16 (br d, J=8.7 Hz, 1H), 7.88 (br s, 1H), 7.48-7.36 (m, 3H), 7.31-7.14 (m, 6H), 4.75 (h, J=6.7 Hz, 1H), 4.08 (s, 3H), 4.04 (q, J=7.0 Hz, 2H), 3.56-3.42 (sym. m, 1H), 3.11-2.99 (sym. m, 2H), 2.55-2.39 (sym. m, 2H), 1.40 (t, J=7.0 Hz, 3H).

Example 154: Preparation of N-((1S,3r)-3-(5-(5-ethoxypyridin-2-yl)-4-(2-fluorophenyl)-4H-1,2,4-triazol-3-yl)cyclobutyl)quinoxaline-5-carboxamide

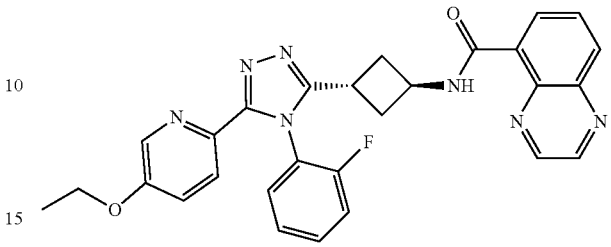

The title compound was prepared according to the general procedure F as an off-white powder (20.4 mg, 79% yield).

LC/MS (ESI) m/z for $C_{28}H_{24}FN_7O_2$ 509 (calcd) 510 ([M+H]$^+$, found).

$^1$H NMR (400 MHz, Chloroform-d) δ 10.68 (br d, J=5.9 Hz, 1H), 8.97 (d, J=1.9 Hz, 1H), 8.89-8.83 (m, 2H), 8.26 (dd, J=8.3, 1.6 Hz, 1H), 8.16 (d, J=8.7 Hz, 1H), 7.94-7.86 (m, 2H), 7.47-7.39 (m, 1H), 7.25-7.13 (m, 4H), 4.88-4.78 (sym. m, 1H), 4.04 (q, J=7.0 Hz, 2H), 3.57-3.48 (sym. m, 1H), 3.13-3.03 (sym. m, 2H), 2.60-2.45 (sym. m, 2H), 1.40 (t, J=7.0 Hz, 3H).

Example 155: Preparation of N-((1S,3r)-3-(5-(5-ethoxypyridin-2-yl)-4-(2-fluorophenyl)-4H-1,2,4-triazol-3-yl)cyclobutyl)-6-fluoroquinoline-2-carboxamide

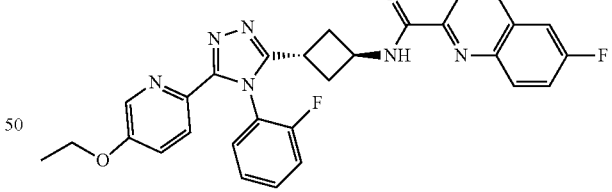

The title compound was prepared according to the general procedure F as a whitish solid (10.9 mg, 41% yield).

LC/MS (ESI) m/z for $C_{29}H_{24}F_2N_6O_2$ 526 (calcd) 527 ([M+H]$^+$, found).

$^1$H NMR (400 MHz, Chloroform-d) δ 8.35 (d, J=7.0 Hz, 1H), 8.32-8.21 (m, 2H), 8.17 (d, J=8.8 Hz, 1H), 8.11 (dd, J=9.2, 5.3 Hz, 1H), 7.88 (d, J=2.1 Hz, 1H), 7.54 (ddd, J=9.3, 8.2, 2.7 Hz, 1H), 7.49 (dd, J=8.7, 2.8 Hz, 1H), 7.47-7.41 (m, 1H), 7.25-7.15 (m, 4H), 4.83 (h, J=7.2 Hz, 1H), 4.04 (q, J=6.9 Hz, 2H), 3.56-3.45 (apparent hept, 1H), 3.14-3.00 (sym. m, 2H), 2.61-2.45 (sym. m, 2H), 1.40 (t, J=7.0 Hz, 3H).

Example 156: Preparation of N-((1S,3r)-3-(5-(5-ethoxypyridin-2-yl)-4-(2-fluorophenyl)-4H-1,2,4-triazol-3-yl)cyclobutyl)-1H-indazole-7-carboxamide

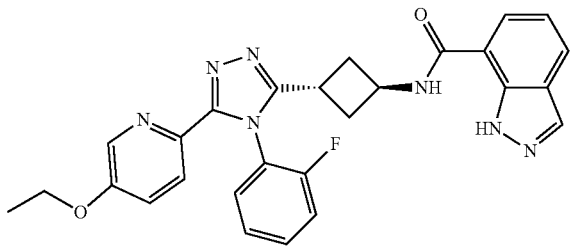

The title compound was prepared according to the general procedure F as a whitish solid (19.4 mg, 77% yield).

LC/MS (ESI) m/z for $C_{27}H_{24}FN_7O_2$ 497 (calcd) 498 ([M+H]$^+$, found).

$^1$H NMR (400 MHz, Chloroform-d) δ 11.59 (br s, 1H), 8.15 (d, J=8.7 Hz, 1H), 8.10 (s, 1H), 7.92 (dd, J=7.9, 0.8 Hz, 1H), 7.88 (d, J=2.9 Hz, 1H), 7.56 (d, J=7.1 Hz, 1H), 7.49-7.41 (m, 1H), 7.26-7.14 (m, 5H), 6.60 (br d, J=6.0 Hz, 1H), 4.86-4.75 (m, 1H), 4.04 (q, J=7.0 Hz, 2H), 3.47 (apparent hept, 1H), 3.13-2.99 (sym. m, 2H), 2.53-2.37 (sym. m, 2H), 1.40 (t, J=7.0 Hz, 3H).

Example 157: Preparation of N-((1S,3r)-3-(5-(5-ethoxypyridin-2-yl)-4-(2-fluorophenyl)-4H-1,2,4-triazol-3-yl)cyclobutyl)-1H-pyrrolo[3,2-c]pyridine-2-carboxamide

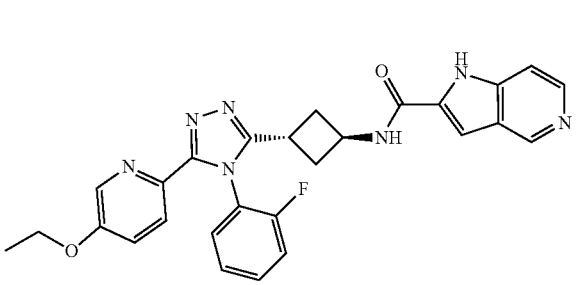

The title compound was prepared according to the general procedure F as a pale yellow solid (18.6 mg, 72% yield).

LC/MS (ESI) m/z for $C_{27}H_{24}FN_7O_2$ 497 (calcd) 498 ([M+H]$^+$, found).

$^1$H NMR (400 MHz, Chloroform-d) δ 9.87 (br s, 1H), 8.97 (s, 1H), 8.37 (d, J=5.8 Hz, 1H), 8.13 (d, J=8.7 Hz, 1H), 7.89 (d, J=2.9 Hz, 1H), 7.50-7.41 (m, 1H), 7.33 (d, J=5.8 Hz, 1H), 7.25-7.15 (m, 4H), 6.97 (s, 1H), 6.76 (d, J=6.6 Hz, 1H), 4.84 (h, J=7.0 Hz, 1H), 4.04 (q, J=7.0 Hz, 2H), 3.44 (tt, J=9.4, 5.2 Hz, 1H), 3.10-2.93 (sym. m, 2H), 2.59-2.41 (sym. m, 2H), 1.40 (t, J=7.0 Hz, 3H).

Example 158: Preparation of N-((1S,3r)-3-(5-(5-ethoxypyridin-2-yl)-4-(2-fluorophenyl)-4H-1,2,4-triazol-3-yl)cyclobutyl)-5-methy-[1,2,4]triazolo[1,5-a]pyrimidine-7-carboxamide

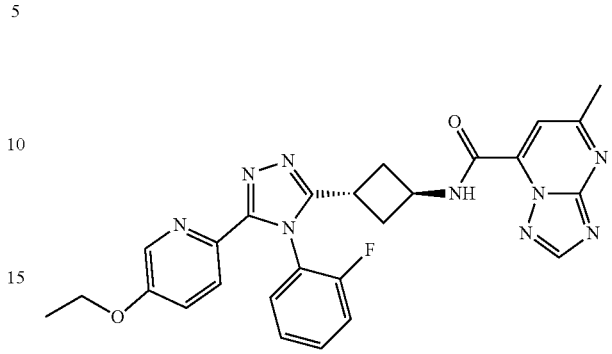

The title compound was prepared according to the general procedure F as a pale yellow solid (14.6 mg, 56% yield).

LC/MS (ESI) m/z for $C_{26}H_{24}FN_9O_2$ 513 (calcd) 514 ([M+H]$^+$, found).

$^1$H NMR (400 MHz, Chloroform-d) δ 8.60 (s, 1H), 8.24 (d, J=7.5 Hz, 1H), 8.16 (d, J=8.8 Hz, 1H), 7.88 (d, J=2.8 Hz, 1H), 7.86 (s, 1H), 7.50-7.43 (m, 1H), 7.26-7.16 (m, 4H), 4.84 (h, J=7.3 Hz, 1H), 4.04 (q, J=7.0 Hz, 2H), 3.46 (tt, J=9.9, 5.8 Hz, 1H), 3.15-3.06 (sym. m, 1H), 3.06-2.96 (sym. m, 1H), 2.93 (s, 3H), 2.48-2.31 (sym. m, 2H), 1.40 (t, J=7.0 Hz, 3H).

Example 159: Preparation of N-((1S,3r)-3-(5-(5-ethoxypyridin-2-yl)-4-(2-fluorophenyl)-4H-1,2,4-triazol-3-yl)cyclobutyl)-7-fluoroquinoxaline-5-carboxamide

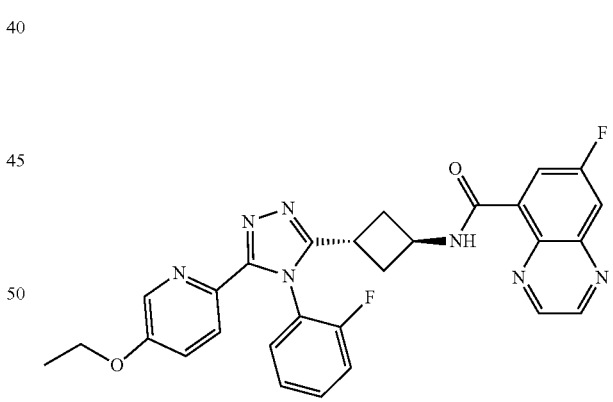

The title compound was prepared according to the general procedure F as a yellow solid (18.2 mg, 68% yield).

LC/MS (ESI) m/z for $C_{28}H_{23}F_2N_7O_2$ 527 (calcd) 528 ([M+H]$^+$, found).

$^1$H NMR (400 MHz, Chloroform-d) δ 10.62 (d, J=5.8 Hz, 1H), 8.96 (d, J=1.8 Hz, 1H), 8.82 (d, J=1.9 Hz, 1H), 8.64 (dd, J=9.6, 3.1 Hz, 1H), 8.17 (br s, 1H), 7.89 (br s, 1H), 7.87 (dd, J=7.9, 3.1 Hz, 1H), 7.48-7.39 (m, 1H), 7.25-7.14 (m, 4H), 4.83 (h, J=6.9 Hz, 1H), 4.04 (q, J=6.9 Hz, 2H), 3.52 (tt, J=10.1, 5.4 Hz, 1H), 3.13-3.01 (sym. m, 2H), 2.53 (dddd, J=15.9, 13.1, 9.7, 6.4 Hz, 2H), 1.40 (t, J=6.9 Hz, 3H).

Example 160: Preparation of N-((1r,3r)-3-(5-(5-ethoxypyridin-2-yl)-4-(pyridin-2-yl)-4H-1,2,4-triazol-3-yl)cyclobutyl)-7-fluoro-1,5-naphthyridine-4-carboxamide

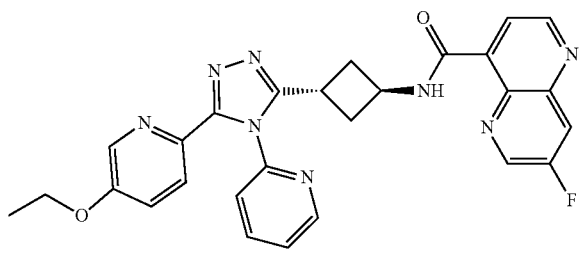

The title compound was prepared according to the general procedure F as a white solid (17.9 mg, 69% yield).

LC/MS (ESI) m/z for $C_{27}H_{23}FN_8O_2$ 510 (calcd) 511 ([M+H]$^+$, found).

$^1$H NMR (400 MHz, Chloroform-d) δ 10.81 (d, J=6.0 Hz, 1H), 9.15 (d, J=4.5 Hz, 1H), 8.92 (d, J=2.9 Hz, 1H), 8.56 (dd, J=4.8, 1.0 Hz, 1H), 8.52 (d, J=4.4 Hz, 1H), 8.20 (dd, J=8.7, 2.8 Hz, 1H), 8.17 (d, J=9.0 Hz, 1H), 7.87 (d, J=2.8 Hz, 1H), 7.79 (td, J=7.7, 1.9 Hz, 1H), 7.37 (dd, J=7.5, 4.8 Hz, 1H), 7.24 (dd, J=8.8, 3.0 Hz, 1H), 7.18 (d, J=8.0 Hz, 1H), 4.80 (h, J=6.6 Hz, 1H), 4.05 (q, J=7.0 Hz, 2H), 3.72 (tt, J=9.2, 5.3 Hz, 1H), 3.06 (ddd, J=13.2, 8.0, 5.3 Hz, 2H), 2.50 (ddd, J=12.6, 9.5, 6.2 Hz, 2H), 1.41 (t, J=7.0 Hz, 3H).

Example 161: Preparation of amine building block AB: (1r,3r)-3-(5-(5-ethoxypyridin-2-yl)-4-(pyridin-3-yl)-4H-1,2,4-triazol-3-yl)cyclobutan-1-amine trihydrochloride

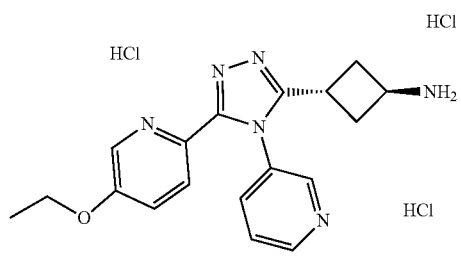

Step (a): crude 5-ethoxy-N-(pyridin-3-yl)picolinamide was prepared according to the general procedure A, method c) as an white-orange solid (716 mg, 98% yield).

LC/MS (ESI) m/z for $C_{13}H_{13}N_3O_2$ 243 (calcd) 244 ([M+H]$^+$, found).

$^1$H NMR (400 MHz, Chloroform-d) δ 9.90 (br s, 1H), 8.80 (d, J=2.6 Hz, 1H), 8.41-8.35 (m, 2H), 8.26 (d, J=2.8 Hz, 1H), 8.23 (d, J=8.7 Hz, 1H), 7.35-7.29 (m, 2H), 4.17 (q, J=7.0 Hz, 2H), 1.49 (t, J=7.0 Hz, 3H).

Step (b): 5-ethoxy-N-(pyridin-3-yl)pyridine-2-carbothioamide was prepared following the general procedure B as a yellow solid (641 mg, 86% yield).

LC/MS (ESI) m/z for $C_{13}H_{13}N_3OS$ 259 (calcd) 260 ([M+H]$^+$, found).

$^1$H NMR (400 MHz, Chloroform-d) δ 11.84 (br s, 1H), 8.92 (d, J=2.6 Hz, 1H), 8.83 (ddd, J=8.3, 2.7, 1.4 Hz, 1H), 8.73 (d, J=8.8 Hz, 1H), 8.50 (dd, J=4.7, 1.5 Hz, 1H), 8.20 (d, J=2.9 Hz, 1H), 7.39 (dd, J=8.3, 4.7 Hz, 1H), 7.31 (dd, J=8.8, 2.9 Hz, 1H), 4.18 (q, J=7.0 Hz, 2H), 1.50 (t, J=6.9 Hz, 3H).

Step (c): methyl 5-ethoxy-N-(pyridin-3-yl)pyridine-2-carbimidothioate was prepared as a yellow oil (377 mg, 90% purity, 51% yield) employing an alternative method to the general procedure C.

Starting thioamide was dissolved in absolute ethanol (0.1 molar) and the resulting suspension was treated with a 21% ethanolic solution of sodium ethoxide (1.05 equiv.) turning into a solution. After stirring for 1 hour at ambient temperature, the mixture was treated with iodomethane (1.05 equiv.) and it was allowed to stir at ambient temperature for 2 hours observing then complete conversion. The mixture was evaporated to dryness, the residue was resuspended in DCM, diluted with aqueous sodium carbonate and extracted three times with DCM. The organic extracts were dried over sodium sulfate, filtered and evaporated to dryness providing the crude product that was further purified by column chromatography.

LC/MS (ESI) m/z for $C_{14}H_{15}N_3OS$ 273 (calcd) 274 ([M-FH]$^+$, found).

$^1$H NMR (400 MHz, Chloroform-d) δ 8.35-8.21 (br m, 2H), 8.21-7.99 (br m, 1H), 7.26-6.90 (br m, 4H), 4.08 (distorted q, J=6.1, 5.0 Hz, 2H), 2.45 (br s, 3H), 1.43 (t, J=6.9 Hz, 3H).

Step (d): tert-butyl ((1r,3r)-3-(5-(5-ethoxypyridin-2-yl)-4-(pyridin-3-yl)-4H-1,2,4-triazol-3-yl)cyclobutyl)carbamate was prepared according to the general procedure D as a whitish glass (277 mg, 90% purity, 92% yield).

LC/MS (ESI) m/z for $C_{23}H_{28}N_6O_3$ 436 (calcd) 437 ([M+H]$^+$, found).

$^1$H NMR (400 MHz, Chloroform-d) δ 8.69 (dd, J=4.8, 1.5 Hz, 1H), 8.43 (d, J=2.5 Hz, 1H), 8.14 (d, J=8.7 Hz, 1H), 7.86 (d, J=2.9 Hz, 1H), 7.53 (ddd, J=8.1, 2.6, 1.6 Hz, 1H), 7.41 (dd, J=8.2, 4.8 Hz, 1H), 7.22 (dd, J=8.7, 2.9 Hz, 1H), 4.73 (br s, 1H), 4.34 (ht, J=7.1, 1.4 Hz, 1H), 4.04 (q, J=6.9 Hz, 2H), 3.30 (br apparent s, 1H), 2.86 (ddd, J=12.9, 7.9, 5.6 Hz, 2H), 2.26 (br apparent s, 2H), 1.42 (s, 9H), 1.39 (t, J=7.0 Hz, 3H).

Step (e): the crude title compound was prepared according to the general procedure E as a white powdery solid (264 mg, 95% purity, 99% yield).

LC/MS (ESI) m/z for $C_{18}H_{20}N_6O$·336 (calcd) 337 ([M+H]$^+$, found).

$^1$H NMR (400 MHz, DMSO-d6) δ 8.75 (dd, J=5.1, 1.5 Hz, 1H), 8.68 (d, 0.1=2.5 Hz, 1H), 8.33 (br d, J=5.4 Hz, 3H, NH$_2$+HCl), 8.03 (d, J=8.8 Hz, 1H), 7.99 (dt, J=8.2, 2.0 Hz, 1H), 7.95 (d, J=2.8 Hz, 1H), 7.65 (dd, J=8.2, 4.9 Hz, 1H), 7.51 (dd, J=8.8, 2.8 Hz, 1H), 4.10 (q, J=6.9 Hz, 2H), 3.83 (h, J=6.3 Hz, 1H), 3.58 (tt, J=9.8, 5.7 Hz, 1H), 2.73 (ddd, J=13.3, 8.0, 5.5 Hz, 2H), 2.38-2.26 (sym. m, 2H), 1.31 (t, J=7.0 Hz, 3H).

Example 162: Preparation of N-((1r,3r)-3-(5-(5-ethoxypyridin-2-yl)-4-(pyridin-3-yl)-4H-1,2,4-triazol-3-yl)cyclobutyl)-1,5-naphthyridine-4-carboxamide

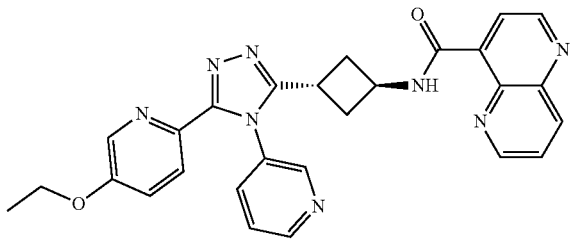

The title compound was prepared according to the general procedure F as a white solid (12.6 mg, 51% yield).

LC/MS (ESI) m/z for $C_{27}H_{24}N_8O_2$ 492 (calcd) 493 ([M+H]$^+$, found).

$^1$H NMR (400 MHz, Chloroform-d) δ 11.31 (d, J=6.0 Hz, 1H), 9.14 (d, J=4.5 Hz, 1H), 8.98 (dd, J=4.3, 1.8 Hz, 1H), 8.68 (dd, J=4.8, 1.5 Hz, 1H), 8.59-8.52 (m, 2H), 8.48 (d, J=2.5 Hz, 1H), 8.17 (d, J=8.8 Hz, 1H), 7.87 (d, J=2.9 Hz, 1H), 7.74 (dd, J=8.6, 4.2 Hz, 1H), 7.58 (ddd, J=8.1, 2.5, 1.5 Hz, 1H), 7.41 (dd, J=8.0, 4.7 Hz, 1H), 7.24 (dd, J=8.7, 2.9 Hz, 1H), 4.87 (ht, J=6.9, 1.5 Hz, 1H), 4.05 (q, J=7.0 Hz, 2H), 3.52 (ttt, J=9.8, 5.2, 1.3 Hz, 1H), 3.09 (ddd, J=13.3, 8.0, 5.4 Hz, 2H), 2.62-2.51 (sym. m, 2H), 1.41 (t, J=7.0 Hz, 3H).

Example 163: Preparation of N-((1r,3r)-3-(5-(5-ethoxypyridin-2-yl)-4-(pyridin-3-yl)-4H-1,2,4-triazol-3-yl)cyclobutyl)-1,5-naphthyridine-2-carboxamide

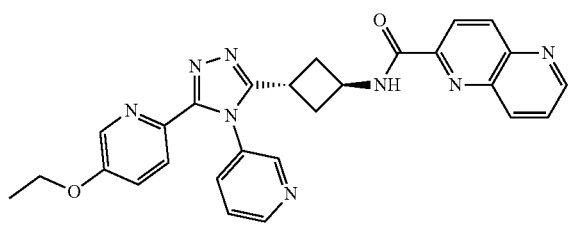

The title compound was prepared according to the general procedure F as a white solid (14.8 mg, 60% yield).

LC/MS (ESI) m/z for $C_{27}H_{24}N_8O_2$ 492 (calcd) 493 ([M+H]$^+$, found).

$^1$H NMR (400 MHz, Chloroform-d) δ 9.05 (dd, J=4.2, 1.7 Hz, 1H), 8.69 (dd, J=4.8, 1.5 Hz, 1H), 8.57-8.49 (m, apparent q), 2H), 8.48 (d, J=2.4 Hz, 1H), 8.42 (dd, J=8.6, 1.7 Hz, 1H), 8.35 (d, J=6.9 Hz, 1H), 8.17 (d, J=8.7 Hz, 1H), 7.87 (d, J=2.9 Hz, 1H), 7.70 (dd, J=8.6, 4.2 Hz, 1H), 7.58 (ddd, J=8.1, 2.6, 1.5 Hz, 1H), 7.42 (dd, J=8.1, 4.7 Hz, 1H), 7.24 (dd, J=8.7, 2.9 Hz, 1H), 4.86 (h, J=7.1 Hz, 1H), 4.05 (q, J=7.0 Hz, 2H), 3.50 (tt, J=9.8, 5.0 Hz, 1H), 3.13-3.02 (sym. m, 2H), 2.61-2.50 (sym. m, 2H), 1.41 (t, J=7.0 Hz, 3H).

Example 164: Preparation of N-((1r,3r)-3-(5-(5-ethoxypyridin-2-yl)-4-(pyridin-3-yl)-4H-1,2,4-triazol-3-yl)cyclobutyl)-7-fluoro-1,5-naphthyridine-4-carboxamide

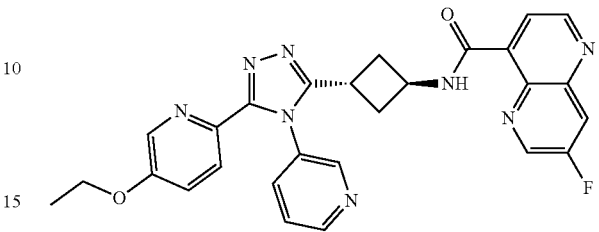

The title compound was prepared according to the general procedure F as a white solid (22 mg, 85% yield).

LC/MS (ESI) m/z for $C_{27}H_{23}FN_8O_2$ 510 (calcd) 511 ([M+H]$^+$, found).

$^1$H NMR (400 MHz, Chloroform-d) δ 10.83 (d, J=6.0 Hz, 1H), 9.15 (d, J=4.4 Hz, 1H), 8.91 (d, J=2.8 Hz, 1H), 8.69 (dd, J=4.8, 1.5 Hz, 1H), 8.52 (d, J=4.4 Hz, 1H), 8.48 (d, J=2.5 Hz, 1H), 8.20 (dd, J=8.7, 2.8 Hz, 1H), 8.17 (d, J=8.5 Hz, 1H), 7.87 (d, J=2.8 Hz, 1H), 7.57 (dt, J=8.1, 2.0 Hz, 1H), 7.41 (dd, J=8.2, 4.8 Hz, 1H), 7.24 (dd, J=8.8, 3.0 Hz, 1H), 4.87 (h, J=7.1 Hz, 1H), 4.05 (q, J=7.0 Hz, 2H), 3.50 (tt, J=9.8, 5.2 Hz, 1H), 3.08 (ddd, J=13.3, 7.9, 5.2 Hz, 2H), 2.55 (ddd, J=12.6, 9.4, 6.2 Hz, 2H), 1.41 (t, J=7.0 Hz, 3H).

Example 165: Preparation of amine building block AC: 3-(5-(5-ethoxypyridin-2-yl)-4-(pyridin-3-yl)-4H-1,2,4-triazol-3-yl)bicyclo[1.1.1]pentan-1-amine trihydrochloride

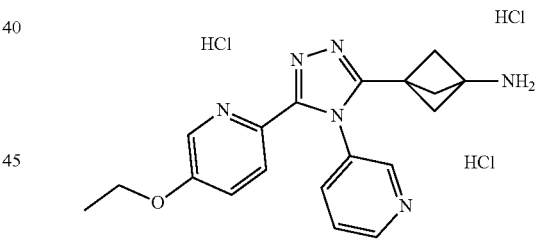

Step (a): crude tert-butyl (3-(5-(5-ethoxypyridin-2-yl)-4-(pyridin-3-yl)-4H-1,2,4-triazol-3-yl)bicyclo[1.1.1]pentan-1-yl)carbamate was prepared according to the general procedure D a pale yellow semisolid (263 mg, =81% purity, 77% yield) from methyl 5-ethoxy-N-(pyridin-3-yl)pyridine-2-carbimidothioate and tert-butyl (3-(hydrazinecarbonyl)bicyclo[1.1.1]pentan-1-yl)carbamate (Example 2).

LC/MS (ESI) m/z for $C_{24}H_{28}N_6O_3$ 448 (calcd) 449 ([M+H]$^+$, found).

$^1$H NMR (400 MHz, Chloroform-d) δ 8.72 (dd, J=4.8, 1.5 Hz, 1H), 8.50 (d, J=2.5 Hz, 1H), 8.12 (d, J=8.8 Hz, 1H), 7.85 (d, J=2.9 Hz, 1H), 7.62 (dt, J=8.1, 2.0 Hz, 1H), 7.43 (dd, J=8.1, 4.8 Hz, 1H), 7.20 (dd, J=8.7, 2.9 Hz, 1H), 4.90 (br s, 1H), 4.03 (q, J=7.0 Hz, 2H), 2.20 (s, 6H), 1.44-1.32 (coinciding s+t, 12H).

Step (b): the crude title compound was prepared according to the general procedure E as a whitish powder (233 mg, ~92% purity, =100% yield).

LC/MS (ESI) m/z for C₁₉H₂₀N₆O·348 (calcd) 349 ([M+H]⁺, found).

¹H NMR (400 MHz, DMSO-d6) δ 8.87 (br s, 3H, NH₂+HCl), 8.77 (dd, J=4.8, 1.5 Hz, 1H), 8.71 (d, J=2.5 Hz, 1H), 8.06-7.99 (m, 2H), 7.93 (d, J=2.9 Hz, 1H), 7.64 (dd, J=8.2, 4.9 Hz, 1H), 7.49 (dd, J=8.8, 2.9 Hz, 1H), 4.09 (q, J=6.9 Hz, 2H), 2.09 (s, 6H), 1.30 (t, J=6.9 Hz, 3H).

Example 166: Preparation of N-(3-(5-(5-ethoxypyridin-2-yl)-4-(pyridin-3-yl)-4H-1,2,4-triazol-3-yl)bicyclo[1.1.1]pentan-1-yl)-1,5-naphthyridine-4-carboxamide

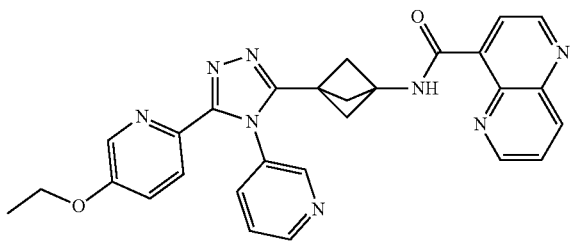

The title compound was prepared according to the general procedure F as a white powder (20.2 mg, 78% yield).

LC/MS (ESI) m/z for C₂₈H₂₄N₈O₂ 504 (calcd) 505 ([M+H]⁺, found).

¹H NMR (400 MHz, Chloroform-d) δ 11.45 (s, 1H), 9.14 (d, J=4.5 Hz, 1H), 8.99 (dd, J=4.1, 1.8 Hz, 1H), 8.74 (dd, J=4.8, 1.5 Hz, 1H), 8.58-8.52 (m, 2H), 8.49 (d, J=4.4 Hz, 1H), 8.14 (d, J=8.8 Hz, 1H), 7.87 (d, J=2.9 Hz, 1H), 7.74 (dd, J=8.6, 4.3 Hz, 1H), 7.69 (ddd, J=8.1, 2.5, 1.5 Hz, 1H), 7.46 (dd, J=8.0, 4.7 Hz, 1H), 7.22 (dd, J=8.8, 2.9 Hz, 1H), 4.04 (q, J=6.9 Hz, 2H), 2.49 (s, 6H), 1.40 (t, J=7.0 Hz, 3H).

Example 167: Preparation of amine building block AD: (1r,3r)-3-(5-(5-ethoxypyridin-2-yl)-4-(pyridin-4-yl)-4H-1,2,4-triazol-3-yl)cyclobutan-1-amine trihydrochloride

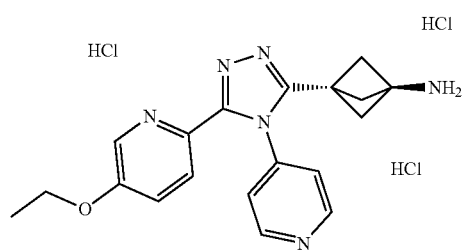

Step (a): crude 5-ethoxy-N-(pyridin-4-yl)picolinamide was prepared according to the general procedure A, method c) as an orange solid (649 mg, 95% purity, 84% yield).

LC/MS (ESI) m/z for C₁₃H₁₃N₃O₂ 243 (calcd) 244 ([M+H]⁺, found).

Step (b): 5-ethoxy-N-(pyridin-4-yl)pyridine-2-carbothioamide was prepared following the general procedure B as a yellow oil (381 mg, 56% yield) crystallising upon standing.

LC/MS (ESI) m/z for C₁₃H₁₃N₃OS 259 (calcd) 260 ([M+H]⁺, found).

Step (c): ethyl 5-ethoxy-N-(pyridin-4-yl)pyridine-2-carbimidothioate was prepared as a pale yellow oil (222 mg, 95% purity, 52% yield) according to the to the general procedure C using iodoethane instead of iodomethane.

LC/MS (ESI) m/z for C₁₅H₁₇N₃OS 287 (calcd) 288 ([M+H]⁺, found).

¹H NMR (400 MHz, Chloroform-d) δ 8.42 (distorted d, J=−6.3 Hz, 2H), 8.29 (d, J=2.9 Hz, 1H), 7.29 (br s, 1H), 7.06 (dd, J=8.7, 2.9 Hz, 1H), 6.71 (distorted d, J=−6.5 Hz, 2H), 4.08 (q, J=7.0 Hz, 2H), 3.00 (q, J=7.4 Hz, 2H), 1.44 (t, J=7.0 Hz, 3H), 1.29 (t, J=7.4 Hz, 3H).

Step (d): tert-butyl ((1r,3r)-3-(5-(5-ethoxypyridin-2-yl)-4-(pyridin-4-yl)-4H-1,2,4-triazol-3-yl)cyclobutyl)carbamate was prepared according to the general procedure D as a white foam (269 mg, 83% yield).

LC/MS (ESI) m/z for C₂₃H₂₈N₆O₃ 436 (calcd) 437 ([M+H]⁺, found).

¹H NMR (400 MHz, Chloroform-d) δ 8.76-8.68 (sym. m, 2H), 8.13 (d, J=8.8 Hz, 1H), 7.87 (d, J=2.9 Hz, 1H), 7.24 (dd, J=8.7, 2.9 Hz, 1H), 7.12-7.06 (sym. m, 2H), 4.73 (br s, 1H), 4.34 (apparent h, J=7.1 Hz, 1H), 4.05 (q, J=7.0 Hz, 2H), 3.31 (tt, J=9.3, 5.0 Hz, 1H), 2.92-2.80 (sym. m, 2H), 1.42 (s, 9H), 1.41 (t, J=7.0 Hz, 3H).

Step (e): the crude title compound was prepared according to the general procedure E as a white powdery solid (262 mg, 90% purity, 100% yield).

LC/MS (ESI) m/z for C₁₈H₂₀N₆O·336 (calcd) 337 ([M+H]⁺, found).

¹H NMR (400 MHz, DMSO-d6) δ 8.81 (d, J=5.4 Hz, 2H), 8.29 (br d, J=3.7 Hz, 3H, NH₂+HCl), 8.03 (d, J=8.8 Hz, 1H), 7.96 (d, J=3.0 Hz, 1H), 7.59 (d, J=5.8 Hz, 2H), 7.52 (dd, J=8.7, 2.9 Hz, 1H), 4.10 (q, J=7.0 Hz, 2H), 3.89-3.78 (m, 1H), 3.58 (tt, J=9.6, 5.5 Hz, 1H), 2.70 (ddd, J=13.1, 7.8, 5.0 Hz, 2H), 2.34 (ddd, J=12.6, 9.4, 5.6 Hz, 2H), 1.31 (t, J=7.0 Hz, 3H).

Example 168: Preparation of N-((1r,3r)-3-(5-(5-ethoxypyridin-2-yl)-4-(pyridin-4-yl)-4H-1,2,4-triazol-3-yl)cyclobutyl)-1,5-naphthyridine-4-carboxamide

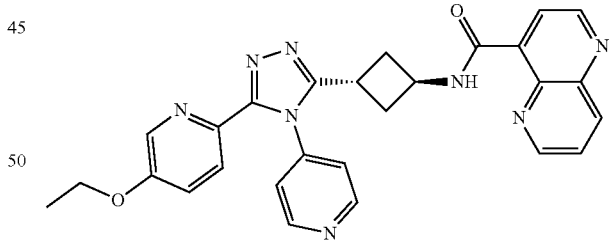

The title compound was prepared according to the general procedure F as a white solid (12.7 mg, 51% yield).

LC/MS (ESI) m/z for C₂₇H₂₄N₈O₂ 492 (calcd) 493 ([M+H]⁺, found).

¹H NMR (400 MHz, Chloroform-d) δ 11.31 (d, J=6.0 Hz, 1H), 9.15 (d, J=4.4 Hz, 1H), 8.97 (dd, J=4.3, 1.8 Hz, 1H), 8.75-8.69 (sym. m, 2H), 8.59-8.52 (m, 2H), 8.17 (d, J=8.8 Hz, 1H), 7.88 (d, J=2.8 Hz, 1H), 7.74 (dd, J=8.5, 4.2 Hz, 1H), 7.26 (dd, J=8.7, 2.9 Hz, 1H), 7.17-7.11 (sym. m, 2H), 4.87 (ht, J=7.0, 1.5 Hz, 1H), 4.06 (q, J=7.0 Hz, 2H), 3.52 (tt, J=9.8, 5.2 Hz, 1H), 3.09 (ddd, J=13.2, 8.0, 5.3 Hz, 2H), 2.63-2.52 (sym. m, 2H), 1.42 (t, J=7.0 Hz, 3H).

Example 169: Preparation of N-((1r,3r)-3-(5-(5-ethoxypyridin-2-yl)-4-(pyridin-4-yl)-4H-1,2,4-triazol-3-yl)cyclobutyl)-1,5-naphthyridine-2-carboxamide

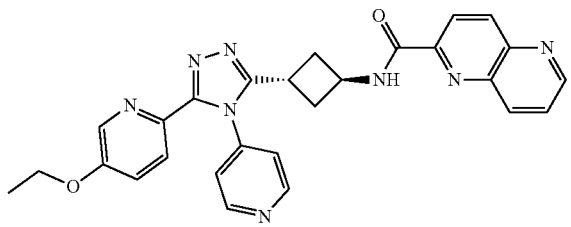

The title compound was prepared according to the general procedure F as a white solid (22.5 mg, 90% yield).

LC/MS (ESI) m/z for $C_{27}H_{24}N_8O_2$ 492 (calcd) 493 ([M+H]$^+$, found).

$^1$H NMR (400 MHz, Chloroform-d) δ 9.06 (dd, J=4.2, 1.7 Hz, 1H), 8.77-8.70 (sym. m, 2H), 8.58-8.48 (m (apparent q), 2H), 8.41 (dd, J=8.7, 1.7 Hz, 1H), 8.35 (d, J=6.9 Hz, 1H), 8.17 (d, J=8.7 Hz, 1H), 7.88 (d, J=3.0 Hz, 1H), 7.70 (dd, J=8.6, 4.2 Hz, 1H), 7.26 (dd, J=8.7, 2.9 Hz, 1H), 7.17-7.10 (sym. m, 2H), 4.87 (h, J=7.2 Hz, 1H), 4.06 (q, J=6.9 Hz, 2H), 3.50 (tdd, J=9.8, 5.6, 4.4 Hz, 1H), 3.08 (ddd, J=13.2, 8.1, 5.1 Hz, 2H), 2.62-2.51 (sym. m, 2H), 1.42 (t, J=7.0 Hz, 3H).

Example 170: Preparation of N-((1r,3r)-3-(5-(5-ethoxypyridin-2-yl)-4-(pyridin-4-yl)-4H-1,2,4-triazol-3-yl)cyclobutyl)-7-fluoro-1,5-naphthyridine-4-carboxamide

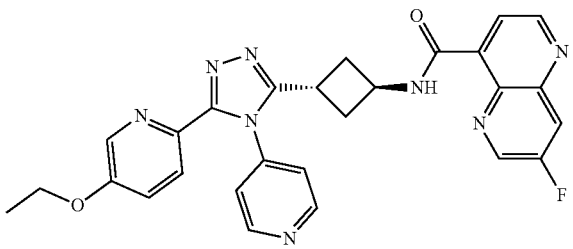

The title compound was prepared according to the general procedure F as a white solid (19.2 mg, 74% yield).

LC/MS (ESI) m/z for $C_{27}H_{23}FN_8O_2$ 510 (calcd) 511 ([M+H]$^+$, found).

$^1$H NMR (400 MHz, Chloroform-d) δ 10.83 (d, J=6.0 Hz, 1H), 9.16 (d, J=4.5 Hz, 1H), 8.91 (d, J=2.9 Hz, 1H), 8.76-8.69 (sym. m, 2H), 8.52 (d, J=4.5 Hz, 1H), 8.20 (dd, J=8.7, 2.9 Hz, 1H), 8.17 (d, J=8.6 Hz, 1H), 7.88 (d, J=3.3 Hz, 1H), 7.25 (dd, J=8.8, 2.8 Hz, 1H), 7.17-7.10 (sym. m, 2H), 4.87 (h, J=7.0 Hz, 1H), 4.06 (q, J=6.9 Hz, 2H), 3.51 (tt, J=9.3, 5.4 Hz, 1H), 3.08 (ddd, J=13.0, 8.0, 5.1 Hz, 2H), 2.56 (ddd, J=12.7, 9.5, 6.5 Hz, 2H), 1.42 (t, J=7.0 Hz, 3H).

Example 171: Preparation of amine building block AE: 3-(5-(5-ethoxypyridin-2-yl)-4-(pyridin-4-yl)-4H-1,2,4-triazol-3-yl)bicyclo[1.1.1]pentan-1-amine trihydrochloride

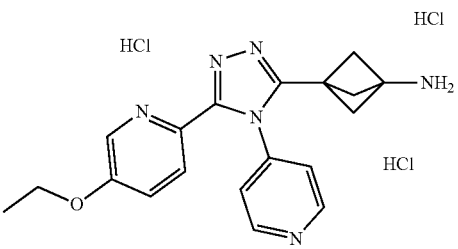

Step (a): tert-butyl (3-(5-(5-ethoxypyridin-2-yl)-4-(pyridin-4-yl)-4H-1,2,4-triazol-3-yl)bicyclo[1.1.1]pentan-1-yl)carbamate was prepared according to the general procedure D as an off-white solid (17 mg, ~85% purity, 98% yield) from ethyl 5-ethoxy-N-(pyridin-4-yl)pyridine-2-carbimidothioate and tert-butyl (3-(hydrazinecarbonyl)bicyclo[1.1.1]pentan-1-yl)carbamate (Example 2).

LC/MS (ESI) m/z for $C_{24}H_{28}N_6O_3$ 448 (calcd) 449 ([M+H]$^+$, found).

$^1$H NMR (400 MHz, Chloroform-d) δ 8.75 (d, J=5.2 Hz, 2H), 8.11 (d, J=8.8 Hz, 1H), 7.84 (d, J=2.9 Hz, 1H), 7.24-7.16 (m, 3H), 4.91 (br s, 1H), 4.03 (q, J=7.0 Hz, 2H), 2.22 (s, 6H), 1.42-1.36 (coinciding s+t, 12H).

Step (b): the crude title compound was prepared according to the general procedure E as a whitish solid (17 mg, ~85% purity, ~100% yield).

LC/MS (ESI) m/z for $C_{19}H_{20}N_6O$·348 (calcd) 349 ([M+H]$^+$, found).

Example 172: Preparation of N-(3-(5-(5-ethoxypyridin-2-yl)-4-(pyridin-4-yl)-4H-1,2,4-triazol-3-yl)bicyclo[1.1.1]pentan-1-yl)-1,5-naphthyridine-4-carboxamide

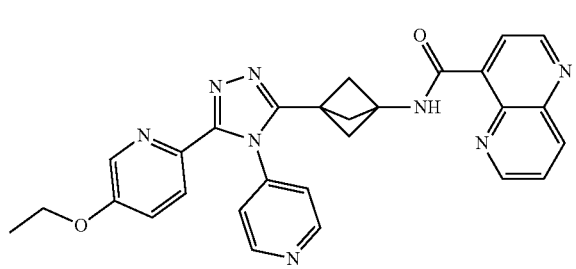

The title compound was prepared according to the general procedure F as a white powder (10.2 mg, 63% yield).

LC/MS (ESI) m/z for $C_{28}H_{24}N_8O_2$ 504 (calcd) 505 ([M+H]$^+$, found).

$^1$H NMR (400 MHz, Chloroform-d) δ 11.45 (s, 1H), 9.14 (d, J=4.5 Hz, 1H), 8.99 (dd, J=4.2, 1.8 Hz, 1H), 8.82-8.75 (sym. m, 2H), 8.55 (dd, J=8.6, 1.8 Hz, 1H), 8.50 (d, J=4.4 Hz, 1H), 8.14 (d, J=8.8 Hz, 1H), 7.86 (d, J=2.8 Hz, 1H), 7.74 (dd, J=8.5, 4.2 Hz, 1H), 7.30-7.26 (sym. m, 2H), 7.23 (dd, J=8.7, 2.9 Hz, 1H), 4.04 (q, J=6.9 Hz, 2H), 2.51 (s, 6H), 1.41 (t, J=7.0 Hz, 3H).

Example 173: Preparation of amine building block AF: (1S,3r)-3-(4-(2-fluorophenyl)-5-phenyl-4H-1,2,4-triazol-3-yl)cyclobutan-1-amine dihydrochloride

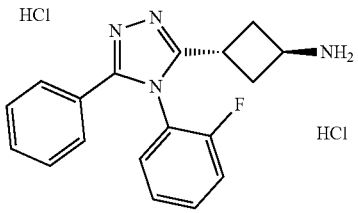

Step (a): crude N-(2-fluorophenyl)benzamide was prepared according to the general procedure A, method c) as a beige solid (2.18 gram, 100% yield).

LC/MS (ESI) m/z for $C_{13}H_{10}FNO$ 215 (calcd) 216 ([M+H]$^+$, found).

Step (b): N-(2-fluorophenyl)benzothioamide was prepared following the general procedure B as a yellow oil (2.28 gram, 98% yield) crystallising upon standing.

LC/MS (ESI) m/z for $C_{13}H_{10}FNS$ 231 (calcd) 232 ([M+H]$^+$, found).

Step (c): methyl N-(2-fluorophenyl)benzimidothioate was prepared as a yellow oil (2.23 gram, 92% yield) employing the general procedure C.

LC/MS (ESI) m/z for $C_{14}H_{12}FNS$ 245 (calcd) 246 ([M+H]$^+$, found).

Step (d): tert-butyl ((1S,3r)-3-(4-(2-fluorophenyl)-5-phenyl-4H-1,2,4-triazol-3-yl)cyclobutyl)carbamate was prepared as a white foam (739 mg, 95% purity, 43% yield) according to the general procedure D with 0.10 equiv. of p-toluenesulfonic acid monohydrate [additionally, ~30% yield of the deprotected amine was also isolated].

LC/MS (ESI) m/z for $C_{23}H_{25}FN_4O_2$ 408 (calcd) 409 ([M+H]$^+$, found).

$^1$H NMR (400 MHz, Chloroform-d) δ 7.50 (tdd, J=7.8, 4.9, 1.8 Hz, 1H), 7.44-7.38 (m, 2H), 7.38-7.31 (m, 1H), 7.31-7.20 (m, 4H), 7.15 (td, J=7.4, 1.8 Hz, 1H), 4.77 (br s, 1H), 4.32 (ht, J=6.9, 1.5 Hz, 1H), 3.33 (br s, 1H), 2.94-2.78 (m, 2H), 2.37-2.10 (br s+m, 2H), 1.42 (s, 9H).

Step (e): the crude title compound was prepared according to the general procedure E as a white solid (665 mg, 100% yield).

LC/MS (ESI) m/z for $C_{18}H_{17}FN_4$·308 (calcd) 309 ([M+H]$^+$, found).

$^1$H NMR (400 MHz, DMSO-d6) δ 8.44 (br d, J=5.3 Hz, 3H, NH$_2$+HCl), 7.72 (td, J=7.8, 1.7 Hz, 1H), 7.66 (tdd, J=7.5, 5.2, 1.7 Hz, 1H), 7.50 (ddd, J=9.9, 8.4, 1.3 Hz, 1H), 7.47-7.41 (m, 2H), 7.41-7.33 (m, 4H), 3.86 (h, J=6.2 Hz, 1H), 3.58 (tt, J=9.8, 5.7 Hz, 1H), 2.84-2.73 (sym. m, 1H), 2.66-2.55 (sym. m, 1H), 2.45-2.30 (sym. m, 2H).

Example 174: Preparation of N-((1S,3r)-3-(4-(2-fluorophenyl)-5-phenyl-4H-1,2,4-triazol-3-yl)cyclobutyl)picolinamide

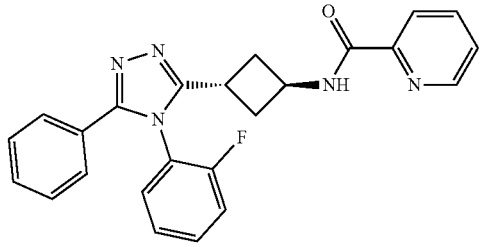

The title compound was prepared according to the general procedure F as a white solid (21.0 mg, 84% yield).

LC/MS (ESI) m/z for $C_{24}H_{20}FN_5O$ 413 (calcd) 414 ([M+H]$^+$, found).

$^1$H NMR (400 MHz, Chloroform-d) δ 8.53 (dq, J=4.8, 1.0 Hz, 1H), 8.23 (br d, J=6.8 Hz, 1H), 8.17 (dt, J=7.9, 1.1 Hz, 1H), 7.84 (td, J=7.7, 1.7 Hz, 1H), 7.53-7.46 (m, 1H), 7.46-7.39 (m, 3H), 7.39-7.32 (m, 1H), 7.29 (dd, J=8.1, 6.5 Hz, 2H), 7.26-7.21 (m, 2H), 7.17 (td, J=7.5, 1.6 Hz, 1H), 4.76 (h, J=7.2 Hz, 1H), 3.49 (tt, J=9.4, 5.6 Hz, 1H), 3.11-2.95 (sym. m, 2H), 2.52-2.40 (sym. m, 2H).

Example 175: Preparation of 5-fluoro-N-((1S,3r)-3-(4-(2-fluorophenyl)-5-phenyl-4H-1,2,4-triazol-3-yl)cyclobutyl)picolinamide

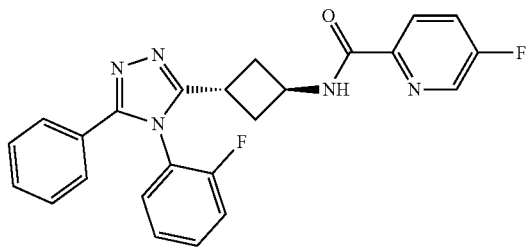

The title compound was prepared according to the general procedure F as a white solid (20.1 mg, 76% yield).

LC/MS (ESI) m/z for $C_{24}H_{19}F_2N_5O$ 431 (calcd) 432 ([M+H]$^+$, found).

$^1$H NMR (400 MHz, Chloroform-d) δ 8.36 (d, J=2.8 Hz, 1H), 8.20 (dd, J=8.7, 4.6 Hz, 1H), 8.05 (br d, J=6.9 Hz, 1H), 7.56-7.46 (m, 2H), 7.46-7.39 (m, 2H), 7.39-7.32 (m, 1H), 7.32-7.21 (m, 4H), 7.17 (td, J=7.5, 1.7 Hz, 1H), 4.76 (ht, J=7.4, 1.6 Hz, 1H), 3.47 (tt, J=9.4, 5.6 Hz, 1H), 3.11-2.95 (sym. m, 2H), 2.51-2.39 (sym. m, 2H).

Example 176: Preparation of N-((1S,3r)-3-(4-(2-fluorophenyl)-5-phenyl-4H-1,2,4-triazol-3-yl)cyclobutyl)-1,5-naphthyridine-4-carboxamide

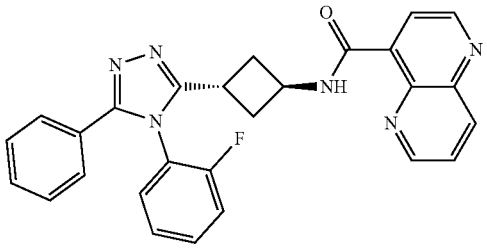

The title compound was prepared according to the general procedure F as a whitish solid (14.3 mg, 61% yield).

LC/MS (ESI) m/z for $C_{27}H_{21}FN_6O$ 464 (calcd) 465 ([M+H]$^+$, found).

$^1$H NMR (400 MHz, Chloroform-d) δ 11.32 (d, J=5.9 Hz, 1H), 9.15 (d, J=4.5 Hz, 1H), 8.98 (dd, J=4.3, 1.8 Hz, 1H), 8.59-8.51 (m, 2H), 7.74 (dd, J=8.5, 4.2 Hz, 1H), 7.53-7.46 (m, 1H), 7.46-7.40 (m, 2H), 7.39-7.33 (m, 1H), 7.33-7.27 (m, 2H), 7.23 (distorted d, J=8.1 Hz, 2H), 7.22-7.15 (m, 1H), 4.85 (ht, J=7.0, 1.5 Hz, 1H), 3.55 (tt, J=9.9, 5.4 Hz, 1H), 3.18-3.08 (sym. m, 1H), 3.08-2.99 (sym. m, 1H), 2.65-2.51 (sym. m, 2H).

Example 177: Preparation of 7-fluoro-N-((1S,3r)-3-(4-(2-fluorophenyl)-5-phenyl-4H-1,2,4-triazol-3-yl)cyclobutyl)-1,5-naphthyridine-4-carboxamide

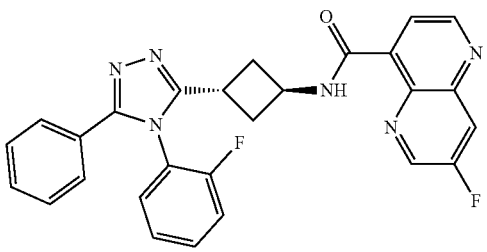

The title compound was prepared according to the general procedure F as a white solid (17.9 mg, 74% yield).

LC/MS (ESI) m/z for $C_{27}H_{20}F_2N_6O$ 482 (calcd) 483 ([M+H]$^+$, found).

$^1$H NMR (400 MHz, Chloroform-d) δ 10.83 (d, J=6.0 Hz, 1H), 9.15 (d, J=4.5 Hz, 1H), 8.92 (d, J=2.9 Hz, 1H), 8.52 (d, J=4.5 Hz, 1H), 8.20 (dd, J=8.6, 2.9 Hz, 1H), 7.54-7.46 (m, 1H), 7.46-7.40 (m, 2H), 7.39-7.33 (m, 1H), 7.33-7.22 (m, 4H), 7.22-7.15 (m, 1H), 4.85 (ht, J=7.0, 1.7 Hz, 1H), 3.53 (tt, J=9.8, 5.3 Hz, 1H), 3.16-2.99 (sym. m, 2H), 2.63-2.50 (sym. m, 2H).

Example 178: Preparation of N-((1S,3r)-3-(4-(2-fluorophenyl)-5-phenyl-4H-1,2,4-triazol-3-yl)cyclobutyl)-1,6-naphthyridine-2-carboxamide

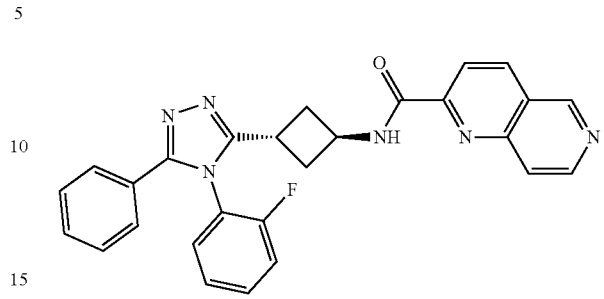

The title compound was prepared according to the general procedure F as a white solid (17.3 mg, 74% yield).

LC/MS (ESI) m/z for $C_{27}H_{21}FN_6O$ 464 (calcd) 465 ([M+H]$^+$, found).

$^1$H NMR (400 MHz, Chloroform-d) δ 9.36 (s, 1H), 8.83 (d, J=5.9 Hz, 1H), 8.47 (distorted dd, J=8.6, 0.8 Hz, 1H), 8.44-8.36 (m, 2H), 7.93 (d, J=5.9 Hz, 1H), 7.54-7.47 (m, 1H), 7.47-7.40 (m, 2H), 7.39-7.33 (m, 1H), 7.33-7.22 (m, 4H), 7.19 (ddd, J=8.2, 7.1, 1.8 Hz, 1H), 4.86 (ht, J=7.4, 1.5 Hz, 1H), 3.52 (tt, J=9.8, 5.3 Hz, 1H), 3.16-3.00 (sym. m, 2H), 2.63-2.50 (sym. m, 2H).

Example 179: Preparation of amine building block AG: (1S,3r)-3-(5-(5-(difluoromethoxy)pyridin-2-yl)-4-(2-fluorophenyl)-4H-1,2,4-triazol-3-yl)cyclobutan-1-amine dihydrochloride

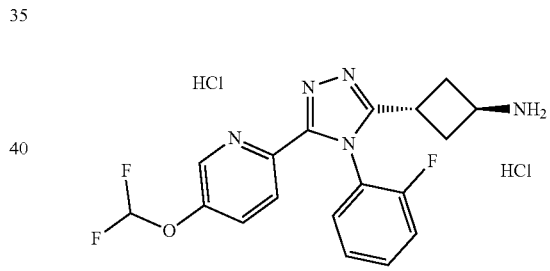

Step (a): crude 5-(difluoromethoxy)-N-(2-fluorophenyl)picolinamide was prepared according to the general procedure A, method c) as a beige solid (563 mg, 99% yield).

LC/MS (ESI) m/z for $C_{13}H_9F_3N_2O_2$ 282 (calcd) 283 ([M+H]$^+$, found).

Step (b): 5-(difluoromethoxy)-N-(2-fluorophenyl)pyridine-2-carbothioamide was prepared following the general procedure 13 as a yellow solid (551 mg, 93% yield).

LC/MS (ESI) m/z for $C_{13}H_9F_3N_2OS$ 298 (calcd) 299 ([M+H]$^+$, found).

Step (c): methyl 5-(difluoromethoxy)-N-(2-fluorophenyl)pyridine-2-carbimidothioate was prepared as a yellow oil (569 mg, 100% yield) employing the general procedure C.

LC/MS (ESI) m/z for $C_{14}H_{11}F_3N_2OS$ 312 (calcd) 313 ([M+H]$^+$, found).

Step (d): tert-butyl ((1S,3r)-3-(5-(5-(difluoromethoxy)pyridin-2-yl)-4-(2-fluorophenyl)-4H-1,2,4-triazol-3-yl)cyclobutyl)carbamate was prepared as an off-white foam (448 mg, 91% yield) according to the general procedure D.

LC/MS (ESI) m/z for $C_{23}H_{24}F_3N_5O_3$ 475 (calcd) 476 ([M+11]$^+$, found).

¹H NMR (400 MHz, Chloroform-d) δ 8.30 (d, J=8.7 Hz, 1H), 8.06 (d, J=2.7 Hz, 1H), 7.53 (dd, J=8.8, 2.7 Hz, 1H), 7.48 (tdd, J=7.6, 4.8, 1.9 Hz, 1H), 7.26-7.14 (m, 3H), 6.51 (t, J=72.4 Hz, 1H), 4.73 (br s, 1H), 4.33 (ht, J=7.1, 1.5 Hz, 1H), 3.37-3.25 (m, 1H), 2.95-2.85 (m, 1H), 2.83 (apparent s, 1H), 2.40-2.10 (m, 2H), 1.42 (s, 9H).

Step (e): the crude title compound was prepared according to the general procedure E as a white solid (447 mg, 91% purity, 100% yield) with some brown tints.

LC/MS (ESI) m/z for $C_{18}H_{16}F_3N_5O$·375 (calcd) 376 ([M+H]⁺, found).

¹H NMR (400 MHz, DMSO-d6) δ 8.37 (br d, J=5.5 Hz, 3H, NH₂+HCl), 8.21 (d, J=8.8 Hz, 1H), 8.17 (d, J=2.8 Hz, 1H), 7.81 (dd, J=8.7, 2.8 Hz, 1H), 7.66-7.52 (m, 2H), 7.47 (ddd, J=9.7, 8.2, 1.3 Hz, 1H), 7.38 (t, J=72.9 Hz, 1H), 7.35 (td, J=7.7, 1.3 Hz, 1H), 3.85 (br h, J=6.4 Hz, 1H), 3.53 (tt, J=9.6, 5.8 Hz, 1H), 2.84-2.73 (sym. m, 1H), 2.64-2.53 (sym. m, 1H), 2.44-2.27 (sym. m, 2H).

Example 180: Preparation of N-((1S,3r)-3-(5-(5-(difluoromethoxy)pyridin-2-yl)-4-(2-fluorophenyl)-4H-1,2,4-triazol-3-yl)cyclobutyl)picolinamide

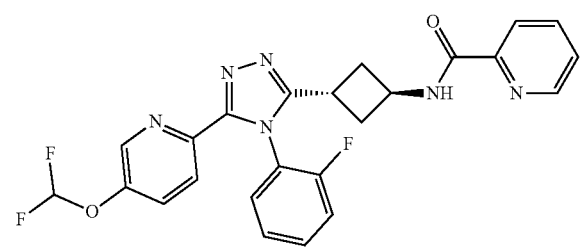

The title compound was prepared according to the general procedure F as a whitish solid (24.9 mg, 86% yield).

LC/MS (ESI) m/z for $C_{24}H_{19}F_3N_6O_2$ 480 (calcd) 481 ([M+H]⁺, found).

¹H NMR (400 MHz, Chloroform-d) δ 8.53 (ddd, J=4.7, 1.6, 1.0 Hz, 1H), 8.32 (d, J=8.7 Hz, 1H), 8.22 (d, J=7.0 Hz, 1H), 8.17 (dt, J=7.8, 1.1 Hz, 1H), 8.07 (d, J=2.8 Hz, 1H), 7.84 (td, J=7.7, 1.7 Hz, 1H), 7.54 (dd, J=8.6, 2.7 Hz, 1H), 7.51-7.44 (m, 1H), 7.42 (ddd, J=7.6, 4.8, 1.2 Hz, 1H), 7.25-7.16 (m, 3H), 6.52 (t, J=72.5 Hz, 1H), 4.78 (h, J=7.2 Hz, 1H), 3.47 (tt, J=9.6, 5.5 Hz, 1H), 3.12-2.96 (sym. m, 2H), 2.54-2.37 (sym. m, 2H).

Example 181: Preparation of N-((1S,3r)-3-(5-(5-(difluoromethoxy)pyridin-2-yl)-4-(2-fluorophenyl)-4H-1,2,4-triazol-3-yl)cyclobutyl)-5-fluoropicolinamide

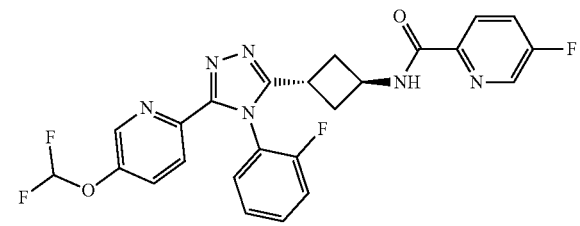

The title compound was prepared according to the general procedure F as a white solid (23.1 mg, 76% yield).

LC/MS (ESI) m/z for $C_{24}H_{18}F_4N_6O_2$ 498 (calcd) 499 ([M+H]⁺, found).

¹H NMR (400 MHz, Chloroform-d) δ 8.36 (d, J=2.8 Hz, 1H), 8.32 (d, J=8.7 Hz, 1H), 8.20 (dd, J=8.7, 4.6 Hz, 1H), 8.07 (d, J=2.7 Hz, 1H), 8.04 (d, J=7.0 Hz, 1H), 7.57-7.44 (m, 3H), 7.26-7.17 (m, 3H), 6.52 (t, J=72.4 Hz, 1H), 4.78 (h, J=7.3 Hz, 1H), 3.45 (tt, J=9.7, 5.3 Hz, 1H), 3.11-2.95 (sym. m, 2H), 2.53-2.36 (sym. m, 2H).

Example 182: Preparation of N-((1S,3r)-3-(5-(5-(difluoromethoxy)pyridin-2-yl)-4-(2-fluorophenyl)-4H-1,2,4-triazol-3-yl)cyclobutyl)-1,5-naphthyridine-4-carboxamide

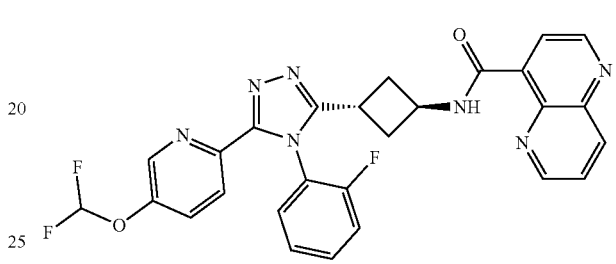

The title compound was prepared according to the general procedure F as a white solid (16.5 mg, 62% yield).

LC/MS (ESI) m/z for $C_{27}H_{20}F_3N_7O_2$ 531 (calcd) 532 ([M+H]⁺, found).

¹H NMR (400 MHz, Chloroform-d) δ 11.31 (d, J=6.0 Hz, 1H), 9.15 (d, J=4.4 Hz, 1H), 8.98 (dd, J=4.3, 1.8 Hz, 1H), 8.59-8.52 (m, 2H), 8.33 (d, J=8.8 Hz, 1H), 8.07 (d, J=2.7 Hz, 1H), 7.74 (dd, J=8.6, 4.2 Hz, 1H), 7.55 (dd, J=8.8, 2.7 Hz, 1H), 7.51-7.43 (m, 1H), 7.25-7.16 (m, 3H), 6.52 (t, J=72.4 Hz, 1H), 4.86 (ht, J=7.0, 1.6 Hz, 1H), 3.53 (tt, J=9.9, 5.2 Hz, 1H), 3.15-3.03 (sym. m, 2H), 2.65-2.49 (sym. m, 2H).

Example 183: Preparation of N-((1S,3r)-3-(5-(5-(difluoromethoxy)pyridin-2-yl)-4-(2-fluorophenyl)-4H-1,2,4-triazol-3-yl)cyclobutyl)-7-fluoro-1,5-naphthyridine-4-carboxamide

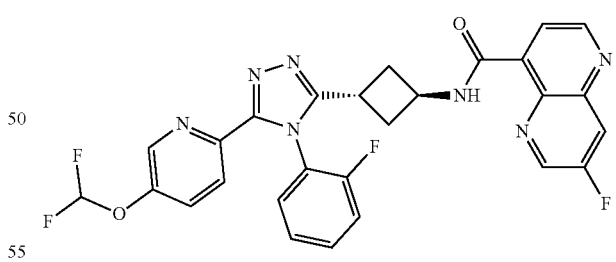

The title compound was prepared according to the general procedure F as a whitish solid (20.4 mg, 74% yield).

LC/MS (ESI) m/z for $C_{27}H_{19}F_4N_7O_2$ 549 (calcd) 550 ([M+H]⁺, found).

¹H NMR (400 MHz, Chloroform-d) δ 10.83 (d, J=6.1 Hz, 1H), 9.15 (d, J=4.4 Hz, 1H), 8.91 (d, J=2.9 Hz, 1H), 8.52 (d, J=4.4 Hz, 1H), 8.33 (d, J=8.7 Hz, 1H), 8.20 (dd, J=8.6, 2.8 Hz, 1H), 8.07 (d, J=2.7 Hz, 1H), 7.55 (dd, J=8.6, 2.7 Hz, 1H), 7.52-7.43 (m, 1H), 7.26-7.17 (m, 3H), 6.53 (t, J=72.4 Hz, 1H), 4.87 (ht, J=7.1, 1.6 Hz, 1H), 3.51 (tt, J=9.5, 5.6 Hz, 1H), 3.16-3.01 (sym. m, 2H), 2.63-2.48 (sym. m, 2H).

Example 184: Preparation of N-((1S,3r)-3-(5-(5-(difluoromethoxy)pyridin-2-yl)-4-(2-fluorophenyl)-4H-1,2,4-triazol-3-yl)cyclobutyl)-1,6-naphthyridine-2-carboxamide

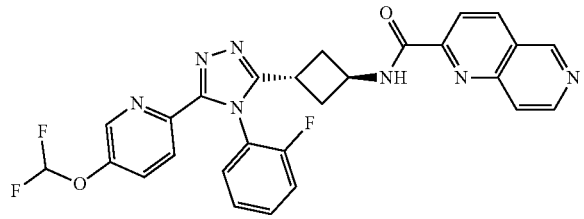

The title compound was prepared according to the general procedure F as a white solid (20.7 mg, 77% yield).

LC/MS (ESI) m/z for $C_{27}H_{20}F_3N_7O_2$ 531 (calcd) 532 ([M+H]$^+$, found).

$^1$H NMR (400 MHz, Chloroform-d) δ 9.36 (s, 1H), 8.83 (d, J=6.0 Hz, 1H), 8.47 (dd, J=8.6, 0.8 Hz, 1H), 8.44-8.36 (m, 2H), 8.33 (d, J=8.7 Hz, 1H), 8.08 (d, J=2.6 Hz, 1H), 7.92 (d, J=6.0 Hz, 1H), 7.55 (dd, J=8.8, 2.8 Hz, 1H), 7.53-7.45 (m, 1H), 7.28-7.17 (m, 3H), 6.53 (t, J=72.4 Hz, 1H), 4.87 (h, J=7.1 Hz, 1H), 3.50 (tt, J=9.8, 5.1 Hz, 1H), 3.16-3.00 (sym. m, 2H), 2.64-2.47 (sym. m, 2H).

Example 185: Preparation of N-((1S,3r)-3-(5-(5-(difluoromethoxy)pyridin-2-yl)-4-(2-fluorophenyl)-4H-1,2,4-triazol-3-yl)cyclobutyl)quinoxaline-5-carboxamide

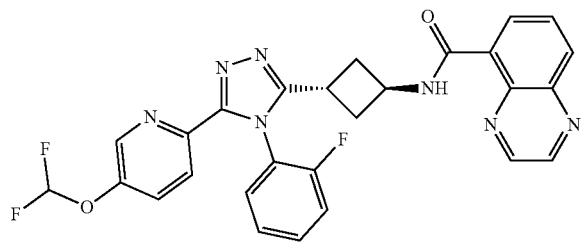

The title compound was prepared according to the general procedure F as a white solid (23.0 mg, 86% yield).

LC/MS (ESI) m/z for $C_{27}H_{20}F_3N_7O_2$ 531 (calcd) 532 ([M+H]$^+$, found).

$^1$H NMR (400 MHz, Chloroform-d) δ 10.67 (d, J=5.9 Hz, 1H), 8.97 (d, J=1.8 Hz, 1H), 8.89-8.83 (m, 2H), 8.33 (d, J=8.8 Hz, 1H), 8.26 (dd, J=8.4, 1.6 Hz, 1H), 8.07 (d, J=2.8 Hz, 1H), 7.90 (dd, J=8.4, 7.4 Hz, 1H), 7.55 (dd, J=8.8, 2.8 Hz, 1H), 7.51-7.42 (m, 1H), 7.26-7.16 (m, 3H), 6.52 (t, J=72.5 Hz, 1H), 4.85 (ht, J=6.9, 1.5 Hz, 1H), 3.52 (tt, J=9.6, 5.3 Hz, 1H), 3.14-3.02 (sym. m, 2H), 2.63-2.47 (sym. m, 2H).

Example 186: Preparation of N-((1S,3r)-3-(5-(5-(difluoromethoxy)pyridin-2-yl)-4-(2-fluorophenyl)-4H-1,2,4-triazol-3-yl)cyclobutyl)-7-fluoroquinoxaline-5-carboxamide

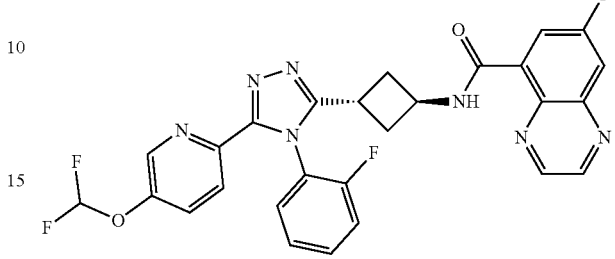

The title compound was prepared according to the general procedure F as a white solid (19.8 mg, 71% yield).

LC/MS (ESI) m/z for $C_{27}H_{19}F_4N_7O_2$ 549 (calcd) 550 ([M+H]$^+$, found).

$^1$H NMR (400 MHz, Chloroform-d) δ 10.63 (d, J=5.9 Hz, 1H), 8.96 (d, J=2.0 Hz, 1H), 8.82 (d, J=1.9 Hz, 1H), 8.64 (dd, J=9.5, 3.1 Hz, 1H), 8.33 (d, J=8.7 Hz, 1H), 8.07 (d, J=2.6 Hz, 1H), 7.87 (dd, J=7.8, 3.1 Hz, 1H), 7.55 (dd, J=8.8, 2.8 Hz, 1H), 7.51-7.42 (m, 1H), 7.25-7.16 (m, 3H), 6.52 (t, J=72.5 Hz, 1H), 4.85 (ht, J=7.1, 1.5 Hz, 1H), 3.51 (tt, J=9.6, 5.3 Hz, 1H), 3.14-3.01 (sym. m, 2H), 2.62-2.47 (sym. m, 2H).

Example 187: Preparation of amine building block AH: (1S,3r)-3-(4-(2-fluorophenyl)-5-(pyridin-2-yl)-4H-1,2,4-triazol-3-yl)cyclobutan-1-amine dihydrochloride

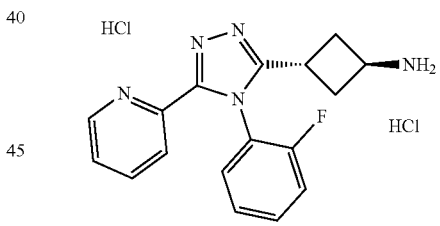

Step (a): crude N-(2-fluorophenyl)picolinamide was prepared as an off-white solid (825 gram, 76% yield) according to the general procedure A, method a) using EDCI/HOAt as coupling reagents.

LC/MS (ESI) m/z for $C_{12}H_9FN_2O$ 216 (calcd) 217 ([M+H]$^+$, found).

Step (b): N-(2-fluorophenyl)pyridine-2-carbothioamide was prepared following the general procedure B as an orange solid (792 mg, 89% yield).

LC/MS (ESI) m/z for $C_{12}H_9FN_2S$ 232 (calcd) 233 ([M+H]$^+$, found).

Step (c): methyl N-(2-fluorophenyl)pyridine-2-carbimidothioate was prepared as a yellow oil (809 mg, 97% yield) employing the general procedure C.

LC/MS (ESI) m/z for $C_{13}H_{11}FN_2S$ 246 (calcd) 247 ([M+H]$^+$, found).

Step (d): tert-butyl 41S,3r)-3-(4-(2-fluorophenyl)-5-(pyridin-2-yl)-4H-1,2,4-triazol-3-yl) cyclobutyl)carbamate was prepared as a light-brown foam (653 mg, 77% yield) according to the general procedure D.

LC/MS (ESI) m/z for $C_{22}H_{24}FN_5O_2$ 409 (calcd) 410 ([M+1-1]$^+$, found).

1H NMR (400 MHz, Chloroform-d) δ 8.23 (dt, J=8.1, 1.1 Hz, 1H), 8.20 (dt, J=4.8, 1.4 Hz, 1H), 7.74 (td, J=7.8, 1.8 Hz, 1H), 7.46 (tdd, J=7.9, 5.0, 2.2 Hz, 1H), 7.25-7.14 (m, 4H), 4.73 (br s, 1H), 4.39-4.27 (m, 1H), 3.38-3.26 (m, 1H), 2.95-2.78 (m+br s, 2H), 2.40-2.10 (br s+m, 2H), 1.42 (s, 9H).

Step (e): the crude title compound was prepared according to the general procedure E as a purple glass (661 mg, 89% purity, 100% yield).

LC/MS (ESI) m/z for $C_{17}H_{16}FN_5$·309 (calcd) 310 ([M+H]$^+$, found).

$^1$H NMR (400 MHz, DMSO-d6) δ 8.35 (br s, 3H, NH$_2$+HCl), 8.26 (d, J=4.6 Hz, 1H), 8.12 (d, J=7.9 Hz, 1H), 7.94 (td, J=7.7, 1.8 Hz, 1H), 7.64-7.50 (m, 2H), 7.45 (t, J=8.5 Hz, 1H), 7.41-7.30 (m, 2H), 3.86 (br dq, J=11.7, 6.8 Hz, 1H), 3.54 (tt, J=9.5, 5.4 Hz, 1H), 2.78 (br dt, J=12.2, 6.9 Hz, 1H), 2.64-2.53 (m, 1H), 2.44-2.26 (m, 2H).

Example 188: Preparation of N-((1S,3r)-3-(4-(2-fluorophenyl)-5-(pyridin-2-yl)-4H-1,2,4-triazol-3-yl)cyclobutyl)picolinamide

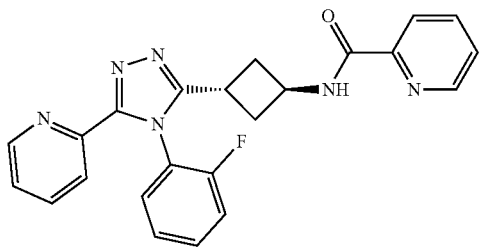

The title compound was prepared according to the general procedure F as a white solid (21.5 mg, 86% yield).

LC/MS (ESI) m/z for $C_{23}H_{19}FN_6O$ 414 (calcd) 415 ([M+H]$^+$, found).

$^1$H NMR (400 MHz, Chloroform-d) δ 8.53 (dq, J=4.8, 1.0 Hz, 1H), 8.25 (dt, J=7.9, 1.1 Hz, 1H), 8.24-8.18 (m, 2H), 8.17 (dt, J=7.8, 1.1 Hz, 1H), 7.84 (td, J=7.7, 1.7 Hz, 1H), 7.76 (td, J=7.8, 1.8 Hz, 1H), 7.49-7.40 (m, 2H), 7.25-7.14 (m, 4H), 4.78 (ht, J=7.0, 1.6 Hz, 1H), 3.55-3.43 (m, 1H), 3.12-2.97 (sym. m, 2H), 2.54-2.37 (sym. m, 2H).

Example 189: Preparation of 5-fluoro-N-((1S,3r)-3-(4-(2-fluorophenyl)-5-(pyridin-2-yl)-4H-1,2,4-triazol-3-yl)cyclobutyl)picolinamide

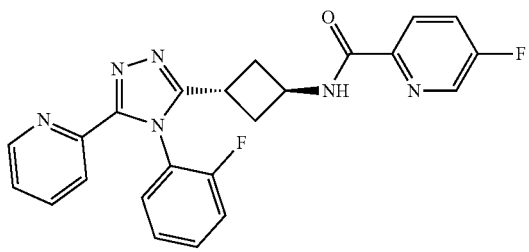

The title compound was prepared according to the general procedure F as a white solid (19.5 mg, 74% yield).

LC/MS (ESI) m/z for $C_{23}H_{18}F_2N_6O$ 432 (calcd) 433 ([M+H]$^+$, found).

$^1$H NMR (400 MHz, Chloroform-d) δ 8.36 (d, J=2.8 Hz, 1H), 8.25 (d, J=8.0 Hz, 1H), 8.20 (dd, J=8.7, 4.6 Hz, 2H), 8.04 (br d, J=7.0 Hz, 1H), 7.76 (td, J=7.7, 1.7 Hz, 1H), 7.52 (td, J=8.3, 2.8 Hz, 1H), 7.49-7.42 (m, 1H), 7.25-7.15 (m, 4H), 4.78 (h, J=7.2 Hz, 1H), 3.47 (tt, J=9.7, 5.3 Hz, 1H), 3.11-2.96 (sym. m, 2H), 2.53-2.36 (sym. m, 2H).

Example 190: Preparation of N-((1S,3r)-3-(4-(2-fluorophenyl)-5-(pyridin-2-yl)-4H-1,2,4-triazol-3-yl)cyclobutyl)-1,5-naphthyridine-4-carboxamide

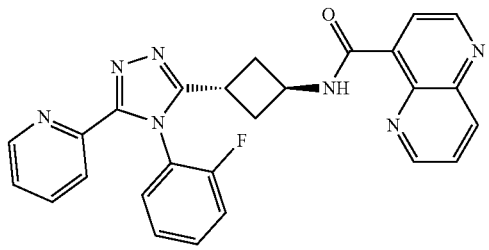

The title compound was prepared according to the general procedure F as a white solid (18 mg, 77% yield).

LC/MS (ESI) m/z for $C_{26}H_{20}FN_7O$ 465 (calcd) 466 ([M+H]$^+$, found).

$^1$H NMR (400 MHz, Chloroform-d) δ 11.31 (d, J=6.0 Hz, 1H), 9.14 (d, J=4.5 Hz, 1H), 8.98 (dd, J=4.2, 1.8 Hz, 1H), 8.59-8.52 (m, 2H), 8.26 (dt, J=7.7, 1.1 Hz, 1H), 8.22 (dt, J=4.8, 1.4 Hz, 1H), 7.80-7.71 (m, 2H), 7.49-7.40 (m, 1H), 7.26-7.15 (m, 4H), 4.91-4.80 (sym. m, 1H), 3.55 (tt, J=9.1, 5.6 Hz, 1H), 3.16-3.03 (sym. m, 2H), 2.65-2.49 (sym. m, 2H).

Example 191: Preparation of 7-fluoro-N-((1S,3r)-3-(4-(2-fluorophenyl)-5-(pyridin-2-yl)-4H-1,2,4-triazol-3-yl)cyclobutyl)-1,5-naphthyridine-4-carboxamide

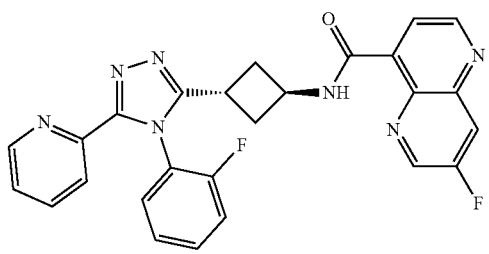

The title compound was prepared according to the general procedure F as a white solid (17.2 mg, 70% yield).

LC/MS (ESI) m/z for $C_{26}H_{19}F_2N_7O$ 483 (calcd) 484 ([M+H]$^+$, found).

$^1$H NMR (400 MHz, Chloroform-d) δ 10.83 (d, J=6.0 Hz, 1H), 9.15 (d, J=4.5 Hz, 1H), 8.91 (d, J=2.8 Hz, 1H), 8.52 (d, J=4.4 Hz, 1H), 8.26 (dt, J=7.9, 1.0 Hz, 1H), 8.24-8.16 (m, 2H), 7.77 (td, J=7.8, 1.8 Hz, 1H), 7.50-7.42 (m, 1H), 7.25-7.15 (m, 4H), 4.87 (ht, J=6.8, 1.6 Hz, 1H), 3.53 (tt, J=9.3, 5.6 Hz, 1H), 3.15-3.02 (sym. m, 2H), 2.63-2.47 (sym. m, 2H).

Example 192: Preparation of N-((1S,3r)-3-(4-(2-fluorophenyl)-5-(pyridin-2-yl)-4H-1,2,4-triazol-3-yl)cyclobutyl)-1,6-naphthyridine-2-carboxamide

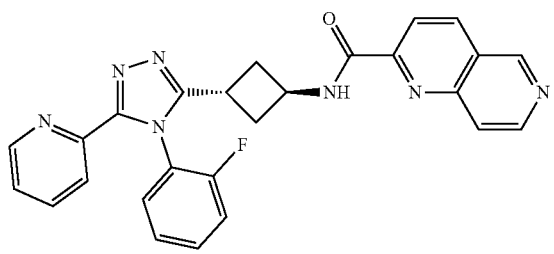

The title compound was prepared according to the general procedure F as a white solid (17.6 mg, 75% yield).

LC/MS (ESI) m/z for $C_{26}H_{20}FN_7O$ 465 (calcd) 466 ([M-FH]+, found).

$^1$H NMR (400 MHz, Chloroform-d) δ 9.36 (s, 1H), 8.83 (d, J=6.0 Hz, 1H), 8.47 (distorted dd, J=8.5, 0.8 Hz, 1H), 8.44-8.36 (m, 2H), 8.27 (d, J=8.0 Hz, 1H), 8.22 (d, J=4.8 Hz, 1H), 7.93 (d, J=5.9 Hz, 1H), 7.77 (td, J=7.8, 1.7 Hz, 1H), 7.51-7.43 (m, 1H), 7.26-7.16 (m, 4H), 4.87 (h, J=7.4 Hz, 1H), 3.52 (tt, J=9.7, 5.0 Hz, 1H), 3.17-3.01 (sym. m, 2H), 2.63-2.47 (sym. m, 2H).

Example 193: Preparation of N-((1S,3r)-3-(4-(2-fluorophenyl)-5-(pyridin-2-yl)-4H-1,2,4-triazol-3-yl)cyclobutyl)quinoxaline-5-carboxamide

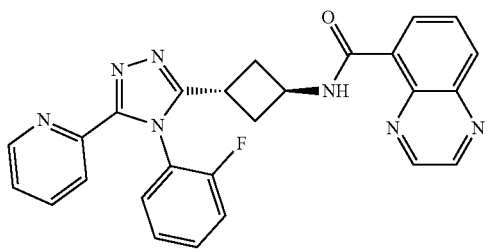

The title compound was prepared according to the general procedure F as a white solid (19.3 mg, 83% yield).

LC/MS (ESI) m/z for $C_{26}H_{20}FN_7O$ 465 (calcd) 466 ([M+H]+, found).

$^1$H NMR (400 MHz, Chloroform-d) δ 10.68 (d, J=5.8 Hz, 1H), 8.97 (d, J=1.8 Hz, 1H), 8.89-8.83 (m, 2H), 8.26 (dd, J=8.3, 1.5 Hz, 2H), 8.21 (d, J=4.3 Hz, 1H), 7.90 (dd, J=8.4, 7.4 Hz, 1H), 7.76 (td, J=7.8, 1.7 Hz, 1H), 7.49-7.40 (m, 1H), 7.25-7.14 (m, 4H), 4.84 (h, J=6.8 Hz, 1H), 3.54 (tt, J=9.3, 5.7 Hz, 1H), 3.15-3.02 (sym. m, 2H), 2.62-2.47 (sym. m, 2H).

Example 194: Preparation of 7-fluoro-N-((1S,3r)-3-(4-(2-fluorophenyl)-5-(pyridin-2-yl)-4H-1,2,4-triazol-3-yl)cyclobutyl)quinoxaline-5-carboxamide

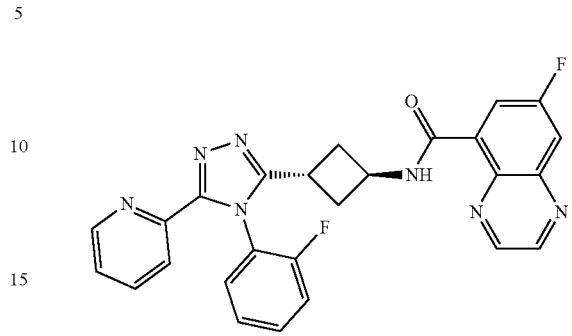

The title compound was prepared according to the general procedure F as a white powder (15.6 mg, 64% yield).

LC/MS (ESI) m/z for $C_{26}H_{19}F_2N_7O$ 483 (calcd) 484 ([M+H]+, found).

$^1$H NMR (400 MHz, Chloroform-d) δ 10.63 (d, J=5.8 Hz, 1H), 8.96 (d, J=1.8 Hz, 1H), 8.83 (d, J=1.8 Hz, 1H), 8.64 (dd, J=9.6, 3.1 Hz, 1H), 8.26 (dt, J=8.1, 1.1 Hz, 1H), 8.22 (dd, J=4.8, 1.6 Hz, 1H), 7.87 (dd, J=7.8, 3.1 Hz, 1H), 7.76 (td, J=7.8, 1.8 Hz, 1H), 7.49-7.40 (m, 1H), 7.25-7.14 (m, 4H), 4.84 (ht, J=7.1, 1.5 Hz, 1H), 3.53 (tt, J=9.3, 5.3 Hz, 1H), 3.14-3.02 (sym. m, 2H), 2.55 (dddd, J=16.5, 13.1, 9.8, 6.5 Hz, 2H).

Example 195: Preparation of amine building block AI: (1S,3r)-3-(4-(2-fluorophenyl)-5-(6-methylpyridin-2-yl)-4H-1,2,4-triazol-3-yl)cyclobutan-1-amine dihydrochloride

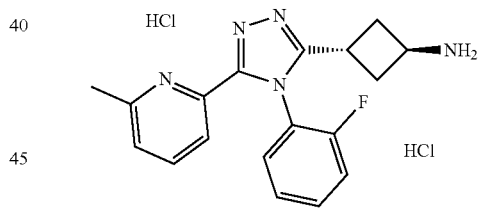

Step (a): crude N-(2-fluorophenyl)-6-methylpicolinamide was prepared as an off-white solid (519 gram, 89% yield) according to the general procedure A, method a)

LC/MS (ESI) m/z for $C_{13}H_{11}FN_2O$ 230 (calcd) 231 ([M+H]+, found).

Step (b): N-(2-fluorophenyl)-6-methylpyridine-2-carbothioamide was prepared following the general procedure B as a yellow solid (475 mg, 86% yield).

LC/MS (ESI) m/z for $C_{13}H_{11}FN_2S$ 246 (calcd) 247 ([M+H]+, found).

Step (c): methyl N-(2-fluorophenyl)-6-methylpyridine-2-carbimidothioate was prepared as a yellow oil (492 mg, 99% yield) employing the general procedure C.

LC/MS (ESI) m/z for $C_{14}H_{13}FN_2S$ 260 (calcd) 261 ([M+H]+, found).

Step (d): tert-butyl ((1S,3r)-3-(4-(2-fluorophenyl)-5-(6-methylpyridin-2-yl)-4H-1,2,4-triazol-3-yl)cyclobutyl)carbamate was prepared as a white solid (405 mg, 93% yield) according to the general procedure D.

LC/MS (ESI) m/z for C₂₃H₂₆FN₅O₂ 423 (calcd) 424 ([M+H]⁺, found).

¹H NMR (400 MHz, Chloroform-d) δ 8.04 (d, J=7.8 Hz, 1H), 7.61 (t, J=7.8 Hz, 1H), 7.46 (tdd, J=7.6, 4.9, 2.1 Hz, 1H), 7.24-7.14 (m, 3H), 7.02 (d, J=7.8 Hz, 1H), 4.74 (br s, 1H), 4.33 (ht, J=7.1, 1.5 Hz, 1H), 3.40-3.28 (m, 1H), 2.96-2.87 (m, 1H), 2.87-2.78 (br s, 1H), 2.38-2.12 (br s+m, 2H), 2.06 (s, 3H), 1.42 (s, 9H).

Step (e): the crude title compound was prepared according to the general procedure E as a colourless glass (396 mg, 92% purity, ~100% yield).

LC/MS (ESI) m/z for C₁₈H₁₈FN₅·323 (calcd) 324 ([M+H]⁺, found).

¹H NMR (400 MHz, DMSO-d6) δ 8.40 (d, J=3.3 Hz, 3H, NH₂+HCl), 7.93 (d, J=7.8 Hz, 1H), 7.81 (t, J=7.8 Hz, 1H), 7.62 (tdd, J=7.5, 5.1, 1.7 Hz, 1H), 7.54 (td, J=7.7, 1.7 Hz, 1H), 7.45 (ddd, J=9.8, 8.4, 1.3 Hz, 1H), 7.35 (td, J=7.6, 1.3 Hz, 1H), 7.24 (d, J=7.6 Hz, 1H), 3.86 (h, J=6.6 Hz, 1H), 3.57 (tt, J=9.4, 5.6 Hz, 1H), 2.85-2.75 (sym. m, 1H), 2.65-2.55 (sym. m, 1H), 2.46-2.29 (sym. m, 2H), 2.03 (s, 3H).

Example 196: Preparation of N-((1S,3r)-3-(4-(2-fluorophenyl)-5-(6-methylpyridin-2-yl)-4H-1,2,4-triazol-3-yl)cyclobutyl)picolinamide

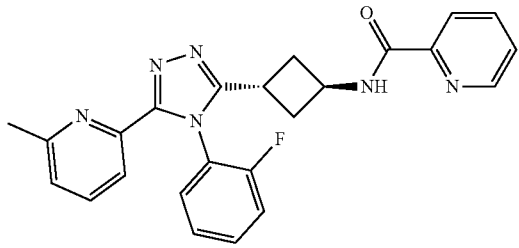

The title compound was prepared according to the general procedure F as a white solid (22.0 mg, 85% yield).

LC/MS (ESI) m/z for C₂₄H₂₁FN₆O 428 (calcd) 429 ([M+H]⁺, found).

¹H NMR (400 MHz, Chloroform-d) δ 8.53 (dq, J=4.9, 1.0 Hz, 1H), 8.23 (d, J=7.0 Hz, 1H), 8.17 (dt, J=7.8, 1.2, 1.2 Hz, 1H), 8.05 (d, J=7.7 Hz, 1H), 7.84 (td, J=7.7, 1.7 Hz, 1H), 7.62 (t, J=7.8 Hz, 1H), 7.49-7.39 (m, 2H), 7.24-7.15 (m, 3H), 7.03 (d, J=7.7 Hz, 1H), 4.77 (ht, J=7.2, 1.6 Hz, 1H), 3.50 (tt, J=9.7, 5.1 Hz, 1H), 3.13-2.98 (sym. m, 2H), 2.54-2.38 (sym. m, 2H), 2.07 (s, 3H).

Example 197: Preparation of 5-fluoro-N-((1S,3r)-3-(4-(2-fluorophenyl)-5-(6-methylpyridin-2-yl)-4H-1,2,4-triazol-3-yl)cyclobutyl)picolinamide

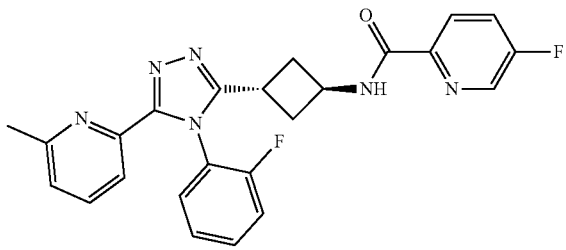

The title compound was prepared according to the general procedure F as a white solid (20.1 mg, 75% yield).

LC/MS (ESI) m/z for C₂₄H₂₀F₂N₆O 446 (calcd) 447 ([M+H]⁺, found).

¹H NMR (400 MHz, Chloroform-d) δ 8.36 (d, J=2.8 Hz, 1H), 8.20 (dd, J=8.7, 4.6 Hz, 1H), 8.09-8.00 (m, 2H), 7.62 (t, J=7.8 Hz, 1H), 7.52 (td, J=8.4, 2.8 Hz, 1H), 7.49-7.42 (m, 1H), 7.25-7.15 (m, 3H), 7.03 (d, J=7.6 Hz, 1H), 4.77 (ht, J=7.1, 1.7 Hz, 1H), 3.48 (tt, J=9.4, 5.3 Hz, 1H), 3.12-2.97 (sym. m, 2H), 2.53-2.37 (sym. m, 2H), 2.07 (s, 3H).

Example 198: Preparation of N-((1S,3r)-3-(4-(2-fluorophenyl)-5-(6-methylpyridin-2-yl)-4H-1,2,4-triazol-3-yl)cyclobutyl)-1,5-naphthyridine-4-carboxamide

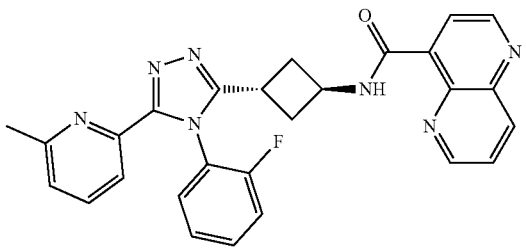

The title compound was prepared according to the general procedure F as a white solid (17 mg, 70% yield).

LC/MS (ESI) m/z for C₂₇H₂₂FN₇O 479 (calcd) 480 ([M+H]⁺, found).

¹H NMR (400 MHz, Chloroform-d) δ 11.31 (br d, J=6.0 Hz, 1H), 9.14 (d, J=4.4 Hz, 1H), 8.98 (dd, J=4.3, 1.7 Hz, 1H), 8.59-8.52 (m, 2H), 8.07 (d, J=7.8 Hz, 1H), 7.74 (dd, J=8.6, 4.2 Hz, 1H), 7.63 (t, J=7.8 Hz, 1H), 7.49-7.41 (m, 1H), 7.26-7.15 (m, 3H), 7.03 (d, J 7.6 Hz, 1H), 4.86 (ht, J=7.1, 1.6 Hz, 1H), 3.56 (tt, J=9.7, 5.0 Hz, 1H), 3.16-3.04 (sym. m, 2H), 2.65-2.50 (sym. m, 2H), 2.08 (s, 3H).

Example 199: Preparation of 7-fluoro-N-((1S,3r)-3-(4-(2-fluorophenyl)-5-(6-methylpyridin-2-yl)-4H-1,2,4-triazol-3-yl)cyclobutyl)-1,5-naphthyridine-4-carboxamide

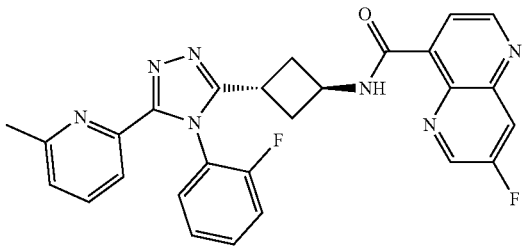

The title compound was prepared according to the general procedure F as a white solid (17.5 mg, 70% yield).

LC/MS (ESI) m/z for C₂₇H₂₁F₂N₇O 497 (calcd) 498 ([M+H]⁺, found).

¹H NMR (400 MHz, Chloroform-d) δ 10.83 (br d, J=6.0 Hz, 1H), 9.15 (d, J=4.4 Hz, 1H), 8.91 (d, J=2.8 Hz, 1H), 8.53 (d, J=4.5 Hz, 1H), 8.20 (dd, J=8.6, 2.9 Hz, 1H), 8.07 (d, J 7.8 Hz, 1H), 7.63 (t, J=7.8 Hz, 1H), 7.50-7.41 (m, 1H), 7.26-7.15 (m, 3H), 7.03 (d, J=7.6 Hz, 1H), 4.86 (ht, J=7.0, 1.6 Hz, 1H), 3.54 (tt, J=9.2, 5.3 Hz, 1H), 3.16-3.03 (sym. m, 2H), 2.63-2.48 (sym. m, 2H), 2.08 (s, 3H).

Example 200: Preparation of N-((1S,3r)-3-(4-(2-fluorophenyl)-5-(6-methylpyridin-2-yl)-4H-1,2,4-triazol-3-yl)cyclobutyl)-1,6-naphthyridine-2-carboxamide

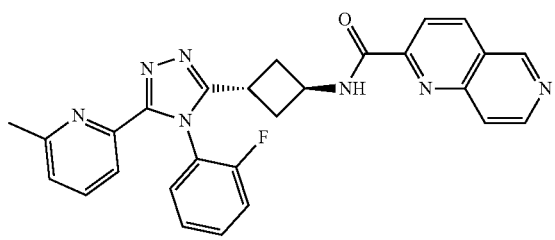

The title compound was prepared according to the general procedure F as a white solid (19.0 mg, 78% yield).

LC/MS (ESI) m/z for $C_{27}H_{22}FN_7O$ 479 (calcd) 480 ([M+H]$^+$, found).

$^1$H NMR (400 MHz, Chloroform-d) δ 9.36 (d, J=1.0 Hz, 1H), 8.83 (d, J=6.0 Hz, 1H), 8.46 (distorted dd, J=8.6, 0.8 Hz, 1H), 8.44-8.36 (m, 2H), 8.07 (d, J=7.8 Hz, 1H), 7.93 (dt, J=5.9, 1.0 Hz, 1H), 7.63 (t, J=7.8 Hz, 1H), 7.51-7.43 (m, 1H), 7.26-7.16 (m, 3H), 7.04 (d, J=7.6 Hz, 1H), 4.87 (ht, J=7.2, 1.5 Hz, 1H), 3.54 (tt, J=9.7, 5.3 Hz, 1H), 3.17-3.02 (sym. m, 2H), 2.63-2.48 (sym. m, 2H), 2.08 (s, 3H).

Example 201: Preparation of N-((1S,3r)-3-(4-(2-fluorophenyl)-5-(6-methylpyridin-2-yl)-4H-1,2,4-triazol-3-yl)cyclobutyl)quinoxaline-5-carboxamide

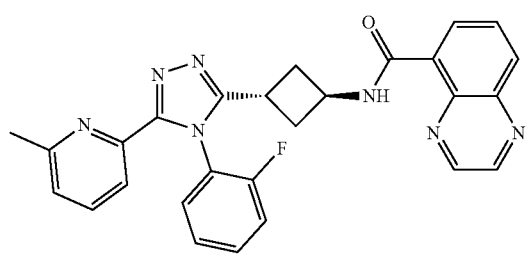

The title compound was prepared according to the general procedure F as a white powder (20.7 mg, 86% yield).

LC/MS (ESI) m/z for $C_{27}H_{22}FN_7O$ 479 (calcd) 480 ([M+H]$^+$, found).

$^1$H NMR (400 MHz, Chloroform-d) δ 10.68 (d, J=5.7 Hz, 1H), 8.96 (d, J=1.9 Hz, 1H), 8.90-8.82 (m, 2H), 8.26 (dd, J=8.4, 1.6 Hz, 1H), 8.07 (d, J=7.8 Hz, 1H), 7.90 (dd, J=8.4, 7.4 Hz, 1H), 7.63 (t, J=7.8 Hz, 1H), 7.49-7.41 (m, 1H), 7.26-7.14 (m, 3H), 7.03 (d, J=7.7 Hz, 1H), 4.84 (ht, J=7.0, 1.7 Hz, 1H), 3.56 (tt, J=9.9, 5.4 Hz, 1H), 3.15-3.05 (sym. m, 2H), 2.62-2.48 (sym. m, 2H), 2.07 (s, 3H).

Example 202: Preparation of 7-fluoro-N-((1S,3r)-3-(4-(2-fluorophenyl)-5-(6-methylpyridin-2-yl)-4H-1,2,4-triazol-3-yl)cyclobutyl)quinoxaline-5-carboxamide

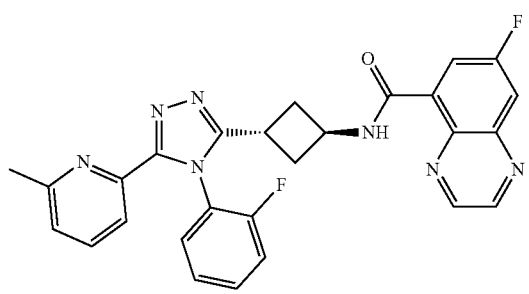

The title compound was prepared according to the general procedure F as a white solid (18.2 mg, 73% yield).

LC/MS (ESI) m/z for $C_{27}H_{21}F_2N_7O$ 497 (calcd) 498 ([M+H]$^+$, found).

$^1$H NMR (400 MHz, Chloroform-d) δ 10.63 (d, J=5.9 Hz, 1H), 8.96 (d, J=1.9 Hz, 1H), 8.83 (d, J=1.8 Hz, 1H), 8.64 (dd, J=9.5, 3.1 Hz, 1H), 8.06 (d, J=7.8 Hz, 1H), 7.87 (dd, J=7.8, 3.1 Hz, 1H), 7.63 (t, J=7.8 Hz, 1H), 7.49-7.41 (m, 1H), 7.24-7.15 (m, 3H), 7.03 (d, J=7.7 Hz, 1H), 4.84 (ht, J=7.1, 1.5 Hz, 1H), 3.54 (tt, J=9.3, 5.3 Hz, 1H), 3.14-3.04 (sym. m, 2H), 2.61-2.48 (sym. m, 2H), 2.07 (s, 3H).

Example 203—IC$_{50}$ Values

Cellular IC$_{50}$ and biochemical IC$_{50}$ values for the following compounds were determined in accordance with the following protocol (see also Anumala et al., Discovery of Novel Series of Tankyrase Inhibitors by a Hybridization Approach J. Med. Chem. 2017):

IC$_{50}$ calculations:

XLfit (idbs) was used to determine the IC50-values in inhibition experiments. The following formula was chosen to fit the data points (Langmuir Binding Isotherm):

$$\text{fit}=((A+(B*x))+4(C-B)*(1-\exp((-1*D)*x)))/D)), \text{res}=(y-\text{fit})$$

TABLE 1

| Compound Example No. | Biochemical IC$_{50}$ TNKS2 (nM) | Cellular IC$_{50}$ HEK293 (nM) |
|---|---|---|
| 4 | 5.4 | 1 |
| 5 | 0.85 | 1 |
| 6 | 680 | 1300 |
| 7 | 350 | 750 |
| 8 | 57 | 70 |
| 9 | 18 | 50 |
| 10 | 1.5 | 0.2 |
| 11 | 3.5 | 4 |
| 12 | 5.5 | 3 |
| 13 | 6.4 | 30 |
| 14 | 6.7 | 40 |
| 15 | 4.1 | 30 |
| 16 | 1700 | 7680 |
| 17 | 2.7 | 2.4 |
| 18 | 37 | 57 |
| 19 | 3 | 0.86 |
| 21 | 1.8 | 0.5 |
| 41 | 2 | 0.65 |
| 42 | 5.9 | 20 |

TABLE 1-continued

| Compound Example No. | Biochemical IC$_{50}$ TNKS2 (nM) | Cellular IC$_{50}$ HEK293 (nM) |
|---|---|---|
| 22 | 3.8 | 25 |
| 23 | 3.8 | 100 |
| 43 | 7.9 | 82 |
| 52 | 9.5 | 73 |
| 54 | 7 | 17 |
| 93 | 6.8 | 9.5 |
| 55 | 2 | 0.814 |
| 44 | 13 | 50 |
| 56 | 10 | 62 |
| 25 | 29 | 127 |
| 26 | 3.3 | 3.9 |
| 27 | 250 | 470 |
| 28 | 51 | 240 |
| 68 | 5.2 | 65 |
| 69 | 2 | 0.712 |
| 72 | 14 | 30 |
| 70 | 8.5 | 48 |
| 32 | 49 | 229 |
| 33 | 3.1 | 4.3 |
| 34 | 290 | 921 |
| 35 | 120 | 580 |
| 88 | 47 | 93 |
| 81 | 4.6 | 37 |
| 79 | 27 | 140 |
| 75 | 12 | 27 |
| 89 | 2.7 | 2.4 |
| 82 | 0.73 | 0.81 |
| 78 | 2 | 1.1 |
| 76 | 2 | 1.1 |
| 57 | 2 | 0.17 |
| 94 | 2.7 | 0.45 |
| 29 | 2 | 1.3 |
| 62 | 1.3 | 2.1 |
| 56 | 2 | 5.9 |
| 30 | 2 | 16 |
| 58 | 2 | 10 |
| 59 | 2.4 | 9.5 |
| 37 | 25 | 88 |
| 49 | 1.1 | 0.42 |
| 48 | 1.3 | 0.17 |
| 60 | 2.1 | 1.1 |
| 95 | 3.5 | 0.48 |
| 64 | 1.4 | 3 |
| 91 | 280 | 355 |
| 53 | 3.7 | 13 |
| 38 | 45 | 46 |
| 39 | 28 | 16 |
| 65 | 1.4 | 10 |
| 66 | 35 | 122 |
| 86 | 2.2 | 1.7 |
| 84 | 1.6 | 1 |
| 50 | 1.6 | 0.23 |
| 96 | 1.5 | 5.0 |
| 97 | 2.5 | 7.5 |
| 98 | 4.9 | 14 |
| 99 | 5.4 | 18 |
| 71 | — | 1.8 |
| 83 | 2.4 | 1 |
| 73 | 7 | 102 |
| 130 | 4.8 | 1.4 |
| 131 | 4.5 | 0.66 |
| 132 | 6.6 | 39 |
| 134 | 3.7 | 4.5 |
| 136 | 6.6 | 16 |
| 137 | 4.9 | 10 |
| 113 | 5.6 | 74 |
| 106 | 8.6 | 49 |
| 111 | 12 | 110 |
| 128 | 37 | 230 |
| 148 | 5 | 8 |
| 157 | 4.4 | 34 |
| 152 | 19 | 144 |
| 149 | 7.4 | 27 |
| 150 | 9.5 | 16 |
| 154 | 1.8 | 0.53 |
| 158 | 26 | 44 |
| 159 | 1.5 | 1.5 |
| 129 | 210 | 649 |
| 115 | 10 | 57 |
| 116 | 4.5 | 47 |
| 120 | 18 | 65 |
| 117 | 87 | 550 |
| 118 | 12 | 100 |
| 100 | 8.2 | 48 |
| 101 | 22 | 96 |
| 119 | 5 | 39 |
| 125 | 28 | 70 |
| 126 | 4.1 | 27 |
| 127 | 4.3 | 9.1 |
| 103 | 4.5 | 25 |
| 102 | 190 | 919 |
| 104 | 6.4 | 14 |
| 147 | 19 | 78 |
| 155 | 9.1 | 12 |
| 156 | 21 | 67 |
| 153 | 13 | 56 |
| 151 | 14 | 35 |
| 135 | 1.9 | 0.33 |
| 141 | 2.9 | 1.1 |
| 139 | 8.7 | 4 |
| 143 | 11 | 94 |
| 144 | 9.2 | 12 |
| 140 | 13 | 83 |
| 114 | 20 | 230 |
| 146 | 16 | 80 |
| 122 | 13 | 20 |
| 166 | 9.6 | 30 |
| 172 | 9.4 | 43 |
| 142 | 23 | 55 |
| 107 | 5.7 | 32 |
| 109 | 800 | 4700 |
| 188 | 22 | 33 |
| 189 | 14 | 17 |
| 190 | 2.4 | 1.6 |
| 191 | 1.8 | 3.4 |
| 192 | 4.3 | 5.3 |
| 193 | 1.6 | 0.286 |
| 194 | 2 | 0.794 |
| 196 | 16 | 37 |
| 197 | 21 | 25 |
| 198 | 2.2 | 1.6 |
| 199 | 2.2 | 1.8 |
| 200 | 4 | 12 |
| 201 | 1.7 | 1.5 |
| 202 | 1.6 | 0.169 |
| 174 | 216 | 789 |
| 175 | 150 | 499 |
| 176 | 3.6 | 28 |
| 177 | 3.8 | 25 |
| 178 | 21 | 165 |
| 180 | 8.8 | 36 |
| 181 | 7.4 | 27 |
| 182 | 2.9 | 0.61 |
| 183 | 2 | 1.5 |
| 184 | 3.4 | 10 |
| 185 | 1.9 | 1.2 |
| 186 | 2.4 | 0.508 |
| 124 | 5.8 | 36 |
| 160 | 22 | 9 |
| 162 | 4.5 | 16 |
| 164 | 5.8 | 9 |
| 168 | 5.4 | 13 |
| 170 | 2.9 | 6 |
| 163 | 14 | 71 |
| 169 | 28 | 58 |

The invention claimed is:

1. A compound of general formula (I), or a tautomer, stereoisomer, pharmaceutically acceptable salt or pro-drug thereof:

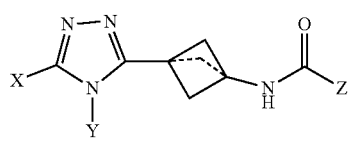

(I)

wherein:
a dashed line indicates an optional bond;
X represents:
  a 5- or 6-membered, unsaturated heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$ (where each R is independently H or $C_{1-6}$ alkyl;
  a $C_{3-5}$ cycloalkyl group optionally substituted by one or more substituents independently selected from $C_{1-6}$ alkyl, $C_{1-6}$ haloalkyl, and $C_{1-6}$ alkoxy; or
  an aryl group optionally substituted by one or more substituents independently selected from halogen, $C_{1-6}$ alkyl, $C_{1-6}$ haloalkyl, and $C_{1-6}$ alkoxy;
Y represents:
  an aryl or heteroaryl group optionally substituted by one or more substituents independently selected from halogen, $C_{1-6}$ alkyl, $C_{1-6}$ haloalkyl, and $C_{1-6}$ alkoxy;
  a 5- or 6-membered, saturated heterocyclic group optionally substituted by one or more substituents independently selected from $C_{1-6}$ alkyl, $C_{1-6}$ haloalkyl, and $C_{1-6}$ alkoxy; or
  a $C_{3-6}$ cycloalkyl group optionally substituted by one or more substituents independently selected from $C_{1-6}$ alkyl, $C_{1-6}$ haloalkyl, and $C_{1-6}$ alkoxy; and
Z represents:
  an aryl group optionally substituted by one or more substituents independently selected from halogen, $C_{1-6}$ alkyl, $C_{1-6}$ haloalkyl, $C_{1-6}$ alkoxy, CN, —$NO_2$, —$N_2$, and —$SO_2R$ (where each R is independently H or $C_{1-6}$ alkyl; or
  an unsaturated, 5- to 10-membered mono- or bicyclic heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$ (where each R is independently H or $C_{1-6}$ alkyl.

2. The compound of claim 1, wherein X represents:
a 5- or 6-membered, unsaturated heterocyclic group optionally substituted by one or more substituents independently selected from halogen, $C_{1-6}$ alkyl, $C_{1-6}$ haloalkyl, $C_{1-6}$ alkoxy, —CN, —$NO_2$, —$N(R)_2$, and —$SO_2R$ (where each R is independently H or $C_{1-6}$ alkyl); or
a $C_{3-5}$ cycloalkyl group optionally substituted by one or more substituents independently selected from $C_{1-6}$ alkyl, $C_{1-6}$ haloalkyl, and $C_{1-6}$ alkoxy.

3. The compound of claim 1, wherein X is an optionally substituted, 5- or 6-membered, unsaturated heterocyclic group.

4. The compound of claim 3, wherein X is selected from any of the following groups: pyridine, pyrimidine, pyrrole, pyrazine, thiazole, pyrazole, imidazole and thiophene.

5. The compound of claim 1, wherein X is selected from any of the following groups:

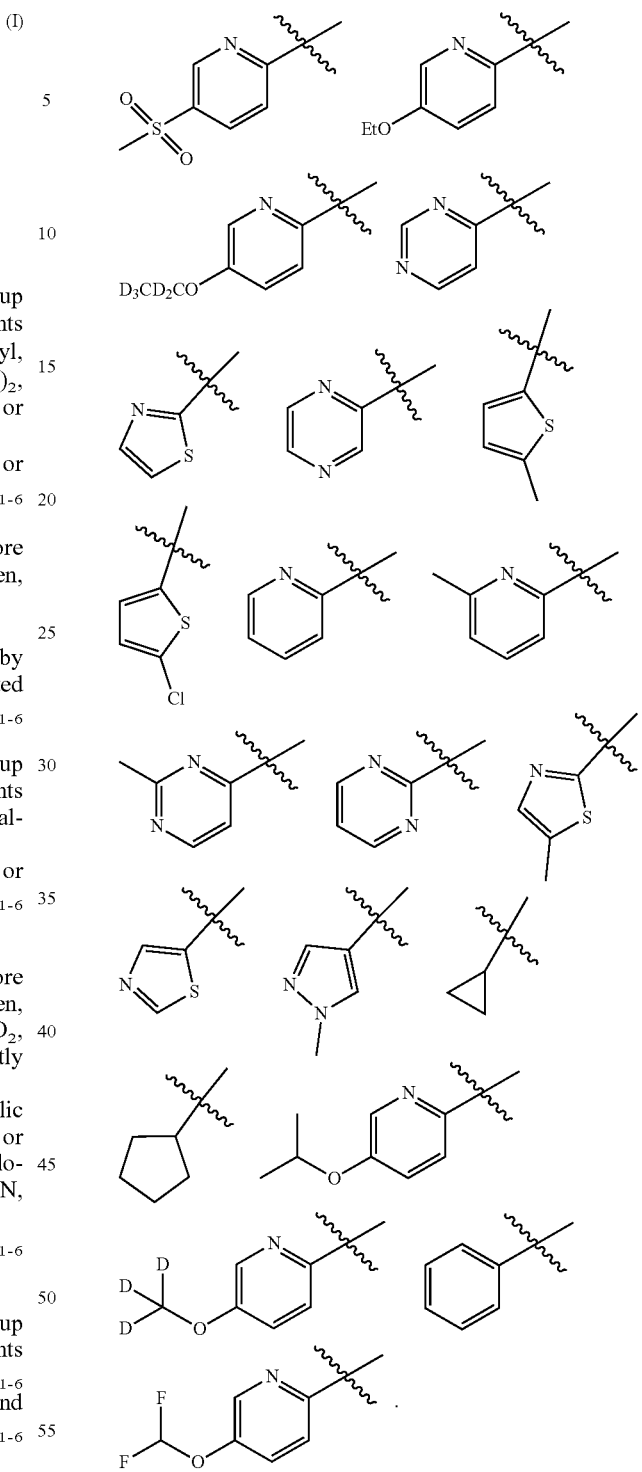

6. The compound of claim 1, wherein Y is an optionally substituted, aryl or heteroaryl group.

7. The compound of claim 6, wherein Y is a phenyl group optionally substituted by one or two substituents selected from the group consisting of: $C_{1-3}$ alkyl, $C_{1-3}$ alkoxy, $C_{1-3}$ haloalkyl, and halogen.

8. The compound of claim 6, wherein Y is an optionally substituted heteroaryl group.

9. The compound of claim 8, wherein Y is a pyridine or thiophene ring, optionally substituted by one or two substituents selected from the group consisting of: $C_{1-3}$ alkyl, $C_{1-3}$ alkoxy, $C_{1-3}$ haloalkyl, and halogen.

10. The compound as claimed in of claim 1, wherein Y is selected from any of the following groups:

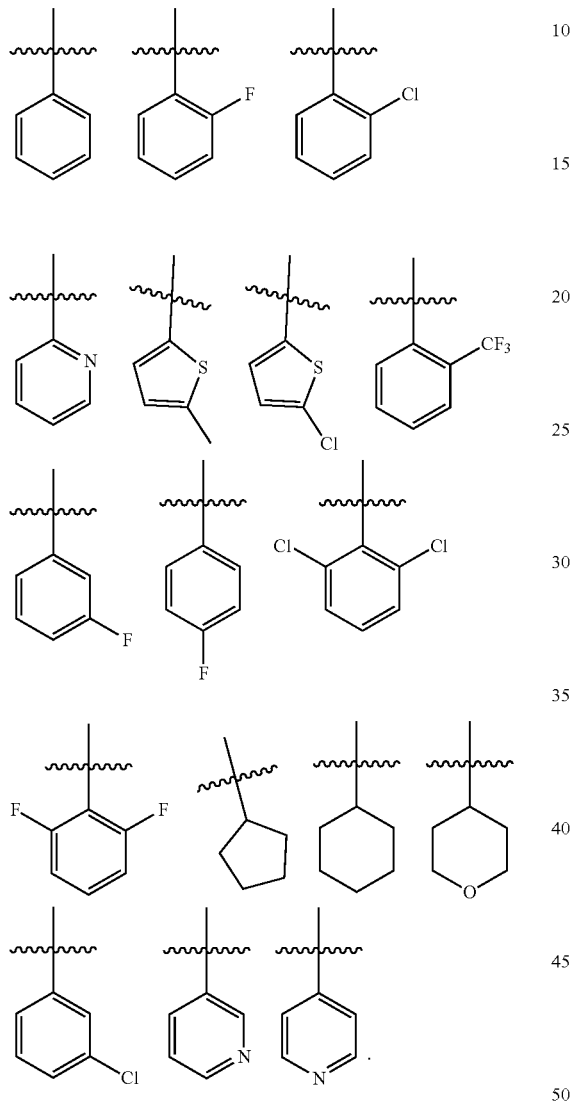

11. The compound of claim 1, wherein Z represents an optionally substituted aryl group.

12. The compound of claim 11, wherein Z is a phenyl group optionally substituted by one or two substituents independently selected from $C_{1-3}$ alkyl, $C_{1-3}$ alkoxy, $C_{1-3}$ haloalkyl, and halogen.

13. The compound of claim 1, wherein Z is an optionally substituted, unsaturated 5- to 10-membered mono- or bicyclic heterocyclic group.

14. The compound of claim 13, wherein Z is a 6-membered, 5-5 fused, 5-6 fused, or 6-6 fused unsaturated heterocyclic ring containing one, two or three heteroatoms.

15. The compound of claim 14, wherein Z is selected from any of the following groups:

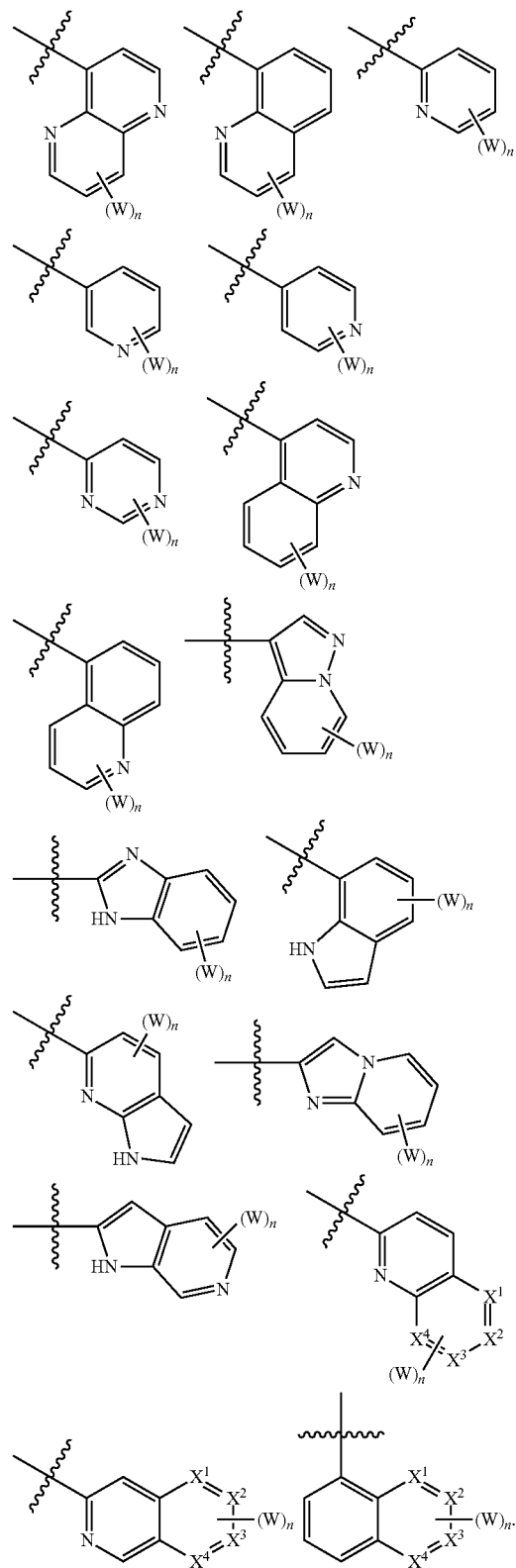

wherein n is 0, 1 or 2;
W is a substituent group selected from halogen, $C_{1-6}$ alkyl, $C_{1-6}$ haloalkyl, $C_{1-6}$ alkoxy, —CN, —$NO_2$, —$N(R)_2$, and —$SO_2R$ (where each R is independently H or $C_{1-6}$ alkyl; and either $X^1$, $X^2$, $X^3$ and $X^4$ are each CH; or one of $X^1$, $X^2$, $X^3$ and $X^4$ is N and the remaining three of $X^1$, $X^2$, $X^3$ and $X^4$ are CH; or two of $X^1$, $X^2$, $X^3$ and $X^4$ are N and the remaining two of $X^1$, $X^2$, $X^3$ and $X^4$ are CH.

16. The compound of claim 15, wherein n is 0.

17. The compound of claim 15, wherein n is 1 or 2 and each W may independently be selected from halogen, $C_{1-3}$ alkyl, $C_{1-3}$ alkoxy, and —CN.

18. The compound of claim 1, wherein Z is selected from optionally substituted phenyl, pyridine, pyrimidine, quinoline, 1,5-napthyridine, benzimidazole, pyrazolo[1,5-a]pyridine, and benzodiazine.

19. The compound of claim 1, wherein Z is selected from any of the following groups:

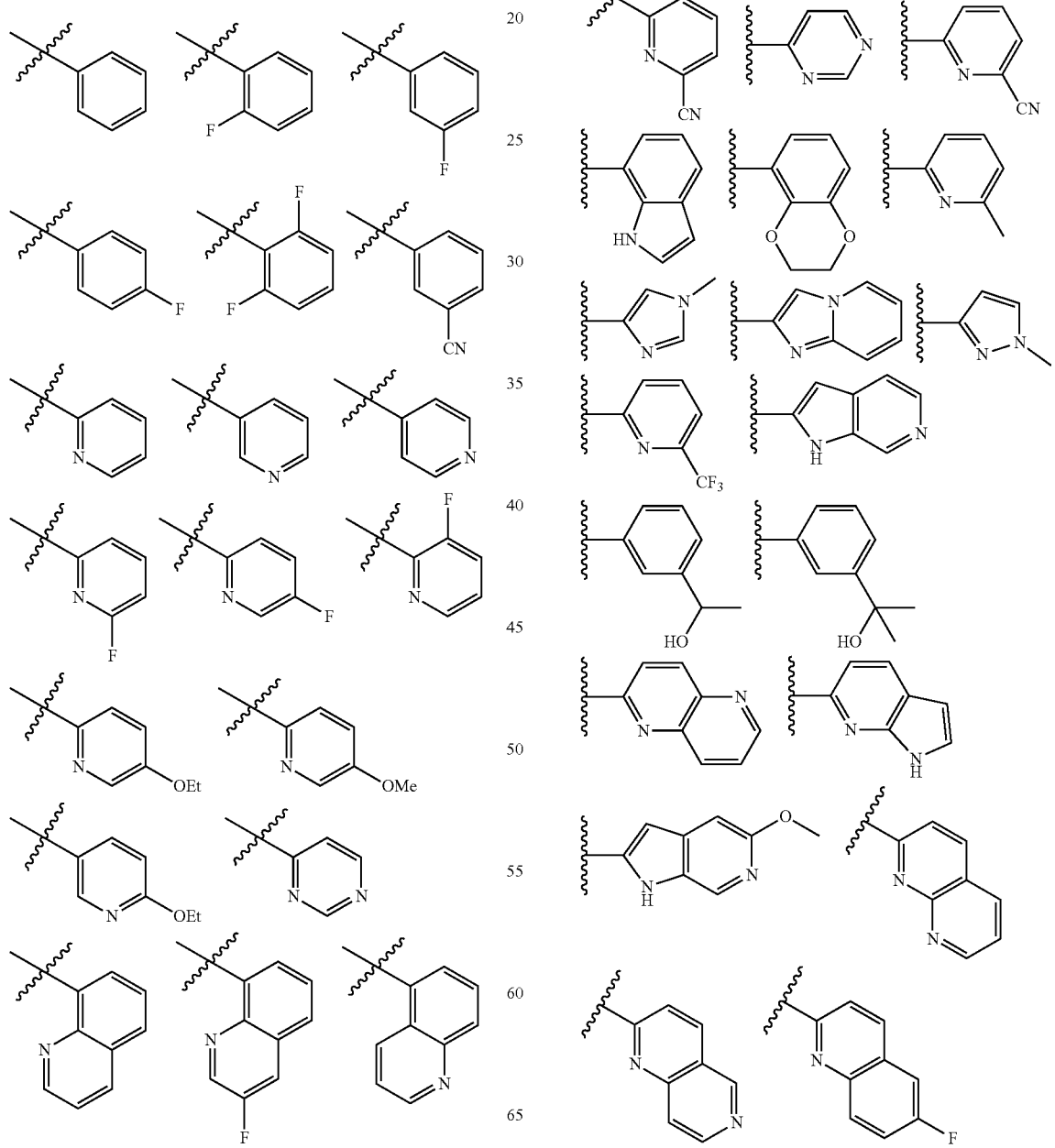

-continued

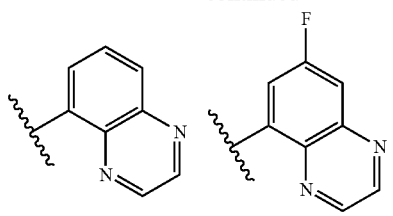
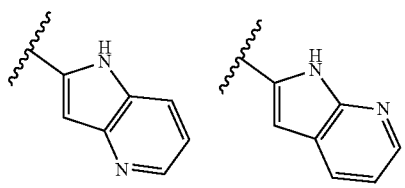
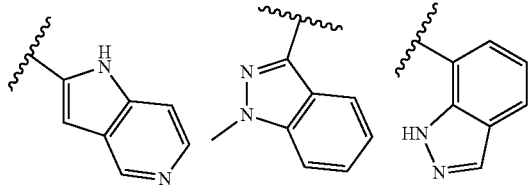

-continued

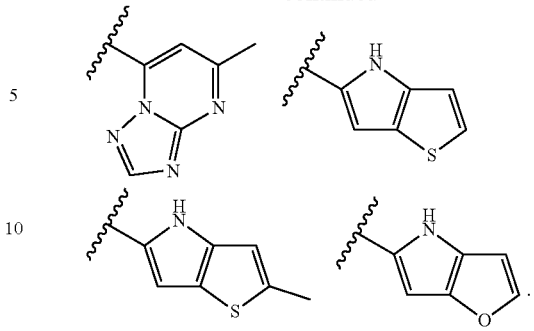

20. The compound of claim 1 having the general formula (Ia), or a tautomer, stereoisomer, pharmaceutically acceptable salt or pro-drug thereof:

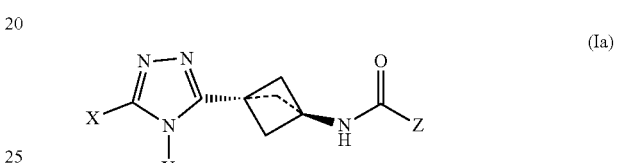

(Ia)

wherein X, Y and Z are as defined in claim 1.

21. The compound of claim 1 selected from any of the following compounds, or a tautomer, a stereoisomer, a pharmaceutically acceptable salt or a pro-drug thereof:

| Example No. (where applicable) | Structure |
|---|---|
| 4 | 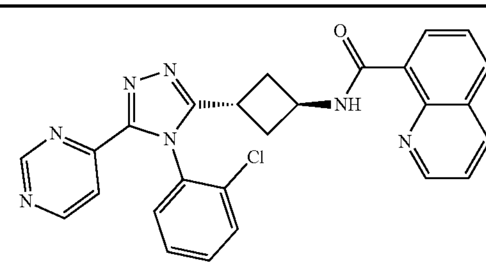 |
| 5 | 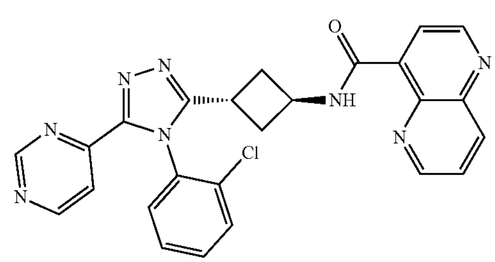 |
| 6 | 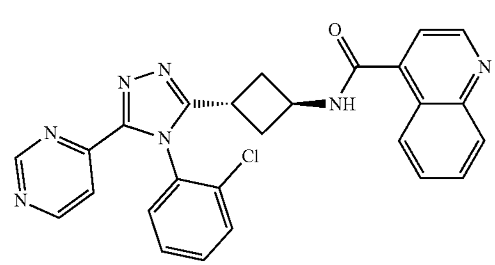 |

-continued
| Example No. (where applicable) | Structure |
|---|---|
| 7 | 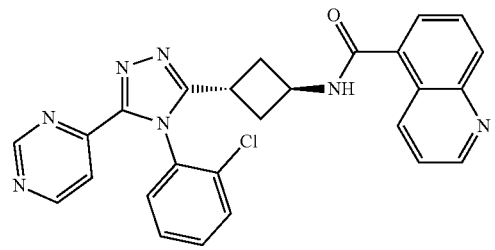 |
| 8 | 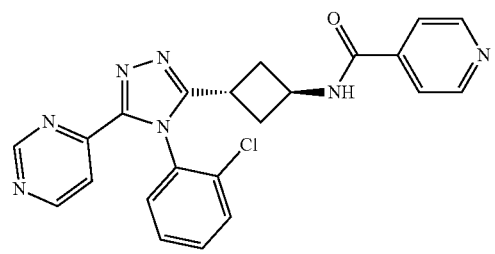 |
| 9 | 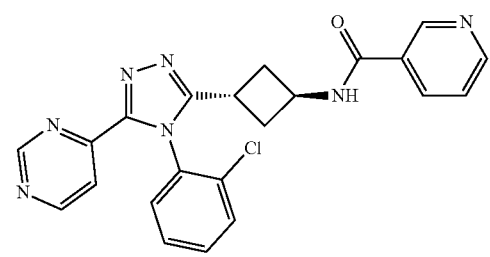 |
| 10 | 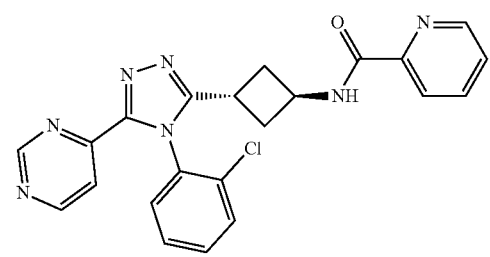 |
| 11 | 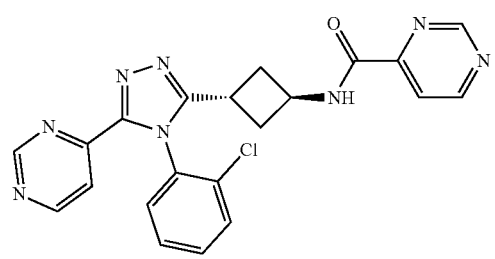 |
| 12 | 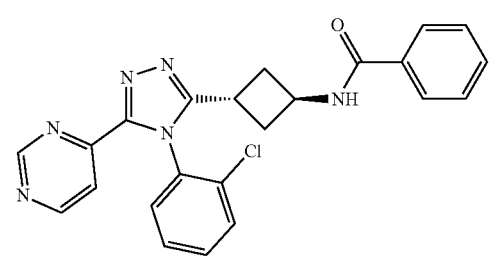 |

-continued
| Example No.<br>(where applicable) | Structure |
|---|---|
| 13 | 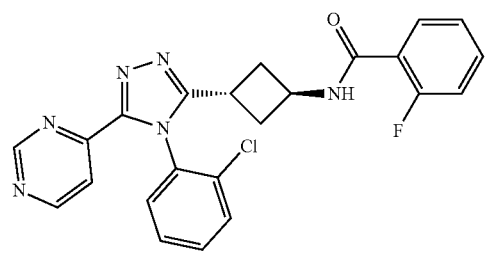 |
| 14 | 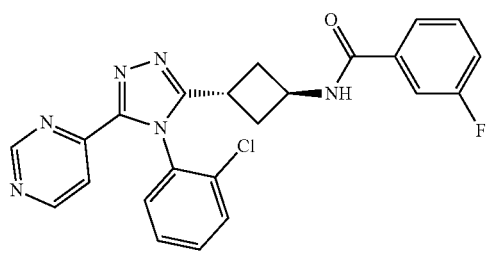 |
| 15 | 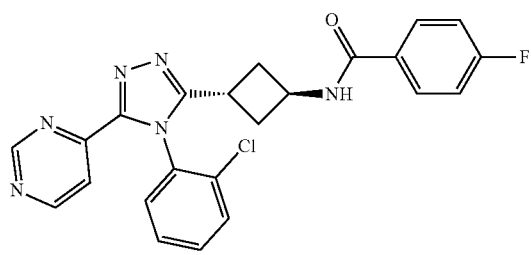 |
| 16 | 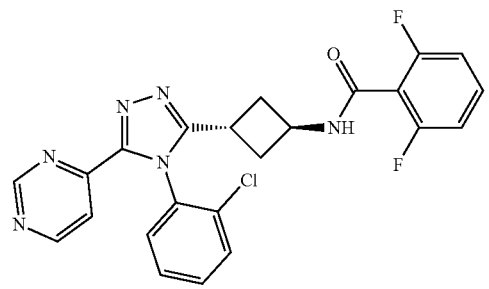 |
| 17 | 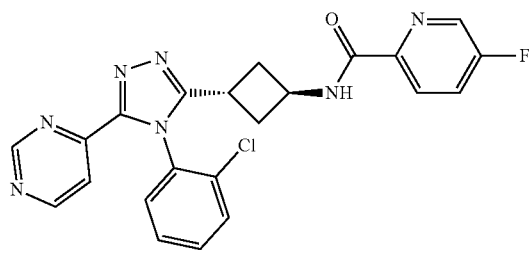 |

-continued
| Example No. (where applicable) | Structure |
|---|---|
| 18 | 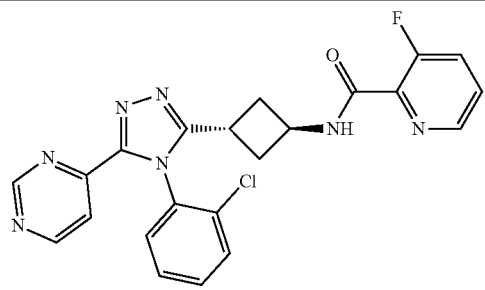 |
| 19 | 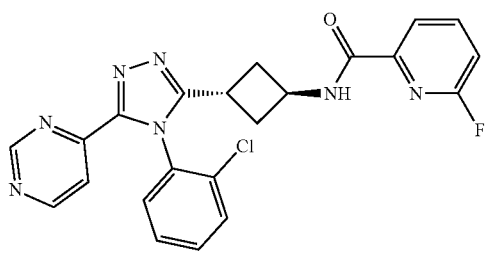 |
| 21 | 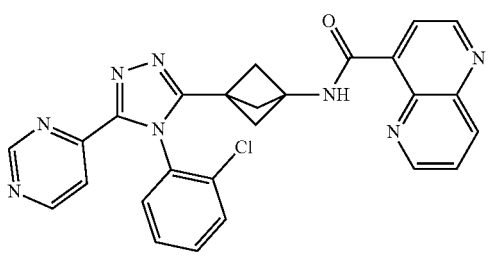 |
| 22 | 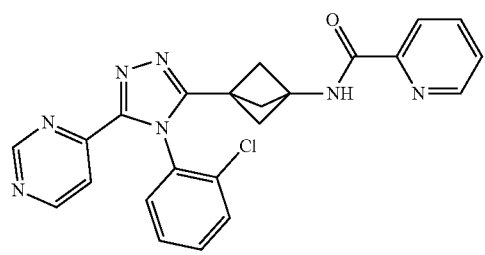 |
| 23 | 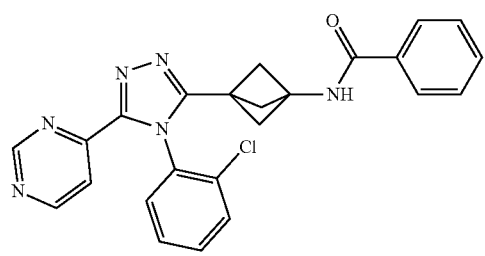 |
| 25 | 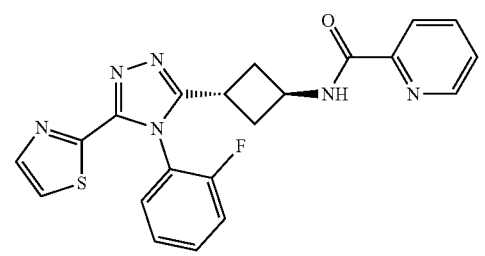 |

-continued
| Example No. (where applicable) | Structure |
|---|---|
| 26 | 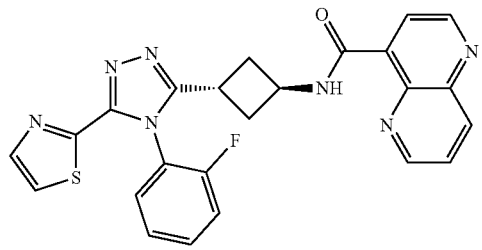 |
| 27 | 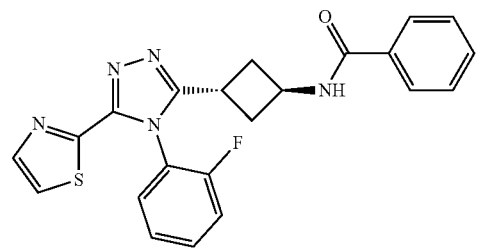 |
| 28 | 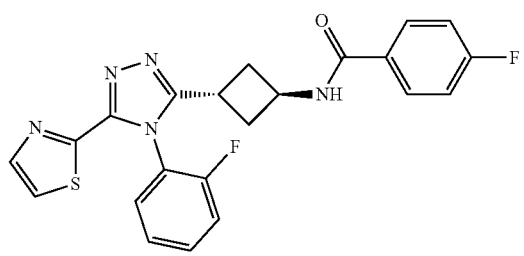 |
| 29 | 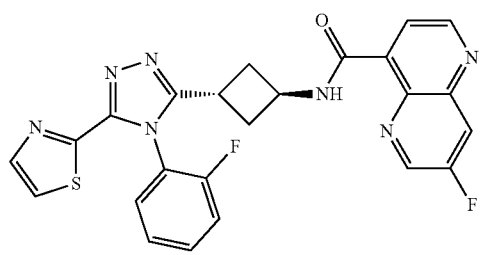 |
| 30 | 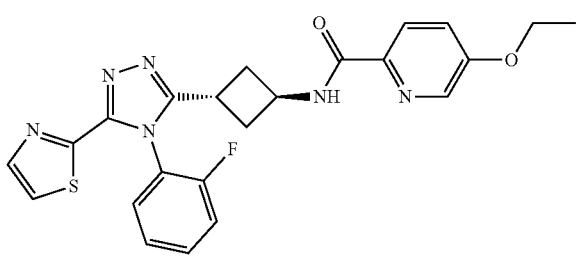 |
| 32 | 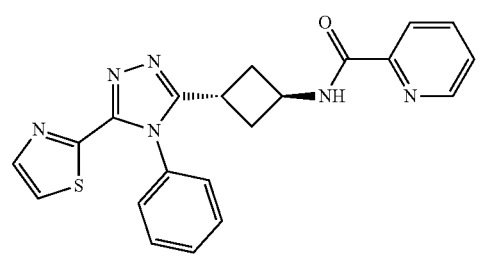 |

-continued
| Example No.<br>(where applicable) | Structure |
|---|---|
| 33 | 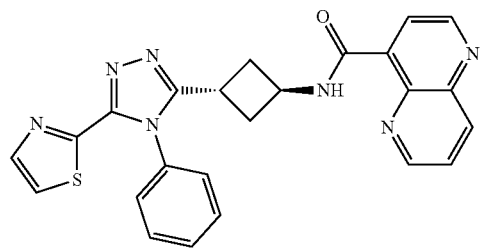 |
| 34 | 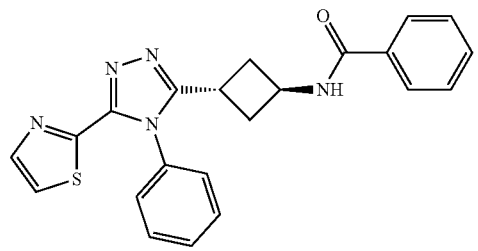 |
| 35 | 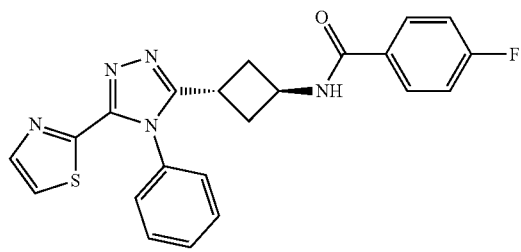 |
| 37 | 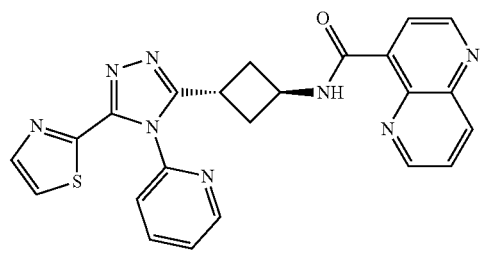 |
| 38 | 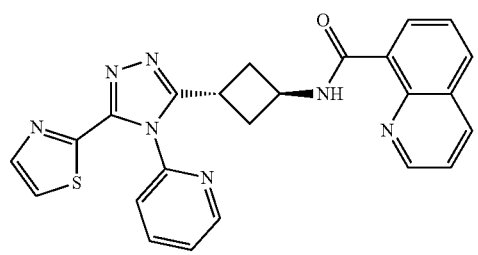 |
| 39 | 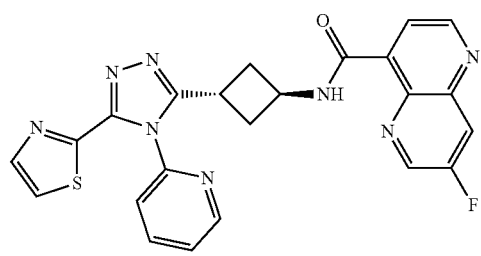 |

-continued
| Example No. (where applicable) | Structure |
|---|---|
| 41 | 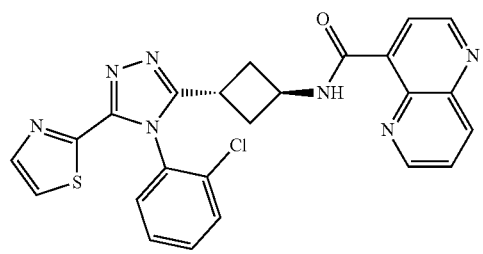 |
| 42 | 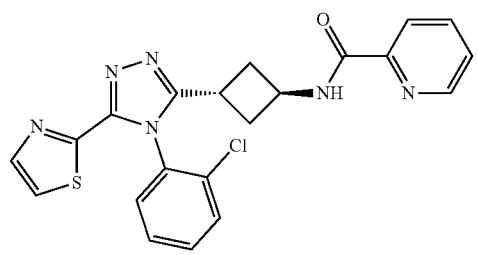 |
| 43 | 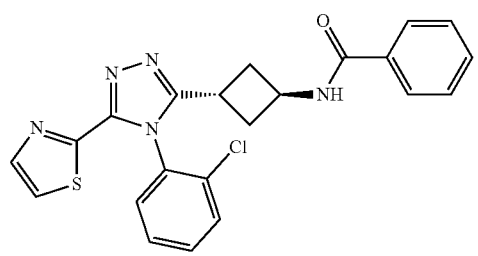 |
| 44 | 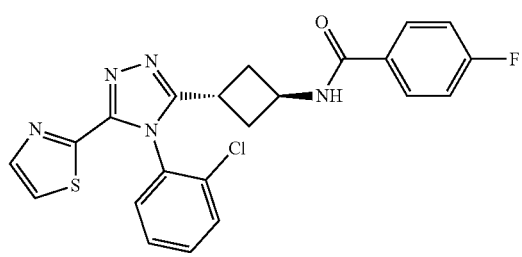 |
| 46 | 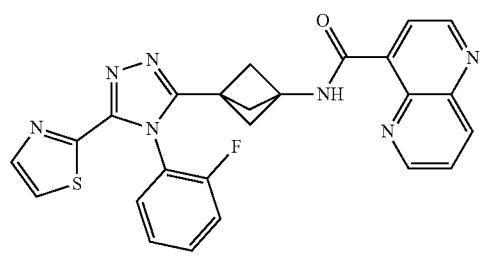 |
| 48 | 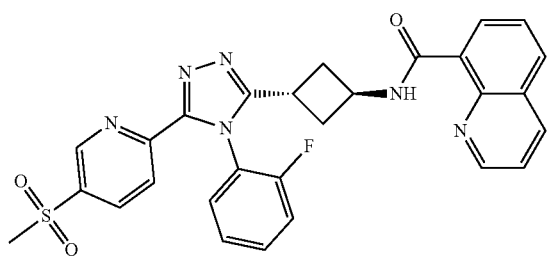 |

| Example No. (where applicable) | Structure |
|---|---|
| 49 | 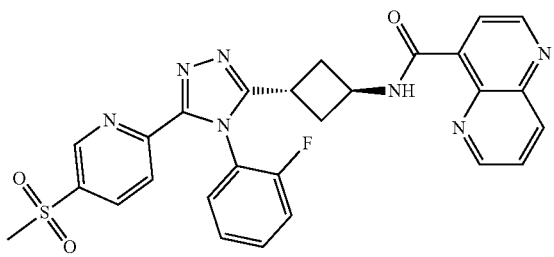 |
| 50 | 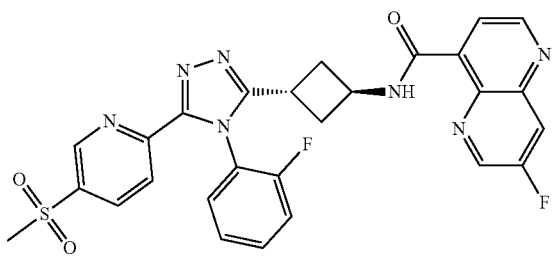 |
| 52 | 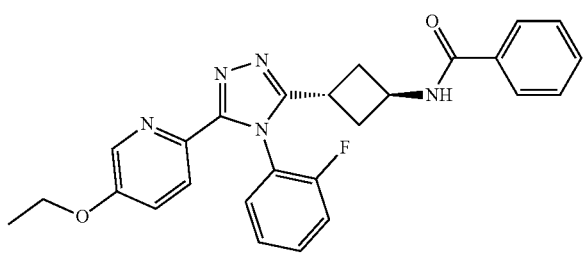 |
| 53 | 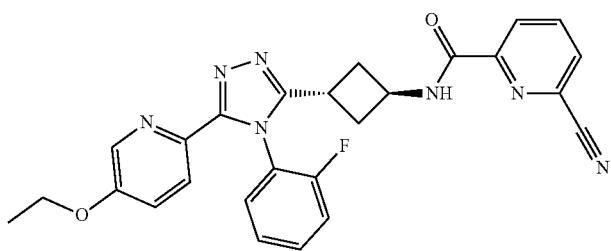 |
| 54 | 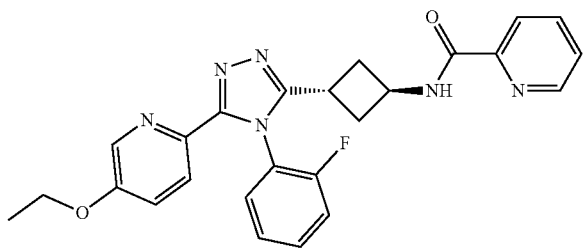 |
| 55 | 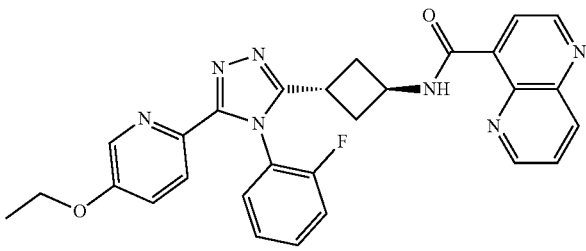 |

-continued
| Example No. (where applicable) | Structure |
|---|---|
| 56 | 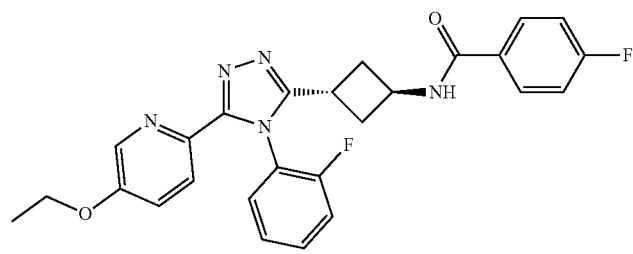 |
| 57 | 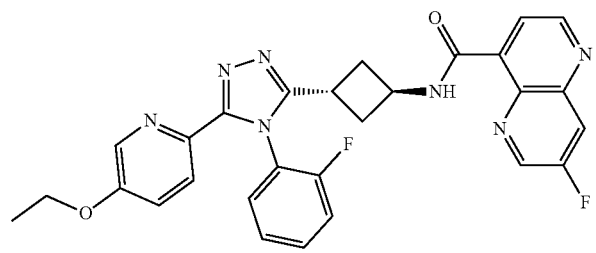 |
| 58 | 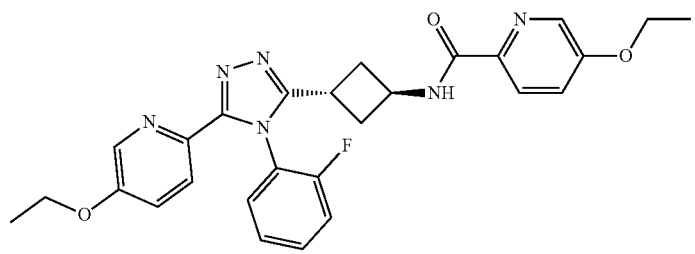 |
| 59 | 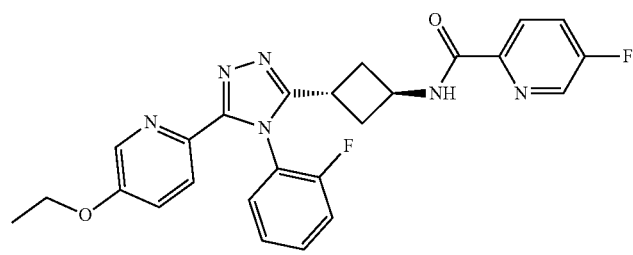 |
| 60 | 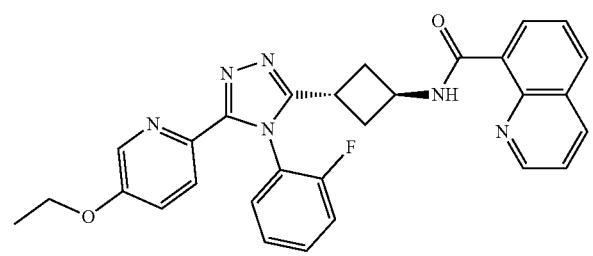 |
| 62 | 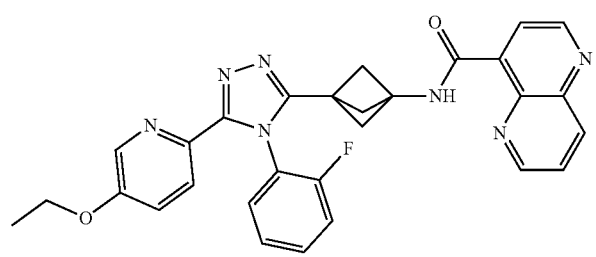 |

| Example No. (where applicable) | Structure |
|---|---|
| 64 | 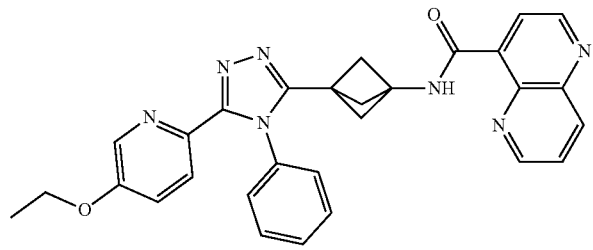 |
| 65 | 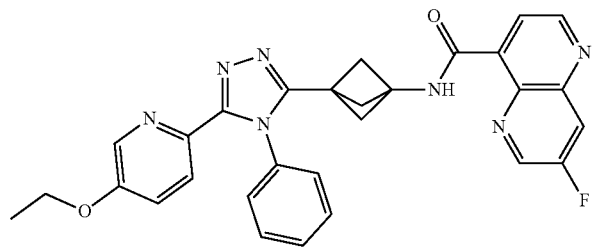 |
| 66 | 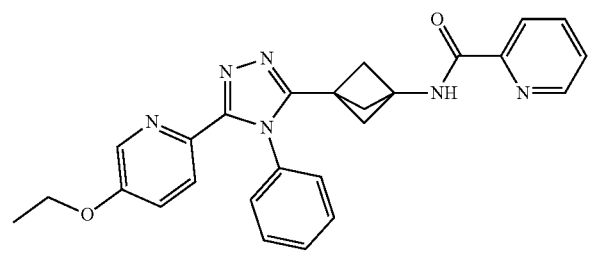 |
| 68 | 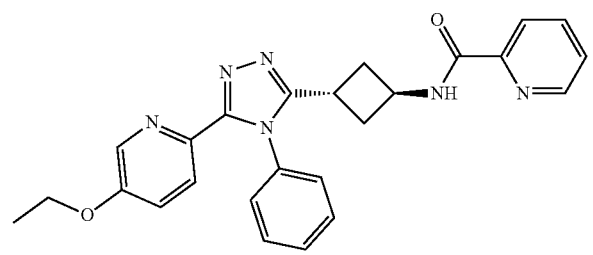 |
| 69 | 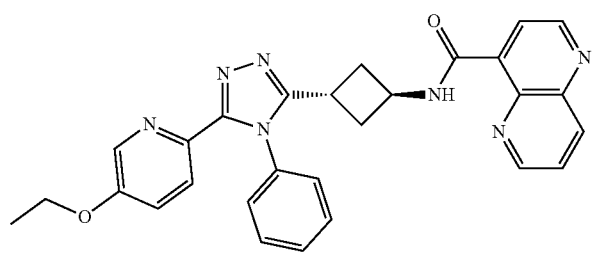 |
| 70 | 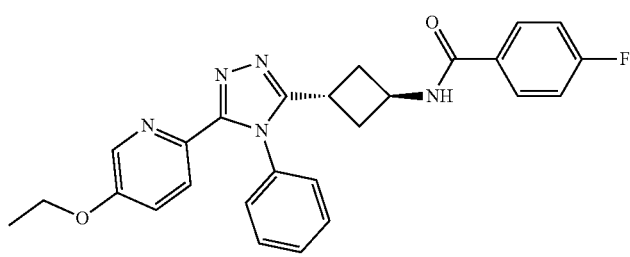 |

-continued
| Example No. (where applicable) | Structure |
|---|---|
| 71 | 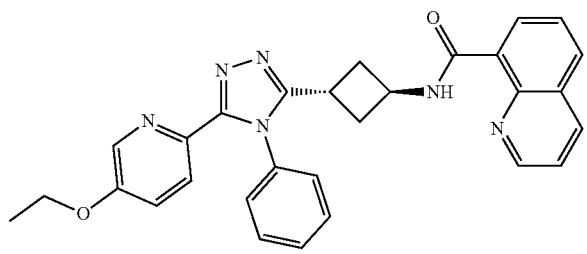 |
| 72 | 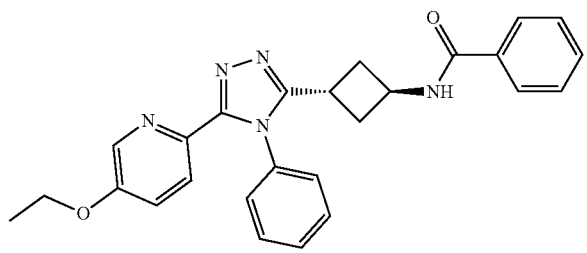 |
| 73 | 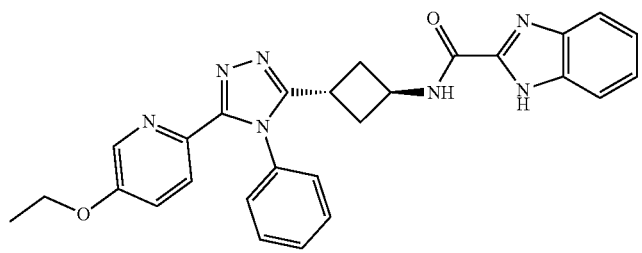 |
| 75 | 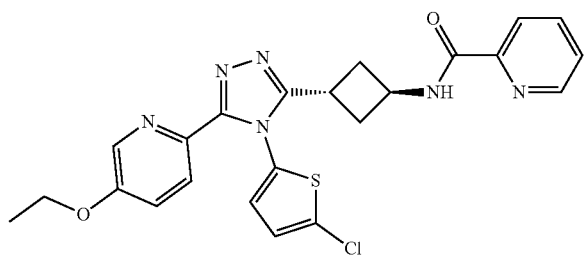 |
| 76 | 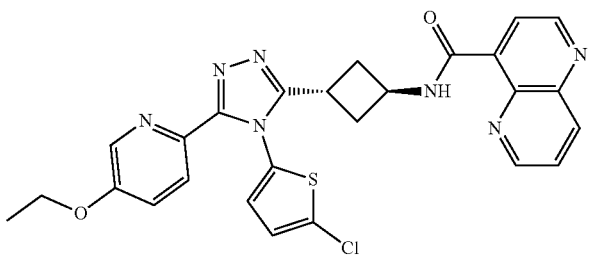 |
| 78 | 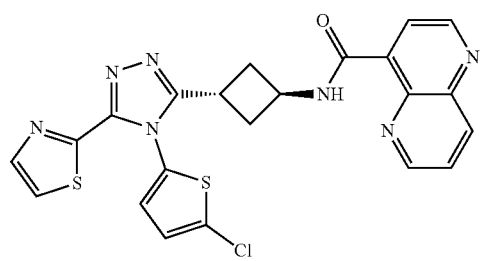 |

| Example No. (where applicable) | Structure |
|---|---|
| 79 | 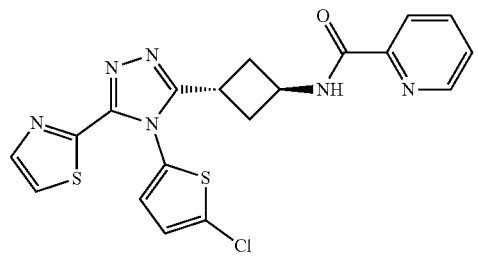 |
| 81 | 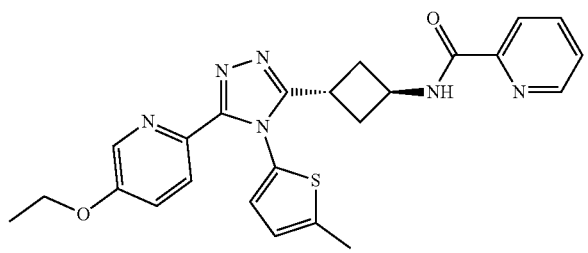 |
| 82 | 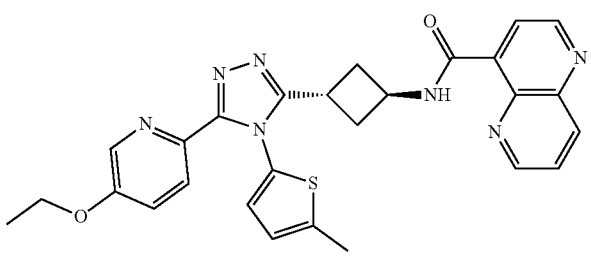 |
| 83 | 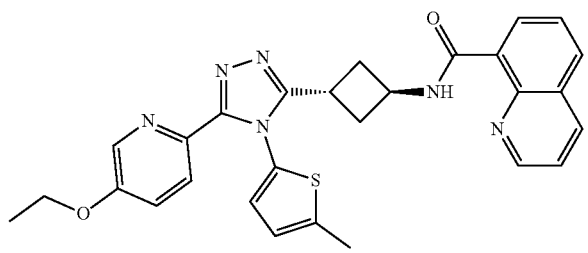 |
| 84 | 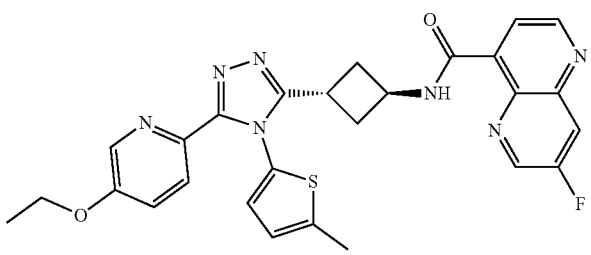 |
| 86 | 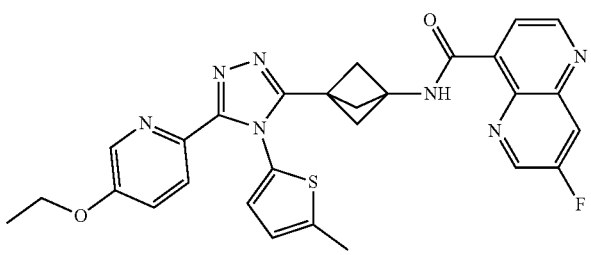 |

US 11,926,614 B2
231                                                                                   232
-continued
| Example No. (where applicable) | Structure |
|---|---|
| 88 | 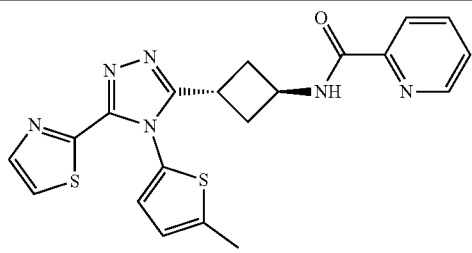 |
| 89 | 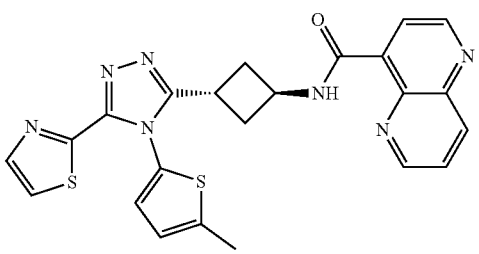 |
| 91 | 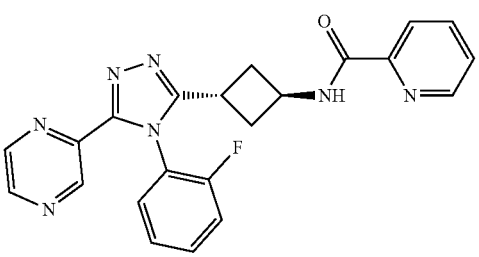 |
| 93 | 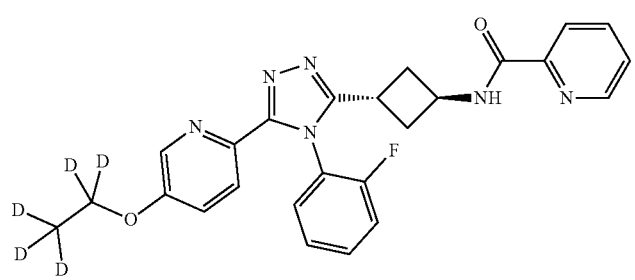 |
| 94 | 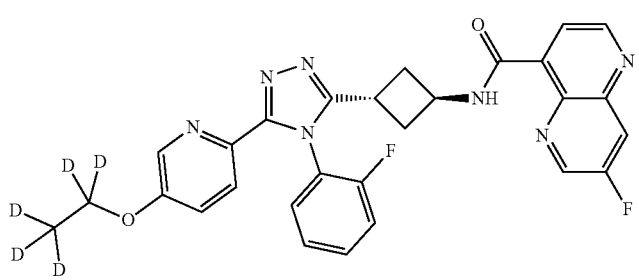 |
| 95 | 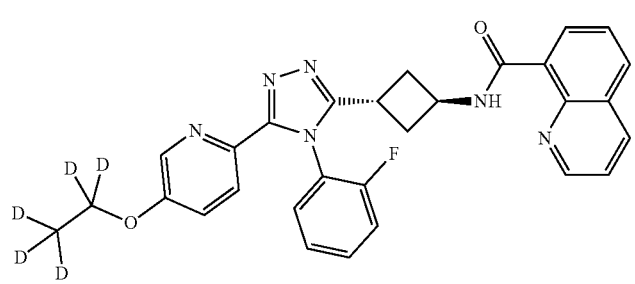 |

| Example No. (where applicable) | Structure |
|---|---|
| 96 | 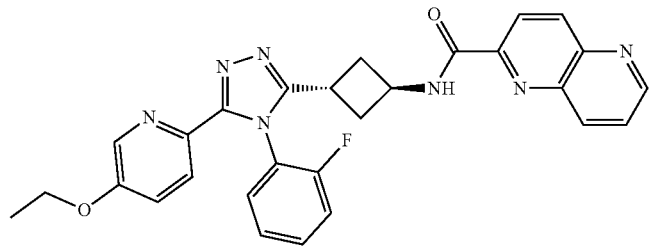 |
| 97 | 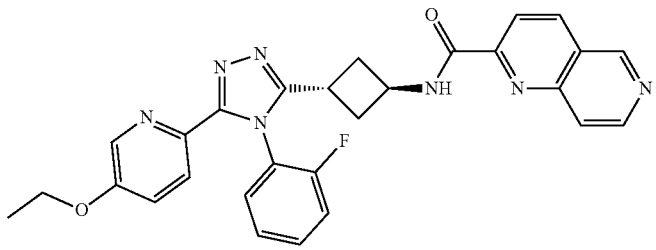 |
| 98 | 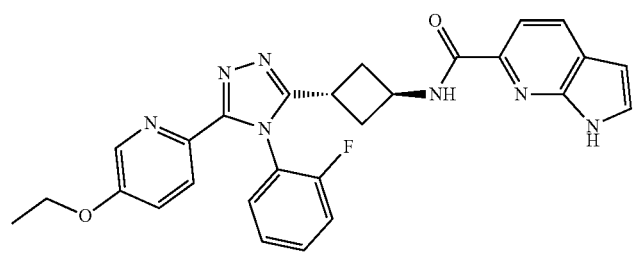 |
| 99 | 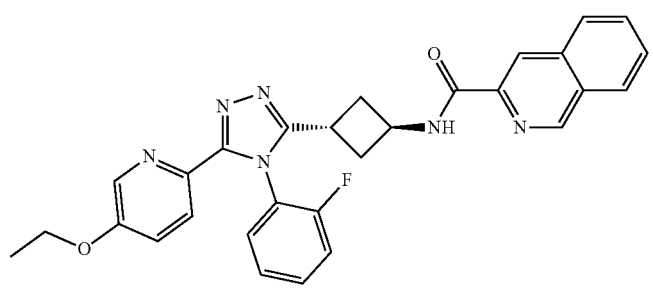 |
| 100 | 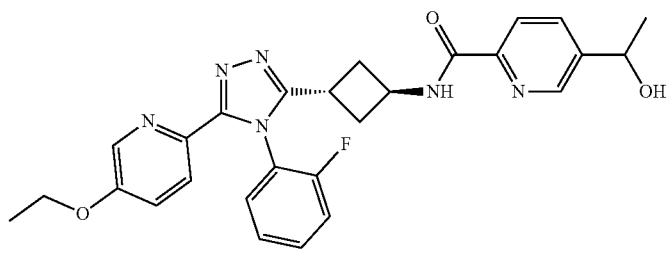 |
| 101 | 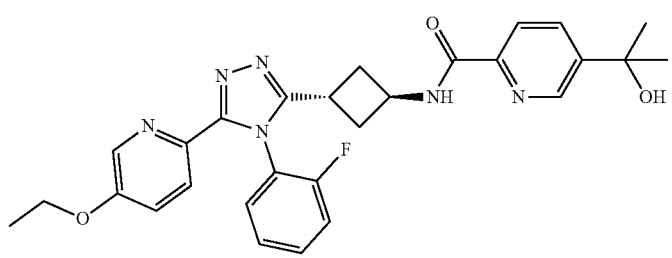 |

| Example No. (where applicable) | Structure |
|---|---|
| 102 | 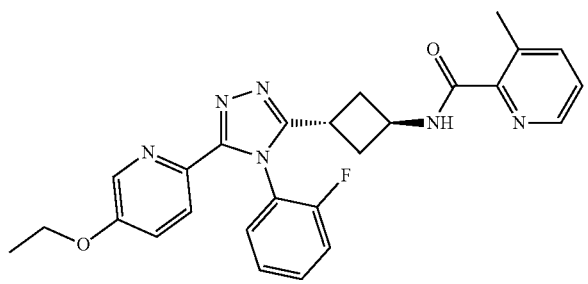 |
| 103 | 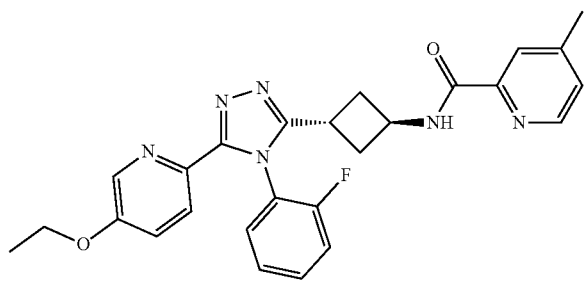 |
| 104 | 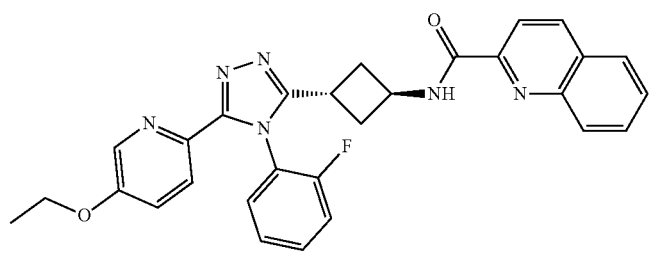 |
| 106 | 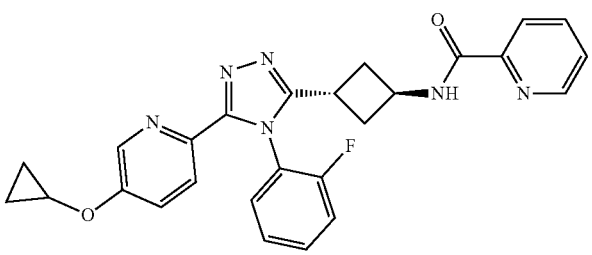 |
| 107 | 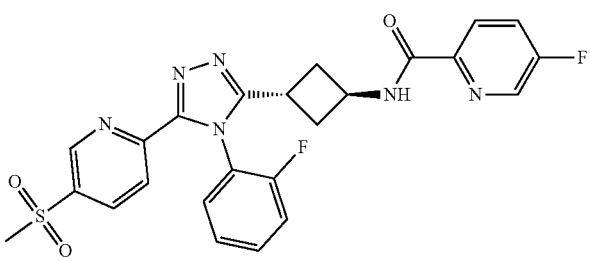 |

| Example No. (where applicable) | Structure |
|---|---|
| 109 | 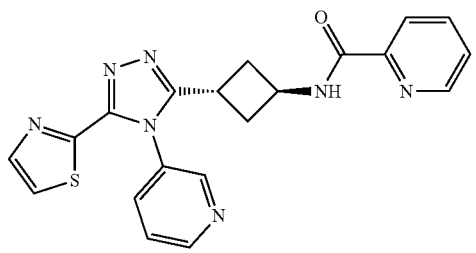 |
| 111 | 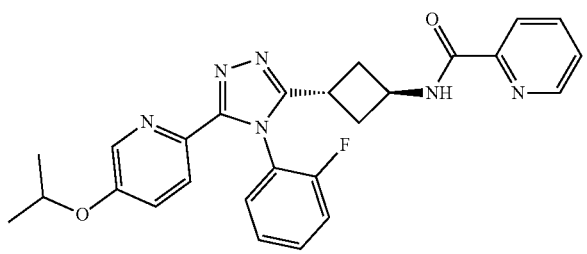 |
| 113 | 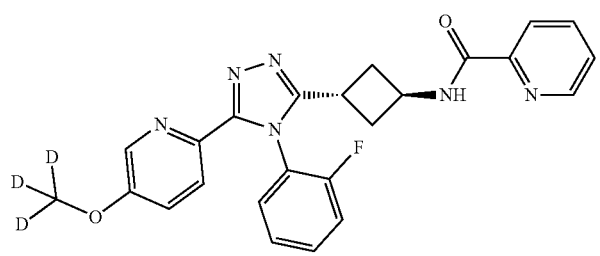 |
| 114 | 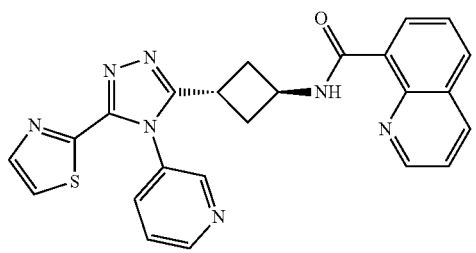 |
| 115 | 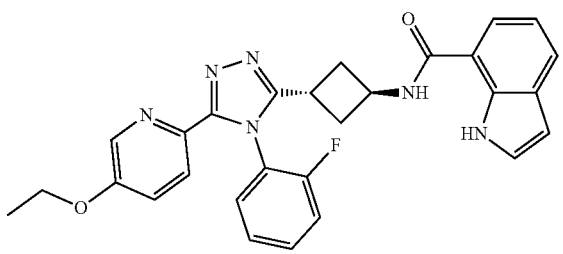 |
| 116 | 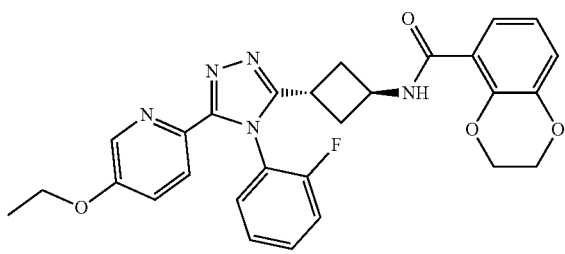 |

| Example No. (where applicable) | Structure |
|---|---|
| 117 | 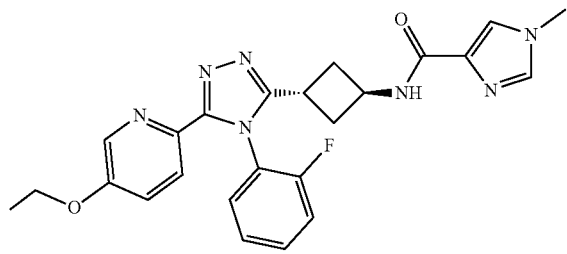 |
| 118 | 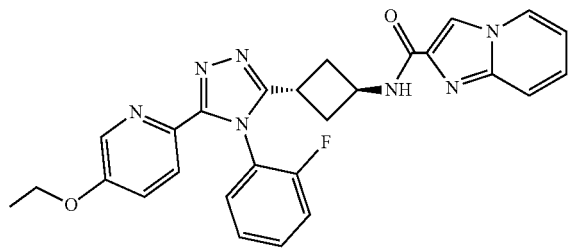 |
| 119 | 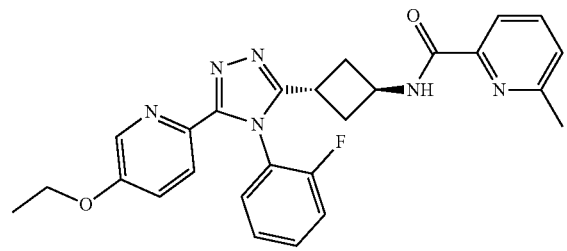 |
| 120 | 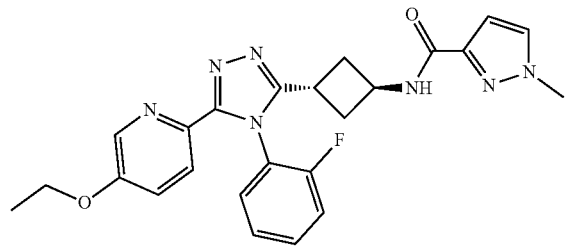 |
| 122 | 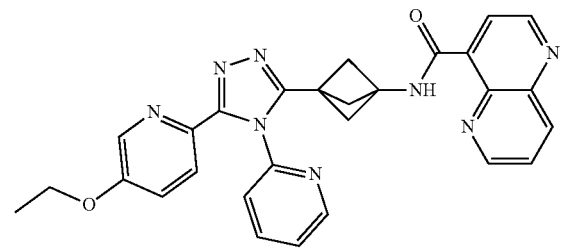 |
| 124 | 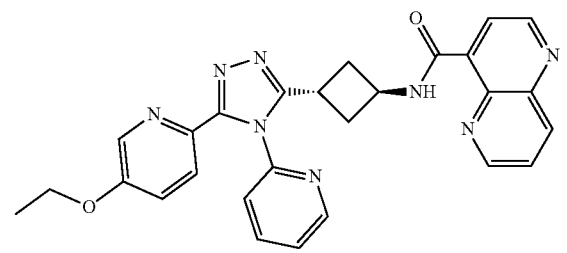 |

-continued
| Example No. (where applicable) | Structure |
|---|---|
| 125 | 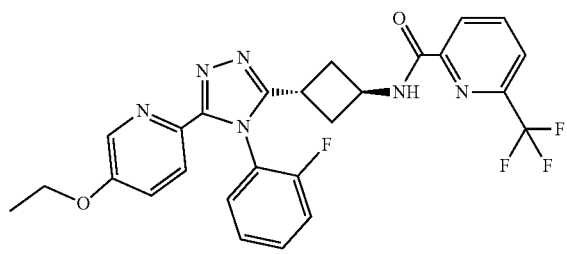 |
| 126 | 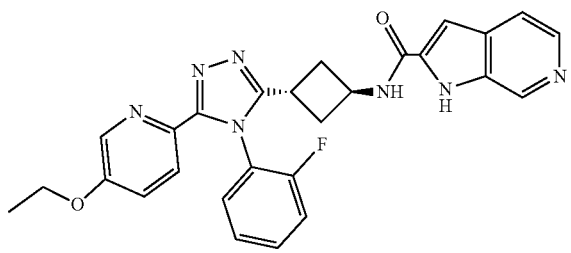 |
| 127 | 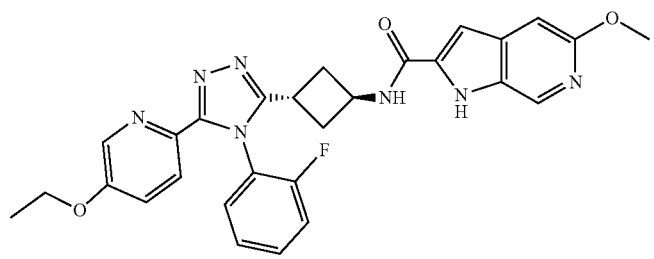 |
| 128 | 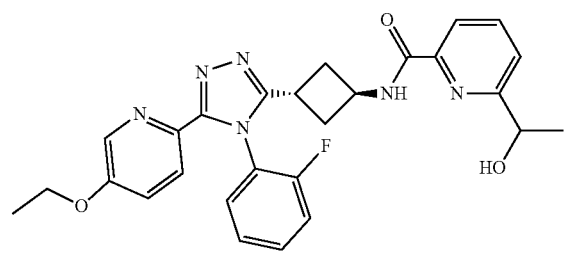 |
| 129 | 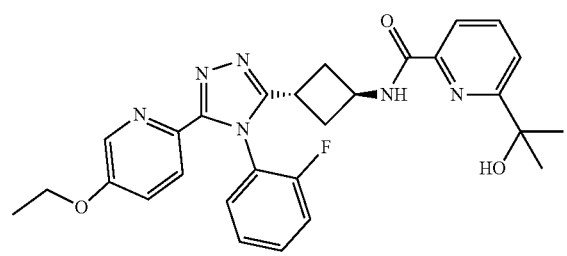 |
| 130 | 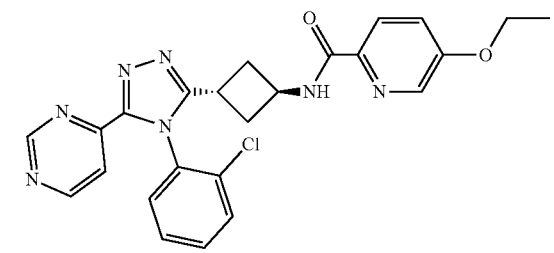 |

| Example No. (where applicable) | Structure |
|---|---|
| 131 | 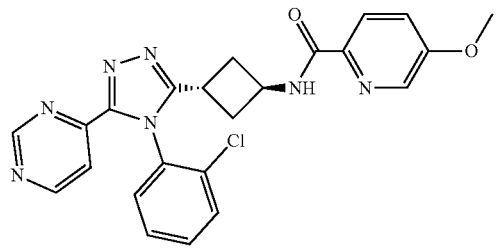 |
| 132 | 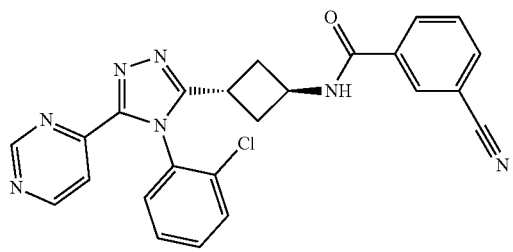 |
| 134 | 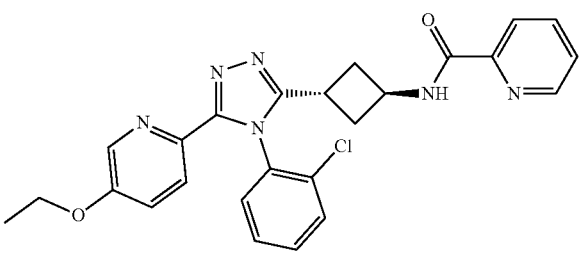 |
| 135 | 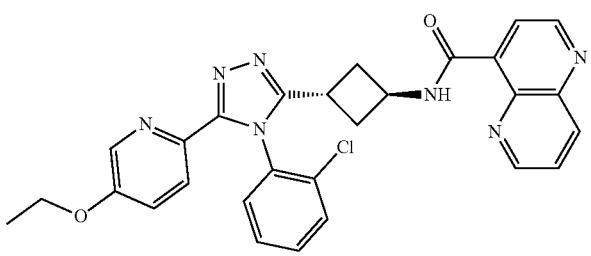 |
| 136 | 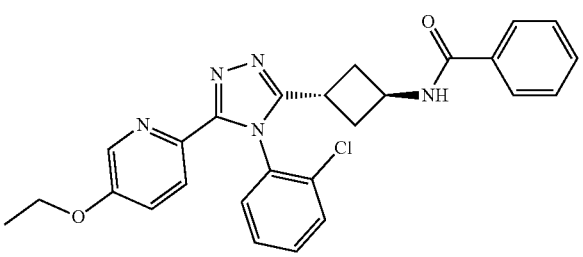 |
| 137 | 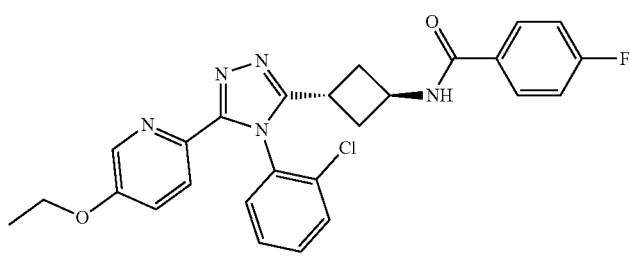 |

| Example No. (where applicable) | Structure |
|---|---|
| 139 | 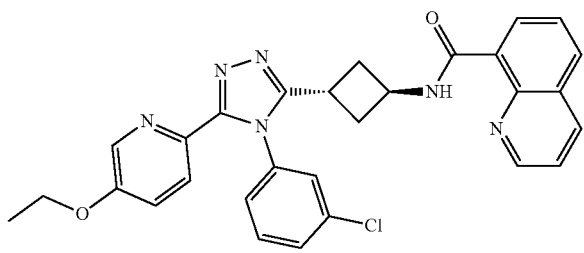 |
| 140 | 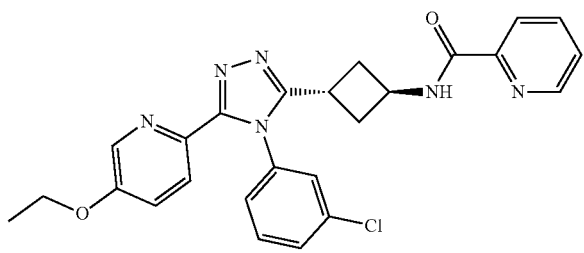 |
| 141 | 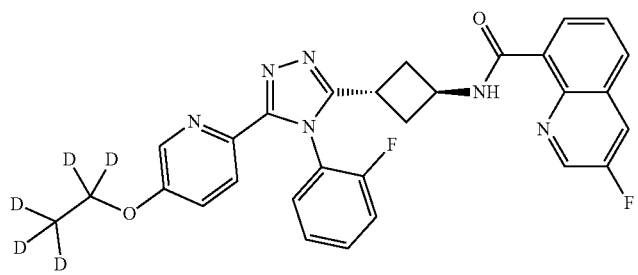 |
| 142 | 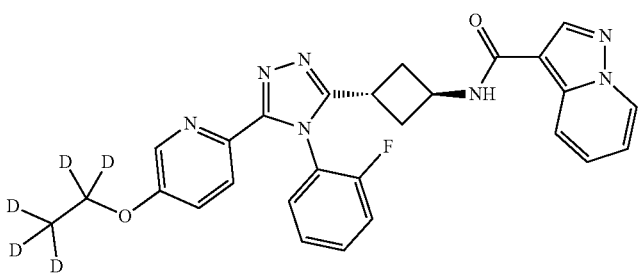 |
| 143 | 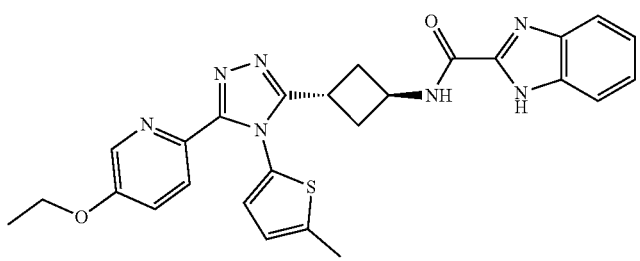 |
| 144 | 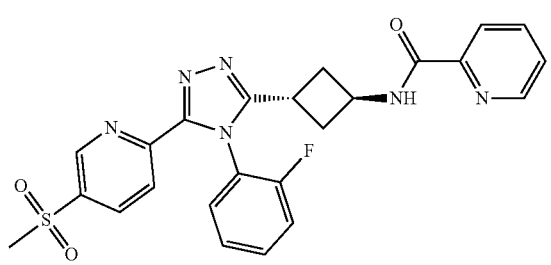 |

| Example No. (where applicable) | Structure |
|---|---|
| 146 | 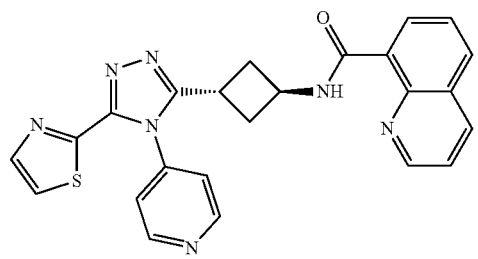 |
| 147 | 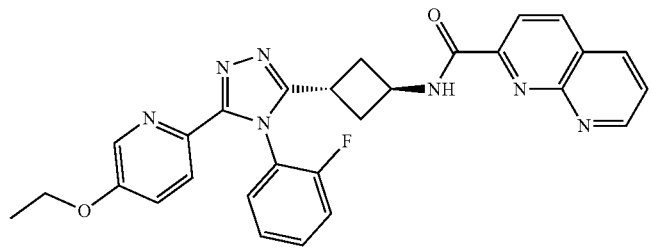 |
| 148 | 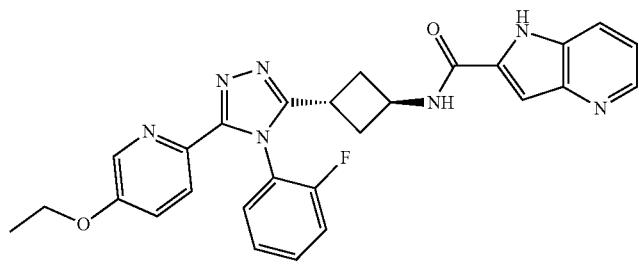 |
| 149 | 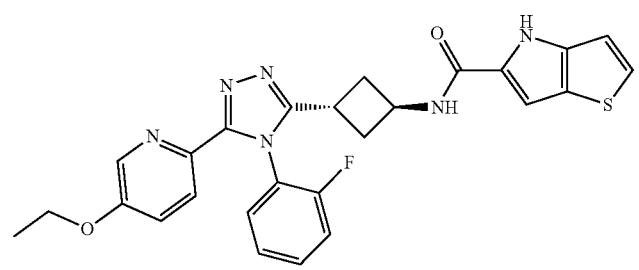 |
| 150 | 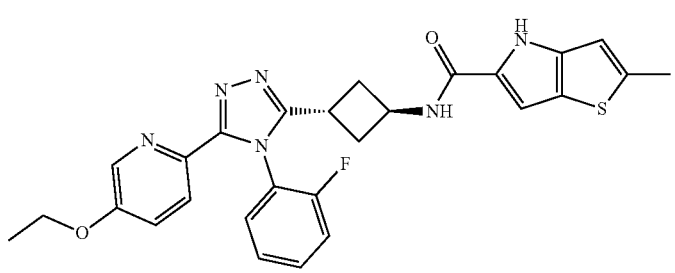 |

| Example No. (where applicable) | Structure |
|---|---|
| 151 | 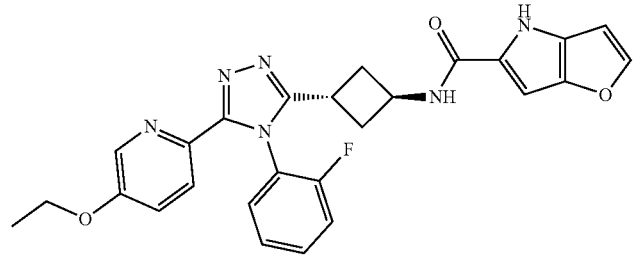 |
| 152 | 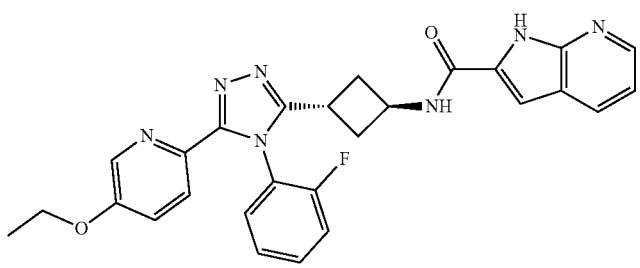 |
| 153 | 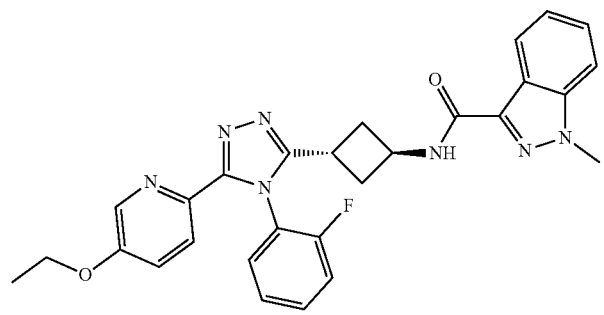 |
| 154 | 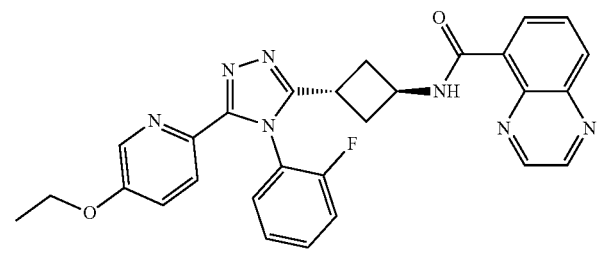 |
| 155 | 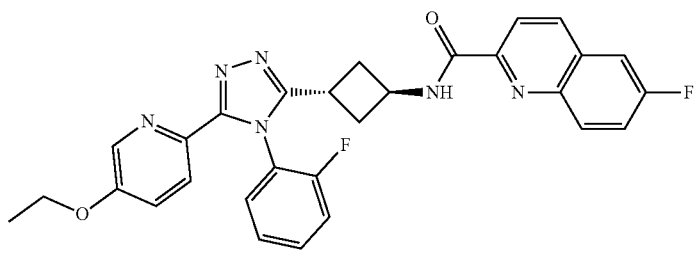 |

| Example No. (where applicable) | Structure |
|---|---|
| 156 | 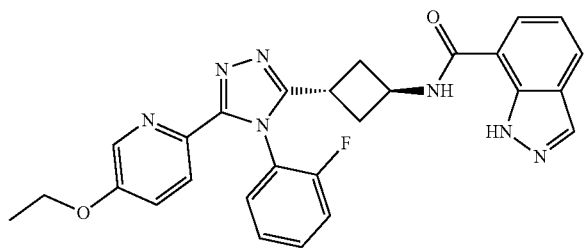 |
| 157 | 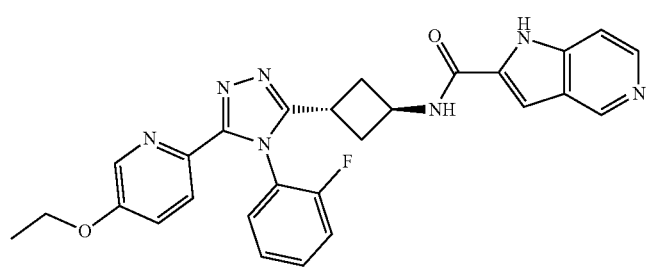 |
| 158 | 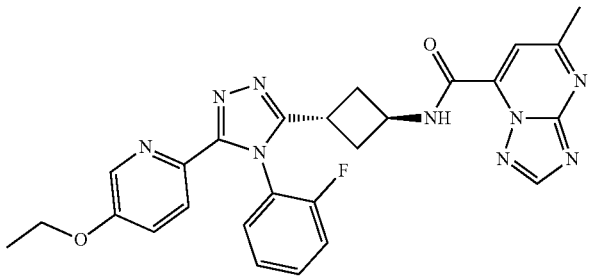 |
| 159 | 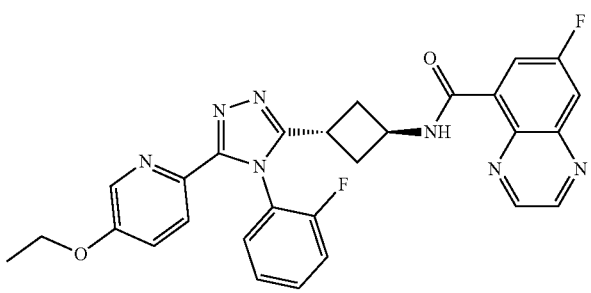 |
| 160 | 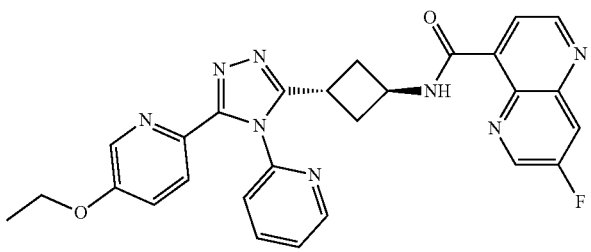 |

| Example No. (where applicable) | Structure |
|---|---|
| 162 | 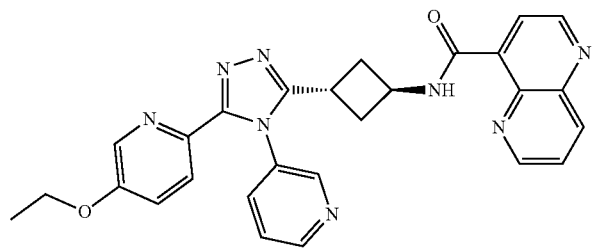 |
| 163 | 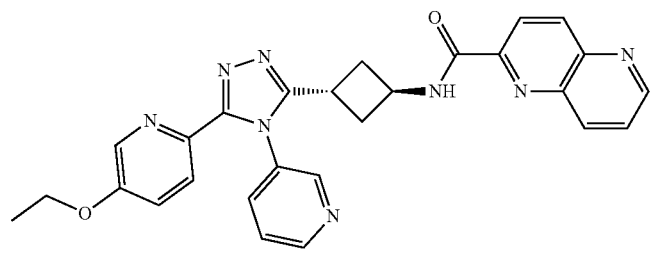 |
| 164 | 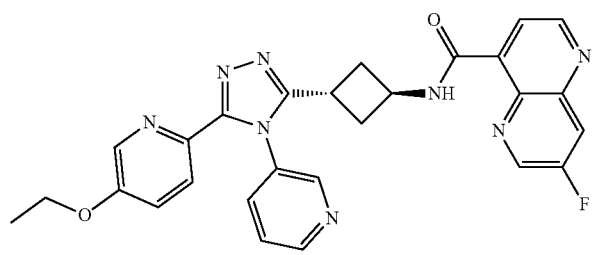 |
| 166 | 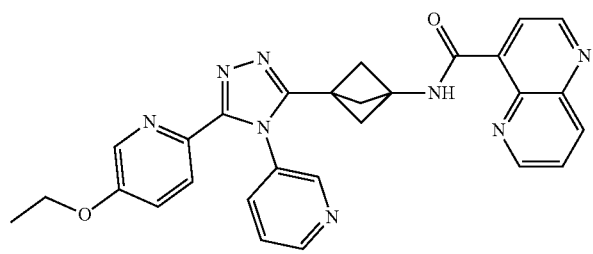 |
| 168 | 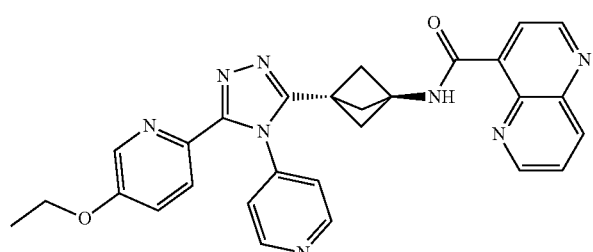 |
| 169 | 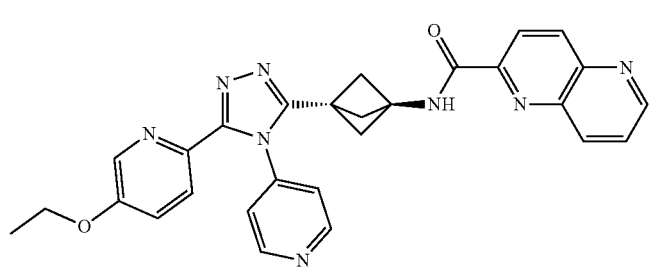 |

| Example No. (where applicable) | Structure |
|---|---|
| 170 | 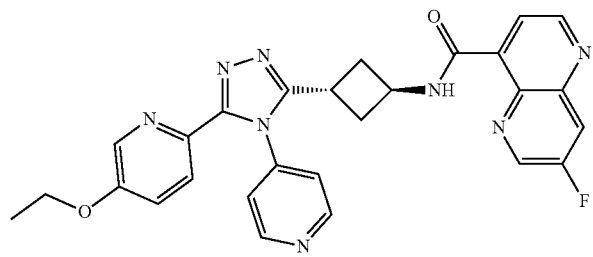 |
| 172 | 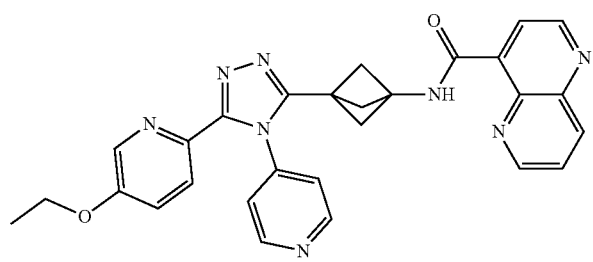 |
| 174 | 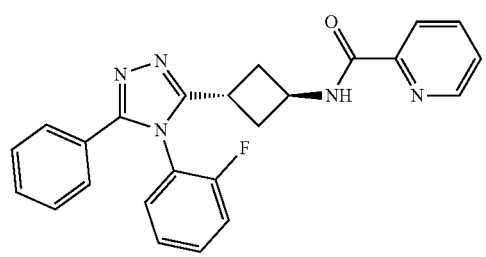 |
| 175 | 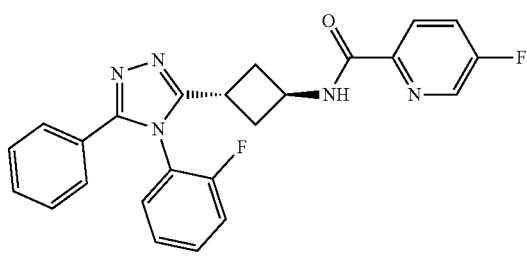 |
| 176 | 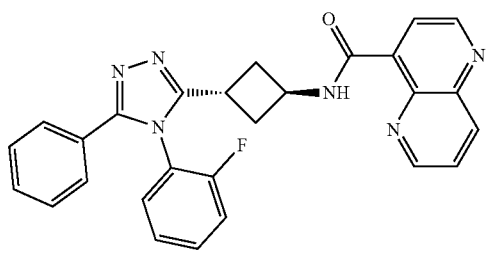 |
| 177 | 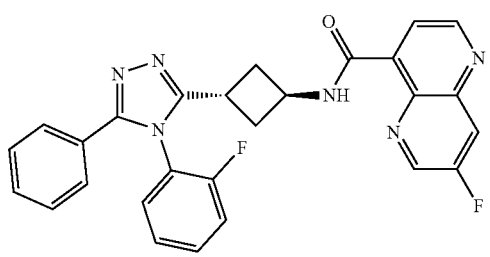 |

| Example No. (where applicable) | Structure |
|---|---|
| 178 | 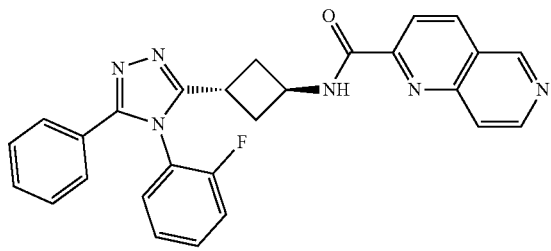 |
| 180 | 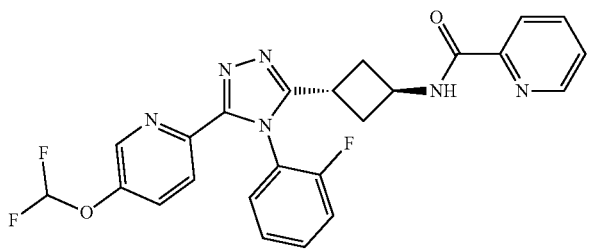 |
| 181 | 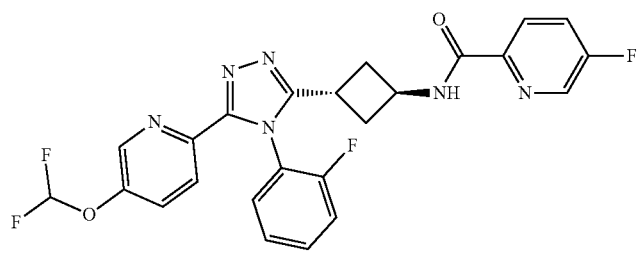 |
| 182 | 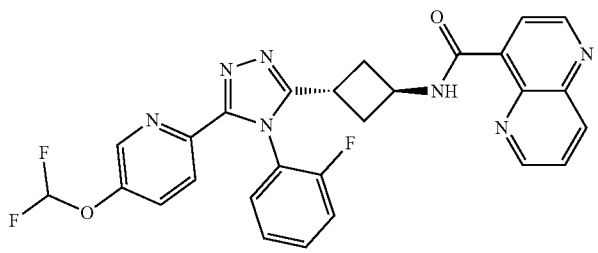 |
| 183 | 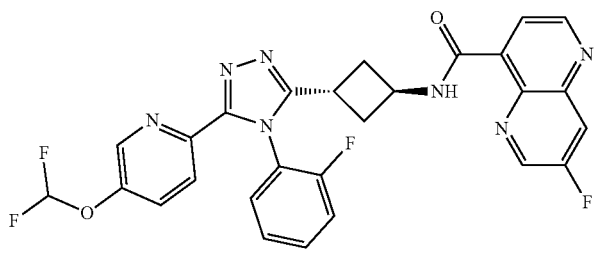 |
| 184 | 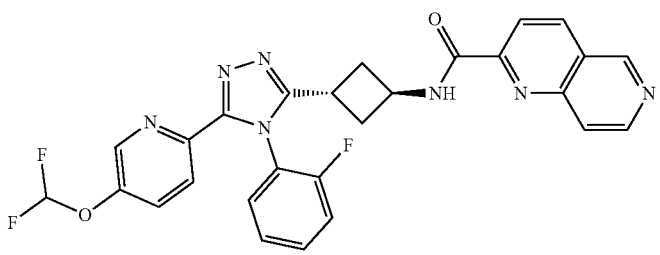 |

| Example No. (where applicable) | Structure |
|---|---|
| 185 | 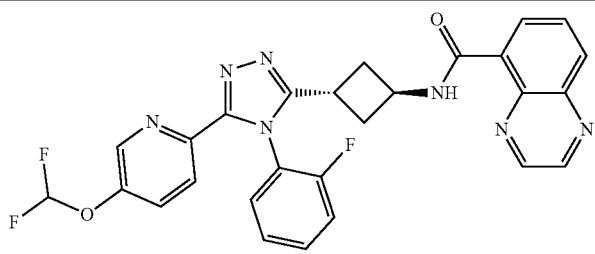 |
| 186 | 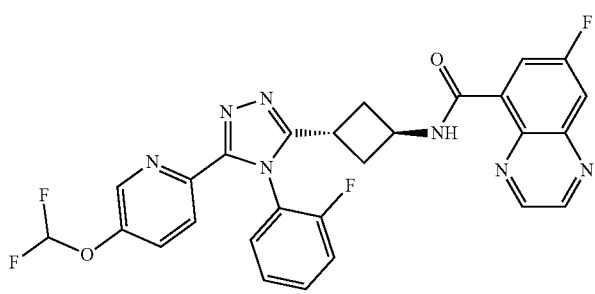 |
| 188 | 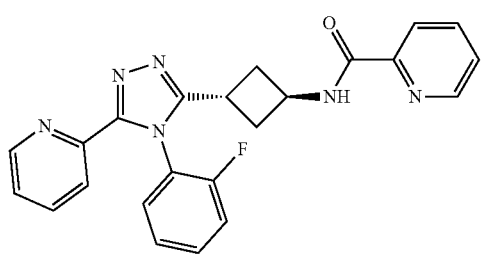 |
| 189 | 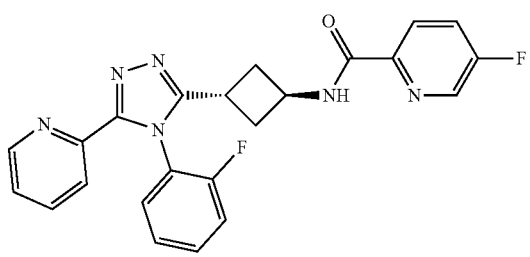 |
| 190 | 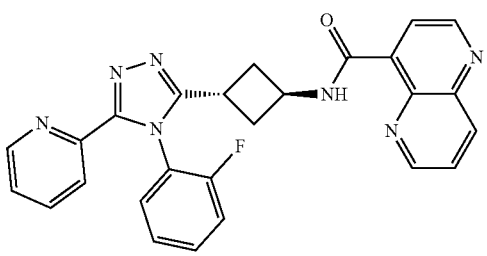 |
| 191 | 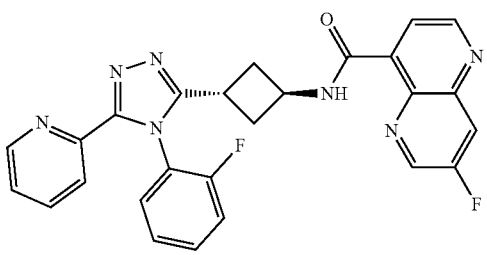 |

-continued
| Example No. (where applicable) | Structure |
|---|---|
| 192 | 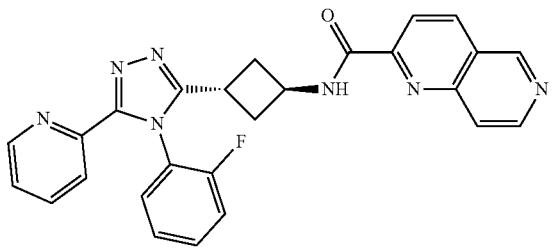 |
| 193 | 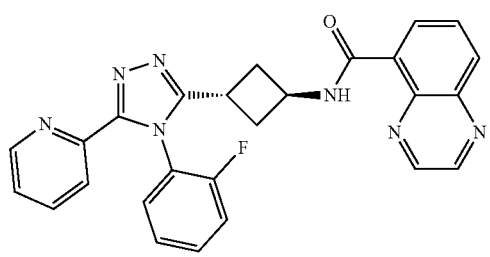 |
| 194 | 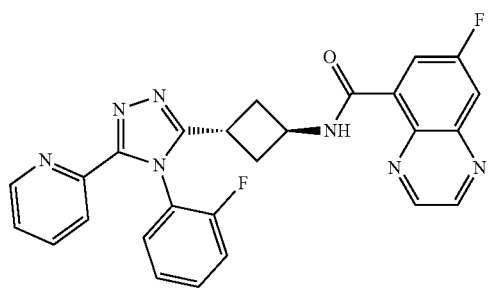 |
| 196 | 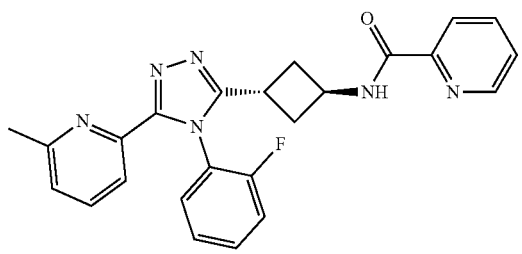 |
| 197 | 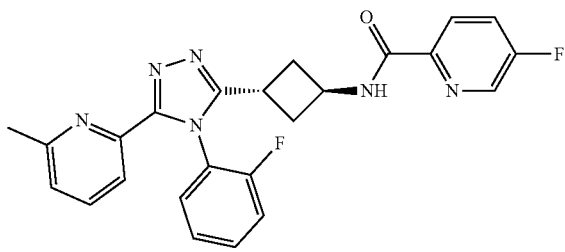 |
| 198 | 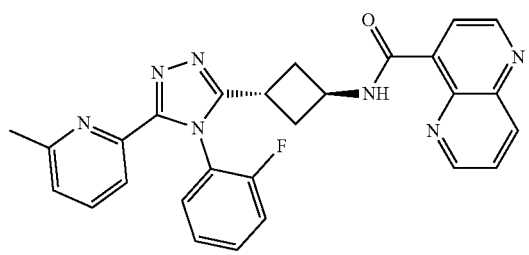 |

-continued

| Example No. (where applicable) | Structure |
|---|---|
| 199 | 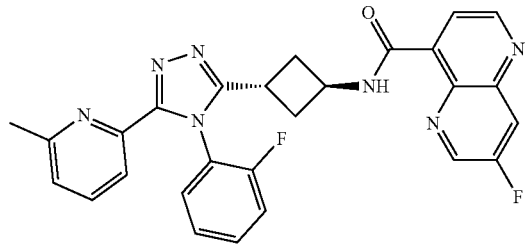 |
| 200 | 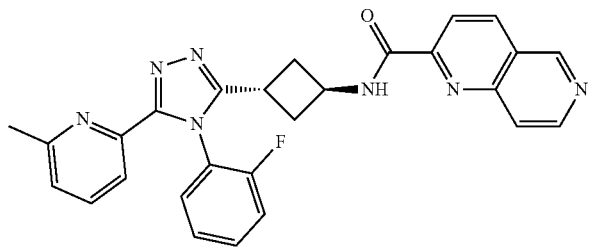 |
| 201 | 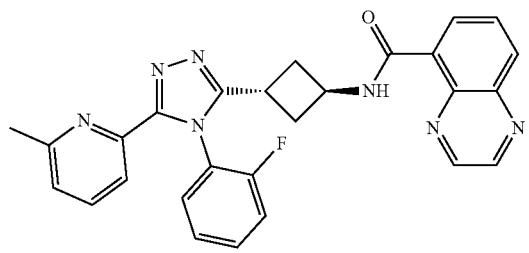 |
| 202 | 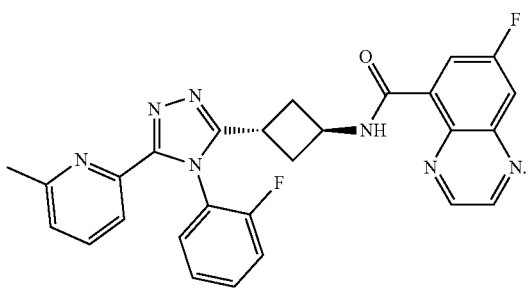 |

22. A pharmaceutical composition comprising a compound as claimed in claim 1, or a tautomer, a stereoisomer, a pharmaceutically acceptable salt, or a pro-drug thereof, together with one or more pharmaceutically acceptable carriers, excipients or diluents.

23. A method of treatment of a disease or disorder responsive to inhibition of tankyrase 1 and/or 2, wherein said disease or disorder is a tumor emerging from colorectal tissue, uterus, pancreas, skin, liver, thyroid, prostate, ovary, stomach, lung, lymphoid, bladder, cervix, thyroid, head and neck, brain, breast or kidney; melanoma; non-regenerative wound healing; or viral infections, fibrosis, or metabolic conditions, said method comprising the step of administering a compound as claimed in claim 1, or a tautomer, a stereoisomer, a pharmaceutically acceptable salt, or pro-drug thereof.

* * * * *